(12) United States Patent
Lehmann-Lintz et al.

(10) Patent No.: US 7,592,373 B2
(45) Date of Patent: *Sep. 22, 2009

(54) AMIDE COMPOUNDS WITH MCH ANTAGONISTIC ACTIVITY AND MEDICAMENTS COMPRISING THESE COMPOUNDS

(75) Inventors: Thorsten Lehmann-Lintz, Ochsenhausen (DE); Ralf R. H. Lotz, Schemmerhofen (DE); Philipp Lustenberger, Warthausen (DE); Stephan Georg Mueller, Warthausen (DE); Gerald Juergen Roth, Biberach (DE); Klaus Rudolf, Warthausen (DE); Marcus Schindler, Biberach (DE); Dirk Stenkamp, Biberach (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 500 days.

This patent is subject to a terminal disclaimer.

(21) Appl. No.: 11/021,897

(22) Filed: Dec. 23, 2004

(65) Prior Publication Data

US 2005/0267093 A1 Dec. 1, 2005

Related U.S. Application Data

(60) Provisional application No. 60/538,593, filed on Jan. 23, 2004.

(30) Foreign Application Priority Data

Dec. 23, 2003 (DE) ................ 103 60 745

(51) Int. Cl.
C07C 233/29 (2006.01)
C07C 235/24 (2006.01)
C07D 209/18 (2006.01)
A61K 31/40 (2006.01)
A61K 31/167 (2006.01)
A61K 31/404 (2006.01)
A61P 3/04 (2006.01)

(52) U.S. Cl. .............. 514/613; 514/318; 514/330; 514/415; 514/539; 514/622; 546/194; 546/227; 546/233; 548/510; 548/568; 558/414; 560/43; 564/123; 564/182

(58) Field of Classification Search ............ 514/613; 564/123

See application file for complete search history.

(56) References Cited

U.S. PATENT DOCUMENTS

| 6,258,953 | B1 | 7/2001 | Howard et al. |
|---|---|---|---|
| 6,366,268 | B1 | 4/2002 | Forrest et al. |
| 7,351,719 | B2 * | 4/2008 | Stenkamp et al. ........ 514/318 |
| 2002/0052383 | A1 | 5/2002 | Bakthavatchalam et al. |
| 2003/0192132 | A1 | 10/2003 | Chassot et al. |
| 2004/0082780 | A1 | 4/2004 | Doherty et al. |
| 2004/0142953 | A1 | 7/2004 | Delorme et al. |
| 2004/0220191 | A1 | 11/2004 | Schwink et al. |
| 2005/0009815 | A1 | 1/2005 | DeVita et al. |
| 2005/0026915 | A1 | 2/2005 | DeVita et al. |

FOREIGN PATENT DOCUMENTS

| EP | 0 237 678 A1 | 9/1987 |
|---|---|---|
| EP | 0 810 220 A1 | 12/1997 |
| EP | 1 283 199 A1 | 2/2003 |
| JP | 04054118 * | 2/1992 |
| JP | 2000086603 | 3/2000 |
| WO | WO 98/38156 | 9/1998 |
| WO | WO 99/02497 A2 | 1/1999 |
| WO | WO 99/29674 | 6/1999 |
| WO | WO 00/05223 | 2/2000 |
| WO | WO 00/06153 | 2/2000 |
| WO | WO 00/49005 | 8/2000 |
| WO | WO 01/02344 | 1/2001 |
| WO | WO 01/21577 | 3/2001 |
| WO | WO 01 55066 A2 | 8/2001 |
| WO | WO 01/82925 | 8/2001 |
| WO | WO 02 04433 A2 | 1/2002 |
| WO | WO 02/06245 A1 | 1/2002 |
| WO | WO 02 28182 A1 | 4/2002 |
| WO | WO02/051809 A1 | 7/2002 |
| WO | WO02/057233 A1 | 7/2002 |
| WO | WO 02/079144 A1 | 10/2002 |
| WO | WO 02/092068 | 11/2002 |
| WO | WO 03 013247 A1 | 2/2003 |

(Continued)

OTHER PUBLICATIONS

Baker, et al., J. Med. Chem., 1967, 10(6)1113-22, especially p. 1116.*

(Continued)

Primary Examiner—Golam M. M. Shameem
Assistant Examiner—Susannah Chung
(74) Attorney, Agent, or Firm—Michael P. Morris; Mary-Ellen M. Devlin; Timothy X. Witkowski

(57) ABSTRACT

Compounds of formula (I)

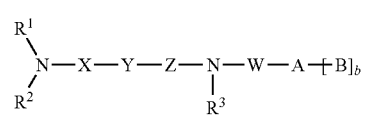

wherein A, B, b, W, X, Y, Z, $R^1$, $R^2$, and $R^3$ have the meanings given in claim 1, pharmaceutical compositions these compounds, and methods of preventing or treating metabolic disorders and/or eating disorders, particularly obesity, bulimia, anorexia, hyperphagia, and diabetes using these compounds.

18 Claims, No Drawings

FOREIGN PATENT DOCUMENTS

| | | |
|---|---|---|
| WO | WO 03/014111 A1 | 2/2003 |
| WO | WO 03/018579 A1 | 3/2003 |
| WO | WO 03/024448 A2 | 3/2003 |
| WO | WO 03/032980 A1 | 4/2003 |
| WO | WO 03/033476 A1 | 4/2003 |
| WO | WO 03/035055 | 5/2003 |
| WO | WO 03/045313 A2 | 6/2003 |
| WO | WO 03/045920 A1 | 6/2003 |
| WO | WO 03/049702 A2 | 6/2003 |
| WO | WO 03 050087 A2 | 6/2003 |
| WO | WO 2004/024702 A1 | 3/2004 |
| WO | WO 2004/037751 A2 | 5/2004 |
| WO | WO 2004/039764 A1 | 5/2004 |
| WO | WO 2004/039780 A1 | 5/2004 |
| WO | WO 2004/069823 A1 | 8/2004 |
| WO | WO 2004/072018 | 8/2004 |
| WO | WO 2004/072025 A2 | 8/2004 |
| WO | WO2005/085221 A1 | 9/2005 |

OTHER PUBLICATIONS

Yamakawa, et al., Macromolecules, 1999, 32(25), 8363-8369, especially p. 8365.*

Yanyun Chen, et al. "Targeted Disruption of the Melanin-Concentrating Hormone Receptor-1 Results in Hyperphagia and Resistance to Diet-Induced Obesity", Endocrinology 143(7):2469-2477 2002.

Daqing Qu, et al. "A Role for melanin-concentrating hormone in the central regulation of feeding behaviour" Nature vol. 380, pp. 243-247 1996.

Masako Shimada, et al. "Mice lacking melanin-concentrating hormone are hypophagic and lean" Nature vol. 396, pp. 670-674 1998.

Beth Borowsky, et al. "Antidepressant, anxlolytic and anorectic effects of a melanin-concentrating hormone-1 receptor antagonist" Nature Medicine vol. 8, No. 8, pp. 825-830, 2002.

Donald J. Marsh, et al. "Melanin-concentrating hormone 1 receptor-deficient mice are lean, hyperactive, and hyperphagic and have altered metabolism" PNAS, vol. 99, No. 5, pp. 3240-3245, 2002.

Shiro Takekawa, et al. "T-226296: a novel, orally active and selective melanin-concentrating hormone receptor antagonist" E. Journal of Pharm. vol. 438, pp. 129-13, 2002.

J. Krapcho, et al; "Immunosuppressive Activity of 2'-(3-Dimethylaminopropylthio) cinnamanilide (Cinanserin) and Relateld Compounds" J. Med. Chemistry. 1969, 12(1), 164-166.

Stenkamp, D. et al; U.S. Appl. No. 11/104,915—Alkyne Compounds with MCH Antagonistic Activity and Medicaments Comprising These Compounds filed Apr. 13, 2005.

Stenkamp, D. et al; U.S. Appl. No. 11/105,010—Alkyne Compounds with MCH Antagonistic Activity and Medicaments Comprising These Compounds filed Apr. 13, 2005.

Stenkamp, D. et al; U.S. Appl. No. 11/104,914—Alkyne Compounds with MCH Antagonistic Activity and Medicaments Comprising These Compounds filed Apr. 13, 2005.

Stenkamp, D. et al; U.S. Appl. No. 11/104,632- Alkyne Compounds with MCH Antagonistic Activity and Medicaments Comprising These Compounds filed Apr. 13, 2005.

Stenkamp, D. et al; U.S. Appl. No. 11/104,889—Alkyne Compounds with MCH Antagonistic Activity and Medicaments Comprising These Compounds filed Apr. 13, 2005.

Tetsuo, Sato, et al; Japanese Abstract 2002193800; VEGF Receptor antagonists for treatament of neoangiogenesis-related diseases.

* cited by examiner

AMIDE COMPOUNDS WITH MCH ANTAGONISTIC ACTIVITY AND MEDICAMENTS COMPRISING THESE COMPOUNDS

RELATED APPLICATIONS

This application claims benefit of U.S. Ser. No. 60/538,593, filed Jan. 23, 2004, and claims priority to German Application No. 103 60 745.5, filed Dec. 23, 2003, each of which is hereby incorporated by reference in its entirety.

FIELD OF THE INVENTION

The present invention relates to new amide compounds, the physiologically acceptable salts thereof, as well as their use as MCH antagonists and their use in preparing a pharmaceutical preparation which is suitable for the prevention and/or treatment of symptoms and/or diseases caused by MCH or causally connected with MCH in some other way. The invention further relates to the use of a compound according to the invention for influencing eating behavior and for reducing bodyweight and/or for preventing an increase in the bodyweight of a mammal. The invention also relates to compositions and medicaments containing a compound according to the invention, and processes for preparing them. Further objects of this invention relate to processes for preparing the compounds according to the invention.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialized countries, have promoted morbid overweight (also known as corpulence or obesity) in recent decades. In affected people, obesity leads directly to restricted mobility and a reduction in the quality of life. There is the additional factor that obesity often leads to other diseases such as, for example, diabetes, dyslipidemia, high blood pressure, arteriosclerosis, and coronary heart disease. Moreover, high bodyweight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases. For simplicity's sake, in the present invention, individuals with a Body Mass Index (BMI), which is defined as the bodyweight measured in kilograms divided by the height (in meters) squared, above a value of 25 and more particularly above 30, are preferably regarded as suffering from obesity.

Apart from physical activity and a change in nutrition, there is currently no convincing treatment option for effectively reducing bodyweight. As obesity is a major risk factor in the development of serious and even life-threatening diseases, however, it is all the more important to have access to pharmaceutical active substances for the prevention and/or treatment of obesity. One approach which has been proposed very recently is the therapeutic use of MCH antagonists (cf. inter alia WO 01/21577 and WO 01/82925).

Melanin-concentrating hormone (MCH) is a cyclic neuropeptide consisting of 19 amino acids. It is synthesized predominantly in the hypothalamus in mammals and from there travels to other parts of the brain by the projections of hypothalamic neurons. Its biological activity is mediated in humans through two different glycoprotein-coupled receptors (GPCRs) from the family of rhodopsin-related GPCRS, namely the MCH receptors 1 and 2 (MCH-1R, MCH-2R).

Investigations into the function of MCH in animal models have provided good indications for a role of the peptide in regulating the energy balance, i.e., changing metabolic activity and food intake. D. Qu, et al., *A role for melanin-concentrating hormone in the central regulation of feeding behavior*, Nature, 1996, 380(6571): pp. 243-7; M. Shimada, et al., *Mice lacking melanin-concentrating hormone are hypophagic and lean*, Nature, 1998, 396(6712): pp. 670-4. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the G-Galpha i-coupled MCH-1R [B. Borowsky, et al., *Antidepressant, anxiolytic and anorectic effects of a melanin-concentrating hormone-1 receptor antagonist*, Nat Med, 2002, 8(8): pp. 825-30; Y. Chen, et al., *Targeted disruption of the melanin-concentrating hormone receptor-1 results in hyperphagia and resistance to diet-induced obesity*, Endocrinology, 2002, 143(7): pp. 2469-77; D. J. Marsh, et al., *Melanin-concentrating hormone 1 receptor-deficient mice are lean, hyperactive, and hyperphagic and have altered metabolism*. Proc Natl Acad Sci USA, 2002, 99(5): pp. 3240-5; S. Takekawa, et al., T-226296: *A novel, orally active and selective melanin-concentrating hormone receptor antagonist*. Eur J Pharmacol, 2002, 438(3): pp. 129-35.], as, unlike primates, ferrets, and dogs, no second MCH receptor subtype has hitherto been found in rodents. After losing the MCH-1R, knock-out mice have a lower fat mass, an increased energy conversion and, when fed on a high fat diet, do not put on weight, compared with control animals. Another indication of the importance of the MCH system in regulating the energy balance results from experiments with a receptor antagonist (SNAP-7941). B. Borowsky, et al., Nat Med, 2002, 8(8): pp. 825-30. In long term trials, the animals treated with the antagonist lose significant amounts of weight.

In addition to its anorectic effect, the MCH-LR antagonist SNAP-7941 also achieves additional anxiolytic and antidepressant effects in behavioral experiments on rats. B. Borowsky, et al., Nat Med, 2002, 8(8): pp. 825-30. Thus, there are clear indications that the MCH-MCH-1R system is involved not only in regulating the energy balance but also in affectivity.

In the patent literature, certain amine compounds are proposed as MCH antagonists. Thus, WO 01/21577 (Takeda) describes compounds of formula

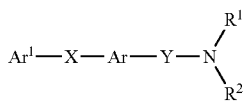

wherein Ar¹ denotes a cyclic group, X denotes a spacer, Y denotes a bond or a spacer, Ar denotes an aromatic ring which may be fused with a non-aromatic ring, $R^1$ and $R^2$ independently of one another denote H or a hydrocarbon group, while $R^1$ and $R^2$ together with the adjacent N atom may form an N-containing hetero ring, and $R^2$ with Ar may also form a spirocyclic ring, R together with the adjacent N atom, and Y may form an N-containing hetero ring, as MCH antagonists for the treatment of obesity, inter alia.

Moreover WO 01/82925 (Takeda) also describes compounds of formula

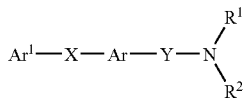

wherein Ar¹ denotes a cyclic group, X and Y represent spacer groups, Ar denotes an optionally substituted fused polycyclic aromatic ring, $R^1$ and $R^2$ independently of one another represent H or a hydrocarbon group, while $R^1$ and $R^2$ together with the adjacent N atom may form an N-containing heterocyclic ring, and $R^2$ together with the adjacent N atom and Y may form an N-containing hetero ring, as MCH antagonists for the treatment of obesity.

EP 0 237 678 A1 describes indole derivatives for the treatment of migraine. Example 4 mentions the compound N-[4-[[(methylamino)sulfonyl]methyl]phenyl]-3-[2-(dimethylamino)ethyl]-1H-indole-5-propanamide oxalate.

JP 2000086603 describes propenamide derivatives which have a 2-hydroxypropoxy group, used as 5-HT1A receptor antagonists.

WO 99/29674 describes N-imidazolyl- and N-triazolylalkylphenylacetamide derivatives as inhibitors of the retinoid metabolism. The substance N-[4-[1-(1H-imidazol-1-yl)-2-methylpropyl]phenyl]-3-phenyl-2-propinamide is mentioned as compound number 198.

J. Krapcho et al., *Immunosuppressive activity of 2'-(3-dimethylaminopropylthio)cinnamanilide (cinanserin) and related compounds*, J. Med. Chem. (1969), 12(1), 164-6, mention inter alia the compound 2'-[[3-(dimethylamino)propyl]thio]-3-phenylpropiolanilide.

WO 01/002344 describes aminobenzoic acid derivatives as VEGF receptor antagonists and mentions, among others, the compound 2-(methylthio)-5-[[3-[4-(octadecylamino)phenyl]-1-oxopropyl]amino]benzoic acid.

JP 04054118 proposes 4-(acylamino)phenols as 5-lipoxygenase inhibitors and mentions among others the compounds 4-amino-N-(4-hydroxy-3,5-dimethylphenyl)benzenepropanamide as well as 4-(dimethylamino)-N-(4-hydroxy-3,5-dimethylphenyl)benzenepropanamide.

The preparation of [[(benzoxyzolylalkanoyl)amino]phenyl]alkanoates and their suitability as integrin receptor ligands are described in WO 00/049005. Mention is made inter alia of the compound β-methyl-4-[[3-[2-[(2-methylphenyl)amino]-6-benzoxazolyl]-1-oxopropylamino]benzenepropanoic acid.

WO 00/005223 describes benzoxazole derivatives as inhibitors of the interaction between VCAM-1 and/or fibronectin and the integrin receptor VLA-4. Mention is made inter alia of the compound 4-[3-[[1-oxo-3-[2-(phenylamino)-6-benzoxazolyl]propyl]amino]phenoxy]-butanoic acid.

The preparation of carboxylic acid derivatives as EDG-1 receptor agonists is described in WO 02/092068. Mention is made inter alia of 2-chloro-5-[[1-oxo-3-[4-[(5-phenylpentyl)amino]phenyl]propyl]amino]benzoic acid and the corresponding methyl ester.

Published International Application WO 2004/072018 proposes amine derivatives as antagonists of the MCH receptor. As well as compounds covered by general formula

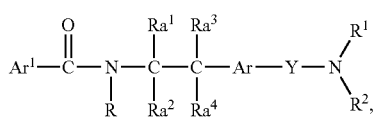

a number of different individual compounds are also published.

The aim of the present invention is to provide new amide compounds, particularly those which are effective as MCH antagonists.

The invention also sets out to provide new amide compounds which can be used to influence the eating habits of mammals and achieve a reduction in bodyweight, particularly in mammals, and/or prevent an increase in bodyweight.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the amide compounds according to the invention. Other aims of the present invention will be immediately apparent to the skilled man from the foregoing remarks and those that follow.

SUMMARY OF THE INVENTION

In a first aspect the present invention relates to amide compounds of general formula I

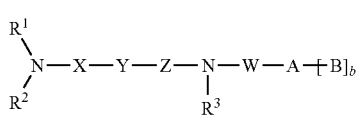

wherein:
$R^1$ and $R^2$ independently of one another denote H, a $C_{1-8}$-alkyl, or $C_{3-7}$-cycloalkyl group optionally mono- or polysubstituted by the group $R^{11}$, while a —CH$_2$— group in position 3 or 4 of a 5-, 6-, or 7-membered cycloalkyl group may be replaced by —O—, —S—, —NR$^{13}$-, or a phenyl or pyridinyl group optionally mono- or polysubstituted by the group $R^{12}$ and/or monosubstituted by nitro, or $R^1$ and $R^2$ form a $C_{2-8}$-alkylene bridge, wherein
- one or two —$CH_2$— groups independently of one another may be replaced by —CH=N— or —CH=CH— and/or
- one or two —$CH_2$— groups independently of one another may be replaced by —O—, —S—, —SO—, —($SO_2$)—, —C=N—O—$R^{18}$, —CO—, —C(=$CH_2$)—, or —$NR^{13}$— in such a way that heteroatoms are not directly joined together, and that a group —C=N—O—$R^{18}$ or —CO— is not directly linked to the group $R^1R^2N$—,
- while in the alkylene bridge defined hereinbefore one or more H atoms may be replaced by $R^{14}$, and the alkylene bridge defined hereinbefore may be substituted by one or two identical or different carbo- or heterocyclic groups Cy such that the bond between the alkylene bridge and the group Cy is made
- via a single or double bond,
- via a common C atom forming a spirocyclic ring system,
- via two common adjacent C and/or N atoms forming a fused bicyclic ring system, or
- via three or more C and/or N atoms forming a bridged ring system;

$R^3$ denotes H, $C_{1-6}$-alkyl, $C_{3-7}$-cycloalkyl, $C_{3-7}$-cycloalkyl-$C_{1-4}$-alkyl, or phenyl-$C_{1-3}$-alkyl;

X denotes a single bond or a $C_{1-8}$-alkylene bridge, wherein:
- a —$CH_2$— group which is not directly linked to the group $R^1R^2N$— may be replaced by —CH=CH— or —C≡C— and/or
- one or two non-adjacent —$CH_2$— groups, which are not directly linked to the group $R^1R^2N$—, may be replaced independently of one another by —O—, —S—, —(SO)—, —($SO_2$)—, —CO—, or —$NR^4$— in such a way that in each case two O, S, or N atoms or an O and an S atom are not directly joined together,
- while the bridge X may be connected to $R^1$ including the N atom linked to $R^1$ and X, forming a heterocyclic group, while the bridge X may additionally also be connected to $R^2$ including the N atom connected to $R^2$ and X, forming a heterocyclic group, and
- while two C atoms or a C and an N atom of the alkylene bridge may be joined together by an additional $C_{1-4}$-alkylene bridge, and
- a C atom may be substituted with $R^{10}$ and/or one or two C atoms may be substituted in each case by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, and W denotes a single bond, while Z denotes —C=C—C(=O)—, —$CR^{7a}R^{7c}$—C(=O)—, or —$CR^{7a}R^{7b}$—$CR^{7c}R^{7d}$—C(=O)—, or W denotes —C(=O)—C=C—, while Z denotes a single bond; and Y has one of the meanings given for Cy,
- while X may be connected to Y, forming a carbo- or heterocyclic group fused to Y, and/or
- optionally $R^1$ may be connected to Y, including the group X and the N atom connected to $R^1$ and X, forming a heterocyclic group fused to Y, and A has one of the meanings given for Cy, while if the index b has the value 0, the group Cy does not have an amino group as substituent in the ortho position to the bridge W;
B has one of the meanings given for Cy,
b denotes the value 0 or 1, Cy denotes a carbo- or heterocyclic group selected from one of the following meanings
- a saturated 3- to 7-membered carbocyclic group,
- a unsaturated 4- to 7-membered carbocyclic group,
- a phenyl group,
- a saturated 4- to 7-membered or unsaturated 5- to 7-membered heterocyclic group with an N, O, or S atom as heteroatom,
- a saturated or unsaturated 5- to 7-membered heterocyclic group with two or more N atoms or with one or two N atoms and one O or S atom as heteroatoms,
- an aromatic heterocyclic 5- or 6-membered group with one or more identical or different heteroatoms selected from N, O, and/or S,
- while the abovementioned 4,5-, 6-, or 7-membered groups may be fused to a phenyl or pyridine ring via two common adjacent C atoms, and
- in the abovementioned 5-, 6-, or 7-membered groups one or two non-adjacent —$CH_2$— groups may independently of one another be replaced by a —CO—, —C(=$CH_2$)—, —(SO)—, or —($SO_2$)— group, and
- the abovementioned saturated 6- or 7-membered groups may also occur as bridged ring systems with an imino, N-($C_{1-4}$-alkyl)-imino, methylene, $C_{1-4}$-alkylmethylene, or di-($C_{1-4}$-alkyl)methylene bridge, and
- the abovementioned cyclic groups may be mono- or polysubstituted by $R^{20}$ at one or more C atoms, in the case of a phenyl group may also additionally be monosubstituted by nitro, and/or one or more NH groups may be substituted by $R^{21}$;

$R^4$ has one of the meanings given for $R^{17}$ or denotes $C_{2-6}$-alkenyl or $C_{3-6}$-alkynyl,
$R^{7a}$ and $R^{7c}$ denote H, F, Cl, $C_{1-4}$-alkyl, or $CF_3$,
$R^{7b}$ and $R^{7d}$ denote H, F, $C_{1-4}$-alkyl, while $R^{7b}$ and $R^{7d}$ representing alkyl may be joined together to form a cyclopropyl group;
$R^{10}$ denotes hydroxy, hydroxy-$C_{1-3}$-alkyl, $C_{1-4}$-alkoxy, $C_{1-4}$-alkoxy-$C_{1-3}$-alkyl, carboxy, $C_{1-4}$-alkoxycarbonyl, amino, $C_{1-4}$-alkylamino, di-($C_{1-4}$-alkyl)amino, cyclo-$C_{3-6}$-alkyleneimino, amino-$C_{1-3}$-alkyl, $C_{1-4}$-alkylamino-$C_{1-3}$-alkyl, di-($C_{1-4}$-alkyl)amino-$C_{1-3}$-alkyl, cyclo-$C_{3-6}$-alkyleneimino-$C_{1-3}$-alkyl, amino-$C_{1-3}$-alkoxy, $C_{1-4}$-alkylamino-$C_{1-3}$-alkoxy, di-($C_{1-4}$-alkyl)amino-$C_{1-3}$-alkoxy, cyclo-$C_{3-6}$-alkyleneimino-$C_{1-3}$-alkoxy, aminocarbonyl, $C_{1-4}$-alkylaminocarbonyl, di-($C_{1-4}$-alkyl)aminocarbonyl, or cyclo-$C_{3-6}$-alkyleneiminocarbonyl;
$R^{11}$ denotes $C_{2-6}$-alkenyl, $C_{2-6}$-alkynyl, $R^{15}$—O—, $R^{15}$—O—$C_{1-3}$-alkyl, $R^{15}$—O—CO—, $R^{15}$—CO—O—, $R^{16}R^{17}N$—, cyano, $R^{18}R^{19}N$—CO—, or Cy;
$R^{12}$ has one of the meanings given for $R^{20}$;
$R^{13}$ has one of the meanings given for $R^{17}$, with the exception of carboxy;
$R^{14}$ denotes halogen, $C_{1-6}$-alkyl, $C_{2-6}$-alkenyl, $C_{2-6}$-alkynyl, $R^{15}$—O—, $R^{15}$—O—CO—, $R^{15}$—CO—, $R^{15}$—CO—O—, $R^{16}R^{17}N$, $R^{18}R^{19}N$—CO, $R^{15}$—O—$C_{1-3}$-alkyl, $R^{15}$—O—CO-$C_{1-3}$-alkyl, $R^{15}$—O—CO—NH—, $R^{15}$—$SO_2$—NH, $R^{15}$—O—CO—NH—$C_{1-3}$-alkyl, $R^{15}$—$SO_2$—NH—$C_{1-3}$-alkyl, $R^{15}$—CO—$C_{1-3}$-alkyl, $R^{15}$—CO—O—$C_{1-3}$-alkyl, $R^{16}R^{17}$N-$C_{1-3}$-alkyl, $R^{18}R^{19}N$—CO—$C_{1-3}$-alkyl, or Cy-$C_{1-3}$-alkyl;
$R^{15}$ denotes H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl, or pyridinyl-$C_{1-3}$-alkyl;
$R^{16}$ denotes H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, hydroxy-$C_{2-3}$-alkyl, $C_{1-4}$-alkoxy-$C_{2-3}$-alkyl, amino- $C_{2-6}$-alkyl, $C_{1-4}$-alkylamino-$C_{2-6}$-alkyl, di-($C_{1-4}$-alkyl) amino-$C_{2-6}$-alkyl, or cyclo-$C_{3-6}$-alkyleneimino-$C_{2-6}$-alkyl;

$R^{17}$ has one of the meanings given for $R^{16}$ or denotes phenyl, phenyl-$C_{1-3}$-alkyl, pyridinyl, dioxolan-2-yl, —CHO, $C_{1-4}$-alkylcarbonyl, carboxy, hydroxycarbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N-($C_{1-4}$-alkylcarbonyl)-N-($C_{1-4}$-alkyl)amino-$C_{2-3}$-alkyl, $C_{1-4}$-alkylsulfonyl, $C_{1-4}$-alkylsulfonylamino-$C_{2-3}$-alkyl, or N-($C_{1-4}$-alkylsulfonyl)-N($C_{1-4}$-alkyl)amino-$C_{2-3}$-alkyl;

$R^{18}$ and $R^{19}$ independently of one another denote H or $C_{1-6}$-alkyl;

$R^{20}$ denotes halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl, or has one of the meanings given for $R^{22}$;

$R^{21}$ denotes $C_{1-4}$-alkyl, hydroxy-$C_{2-3}$-alkyl, $C_{1-4}$-alkoxy-$C_{2-6}$-alkyl, $C_{1-4}$-alkylamino-$C_{2-6}$-alkyl, di-($C_{1-4}$-alkyl) amino-$C_{2-6}$-alkyl, cyclo-$C_{3-6}$-alkyleneimino-$C_{2-6}$-alkyl, phenyl-$C_{1-3}$-alkyl, $C_{1-4}$-alkyl-carbonyl, $C_{1-4}$-alkoxy-carbonyl, or $C_{1-4}$-alkylsulfonyl;

$R^{22}$ denotes phenyl-$C_{1-3}$-alkoxy, cyclo-$C_{3-6}$-alkyleneimino-$C_{2-4}$-alkoxy, OHC, HO—N=HC, $C_{1-4}$-alkoxy-N=HC, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)aminocarbonyl, cyclo-$C_{3-6}$-alkylaminocarbonyl, cyclo-$C_{3-6}$-alkyleneiminocarbonyl, cyclo-$C_{3-6}$-alkyleneimino-$C_{2-4}$-alkylaminocarbonyl, phenylaminocarbonyl, $C_{1-4}$-alkyl-sulfonyl, $C_{1-4}$-alkyl-sulfinyl, $C_{1-4}$-alkyl-sulfonylamino, amino, $C_{1-4}$-alkylamino, di-($C_{1-4}$-alkyl)amino, $C_{1-4}$-alkyl-carbonylamino, cyclo-$C_{3-6}$-alkyleneimino, phenyl-$C_{1-3}$-alkylamino, N-($C_{1-4}$-alkyl)phenyl-$C_{1-3}$-alkylamino, acetylamino, propionylamino, phenylcarbonylamino, phenylcarbonylmethylamino, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, or alkylaminocarbonylamino-, while in the abovementioned groups and radicals, particularly in A, B, W, X, Y, Z, $R^1$ to $R^4$, $R^{7a}$, $R^{7b}$, $R^{7c}$, $R^{7d}$, and $R^{10}$ to $R^{22}$, in each case one or more C atoms may additionally be mono- or polysubstituted by F and/or in each case one or two C atoms independently of one another may additionally be monosubstituted by Cl or Br and/or in each case one or more phenyl rings may independently of one another additionally comprise one, two, or three substituents selected from the group F, Cl, Br, I, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)amino, acetylamino, aminocarbonyl, cyano, difluoromethoxy, trifluoromethoxy, amino-$C_{1-3}$-alkyl, $C_{1-3}$-alkylamino-$C_{1-3}$-alkyl, and di-($C_{1-3}$-alkyl)amino-$C_{1-3}$-alkyl and/or may be monosubstituted by nitro, and the H atom of a carboxy group present or an H atom bound to an N atom in each case may be replaced by a group which can be cleaved in vivo, the tautomers, the diastereomers, the enantiomers, the mixtures thereof and the salts thereof, while the following compounds according to provisos (M1) to (M14) are not included:

(M1) N-[4-[[(methylamino)sulfonyl]methyl]phenyl]-3-[2-(dimethylamino)ethyl]-1H-indole-5-propanamide oxalate, (M2) 3-[2-[3-[3.6-dihydro-4-(2-naphthyl)-1 (2H)pyridinyl]-2-hydroxypropoxy]phenyl]-N-methyl-N-phenyl-2-propenamide, (M3) 3-[2-[2-hydroxy-3-[4-(1-naphthyl)-1-piperidinyl]propoxy]phenyl]-N-methyl-N-phenyl-2-propenamide, (M4) 3-[2-[2-hydroxy-3-[4-(2-naphthyl)-1-piperidinyl]propoxy]phenyl]-N-methyl-N-phenyl-2-propenamide, (M5) 3-[2-[2-hydroxy-3-[4-(2-naphthalyl)-1-piperidinyl] propoxy]phenyl]-N-phenyl-2-propenamide, (M6) N-[4-[1-(1H-imidazol-1-yl)-2-methylpropyl]phenyl]-3-phenyl-2-propinamide, (M7) 2'-[[3-(dimethylamino)propyl]thio]-3-phenylpropiolanilide, (M8) 2-(methylthio)-5-[[3-[4-(octadecylamino)phenyl]-1-oxopropyl]amino]benzoic acid, including the trifluoroacetate salt, (M9) 4-amino-N-(4-hydroxy-3,5-dimethylphenyl)benzenepropanamide, (M10) 4-(dimethylamino)-N-(4-hydroxy-3,5-dimethylphenyl)benzenepropanamide, (M11) β-methyl-4-[[3-[2-[(2-methylphenyl)amino]-6-benzoxazolyl]-1-oxopropylamino]-benzenepropanoic acid, (M12) 4-[3-[[1-oxo-3-[2-(phenylamino)-6-benzoxazolyl] propyl]amino]phenoxy]butanoic acid, (M13) 2-chloro-5-[[1-oxo-3-[4-[(5-phenylpentyl)amino] phenyl]propyl]amino]benzoic acid, (M14) methyl 2-chloro-5-[[1-oxo-3-[4-[(5-phenylpentyl)amino]phenyl]propyl]amino]-benzoate.

In view of the individual compounds disclosed in WO 2004/072018, the following compounds are preferably not included either according to the invention: N-(4-pentylphenyl)-3-(4-pyrrolidin-1-ylmethylphenyl)propionamide, N-(4-bromophenyl)-3-(4-pyrrolidin-1-ylmethylphenyl)propionamide, N-(4'-chlorobiphenyl-4-yl)-3-(4-pyrrolidin-1-ylmethylphenyl)propionamide, N-(4-bromophenyl)-3-(4-pyrrolidin-1-ylmethylphenyl)acrylamide, N-(4'-chlorobiphenyl-4-yl)-3-(4-pyrrolidin-1-ylmethylphenyl) acrylamide, N-(4-bromo-2-fluorophenyl)-3-(4-pyrrolidin-1-ylmethylphenyl)propionamide, and N-(4'-chloro-3-fluorobiphenyl-4-yl)-3-(4-pyrrolidin-1-ylmethylphenyl) propionamide.

The compounds according to the present invention, including the physiologically acceptable salts, are especially effective as antagonists of the MCH receptor, particularly the MCH-1 receptor, and exhibit very good affinity in MCH receptor binding studies. In addition, the compounds according to the invention have a high to very high selectivity with regard to the MCH receptor. Generally the compounds according to the invention have low toxicity, they are well-absorbed when administered by an oral route, and have good intracerebral transitivity, particularly brain accessibility.

The invention also relates to the compounds in the form of the individual optical isomers, mixtures of the individual diastereomers, enantiomers, or racemates, in the form of the tautomers and in the form of the free bases or the corresponding acid addition salts with pharmacologically safe acids. The subject of the invention also includes the compounds according to the invention, including their salts, wherein one or more hydrogen atoms are replaced by deuterium.

This invention also includes the physiologically acceptable salts of the amide compounds according to the invention as described above and hereinafter.

Also covered by this invention are compositions containing at least one amide compound according to the invention and/or a salt according to the invention optionally together with one or more physiologically acceptable excipients.

Also covered by this invention are pharmaceutical compositions containing at least one amide compound according to the invention and/or a salt according to the invention optionally together with one or more inert carriers and/or diluents.

The invention also relates to the use of at least one amide compound according to the invention and/or a salt according to the invention, including the compounds excluded by provisos (M1) to (M14), for influencing the eating behavior of a mammal.

The invention also relates to the use of at least one amide compound according to the invention and/or a salt according to the invention, including the compounds excluded by provisos (M1) to (M14), for reducing the bodyweight and/or for preventing an increase in the bodyweight of a mammal.

The invention also relates to the use of at least one amide compound according to the invention and/or a salt according to the invention, including the compounds excluded by provisos (M1) to (M14), for preparing a pharmaceutical composition with an MCH-receptor-antagonistic activity, particularly with an MCH-1-receptor-antagonistic activity.

Moreover, the invention relates to the use of at least one amide compound according to the invention and/or a salt according to the invention, including the compounds excluded by provisos (M1) to (M14), for preparing a pharmaceutical composition which is suitable for the prevention and/or treatment of symptoms and/or diseases which are caused by MCH or are otherwise causally connected with MCH.

The invention also relates to the use of at least one amide compound according to the invention and/or a salt according to the invention, including the compounds excluded by provisos (M1) to (M14), for preparing a pharmaceutical composition which is suitable for the prevention and/or treatment of metabolic disorders and/or eating disorders, particularly obesity, bulimia, bulimia nervosa, cachexia, anorexia, anorexia nervosa and hyperphagia.

This invention also relates to the use of at least one amide compound according to the invention and/or a salt according to the invention, including the compounds excluded by provisos (M1) to (M14), for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis, and gonitis.

Moreover, the invention relates to the use of at least one amide compound according to the invention and/or a salt according to the invention, including the compounds excluded by provisos (M1) to (M14), for preparing a pharmaceutical composition which is suitable for the prevention and/or treatment of hyperlipidemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia, and hormonal disorders.

Another object of the invention is the use of at least one amide compound according to the invention and/or a salt according to the invention, including the compounds excluded by provisos (M1) to (M14), for preparing a pharmaceutical composition which is suitable for the prevention and/or treatment of micturition disorders, such as, for example, urinary incontinence, hyperactive urinary bladder, urgency, nycturia, and enuresis.

Furthermore, the invention relates to processes for preparing a pharmaceutical composition according to the invention, characterized in that at least one amide compound according to the invention and/or a salt according to the invention is incorporated in one or more inert carriers and/or diluents by a non-chemical method.

The invention further relates to a pharmaceutical composition containing a first active substance selected from the amide compounds according to the invention and/or the corresponding salts, including the compounds excluded by provisos (M1) to (M14), as well as a second active substance selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of hyperlipidemia, including arteriosclerosis, active substances for the treatment of arthritis, active substances for the treatment of anxiety states, and active substances for the treatment of depression, optionally together with one or more inert carriers and/or diluents.

DETAILED DESCRIPTION OF THE INVENTION

Unless otherwise specified, the groups, residues and substituents, particularly A, B, W, X, Y, Z, $R^1$ to $R^4$, $R^{7a}$, $R^{7b}$, $R^{7c}$, $R^{7d}$, $R^{10}$ to $R^{22}$, and the index b have the meanings given hereinbefore.

If groups, residues and/or substituents occur more than once in a compound, they may have the same or different meanings in each case.

Preferred embodiments of this invention comprise compounds which may in each case be described by the following formulae Ia, Ib, Ic, and Id:

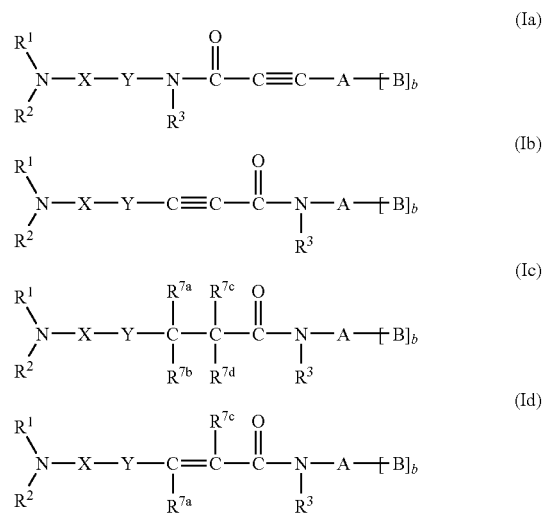

wherein $R^1$, $R^2$, $R^3$, $R^{7a}$, $R^{7b}$, $R^{7c}$, $R^{7d}$, X, Y, A, B, and b have the meanings given above and hereinafter, particularly the meanings stated as being preferred.

Particularly preferred definitions of the groups $R^{7a}$, $R^{7b}$, $R^{7c}$, and $R^{7d}$, are H or methyl, particularly H.

The preferred definitions of the individual groups and substituents given below refer to compounds of formula I according to the invention, particularly in each case to the four embodiments described by formulae Ia, Ib, Ic, and Id.

Preferred meanings of the substituent $R^3$ are H, $C_{1-4}$-alkyl, $C_{3-6}$-cycloalkyl, or $C_{3-6}$-cycloalkyl-$C_{1-3}$-alkyl; particularly H or $C_{1-3}$-alkyl. $R^3$ particularly preferably denotes H or methyl, particularly H.

The substituents $R^1$ and $R^2$ may have the meanings given above and hereinafter as separate groups or may be connected to one another as a bridge. For simplicity's sake, the preferred meanings of $R^1$ and $R^2$ as separate groups will be described first of all and then the preferred meanings of the groups $R^1$ and $R^2$ connected to one another to form a bridge. Preferred compounds according to the invention therefore have one of the preferred meanings of $R^1$ and $R^2$ described below, as separate groups combined with one of the preferred meanings of $R^1$ and $R^2$ described hereinafter as groups connected to one another to form a bridge.

If $R^1$ and $R^2$ are not joined together via an alkylene bridge, $R^1$ and $R^2$ independently of one another preferably denote a $C_{1-8}$-alkyl or $C_{3-7}$-cycloalkyl group optionally mono- or polysubstituted by the group $R^{11}$, while a —$CH_2$— group in position 3 or 4 of a 5-, 6-, or 7-membered cycloalkyl group may be replaced by —O—, —S—, or —$NR^{13}$—, or a phenyl or pyridinyl group optionally mono- or polysubstituted by the group $R^{12}$ and/or monosubstituted by nitro, while one of the groups $R^1$ and $R^2$ may also represent H.

Preferably the groups $R^1$ and $R^2$ independently of one another represent $C_{1-6}$-alkyl, $C_{3-7}$-cycloalkyl, $C_{3-7}$-cycloalkyl-$C_{1-3}$-alkyl, hydroxy-$C_{2-4}$-alkyl, NC—$C_{2-4}$-alkyl, $C_{1-4}$-alkoxy-$C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkylamino-$C_{2-4}$-alkyl, di-($C_{1-4}$-alkyl)amino-$C_{2-4}$-alkyl, cyclo-$C_{3-6}$-alkyleneimino-$C_{2-4}$-alkyl, or pyrrolidin-3-yl, while the NH group may be substituted by $R^{13}$, pyrrolidinyl-$C_{1-3}$-alkyl, while the NH group may be substituted by $R^{13}$, piperidin-3-yl or 4-yl, while the NH group may be substituted by $R^{13}$, piperidinyl-$C_{1-3}$-alkyl, while the NH group may be substituted by $R^{13}$, tetrahydropyran-3-yl or -4-yl, tetrahydropyranyl-C 13-alkyl, tetrahydrofuran-3-yl, tetrahydrofuranyl-$C_{1-3}$-alkyl, phenyl, phenyl-$C_{1-3}$-alkyl, pyridyl, or pyridyl-$C_{1-3}$-alkyl, while in the abovementioned groups and radicals one or more C atoms may be mono- or polysubstituted by F and/or one or two C atoms, particularly one C atom may independently of one another be monosubstituted with Cl or Br, and the phenyl or pyridyl group may be mono- or polysubstituted by the group $R^{12}$ defined hereinbefore and/or may be monosubstituted by nitro, and one of the groups $R^1$ or $R^2$ may also represent H. Preferably the abovementioned cycloalkyl rings may be mono- or polysubstituted by substituents selected from hydroxy, hydroxy-$C_{1-3}$-alkyl, $C_{1-3}$-alkyl, or $C_{1-3}$-alkyloxy, particularly hydroxy, hydroxymethyl, methyl and methoxy. Also preferably the $C_{2-4}$-alkyl bridges contained in hydroxy-$C_{2-4}$-alkyl and $C_{1-4}$-alkoxy-$C_{2-4}$-alkyl may additionally be monosubstituted by hydroxy, hydroxy-$C_{1-3}$-alkyl, $C_{1-3}$-alkyl, or $C_{1-3}$-alkyloxy, particularly hydroxy, hydroxymethyl, methyl, or methoxy. Preferred substituents $R^{12}$ of the abovementioned phenyl or pyridyl groups are selected from among F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)amino, acetylamino, aminocarbonyl, difluoromethoxy, trifluoromethoxy, amino-$C_{1-3}$-alkyl, $C_{1-3}$-alkylamino-$C_{1-3}$-alkyl, and di-($C_{1-3}$-alkyl)amino-$C_{1-3}$-alkyl, while a phenyl group may also be monosubstituted by nitro.

Particularly preferred definitions of the groups $R^1$ and/or $R^2$ are selected from the group consisting of $C_{1-6}$-alkyl, $C_{3-7}$-cycloalkyl, $C_{3-7}$-cycloalkyl-$C_{1-3}$-alkyl, tetrahydropyran-3 or 4-yl, tetrahydropyranyl-$C_{1-3}$-alkyl, and piperidin-3 or 4-yl, while the NH group may be substituted by $R^3$, piperidinyl-$C_{1-3}$-alkyl, while the NH group may be substituted by $R^3$, phenyl, pyridyl, phenyl-$C_{1-3}$-alkyl, pyridyl-$C_{1-3}$-alkyl, hydroxy-$C_{2-4}$-alkyl, $C_{1-4}$-alkoxy-$C_{2-4}$-alkyl, amino-$C_{2-4}$-alkyl, $C_{1-4}$-alkylamino-$C_{2-4}$-alkyl-, and di-($C_{1-4}$-alkyl)amino-$C_{2-4}$-alkyl, while cycloalkyl rings may be mono-, di-, or trisubstituted by substituents selected from hydroxy, hydroxy-$C_{1-3}$-alkyl, $C_{1-3}$-alkyl, or $C_{1-3}$-alkyloxy, particularly hydroxy, hydroxymethyl, methyl, and methoxy, and $C_{2-4}$-alkyl bridges contained in hydroxy-$C_{2-4}$-alkyl- and $C_{1-4}$-alkoxy-$C_{2-4}$-alkyl- may additionally be monosubstituted by hydroxy, hydroxy-$C_{1-3}$-alkyl, $C_{1-3}$-alkyl, or $C_{1-3}$-alkyloxy, particularly hydroxy, hydroxymethyl, methyl, or methoxy, and alkyl groups may be mono- or polysubstituted by F and/or monosubstituted by Cl, and one of the groups $R^1$ and $R^2$ may also represent H.

$R^{13}$ preferably denotes H, $C_{1-6}$-alkyl, $C_{1-4}$-alkylcarbonyl, or $C_{1-4}$-alkyloxycarbonyl. Particularly preferably $R^{13}$ denotes H or $C_{1-4}$-alkyl, particularly H, methyl, ethyl, or propyl.

Most particularly preferred definitions of the groups $R^1$ and/or $R^2$ are selected from the group consisting of methyl, ethyl, n-propyl, isopropyl, n-butyl, isobutyl, cyclopropyl, cyclopentyl, cyclohexyl, cyclopropylmethyl, cyclopentylmethyl, cyclohexylmethyl, phenyl, pyridyl, phenylmethyl, pyridylmethyl, tetrahydropyran-4-yl, tetrahydropyran-4-ylmethyl, and piperidin-4-yl, which may be substituted by $R^{13}$ at the N atom, or piperidin-4-ylmethyl, which may be substituted by $R^{13}$ at the N atom, while the ethyl, propyl, and butyl groups mentioned may be monosubstituted by amino, methylamino, or dimethylamino or mono- or disubstituted by hydroxy, methoxy, or ethoxy, and the abovementioned cycloalkyl rings may be mono- or disubstituted by hydroxy, hydroxymethyl, or methyl, and methyl groups may be mono- or polysubstituted by fluorine, and one of the groups $R^1$ and $R^2$ may also represent H.

Examples of most particularly preferred definitions of the groups $R^1$ and/or $R^2$ are methyl, ethyl, n-propyl, isopropyl, 2-hydroxyethyl, 2-hydroxypropyl, 3-hydroxypropyl, 2-hydroxy-2-methylpropyl, 2-methoxyethyl, 3-aminopropyl, cyclopropyl, cyclopentyl, cyclohexyl, cyclopropylmethyl, (1-hydroxycyclopropyl)methyl, phenyl, pyridyl, phenylmethyl, pyridylmethyl, tetrahydropyran-4-yl, N-methylpiperidin-4-yl, N-(methylcarbonyl)piperidin-4-yl, and N-(tert-butyloxycarbonyl)piperidin-4-yl, while hydroxyalkyl groups may additionally be substituted by hydroxy, and one of the groups $R^1$ or $R^2$ may also represent H.

If the substituent $R^1$ has one of the meanings stated above as being preferred, but not H, the substituent $R^2$ most particularly preferably denotes H, methyl, ethyl, n-propyl, isopropyl, 2-hydroxyethyl, or 2-methoxyethyl.

Compounds according to the invention, particularly those which may be described by formula Ic or Id, are also preferred wherein one or both groups $R^1$ and $R^2$ represent one or more groups selected from 2-hydroxyethyl, 2-hydroxy-2-methylpropyl, 2-methoxyethyl, 3-aminopropyl, cyclopropyl, cyclopentyl, cyclohexyl, cyclopropylmethyl, (1-hydroxycyclopropyl)methyl, phenyl, pyridyl, phenylmethyl, pyridylmethyl, tetrahydropyran-4-yl, N-methylpiperidin-4-yl, N-(methylcarbonyl)piperidin-4-yl, and N-(tert-butyloxycarbonyl)piperidin-4-yl, particularly 2-hydroxyethyl, 2-hydroxy-2-methylpropyl, 2-methoxyethyl, tetrahydropyran-4-yl, cyclopropylmethyl and (1-hydroxycyclopropyl)methyl, while hydroxyalkyl groups may additionally be substituted by hydroxy.

Particularly preferably at least one of the groups $R^1$ or $R^2$, most particularly preferably both groups, have a meaning other than H.

If $R^1$ and $R^2$ form an alkylene bridge, this is preferably a $C_{3-7}$-alkylene bridge, wherein

- a —$CH_2$— group not adjacent to the N atom of the $R^1R^2N$ group may be replaced by —CH=CH— and/or
- a —$CH_2$— group which is preferably not adjacent to the N atom of the $R^1R^2N$— group may be replaced by —O—, —S—, —C(=N—O—$R^{18}$)—, —CO—, —C(=$CH_2$)—, or —$NR^{13}$—, particularly preferably by —O—, —S—, or —$NR^{13}$—, in such a way that heteroatoms are not directly joined together and a group —C=N—O—$R^{18}$ or —CO— is not directly linked to the group $R^1R^2N$—, while in the alkylene bridge defined hereinbefore one or more H atoms may be replaced by $R^{14}$, and the alkylene bridge defined hereinbefore may be substituted by a carbo- or heterocyclic group Cy in such a way that the bond between the alkylene bridge and the group Cy is made via a single or double bond,

- via a common C atom forming a spirocyclic ring system,
- via two common adjacent C and/or N atoms forming a fused bicyclic ring system, or
- via three or more C and/or N atoms forming a bridged ring system.

$R^{13}$ preferably denotes H, $C_{1-6}$-alkyl, $C_{1-4}$-alkylcarbonyl, or $C_{1-4}$-alkyloxycarbonyl. Particularly preferably $R^{13}$ denotes H or $C_{1-6}$-alkyl, particularly H, methyl, ethyl, or propyl.

Also preferably $R^1$ and $R^2$ form an alkylene bridge in such a way that $R^1R^2N$— denotes a group selected from azetidine, pyrrolidine, piperidine, azepan, 2,5-dihydro-1H-pyrrole, 1,2,3,6-tetrahydropyridine, 2,3,4,7-tetrahydro-1H-azepine, 2,3,6,7-tetrahydro-1H-azepine, piperazine wherein the free imine function is substituted by $R^{13}$, piperidin-4-one, piperidin-4-one-oxime, piperidin-4-one-O—$C_{1-4}$-alkyl-oxime, morpholine, and thiomorpholine, particularly a group selected from pyrrolidine, piperidine, 2,5-dihydro-1H-pyrrole, morpholine, thiomorpholine, and piperazine, wherein the free imine function is substituted by $R^{13}$, while according to the general definition of $R^1$ and $R^2$ one or more H atoms may be replaced by $R^{14}$, and/or the above-mentioned groups may be substituted by one or two identical or different carbo- or heterocyclic groups Cy in a manner specified according to the general definition of $R^1$ and $R^2$. Particularly preferred groups Cy for this are phenyl, $C_{3-7}$-cycloalkyl, and aza-$C_{4-7}$-cycloalkyl, particularly phenyl, $C_{3-6}$-cycloalkyl, cyclo-$C_{3-5}$-alkyleneimino, as well as N-$C_{1-4}$-alkyl-(aza-$C_{4-6}$-cycloalkyl), while the cyclic groups Cy may be substituted as specified.

The alkylene bridge formed by $R^1$ and $R^2$, wherein —$CH_2$— groups may be replaced as specified, may be substituted, as described, by one or two identical or different carbo- or heterocyclic groups Cy.

In the event that the alkylene bridge is linked to a group Cy via a single bond, Cy is preferably selected from the group consisting of $C_{3-7}$-cycloalkyl, cyclo-$C_{3-6}$-alkyleneimino, piperazinyl, 1H-imidazole, thienyl, and phenyl, particularly $C_{3-6}$-cycloalkyl, pyrrolidinyl, piperidinyl, and piperazinyl, which may be substituted as specified, and particularly the N atoms may be substituted by $C_{1-4}$-alkyl in each case.

In the event that the alkylene bridge is linked to a group Cy via a common C atom forming a spirocyclic ring system, Cy is preferably selected from the group consisting of $C_{3-7}$-cycloalkyl, aza-$C_{4-8}$-cycloalkyl, oxa-$C_{4-8}$-cycloalkyl, and 2,3-dihydro-1H-quinazolin-4-one, particularly cyclopentyl and cyclohexyl, which may be substituted as specified, and particularly the N atoms may be substituted by $C_{1-4}$-alkyl in each case.

In the event that the alkylene bridge is linked to a group Cy via two common adjacent C and/or N atoms forming a fused bicyclic ring system, Cy is preferably selected from the group consisting of $C_{4-7}$-cycloalkyl, aza-$C_{4-7}$-cycloalkyl, phenyl, and thienyl, particularly phenyl and pyrrolidinyl, which may be substituted as specified, and particularly the N atoms may be substituted by $C_{1-4}$-alkyl in each case.

In the event that the alkylene bridge is linked to a group Cy via three or more C and/or N atoms forming a bridged ring system, Cy preferably denotes $C_{4-8}$-cycloalkane or aza-$C_{4-8}$-cycloalkane, particularly cyclopentane, cyclohexane, pyrrolidine, or piperidine, while the N atoms may be substituted by $C_{1-4}$-alkyl in each case.

Particularly preferably the group

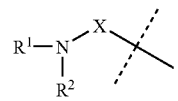

is defined according to one of the following partial formulae

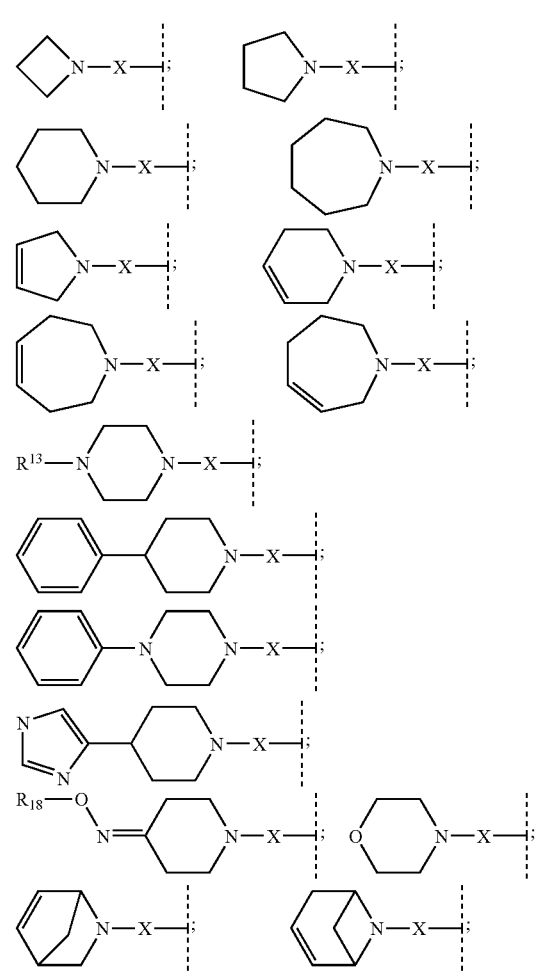

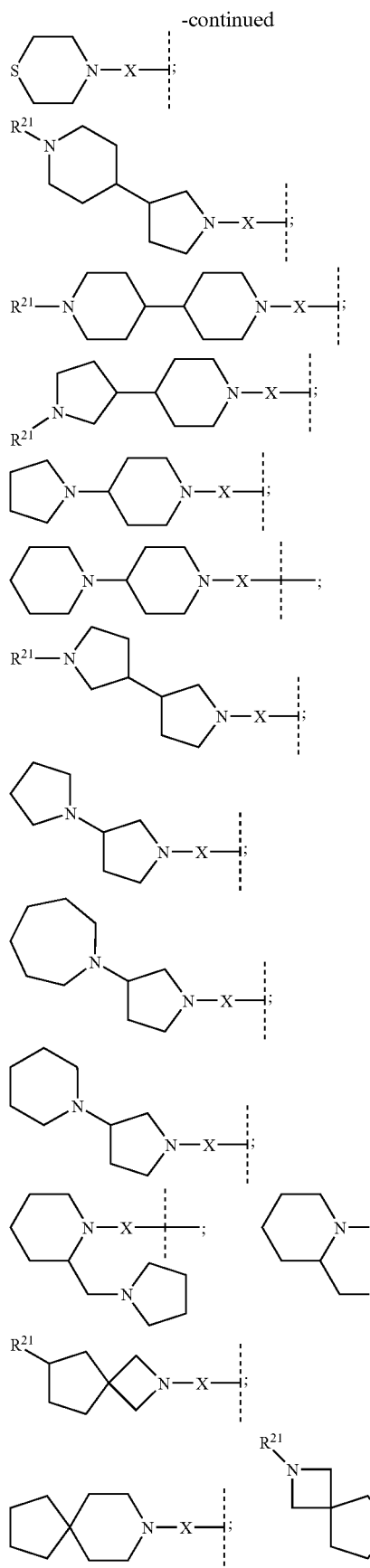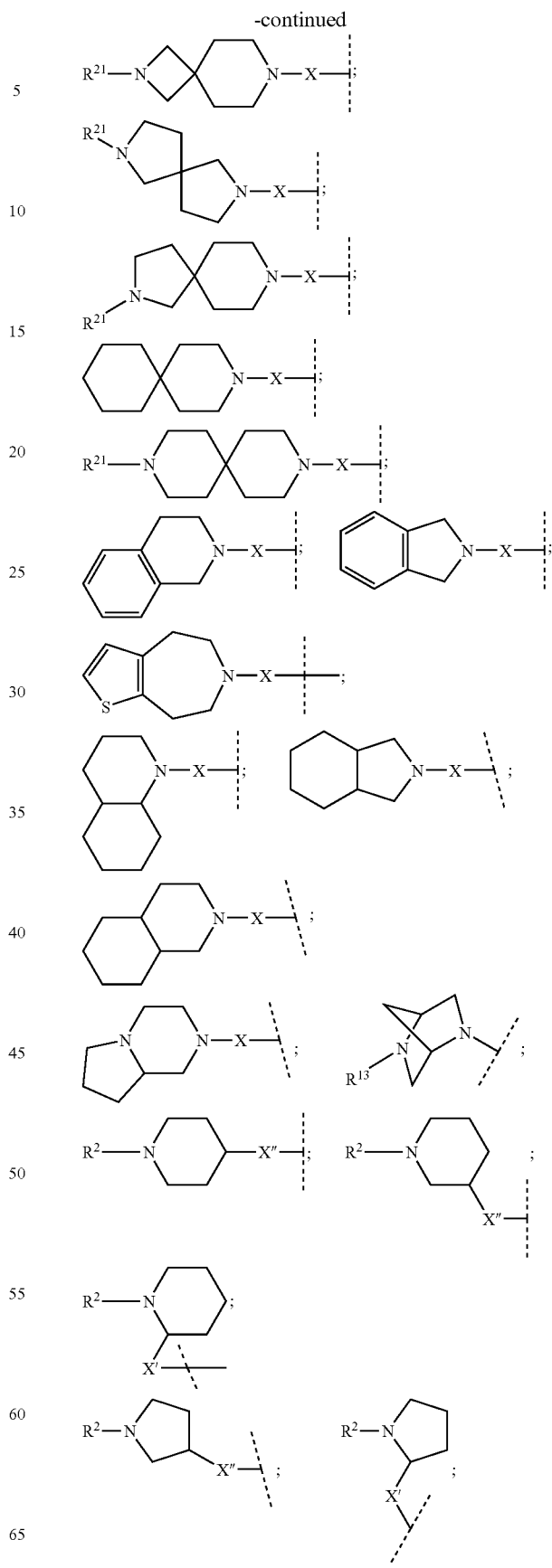

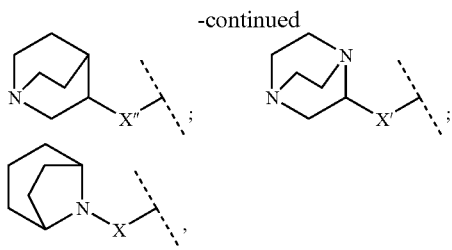

while in the heterocycle formed by the group $R^1R^2N$— one or more H atoms may be replaced by $R^{14}$ and/or a H atom may be substituted by Cy defined as $C_{3-7}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, and the ring connected to the heterocycle formed by the group $R^1R^2N$— may be mono- or polysubstituted at one or more C atoms by $R^{20}$, and in the case of a phenyl ring may also additionally be monosubstituted by nitro and X' and X" independently of one another denote a single bond or $C_{1-3}$-alkylene, and in the event that the group Y is linked to X' or X" via a C atom, may also denote —$C_{1-3}$-alkylene-O—, —$C_{1-3}$-alkylene-NH—, or —$C_{1-3}$-alkylene-N($C_{1-3}$-alkyl)-, and X" additionally also denotes —O—$C_{1-3}$-alkylene, —NH—$C_{1-3}$-alkylene, or —N($C_{1-3}$-alkyl)-$C_{1-3}$-alkylene, and in the event that the group Y is linked to X" via a C atom, also denotes —NH—, —N($C_{1-3}$-alkyl)-, or —O—, while in the meanings given for X' and X" hereinbefore in each case a C atom may be substituted by $R^{10}$, preferably by a hydroxy, ω-hydroxy-$C_{1-3}$-alkyl, ω-($C_{1-4}$-alkoxy)-$C_{1-3}$-alkyl, and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, while two alkyl and/or alkenyl substituents may be joined together, forming a carbocyclic ring system, and in X' and X" independently of one another in each case one or more C atoms may be mono- or polysubstituted by F and/or in each case one or two C atoms independently of one another may be monosubstituted by Cl or Br and wherein $R^2$, $R^{10}$, $R^{13}$, $R^{14}$, $R^{18}$, $R^{20}$, $R^{21}$, and X have the meanings given above and hereinafter.

Preferably X' and X" independently of one another represent a single bond or $C_{1-3}$-alkylene and in the event that the group Y is linked to X' or X" via a C atom, may also denote —$C_{1-3}$-alkylene-O, —$C_{1-3}$-alkylene-NH or —$C_{1-3}$-alkylene-N($C_{1-3}$-alkyl), and X" additionally also denotes —O—$C_{1-3}$-alkylene, —NH—$C_{1-3}$-alkylene, or —N($C_{1-3}$-alkyl)-$C_{1-3}$-alkylene and in the event that the group Y is linked to X" via a C atom, X" also denotes —NH, —N($C_{1-3}$-alkyl)-, or —O—. Particularly preferably X' and X" independently of one another represent a single bond or methylene and in the event that the group Y is linked to X' or X" via a C atom, also represent —$CH_2$—O—, —$CH_2$—NH—, or —$CH_2$—N($C_{1-3}$-alkyl)-, and in the event that the group Y is linked to X" via a C atom, X" also denotes —NH—, —N($C_{1-3}$-alkyl), or —O—.

In the preferred and particularly preferred meanings of $R^1R^2N$— listed above the following definitions of the substituent $R^{14}$ are preferred: F, Cl, Br, $C_{1-4}$-alkyl, $C_{2-4}$-alkenyl, $C_{2-4}$-alkynyl, $C_{3-7}$-cycloalkyl-$C_{1-3}$-alkyl, hydroxy, hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxycarbonyl, hydroxy-carbonyl-$C_{1-3}$-alkyl, $C_{1-4}$-alkoxy-carbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkylamino, $C_{3-7}$-cycloalkylamino, N-($C_{3-7}$-cycloalkyl)-N-($C_{1-4}$-alkyl)amino, di-($C_{1-4}$-alkyl)amino, amino-$C_{1-3}$-alkyl, $C_{1-4}$-alkylamino-$C_{1-3}$-alkyl, $C_{3-7}$-cycloalkylamino-$C_{1-3}$-alkyl, N—($C_{3-7}$-cycloalkyl)-N-($C_{1-4}$-alkyl)amino-$C_{1-3}$-alkyl, di-($C_{1-4}$-alkyl)amino-$C_{1-3}$-alkyl, cyclo-$C_{3-6}$-alkyleneimino-$C_{1-3}$-alkyl, aminocarbonyl, $C_{1-4}$-alkylaminocarbonyl, $C_{3-7}$-cycloalkylaminocarbonyl, N-($C_{3-7}$-cycloalkyl)-N-($C_{1-4}$-alkyl)aminocarbonyl, di-($C_{1-4}$-alkyl)aminocarbonyl, pyridinyl-oxy, pyridinylamino, and pyridinyl-$C_{1-3}$-alkylamino. In the above meanings of the group $R^4$, one or more C atoms may be mono- or polysubstituted by F and/or one or two C atoms independently of one another may be monosubstituted by Cl or Br, and in particular alkyl groups may be mono- or polysubstituted by fluorine.

Most particularly preferred meanings of the substituent $R^{14}$ are F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkoxy, $C_{1-4}$-alkoxy-$C_{1-3}$-alkyl, amino-$C_{1-3}$-alkyl, $C_{1-4}$-alkylamino-$C_{1-3}$-alkyl, $C_{3-7}$-cycloalkylamino-$C_{1-3}$-alkyl, N-($C_{3-7}$-cycloalkyl)-N-($C_{1-4}$-alkyl)amino-$C_{1-3}$-alkyl, di-($C_{1-4}$-alkyl)amino-$C_{1-3}$-alkyl, cyclo-$C_{3-6}$-alkyleneimino-$C_{1-3}$-alkyl, aminocarbonyl, and pyridylamino. In the above meanings of the group $R^4$, one or more C atoms, and particularly alkyl groups, may be mono- or polysubstituted by fluorine.

If in the heterocycle formed by the group $R^1R^2N$— an H atom is replaced by Cy representing $C_{3-7}$-cycloalkyl, which may be mono- or polysubstituted by $R^{20}$, Cy preferably denotes $C_{3-4}$-cycloalkyl and $R^{20}$ preferably denotes F, hydroxy, $C_{1-3}$-alkyl, $CF_3$, $C_{1-3}$-alkyloxy, $OCF_3$, or hydroxy-$C_{1-3}$-alkyl, particularly F, hydroxy, methyl, methoxy, $CF_3$, $OCF_3$, or hydroxymethyl. Particularly preferred meanings of Cy are $C_{3-6}$-cycloalkyl and 1-hydroxy-$C_{3-5}$-cycloalkyl.

Most particularly preferably the group

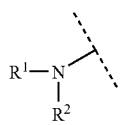

is defined according to one of the following partial formulae

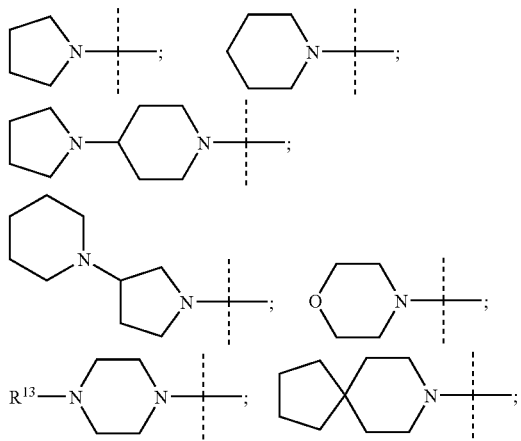

-continued

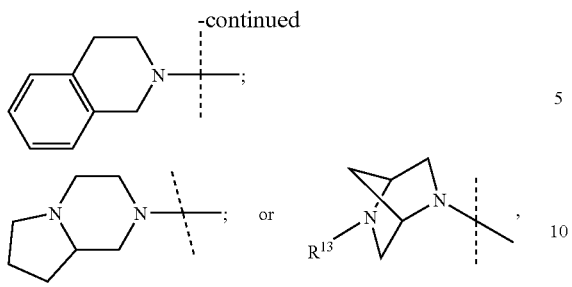

while in the heterocycle formed by the group $R^1R^2N$— one or more H atoms may be replaced by $R^{14}$ and/or an H atom may be replaced by Cy representing $C_{3-6}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, particularly preferably by F, hydroxy, methyl, methoxy, $CF_3$, $OCF_3$, or hydroxymethyl, and the ring connected to the heterocycle formed by the group $R^1R^2N$— may be mono- or polysubstituted, preferably monosubstituted at one or more C atoms by $R^{20}$, or in the case of a phenyl ring may also additionally be monosubstituted by nitro; and $R^{14}$ in each case independently of one another denotes F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms, particularly alkyl groups may additionally be mono- or polysubstituted by F; most particularly preferably denotes methyl, ethyl, propyl, trifluoromethyl, hydroxy, hydroxymethyl, 1-hydroxyethyl, 2-hydroxyethyl, 1-hydroxy-1-methylethyl, 1-hydroxycyclopropyl, methoxy, ethoxy, methoxymethyl, pyridylamino, or aminocarbonyl; and $R^{13}$ is as hereinbefore defined, particularly denotes H or $C_{1-3}$-alkyl.

Compounds according to the invention, particularly those which may be described by formula Ic or Id, are also preferred, wherein the group

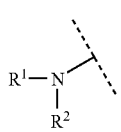

is defined according to one of the following partial formulae

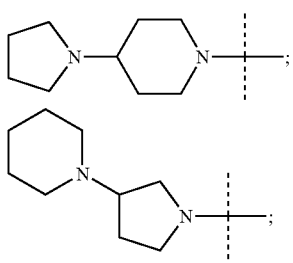

-continued

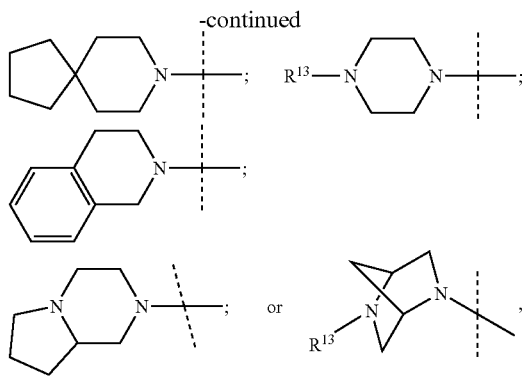

wherein H atoms may be replaced as specified hereinbefore and the ring connected to the heterocycle formed by the group $R^1R^2N$— may be mono- or polysubstituted, preferably monosubstituted at one or more C atoms by $R^{20}$, in the case of a phenyl ring may also additionally be monosubstituted by nitro, or wherein the group

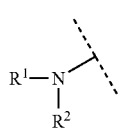

is defined according to one of the following partial formulae

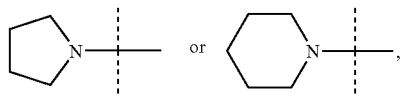

wherein at least one H atom of the heterocycle formed by the group $R^1R^2N$— is substituted by a substituent selected from hydroxy, hydroxy-$C_{1-3}$-alkyl, 1-hydroxy-$C_{3-5}$-cycloalkyl, $C_{1-4}$-alkyloxy and $C_{1-4}$-alkoxy-$C_{1-3}$-alkyl, and wherein additionally one or more, preferably one or two H atoms of the heterocycle formed by the group $R^1R^2N$— may be replaced by the substituent $R^{14}$ defined hereinbefore and/or an H atom of the heterocycle formed by the group $R^1R^2N$— may be replaced by Cy representing $C_{3-6}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, particularly preferably by F, hydroxy, methyl, methoxy, $CF_3$, $OCF_3$, or hydroxymethyl.

Preferably X denotes a $C_{1-6}$-alkylene bridge, wherein
a —$CH_2$ group not adjacent to the N atom of the $R^1R^2N$— group may be replaced by —CH═CH— or —C≡C—; and/or
a —$CH_2$— group not adjacent to the N atom of the $R^1R^2N$ group may be replaced by —O—, —S—, —CO—, or —$NR^4$—, particularly preferably by —O—, —S—, or —$NR^4$—, in such a way that in each case two O, S, or N atoms, or an O and an S atom are not directly joined together,
while $R^4$ may be attached to Y, forming a heterocyclic ring system with one another,
while the bridge X may be connected to $R^1$ including the N atom linked to $R^1$ and X, forming a heterocyclic group, and two C atoms or a C and an N atom of the alkylene bridge may be joined together by an additional $C_{1-4}$-alkylene bridge, and a C atom may be substituted by $R^{10}$ and/or one or two C atoms may each be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together forming a carbocyclic ring system, particularly a cyclopropyl, cyclobutyl, or cyclopentyl group.

Preferably, in the group X a —$CH_2$— group directly adjacent to the group $R^1R^2N$— is not replaced by —O—, —S—, —(SO)—, —($SO_2$)—, —CO—, or —$NR^4$—.

If in the group X one or two —$CH_2$— groups independently of one another are replaced by —O—, —S—, —(SO)—, —($SO_2$)—, —CO—, or —$NR^4$—, these groups are preferably spaced from the $R^1R^2N$— group by an alkylene bridge with at least 2 C atoms.

If in the group X two —$CH_2$ groups independently of one another are replaced by —O—, —S—, —(SO)—, —($SO_2$)—, —CO—, or —$NR^4$—, these groups are preferably separated from one another by an alkylene bridge with at least 2 C atoms.

If in the group X a —$CH_2$— group of the alkylene bridge is replaced according to the invention, this —$CH_2$— group is preferably not directly connected to a heteroatom, a double or triple bond.

Preferably the alkylene bridge X, X', or X" has no imino groups or at most only one imino group. The position of the imino group within the alkylene bridge X, X', or X" is preferably selected so that no aminal function is formed together with the amino group $NR^1R^2$ or another adjacent amino group, or two N atoms are not adjacent to one another.

If in X, X', or X" a C atom is substituted, preferred substituents are selected from among the $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, ω-hydroxy-$C_{1-3}$-alkyl, ω-($C_{1-4}$-alkoxy)-$C_{1-3}$-alkyl, and $C_{1-4}$-alkoxy groups. Moreover, in X, X', or X", a C atom may be disubstituted and/or one or two C atoms may be mono- or disubstituted, while preferred substituents are selected from among $C_{1-4}$-alkyl, $C_{2-4}$-alkenyl, $C_{2-4}$-alkynyl, $C_{3-7}$-cycloalkyl, and $C_{3-7}$-cycloalkyl-$C_{1-3}$-alkyl, and two $C_{1-4}$-alkyl- and/or $C_{2-4}$-alkenyl substituents may also be joined together to form a saturated or monounsaturated carbocyclic ring.

Advantageously the group X representing $C_{2-4}$-alkylenoxy, particularly —$CH_2$—$CH_2$—$CH_2$—O—, has no hydroxy substituent.

Most particularly preferred substituents of one or two C atoms in X, X', or X" are selected from methyl, ethyl, n-propyl, isopropyl, cyclopropyl, or cyclopropylmethyl, while two alkyl substituents on one C atom may also be joined together to form a carbocyclic ring.

In the definitions of the substituents of the bridges X, X', and/or X" and the definitions of the bridges X, X', and/or X" themselves mentioned above and hereinafter, in each case one or more C atoms may additionally be mono- or polysubstituted by F and/or in each case one or two C atoms independently of one another may additionally be monosubstituted by Cl or Br.

If in the group X, X', or X" one or more C atoms are substituted by a hydroxy and/or $C_{1-4}$-alkoxy group, the substituted C atom is preferably not immediately adjacent to another heteroatom.

Preferably X denotes an unbranched $C_{1-4}$-alkylene bridge and in the event that the group Y is linked to X via a C atom, it also denotes —$CH_2$—CH=CH—, —$CH_2$—C≡C—, $C_{2-4}$-alkylenoxy, or $C_{2-4}$-alkylene-$NR^4$, particularly $C_{2-4}$-alkylenoxy or $C_{2-4}$-alkylene-$NR^4$—, while $R^4$ may be connected to Y, forming a heterocyclic ring system, while the bridge X may be connected to $R^1$, including the N atom connected to $R^1$ and X, forming a heterocyclic group, and in X a C atom may be substituted by $R^{10}$ and/or one or two C atoms may be substituted in each case by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, particularly selected from $C_{1-3}$-alkyl, while two alkyl and/or alkenyl substituents may be joined together, forming a carbocyclic ring system, and in the abovementioned groups and radicals one or more C atoms may be mono- or polysubstituted by F and/or one or two C atoms independently of one another may be monosubstituted by Cl or Br and $R^1$, $R^4$, and $R^{10}$ are as hereinbefore defined.

The substituent $R^{10}$ preferably denotes a hydroxy, hydroxy-$C_{1-3}$-alkyl, $C_{1-4}$-alkoxy-$C_{1-3}$-alkyl and/or $C_{1-4}$-alkoxy group, particularly hydroxy, hydroxymethyl, or methoxy.

Preferred meanings of the substituent $R^4$ are H, $C_{1-6}$-alkyl and $C_{3-6}$-alkenyl. Particularly preferably $R^4$ denotes H or $C_{1-3}$-alkyl. If $R^4$ is connected to Y forming a heterocyclic ring system, particularly preferred meanings of $R^4$ are $C_{2-6}$-alkyl and $C_{2-6}$-alkenyl.

In the event that $R^4$ is linked to Y forming a heterocyclic ring system, Y preferably denotes phenyl and $R^4$ preferably denotes $C_{2-6}$-alkyl or $C_{2-6}$-alkenyl. Preferred heterocyclic ring systems are indole, dihydroindole, quinoline, dihydroquinoline, tetrahydroquinoline, and benzoxazole.

Particularly preferably X denotes —$CH_2$—, —$CH_2$—$CH_2$—, or —$CH_2$—$CH_2$—$CH_2$— and in the event that the group Y is linked to X via a C atom (of the group Y), it may also denote —$CH_2$—CH=CH—, —$CH_2$—C≡C—, —$CH_2$—$CH_2$—O—, —$CH_2$—$CH_2$—$CH_2$—O—, —$CH_2$—$CH_2$-$NR^4$—, or —$CH_2$—$CH_2$—$CH_2$—$NR^4$—, particularly —$CH_2$—$CH_2$—O—, —$CH_2$—$CH_2$—$CH_2$—O—, —$CH_2$—$CH_2$-$NR^4$—, or —$CH_2$—$CH_2$—$CH_2$—$NR^4$—, while $R^4$ may be connected to Y, forming a heterocyclic ring system, while the bridge X may be connected to $R^1$, including the N atom linked to $R^1$ and X, forming a heterocyclic group, and in X a C atom may be substituted by $R^{10}$ and/or one or two C atoms independently of one another may each be substituted by one or two identical or different $C_{1-4}$-alkyl groups, while two alkyl groups may be joined together, forming a carbocyclic ring system; preferably in X one or two C atoms may each be substituted independently of one another by one or two identical or different $C_{1-3}$-alkyl groups, while two alkyl groups may be joined together to form a carbocyclic ring system, particularly a cyclopropyl group, and in each case one or more C atoms may be mono- or polysubstituted by F and/or in each case one or two C atoms independently of one another may be monosubstituted by Cl or Br, preferably in each case one or more C atoms may be mono- or polysubstituted by F.

Most particularly preferably, if the group Y is linked to X via a C atom (of the group Y), X denotes —$CH_2$—, —$CH_2$—$CH_2$—, —$CH_2$—$CH_2$—$CH_2$—, 1,1-cyclopropylene, —$CH_2$—$CH_2$—O—, —$CH_2$—$CH_2$-$CH_2$—O—, —$CH_2$—$CH_2$-$NR^4$—, or —$CH_2$—$CH_2$—$CH_2$—$NR^4$—, while these groups are unsubstituted or the alkylene bridge is substituted as specified, preferably mono- or disubstituted by methyl and/or fluorine.

The group $R^4$ preferably only denotes vinyl if $R^4$ is linked to Y forming a heterocyclic ring system.

The group X preferably does not comprise a carbonyl group.

If Y denotes a fused bicyclic ring system, a preferred definition of the group X is a single bond, —$CH_2$—, —$CH_2$—$CH_2$—, or —$CH_2$—$CH_2$—$CH_2$—, particularly a single bond, —$CH_2$— or —$CH_2$—$CH_2$—, most particularly preferably —$CH_2$— or —$CH_2$—$CH_2$—, which may be substituted as specified.

In the event that the index b has the value 1, X particularly preferably denotes —$CH_2$— or 1,1-cyclopropylene. X representing —$CH_2$— may be linked to Y forming a bicyclic ring system as specified, while for this purpose the —$CH_2$— bridge is substituted by $C_{2-3}$-alkyl. The —$CH_2$— bridge may comprise one or two substituents independently of one another selected from the group comprising $C_{1-3}$-alkyl, while two alkyl groups may be joined together, forming a carbocyclic ring system.

In the event that the index b has the value 0, X particularly preferably denotes —$CH_2$—$CH_2$—, —$CH_2$—$CH_2$—O—, —$CH_2$—$CH_2$—$CH_2$—O—, —$CH_2$—$CH_2$—$NR^4$—, or —$CH_2$—$CH_2$—$CH_2$—$NR^4$—, while the abovementioned groups may comprise one or two substituents independently of one another selected from the group comprising $C_{1-3}$-alkyl, while two alkyl groups may be joined together, forming a ring system.

The bridge X may also represent a single bond. Preferably the bridge X only forms a single bond if Y denotes a bicyclic ring system. Also preferably, the bridge X may only represent a single bond if the compound according to the invention can be described according to one of the partial formulae Ia, Ib, or Id, particularly according to one of the partial formulae Ia or Ib, most particularly preferably the partial formula Ib.

The group Y preferably has a meaning selected from among the bivalent cyclic groups phenyl, pyridinyl, naphthyl, tetrahydronaphthyl, indolyl, dihydroindolyl, quinolinyl, dihydroquinolinyl, tetrahydroquinolinyl, isoquinolinyl, dihydroisoquinolinyl, tetrahydroisoquinolinyl, or benzoxazolyl, while the abovementioned cyclic groups may be mono- or polysubstituted at one or more C atoms by $R^{20}$, in the case of a phenyl group may also additionally be monosubstituted by nitro, and/or at one or more N atoms may be substituted by $R^{21}$. $R^1$ may be connected to Y and/or X may be connected to Y as specified hereinbefore.

If the group Y denotes phenyl or pyridinyl, the bridges X and Z are preferably connected to the group Y in the para position.

Particularly preferably the group Y has a meaning selected from among the bivalent cyclic groups

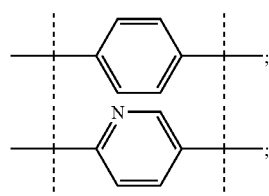

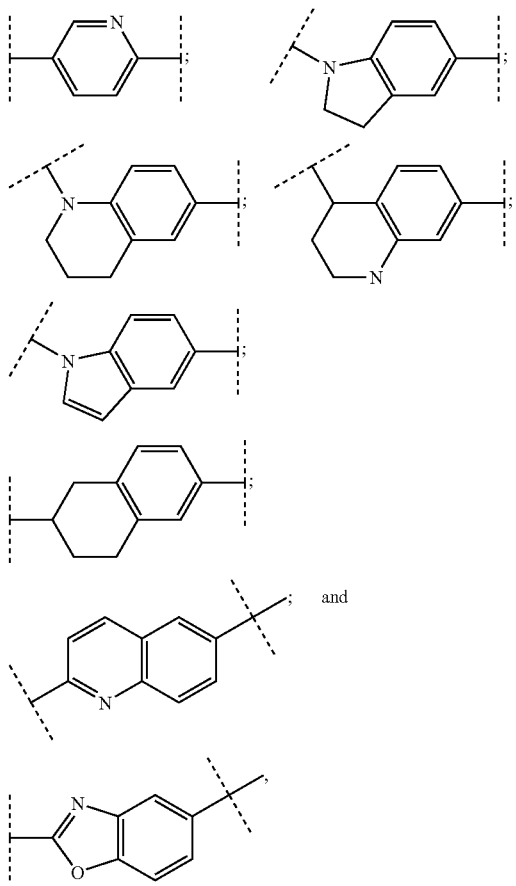

and in particular Y has one of the following meanings

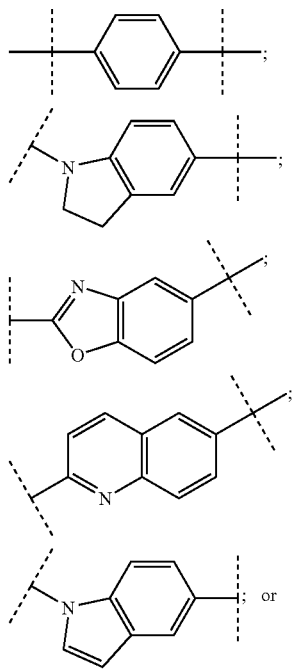

-continued

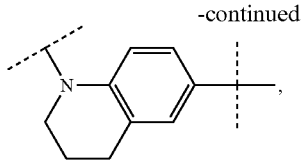

while the abovementioned cyclic groups may be mono- or polysubstituted by $R^{20}$ at one or more C atoms, in the case of a phenyl group may also additionally be monosubstituted by nitro, and/or one or more NH groups may be substituted by $R^{21}$.

The group Y may be linked to the group X forming a carbo- or heterocyclic group fused to Y. Preferred definitions of the groups -X-Y- linked to another are selected from the list comprising:

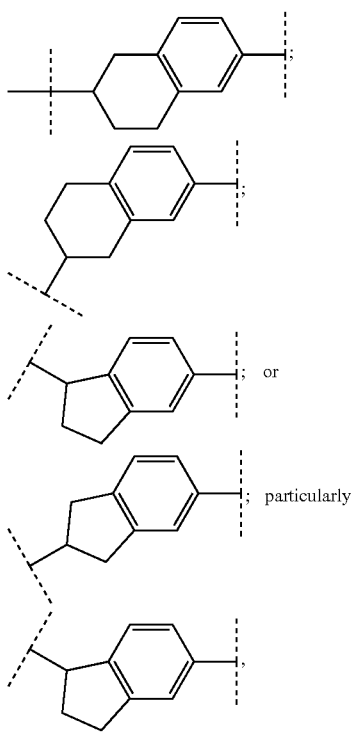

while in the abovementioned bicyclic groups the phenyl ring may be mono- or polysubstituted by $R^{20}$ or may also additionally be monosubstituted by nitro, and the saturated carbocyclic ring may be mono- or disubstituted by $C_{1-3}$-alkyl.

The group Y is preferably unsubstituted or mono- or disubstituted.

Particularly preferred substituents $R^{20}$ of the group Y are selected from the group consisting of fluorine, chlorine, bromine, cyano, nitro, $C_{1-4}$-alkyl, $C_{2-6}$-alkenyl, hydroxy, hydroxy-$C_{1-3}$-alkyl, $C_{1-4}$-alkoxy, trifluoromethyl, trifluoromethoxy, $C_{2-4}$-alkynyl, $C_{1-4}$-alkoxycarbonyl, $C_{1-4}$-alkoxy-$C_{1-3}$-alkyl, $C_{1-4}$-alkoxy-carbonylamino, amino, $C_{1-4}$-alkylamino, di-($C_{1-4}$-alkyl)amino, aminocarbonyl, $C_{1-4}$-alkylaminocarbonyl, di-($C_{1-4}$-alkyl)aminocarbonyl, —CH=N—OH and —CH=N—O—$C_{1-4}$-alkyl.

Most particularly preferred substituents $R^{20}$ of the group Y are selected from the group consisting of fluorine, chlorine, bromine, iodine, cyano, $C_{1-3}$-alkyl, $C_{1-3}$-alkoxy, $C_{1-4}$-alkoxycarbonyl, trifluoromethyl, trifluoromethoxy, amino, or, in the case of a phenyl ring, additionally nitro.

Most particularly preferably the group Y denotes substituted phenylene of the partial formula

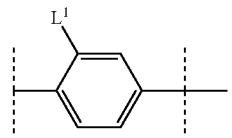

wherein $L^1$ has one of the meanings given hereinbefore for $R^{20}$, preferably F, Cl, Br, I, $CH_3$, $CF_3$, $OCH_3$, $OCF_3$, methoxycarbonyl, ethoxycarbonyl, CN, amino, or $NO_2$, or denotes H.

A preferred meaning of the group A is aryl or heteroaryl.

Preferably the group A is selected from among the cyclic groups phenyl, pyridinyl, or naphthyl, which may be mono- or polysubstituted at one or more C atoms by $R^{20}$, and in the case of a phenyl ring may also additionally be monosubstituted by nitro, while the group A does not contain an amino group as substituent in the ortho position to the bridge W.

Preferably the group A has no substituent selected from the group consisting of $C_{1-4}$-alkyl-sulfonylamino, $C_{1-4}$-alkyl-carbonylamino, $C_{1-4}$-alkyl-sulfonylamino-$C_{1-3}$-alkyl, $C_{1-4}$-alkyl-carbonylamino-$C_{1-3}$-alkyl and phenylcarbonylamino. Other non-preferred substituents are aminocarbonyl, $C_{1-4}$-alkylaminocarbonyl, di-($C_{1-4}$-alkyl)-aminocarbonyl, cyclo-$C_{3-6}$-alkylaminocarbonyl, cyclo-$C_{3-6}$-alkyleneiminocarbonyl, cyclo-$C_{3-6}$-alkyleneimino-$C_{2-4}$-alkylaminocarbonyl, phenylaminocarbonyl, aminocarbonyl-$C_{1-3}$-alkyl, $C_{1-4}$-alkylaminocarbonyl-$C_{1-3}$-alkyl, di-($C_{1-4}$-alkyl)aminocarbonyl-$C_{1-3}$-alkyl, cyclo-$C_{3-6}$-alkylaminocarbonyl-$C_{1-3}$-alkyl, cyclo-$C_{3-6}$-alkyleneiminocarbonyl-$C_{1-3}$-alkyl, cyclo-$C_{3-6}$-alkyleneimino-$C_{2-4}$-alkylaminocarbonyl-$C_{1-3}$-alkyl, and phenylaminocarbonyl-$C_{1-3}$-alkyl.

Moreover, the group A preferably has no substituent selected from the group consisting of nitro and tert-butyloxycarbonylamino in the ortho position to the bridge W in each case.

If b has the value 0, the group A is preferably mono-, di-, or trisubstituted.

If b has the value 1, the group A is preferably unsubstituted or mono- or disubstituted. If b has the value 1 and the group A is monosubstituted, the substituent is preferably in the ortho position relative to the group W.

Most particularly preferably A is one of the following groups

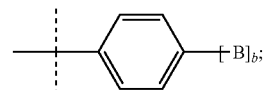

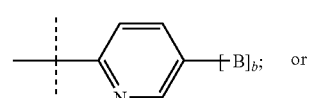

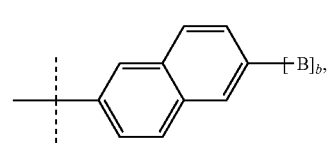

while the groups listed may be mono- or polysubstituted by $R^{20}$ as specified, while if the index b has the value 0, the group A does not have an amino group as substituent in the ortho position to the bridge W. The definitions phenyl and pyridyl given for the group A are preferred when b has the value 1.

Particularly preferred substituents $R^{20}$ of the group A are selected from among fluorine, chlorine, bromine, cyano, $C_{1-4}$-alkyl, $C_{2-6}$-alkenyl, —CHO, hydroxy, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, $C_{1-4}$-alkoxy-$C_{1-3}$-alkyl, $C_{1-4}$-alkoxy-carbonylamino, amino, $C_{1-4}$-alkylamino, di-(C 1-4-alkyl)amino, cyclo-$C_{3-6}$-alkyleneimino, aminocarbonyl, $C_{1-4}$-alkylaminocarbonyl, di-($C_{1-4}$-alkyl)aminocarbonyl, —CH=N—OH, and —CH=N—O—$C_{1-4}$-alkyl.

Most particularly preferred substituents $R^{20}$ of the group A are selected from among fluorine, chlorine, bromine, cyano, $C_{1-4}$-alkyl, $C_{1-4}$-alkoxy, trifluoromethyl, trifluoromethoxy, carboxy, $C_{1-4}$-alkoxycarbonyl, $C_{1-4}$-alkylamino-, and di-($C_{1-4}$-alkyl)amino.

If b has the value 0, a particularly preferred meaning of the group A is substituted phenyl of the partial formula

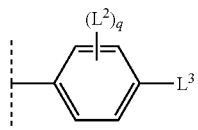

wherein:
$L^2$ has one of the meanings given for $R^{20}$ or denotes H, preferably F, Cl, Br, I, $CH_3$, $CF_3$, $OCH_3$, $OCF_3$, CN, or $NO_2$; particularly preferably F, Cl, or Br;
$L^3$ has one of the meanings given for $R^{20}$ or denotes H, preferably F, Cl, Br, I, $CF_3$, $OCF_3$, CN, $NO_2$, $C_{1-4}$-alkyl, $C_{3-7}$-cycloalkyl, $C_{3-7}$-cycloalkyl-$C_{1-3}$-alkyl, $C_{1-4}$-alkoxy, $C_{3-7}$-cycloalkyl-O, $C_{3-7}$-cycloalkyl-$C_{1-3}$-alkoxy, —COO-$C_{1-4}$-alkyl, or —COOH; particularly preferably F, Cl, Br, $C_{1-4}$-alkyl, $CF_3$, methoxy, $OCF_3$, CN, or $NO_2$; most particularly preferably Cl, Br, $CF_3$, or $NO_2$; and
q has the value 0, 1, or 2,
with the proviso that the phenyl group may only be at most monosubstituted by nitro.

Particularly preferably A is substituted phenyl according to the above partial formula, wherein q denotes 1 or 2 and/or at least one substituent $L^2$ is in the meta position to the substituent $L^3$.

Another preferred partial formula for A, particularly where b has the value 0, is

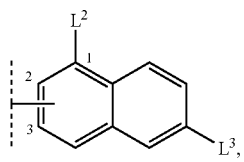

wherein the bond to the group W is effected via the C atom in position number 2 or 3 and $L^2$ and $L^3$ are as hereinbefore defined.

In the event that b has the value 1, a preferred meaning of the group B is aryl or heteroaryl, which may be substituted as specified.

Preferred definitions of the group B are selected from the group consisting of phenyl, pyridyl, thienyl and furanyl. Particularly preferably, the group B denotes phenyl. The group B defined as specified may be mono- or polysubstituted by $R^{20}$, a phenyl group may additionally also be monosubstituted by nitro. Preferably the group B is mono-, di-, or trisubstituted, particularly mono- or disubstituted. In the case of a monosubstitution, the substituent is preferably arranged in the ortho or para position, particularly in the para position to the group A.

Particularly preferred substituents $R^{20}$ of the group B are selected from the group consisting of fluorine, chlorine, bromine, cyano, nitro, $C_{1-4}$-alkyl, hydroxy, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, $C_{1-4}$-alkoxy-$C_{1-3}$-alkyl, $C_{1-4}$-alkoxy-carbonylamino, amino, $C_{1-4}$-alkylamino, di-($C_{1-4}$-alkyl)amino, cyclo-$C_{3-6}$-alkyleneimino, aminocarbonyl, $C_{1-4}$-alkylaminocarbonyl, and di-($C_{1-4}$-alkyl)aminocarbonyl.

Most particularly preferred substituents $R^{20}$ of the group B are selected from the group consisting of fluorine, chlorine, bromine, cyano, $CF_3$, $C_{1-3}$-alkyl, $C_{1-4}$-alkoxy, trifluoromethoxy, and nitro; particularly fluorine, chlorine, bromine, methoxy, $CF_3$, and trifluoromethoxy.

Generally $R^4$ has one of the meanings given for $R^{17}$, preferably one of the meanings given for $R^{16}$.

Particularly preferred meanings of the substituent $R^4$ are H, $C_{1-6}$-alkyl, and $C_{3-6}$-alkenyl. If $R^4$ is linked to Y forming a heterocyclic ring system, particularly preferred meanings of $R^4$ are $C_{2-6}$-alkyl and $C_{2-6}$-alkenyl.

If $R^{11}$ is a $C_{2-6}$-alkenyl or $C_{2-6}$-alkynyl group, the definitions —CH=$CH_2$, —CH=CH($CH_3$), —CH=C($CH_3$)$_2$, —C≡CH and —C≡C—$CH_3$, are preferred.

The substituent $R^{20}$ preferably has none of the following structural elements:
(a) —CO-aryl or —CO-heteroaryl, particularly —CO-phenyl, while heteroaryl, aryl, and phenyl may be substituted,
(b) —C(=NH)—NH, wherein the H atoms may be substituted, and/or
(c) —NH—CO—NH, wherein the H atoms may be substituted.

Generally preferred definitions of the group $R^{20}$ are halogen, hydroxy, cyano, $C_{1-4}$-alkyl, $C_{3-7}$-cycloalkyl, $C_{1-4}$-alkoxy, $C_{1-4}$-alkoxycarbonyl, or amino, while, as hereinbefore defined, in each case one or more C atoms may additionally be mono- or polysubstituted by F and/or in each case one or two C atoms independently of one another may additionally be monosubstituted by Cl or Br. Particularly preferably $R^{20}$ denotes F, Cl, Br, I, OH, cyano, methyl, difluoromethyl, trifluoromethyl, ethyl, n-propyl, isopropyl, methoxy, difluoromethoxy, trifluoromethoxy, ethoxy, n-propoxy, isopropoxy, methoxycarbonyl, ethoxycarbonyl, or amino.

Preferred definitions of the group $R^{21}$ are $C_{1-4}$-alkyl, $C_{1-4}$-alkylcarbonyl, $C_{1-4}$-alkoxycarbonyl, $C_{1-4}$-alkylsulfonyl, —$SO_2$—$NH_2$, —$SO_2$—NH—$C_{1-3}$-alkyl, —$SO_2$—N($C_{1-3}$-alkyl)$_2$, and cyclo-$C_{3-6}$-alkyleneimino-sulfonyl, while, as hereinbefore defined, in each case one or more C atoms may additionally be mono- or polysubstituted by F and/or in each case one or two C atoms independently of one another may additionally be monosubstituted by Cl or Br.

Most particularly preferred meanings of $R^{21}$ are H, $C_{1-4}$-alkyl, $C_{1-4}$-alkylcarbonyl, or $C_{1-4}$-alkoxycarbonyl, particularly H and $C_{1-3}$-alkyl.

Cy preferably denotes a $C_{3-7}$-cycloalkyl, particularly a $C_{5-7}$-cycloalkyl group, a $C_{5-7}$-cycloalkenyl group, pyrrolidinyl, piperidinyl, piperazinyl, morpholinyl, thiomorpholinyl, aryl, or heteroaryl, while aryl or heteroaryl preferably denotes a monocyclic or fused bicyclic ring system, and the abovementioned cyclic groups may be mono- or polysubstituted by $R^{20}$ at one or more C atoms, and in the case of a phenyl group may also additionally be monosubstituted by nitro, and/or one or more NH groups may be substituted by $R^{21}$.

Preferred compounds according to the invention are those wherein one or more of the groups, radicals, substituents and/or indices have one of the meanings specified above as being preferred.

Particularly preferred compounds according to the invention are those wherein:

the bridge X denotes —$CH_2$—, —$CH_2$—$CH_2$—, —$CH_2$—$CH_2$—$CH_2$—, or 1,1-cyclopropylene, and if the group Y is linked to X via a C atom (of the group Y), may also denote —$CH_2$—$CH_2$—O—, —$CH_2$—$CH_2$—$CH_2$—O—, —$CH_2$—$CH_2$-$NR^4$—, or —$CH_2$—$CH_2$—$CH_2$—$NR^4$—, while the groups mentioned for X are unsubstituted or wherein the alkylene bridge as specified is preferably mono- or disubstituted by methyl and/or fluorine, while two methyl groups may be joined together to form a cyclopropyl ring; and the group Y has one of the following meanings

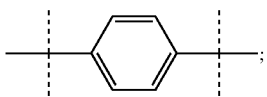

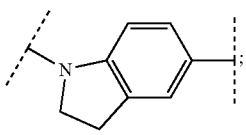

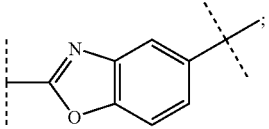

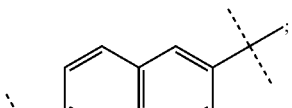

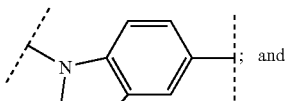

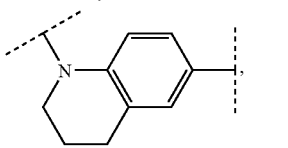

or the group Y is linked to the group X forming a carbo- or heterocyclic group fused to Y, while the group —X—Y— denotes

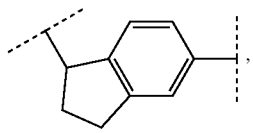

while the abovementioned phenyl rings or the bicyclic groups containing heteroatoms may be mono- or polysubstituted by $R^{20}$ and phenyl rings may also additionally be monosubstituted by nitro, and the saturated carbocyclic ring in the indane skeleton may be mono- or disubstituted by $C_{1-3}$-alkyl, and the group A denotes one of the following partial formulae

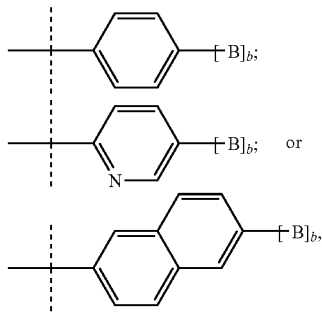

which may be mono- or polysubstituted by $R^{20}$, while if the index b has the value 0, the group A does not have an amino group as substituent in the ortho position to the bridge W, and the group B denotes phenyl, which is mono- or polysubstituted by $R^{20}$; and b denotes the value 0 or 1.

Most particularly preferred according to the invention are those compounds wherein A, B, b, X, Y, Z, $R^1$, $R^2$, $R^3$, and W independently of one another have one or more of the abovementioned preferred meanings.

Preferred groups of compounds according to this invention can be described by the following formulae, particularly preferably by the formulae Ia.1, Ia.2a, Ia.2b, Ia.3, Ia.5, Ia.6, Ia.7, Ia.8, Ib.1, Ib.2, Ic.1, and Id.1:

Ia.1

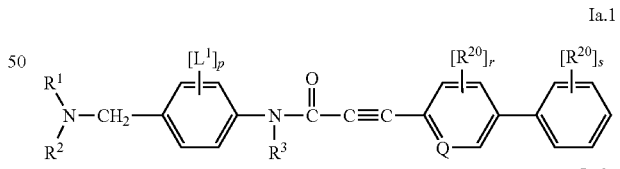

Ia.2a

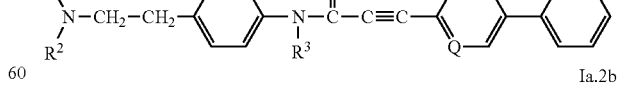

Ia.2b

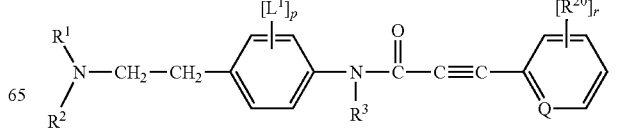

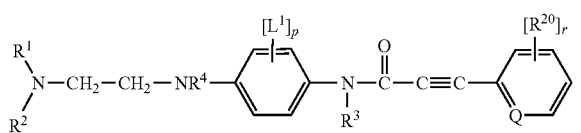 Ia.3

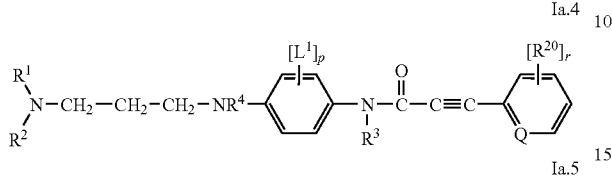 Ia.4

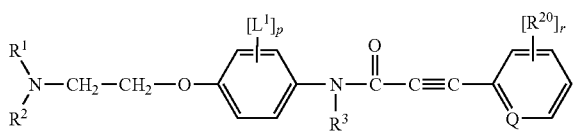 Ia.5

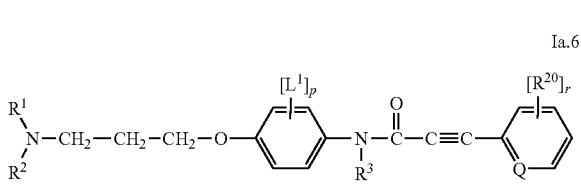 Ia.6

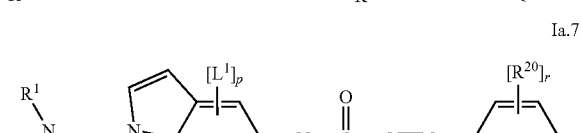 Ia.7

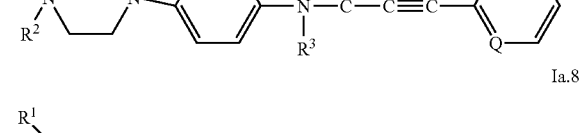 Ia.8

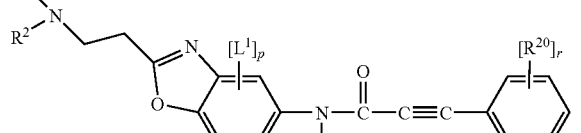 Ia.9

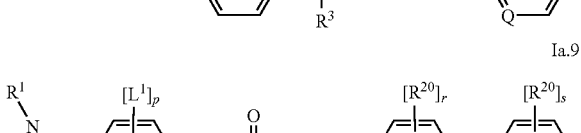 Ib.1

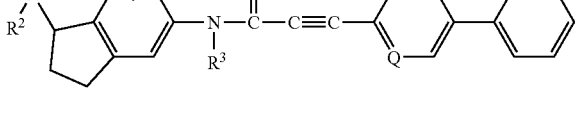 Ib.2

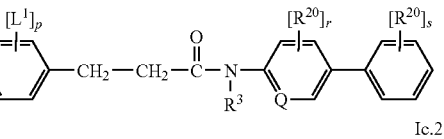 Ic.1

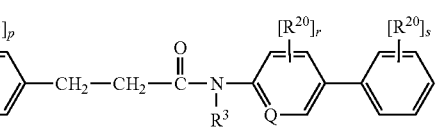 Ic.2

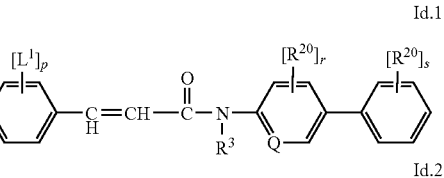 Id.1

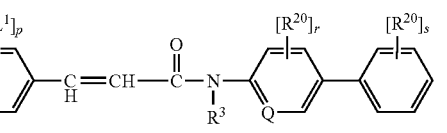 Id.2 while the bridges X contained in formulae Ia.1 to Ia.8, Ib.1, Ic.1 representing —CH$_2$—, —CH$_2$—CH$_2$—, —CH$_2$—CH$_2$—NR$^4$—, —CH$_2$—CH$_2$—CH$_2$—NR$^4$—, —CH$_2$—CH$_2$—O—, and —CH$_2$—CH$_2$—O— may have one or two substituents selected independently of one another from the group consisting of C$_{1-3}$-alkyl and C$_{3-5}$-cycloalkyl, while two alkyl substituents may be joined together to form a C$_{3-6}$-cycloalkyl group; particularly preferably these bridges X, particularly representing —CH$_2$—, may have one or two methyl substituents, while two methyl substituents may be joined together to form a cyclopropyl group; and L$^1$, R$^1$, R$^2$, R$^3$, R$^4$, and R$^{20}$ have the meanings given above and substituents occurring more than once may have identical or different meanings; and particularly R$^1$ and R$^2$ independently of one another are selected from among C$_{1-6}$-alkyl, C$_{3-7}$-cycloalkyl, C$_{3-7}$-cycloalkyl-C$_{1-3}$-alkyl, tetrahydropyran-3 or -4-yl, tetrahydropyranyl-C$_{1-3}$-alkyl, piperidin-3 or -4-yl, wherein the NH group may be substituted by R$^{13}$, piperidinyl-C$_{1-3}$-alkyl, wherein the NH group may be substituted by R$^{13}$, phenyl, pyridyl, phenyl-C$_{1-3}$-alkyl, pyridyl-C$_{1-3}$-alkyl, hydroxy-C$_{2-4}$-alkyl, C$_{1-4}$-alkoxy-C$_{2-4}$-alkyl, amino-C$_{2-4}$-alkyl, C$_{1-4}$-alkylamino-C$_{2-4}$-alkyl and di-(C$_{1-4}$-alkyl)amino-C$_{2-4}$-alkyl, while cycloalkyl rings may be mono-, di-, or trisubstituted by substituents selected from hydroxy, hydroxy-C$_{1-3}$-alkyl, C$_{1-3}$-alkyl, or C$_{1-3}$-alkyloxy, particularly hydroxy, hydroxymethyl, methyl, and methoxy, and C$_{2-4}$-alkyl bridges contained in hydroxy-C$_{2-4}$-alkyl- and C$_{1-4}$-alkoxy-C$_{2-4}$-alkyl may additionally be monosubstituted by hydroxy, hydroxy-C$_{1-3}$-alkyl, C$_{1-3}$-alkyl, or C$_{1-3}$-alkyloxy, particularly hydroxy, hydroxymethyl, methyl, or methoxy, and alkyl groups may be mono- or polysubstituted by F and/or monosubstituted by Cl, and one of the groups R$^1$ and R$^2$ may also represent H; or R$^1$ and R$^2$ are connected to each other in such a way that the group

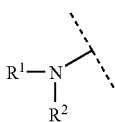

is defined according to one of the following partial formulae

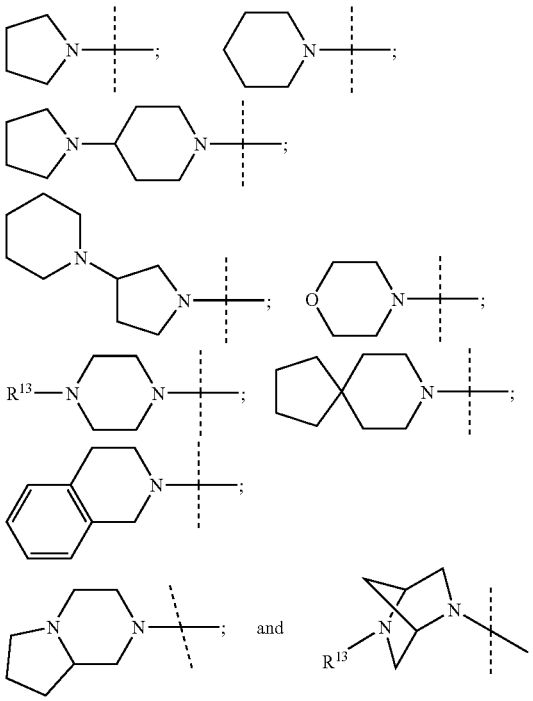

while in the heterocycle formed by the group $R^1R^2N$— one or more H atoms may be replaced by $R^{14}$ and/or a H atom may be replaced by Cy representing $C_{3-6}$-cycloalkyl, which is mono- or polysubstituted by $R^{20}$, particularly with F, hydroxy, $C_{1-3}$-alkyl, $CF_3$, $C_{1-3}$-alkyloxy, $OCF_3$, or hydroxy-$C_{1-3}$-alkyl, particularly preferably with F, hydroxy, methyl, methoxy, $CF_3$, $OCF_3$, or hydroxymethyl, and the ring attached to the heterocycle formed by the group $R^1R^2N$— may be mono- or polysubstituted, preferably monosubstituted at one or more C atoms by $R^{20}$ and, in the case of a phenyl ring, may also additionally be mono-substituted by nitro;

$R^3$ preferably denotes H or methyl; and $R^{14}$ in each case independently of one another denotes F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms may additionally be mono- or polysubstituted by F or in each case a C atom may be monosubstituted by Cl; most particularly preferably denotes methyl, ethyl, propyl, trifluoromethyl, hydroxy, hydroxymethyl, 1-hydroxyethyl, 2-hydroxyethyl, 1-hydroxy-1-methylethyl, methoxy, ethoxy, methoxymethyl, pyridylamino, or aminocarbonyl;

$R^{13}$ denotes H, $C_{1-4}$-alkyl, $C_{1-4}$-alkylcarbonyl, or $C_{1-4}$-alkyloxycarbonyl; particularly preferably denotes H or $C_{1-3}$-alkyl;

Q denotes CH or N, while CH may be substituted by $R^{20}$;

$L^1$ preferably denotes fluorine, chlorine, bromine, cyano, $C_{1-3}$-alkyl, $C_{1-3}$-alkoxy, trifluoromethyl, trifluoromethoxy, $C_{1-4}$-alkoxycarbonyl, amino, or nitro; particularly preferably denotes fluorine, chlorine, bromine, methyl, methoxy, trifluoromethyl, methoxycarbonyl, ethoxycarbonyl, cyano, amino, or nitro;

p has the value 0 or 1;

$R^{20}$ in each case independently of one another preferably denotes fluorine, chlorine, bromine, cyano, nitro, $C_{1-4}$-alkyl, $C_{2-6}$-alkenyl, hydroxy, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, $C_{1-4}$-alkoxy-$C_{1-3}$-alkyl, $C_{1-4}$-alkoxy-carbonylamino, amino, $C_{1-4}$-alkylamino, di-($C_{1-4}$-alkyl)amino, aminocarbonyl, $C_{1-4}$-alkylaminocarbonyl, or di-($C_{1-4}$-alkyl)aminocarbonyl, while if the index b has the value 0, the group Cy does not have an amino group as substituent in the ortho position to the bridge W, particularly preferably $R^{20}$ is selected from fluorine, chlorine, bromine, cyano, nitro, $C_{1-4}$-alkyl, hydroxy, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl-, and $C_{1-4}$-alkoxy-$C_{1-3}$-alkyl, most particularly preferably $R^{20}$ denotes fluorine, chlorine, bromine, cyano, $CF_3$, $C_{1-3}$-alkyl, $C_{1-4}$-alkoxy, trifluoromethoxy, or nitro; and r and s in each case independently of one another have the value 0, 1, 2, or 3, preferably at least one index r or s does not denote the value 0, and the compounds according to provisos (M1) to (M14) are not included.

The groups contained in formulae Ia.1 to Id.2

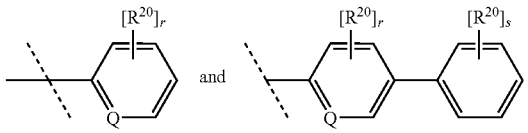

and advantageously have the following substitution pattern:

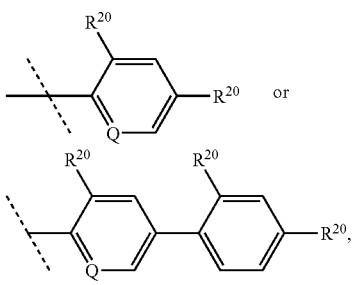

wherein $R^{20}$ has one of the meanings given hereinbefore, including H, and substituents $R^{20}$ occurring more than once may have the same or different meanings, and preferably at least one substituent $R^{20}$ has a meaning other than H.

The compounds listed in the Examples and Tables, including the tautomers, the diastereomers, the enantiomers, the mixtures thereof and the salts thereof, are preferred according to the invention. Particularly preferred compounds are listed below, while the relevant Example number is given in square brackets: 3-(4-piperidin-1-ylmethylphenyl)propynoic acid-(4'-methoxybiphenyl-4-yl)amide [1-8]; 3-{4-[4-(pyridin-2-ylamino)piperidin-1-ylmethyl]phenyl}propynoic acid-(4'-methoxybiphenyl-4-yl)amide [1-11]; 3-(4-pyrrolidin-1-ylmethylphenyl)propynoic acid-(4'-chloro-3-fluorobiphenyl-4-yl)amide [1.17]; 3-[4-(4-methylpiperidin-1-ylmethyl)phenyl]propynoic acid-(4'-chloro-2'-fluorobiphenyl-4-yl)amide [1-18]; 3-[4-((R)-2-hydroxymethylpyrrolidin-1-ylmethyl)phenyl]propynoic acid-(4'-chloro-3-fluorobiphenyl-4-yl)amide [1-20]; 3-[4-(4-hydroxypiperidin-1-ylmethyl)phenyl]propynoic acid-(4'-chloro-3-fluorobiphenyl-4-yl)amide [1-21]; 3-(4-pyrrolidin-1-ylmethylphenyl)propynoic acid-(4'-chlorobiphenyl-4-yl)methylamide [1-23]; 3-(4-pyrrolidin-1-ylmethylphenyl)propynoic acid-(4'-chlorobiphenyl-4-yl)amide [1-33]; 3-{4-[4-(1-hydroxy-1-methylethyl)piperidin-1-ylmethyl]phenyl}propynoic acid-(4'-chlorobiphenyl-4-yl)amide [1-34]; 3-[4-(4-methylpiperidin-1-ylmethyl)phenyl]propynoic acid-(4'-chlorobiphenyl-4-yl)amide [1-35]; 3-[4-(4-methoxypiperidin-1-ylmethyl)phenyl]propynoic acid-(4'-chlorobiphenyl-4-yl)amide [1-36]; 3-[4-(4-hydroxy-4-methylpiperidin-1-ylmethyl)phenyl]propynoic acid-(4'-chlorobiphenyl-4-yl)amide [1-37]; 3-(4-piperidin-1-ylmethylphenyl)propynoic acid-(4'-chlorobiphenyl-4-yl)amide [1-38]; 3-{4-[(cyclohexylethylamino)methyl]phenyl}propynoic acid-(4'-chlorobiphenyl-4-yl)amide [1-52]; 3-{4-[cyclopentylmethylamino)methyl]phenyl}propynoic acid-(4'-chlorobiphenyl-4-yl)amide [1-425]; 3-(1-pyrrolidin-1-ylindan-5-yl)propynoic acid-(4'-chlorobiphenyl-4-yl)amide [2-3]; 3-(4'-chlorobiphenyl-4-yl)propynoic acid-(4-piperidin-1-ylmethylphenyl)amide [3-6]; 3-(4'-chlorobiphenyl-4-yl)propynoic acid-[4-(4-methoxypiperidin-1-ylmethyl)phenyl]amide [3-13]; 3-(4'-chlorobiphenyl-4-yl)propynoic acid-[4-(4-methylpiperidin-1-ylmethyl)phenyl]amide [3-14]; 3-(4'-chlorobiphenyl-4-yl)propynoic acid-{4-[(cyclopropylmethylmethylamino)methyl]phenyl}amide [3-15]; 3-(4'-chlorobiphenyl-4-yl)propynoic acid-[4-(4-hydroxy-4-trifluoromethylpiperidin-1-ylmethyl)phenyl]amide [3-17]; 3-(4'-chlorobiphenyl-4-yl)propynoic acid-[4-(4-hydroxy-1-piperidin-1-ylmethyl)phenyl]amide [3-18]; 3-[5-(4-chlorophenyl)pyridin-2-yl]propynoic acid-(4-piperidin-1-ylmethylphenyl)amide [3-25]; 3-[5-(4-chlorophenyl)pyridin-2-yl]propynoic acid-[4-(3,5-dimethylpiperidin-1-ylmethyl)phenyl]amide [3-29]; 3-(2-chloro-4-trifluoromethylphenyl)propynoic acid-[4-(2-diethylaminoethoxy)phenyl]amide [3-38]; 3-(2,4-dichlorophenyl)propynoic acid-[3-chloro-4-(2-diethylaminoethoxy)phenyl]amide [4-1]; 3-(2,4-dichlorophenyl)propynoic acid-[3-methoxy-4-(2-diethylaminoethoxy)phenyl]amide hydrochloride [4-7]; 3-(4-chlorophenyl)propynoic acid-[1-(2-pyrrolidin-1-ylethyl)-1H-indol-5-yl]amide [4-10]; 3-(2-chloro-4-trifluoromethylphenyl)propynoic acid-[1-(2-pyrrolidin-1-ylethyl)-1H-indol-5-yl]amide [4-11]; 3-(2-chloro-4-trifluoromethylphenyl)propynoic acid-[3-bromo-4-(2-diethylaminoethoxy)phenyl]amide [4-15]; 3-(2-chloro-4-trifluoromethylphenyl)propynoic acid-[3-nitro-4-(2-diethylaminoethoxy)phenyl]amide [4-17]; 3-(2-chloro-4-trifluoromethylphenyl)propynoic acid-[3-methoxy-4-(2-diethylaminoethoxy)phenyl]amide hydrochloride [4-20]; 3-(2-chloro-4-trifluoromethylphenyl)propynoic acid-[3-methyl-4-(2-diethylaminoethoxy)phenyl]amide [4-21]; 3-(2-chloro-4-trifluoromethylphenyl)propynoic acid-[4-(3-diethylaminoethoxy)-3-fluorophenyl]amide [4-25]; 3-(2-chloro-4-trifluoromethylphenyl)propynoic acid-{3-chloro-4-[2-(4-methylpiperidin-1-yl)ethylamino]phenyl}amide [4-27]; 3-(2-chloro-4-trifluoromethylphenyl)propynoic acid-[3-chloro-4-(2-diethylaminoethyl)phenyl]amide [4-31]; 3-(4-bromo-2-chlorophenyl)propynoic acid-[3-chloro-4-(2-diethylaminoethoxy)phenyl]amide [4-35]; 3-(2-chloro-4-trifluoromethylphenyl)propynoic acid-{3-methoxy-4-[2-(4-methylpiperidin-1-yl)ethoxy]phenyl}amide [4-270]; 3-(2-chloro-4-trifluoromethylphenyl)propynoic acid-{4-[2-(3,5-dimethylpiperidin-1-yl)ethoxy]-3-methoxyphenyl}amide [4-271]; 3-(2-chloro-4-trifluoromethylphenyl)propynoic acid-{4-[2-(2,6-dimethylpiperidin-1-yl)ethoxy]-3-methoxyphenyl}amide [4-277]; 3-(2-chloro-4-trifluoromethylphenyl)propynoic acid-{4-[2-(cyclopropylmethylmethylamino)ethoxy]-3-methoxyphenyl}amide hydrochloride [4-278]; 3-(2-chloro-4-trifluoromethylphenyl)propynoic acid-{4-[2-(cyclopropylmethylpropylamino)ethoxy]-3-methoxyphenyl}amide hydrochloride [4-279]; (E)-N-(4'-chlorobiphenyl-4-yl)-3-[4-(4-methylpiperidin-1-ylmethyl)phenyl]acrylamide [5-2]; (E)-N-(4'-chlorobiphenyl-4-yl)-3-[4-(4-methoxypiperidin-1-ylmethyl)phenyl]acrylamide [5-4]; 1-{4-[(E)-2-(4'-chlorobiphenyl-4-ylcarbamoyl)vinyl]benzyl}piperidine-4-carboxylic acid amide [5-6]; (E)-N-(4'-chlorobiphenyl-4-yl)-3-(4-{[methyl-(tetrahydropyran-4-yl)amino]methyl}phenyl)acrylamide [5-7]; (E)-N-(4'-chlorobiphenyl-4-yl)-3-[4-(4-hydroxymethylpiperidin-1-ylmethyl)phenyl]acrylamide [5-8]; (E)-N-(4'-chlorobiphenyl-4-yl)-3-[4-((S)-3-hydroxypyrrolidin-1-ylmethyl)phenyl]acrylamide [5-9]; (E)-N-(4'-chlorobiphenyl-4-yl)-3-(4-pyrrolidin-1-ylmethylphenyl)acrylamide [5-13]; (E)-N-(4'-chlorobiphenyl-4-yl)-3-(4-cyclopropylaminomethylphenyl)acrylamide [5-14]; (E)-N-(4'-chlorobiphenyl-4-yl)-3-{4-[(cyclopropylmethylmethylamino)methyl]phenyl}acrylamide [5-17]; (E)-N-(4'-chlorobiphenyl-4-yl)-3-{4-[(cyclohexylmethylamino)methyl]phenyl}acrylamide [5-19]; (E)-N-(4'-chlorobiphenyl-4-yl)-3-{4-[(cyclohexylmethylamino)methyl]phenyl}acrylamide [5-21]; (E)-N-(4'-chlorobiphenyl-4-yl)-3-[4-(2,6-dimethylmorpholin-4-ylmethyl)phenyl]acrylamide [5-23]; (E)-3-[4-(8-azaspiro[4.5]dec-8-ylmethyl)phenyl]-N-(4'-chlorobiphenyl-4-yl)acrylamide [5-25]; (E)-N-(4'-chlorobiphenyl-4-yl)-3-(4-{[(2-hydroxy-2-methylpropyl)-(2-methoxyethyl)amino]methyl}phenyl)acrylamide [5-27]; (E)-N-(4'-chlorobiphenyl-4-yl)-3-[4-(3-piperidin-1-ylpyrrolidin-1-ylmethyl)phenyl]acrylamide [5-28]; N-(4'-chlorobiphenyl-4-yl)-3-[4-(4-methylpiperidin-1-ylmethyl)phenyl]propionamide [6-2]; N-(4'-chlorobiphenyl-4-yl)-3-[4-(4-methoxypiperidin-1-ylmethyl)phenyl]propionamide [6-3]; N-(4'-chlorobiphenyl-4-yl)-3-(4-morpholin-4-ylmethylphenyl)propionamide [64]; 1-{4-[2-(4'-chlorobiphenyl-4-ylcarbamoyl)ethyl]benzyl}piperidine-4-carboxylic acid amide [6-5]; N-(4'-chlorobiphenyl-4-yl)-3-[4-(4-hydroxymethylpiperidin-1-ylmethyl)phenyl]propionamide [6-6]; N-(4'-chlorobiphenyl-4-yl)-3-[4-((S)-3-hydroxypyrrolidin-1-ylmethyl)phenyl]propionamide [6-7]; N-(4'-chlorobiphenyl-4-yl)-3-[4-((R)-2-hydroxymethylpyrrolidin-1-ylmethyl)phenyl]propionamide [6-8]; N-(4'-chlorobiphenyl-4-yl)-3-[4-(4-hydroxy-4-methylpiperidin-1-ylmethyl)phenyl]propionamide [6-9]; N-(4'-chlorobiphenyl-4-yl)-3-(4-pyrrolidin-1-ylmethylphenyl)propionamide [6-11]; N-(4'-chlorobiphenyl-4-yl)-3-(4-{[methyl-(tetrahydropyran-4-yl)amino]methyl}phenyl)propionamide [6-12]; N-(4'-chlorobiphenyl-4-yl)-3-{4-[(cyclopropylmethylmethylamino)methyl]phenyl}propionamide [6-13]; N-(4'-chlorobiphenyl-4-yl)-3-(4-{[(2-hydroxy-2-methylpropyl)-(2-methoxyethyl)amino]methyl}phenyl)propionamide [6-14]; N-(4'-chlorobiphenyl- 4-yl)-3-{4-[(cyclopropylmethylamino)methyl]phenyl}propionamide [6-15]; N-(4'-chlorobiphenyl-4-yl)-3-[4-(hexahydropyrrolo[1,2-a]pyrazin-2-ylmethyl)phenyl]propionamide [6-16]; N-(4'-chlorobiphenyl-4-yl)-3-(4-{[(2-methoxyethyl)methylamino]methyl}phenyl)propionamide [6-17]; 3-{4-[(benzylmethylamino)methyl]phenyl}-N-(4'-chlorobiphenyl-4-yl)propionamide [6-18]; N-(4'-chlorobiphenyl-4-yl)-3-(4-{[methyl-(tetrahydropyran-4-ylmethyl)amino]methyl}phenyl)propionamide [6-19]; N-(4'-chlorobiphenyl-4-yl)-3-(4-{[methyl-(2-phenoxyethyl)amino]methyl}phenyl)propionamide [6-20]; N-(4'-chlorobiphenyl-4-yl)-3-[4-(2,6-dimethylmorpholin4-ylmethyl)phenyl]propionamide [6-21]; N-(4'-chlorobiphenyl-4-yl)-3-{4-[(cyclohexylmethylamino)methyl]phenyl}propionamide [6-22]; N-(4'-chlorobiphenyl-4-yl)-3-[4-(5-methyl-2,5-diazabicyclo[2.2.1]hept-2-ylmethyl)phenyl]propionamide [6-23]; N-(4'-chlorobiphenyl-4-yl)-3-[4-(3-piperidin-1-ylpyrrolidin-1-ylmethyl)phenyl]propionamide [6-25]; N-(4'-chlorobiphenyl-4-yl)-3-[4-((3S,5R)-3,5-dimethylpiperidin-1-ylmethyl)phenyl]propionamide [6-26]; 3-(4-{[(3-aminopropyl)methylamino]methyl}phenyl)-N-(4'-chlorobiphenyl-4-yl)propionamide [6-27]; 3-[4-(8-azaspiro[4.5]dec-8-ylmethyl)phenyl]-N-(4'-chlorobiphenyl-4-yl)propionamide [6-28]; N-(4'-chlorobiphenyl-4-yl)-3-[4-((R)-3-hydroxypyrrolidin-1-ylmethyl)phenyl]propionamide [6-29]; N-(4'-chlorobiphenyl-4-yl)-3-{4-[(methylpyridin-3-ylmethylamino)methyl]phenyl}propionamide [6-33]; N-(4'-chlorobiphenyl-4-yl)-3-{4-[(cyclohexylethylamino)methyl]phenyl}propionamide [6-35]; N-(4'-chlorobiphenyl-4-yl)-3-(4-cyclohexylaminomethylphenyl)propionamide [6-39]; N-(4'-chlorobiphenyl-4-yl)-3-{4-[(cyclohexylisopropylamino)methyl]phenyl}propionamide [6-40]; N-(4'-chlorobiphenyl-4-yl)-3-(4-cyclopentylaminomethylphenyl)propionamide [6-41]; and N-(4'-chlorobiphenyl-4-yl)-3-(4-{[ethyl-(2-hydroxy-2-methylpropyl)amino]methyl}phenyl)propionamide [6-42], including the tautomers, the diastereomers, the enantiomers, the mixtures thereof and the salts thereof.

Some expressions used hereinbefore and below to describe the compounds according to the invention will now be defined more fully.

The term halogen denotes an atom selected from among F, Cl, Br, and I, particularly F, Cl, and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, isopropyl, butyl, isobutyl, sec-butyl, tert-butyl, n-pentyl, isopentyl, neopentyl, tert-pentyl, n-hexyl, isohexyl, etc. Substituted alkyl groups, such as, for example, the $C_{2-4}$-alkyl group in hydroxy-$C_{2-4}$-alkyl or $C_{1-4}$-alkoxy-$C_{2-4}$-alkyl, may also be branched or unbranched.

The term $C_{1-n}$-alkylene, where n may have a value of 1 to 8, denotes a saturated, branched or unbranched hydrocarbon bridge with 1 to n C atoms. Examples of such groups include methylene (—$CH_2$—), ethylene (—$CH_2$—$CH_2$—), 1-methylethylene (—$CH(CH_3)$—$CH_2$—), 1,1-dimethylethylene (—$C(CH_3)_2$—$CH_2$—), n-prop-1,3-ylene (—$CH_2$—$CH_2$—$CH_2$—), 1-methylprop-1,3-ylene (—$CH(CH_3)$—$CH_2$—$CH_2$—), 2-methylprop-1,3-ylene (—$CH_2$—$CH(CH_3)$—$CH_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C═C-double bond. Examples of such groups include vinyl, 1-propenyl, 2-propenyl, isopropenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl, etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, isopropynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl, etc.

The term $C_{1-n}$-alkoxy denotes a $C_{1-n}$-alkyl-O— group, wherein $C_{1-n}$-alkyl is defined as above. Examples of such groups include methoxy, ethoxy, n-propoxy, isopropoxy, n-butoxy, isobutoxy, sec-butoxy, tert-butoxy, n-pentoxy, isopentoxy, neopentoxy, tert-pentoxy, n-hexoxy, isohexoxy, etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, etc.

The term $C_{1-n}$-alkylcarbonyl denotes a $C_{1-n}$-alkyl—C(═O)— group, wherein $C_{1-n}$-alkyl is defined as above. Examples of such groups include methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl, etc.

The term $C_{3-n}$-cycloalkyl denotes a saturated mono-, bi-, tri-, or spirocarbocyclic, preferably monocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term $C_{5-n}$-cycloalkenyl denotes a monounsaturated mono-, bi-, tri-, or spirocarbocyclic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(═O) group, wherein $C_{3-n}$-cycloalkyl is as hereinbefore defined.

The term aryl denotes a carbocyclic, aromatic ring system, such as, for example, phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-7}$-alkyleneimino denotes a 4- to 7-membered ring which comprises 3 to 7 methylene units as well as an imino group, while the bond to the residue of the molecule is made via the imino group.

The term cyclo-$C_{3-7}$-alkyleneiminocarbonyl denotes a cyclo-$C_{3-7}$-alkyleneimino ring as hereinbefore defined which is linked to a carbonyl group via the imino group.

The term heteroaryl used in this application denotes a heterocyclic, aromatic ring system which comprises in addition to at least one C atom one or more heteroatoms selected from N, O, and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazolyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated ring systems are 2,3-dihydrobenzofuranyl, pyrolinyl, pyrazolinyl, indolinyl, oxazolidinyl, oxazolinyl, oxazepinyl, etc. Particularly preferably heteroaryl denotes a heteroaromatic mono- or bicyclic ring system.

Terms such as aryl-$C_{1-n}$-alkyl, heteroaryl-$C_{1-n}$-alkyl, etc. refer to $C_{1-n}$-alkyl, as defined above, which is substituted with an aryl or heteroaryl group.

Many of the terms given above may be used repeatedly in the definition of a formula or group and in each case have one of the meanings given above, independently of one another.

The term "unsaturated", for example, in "unsaturated carbocyclic group" or "unsaturated heterocyclic group", as used particularly in the definition of the group Cy, comprises in addition to the mono- or polyunsaturated groups, the corresponding, totally unsaturated groups, but particularly the mono- and diunsaturated groups.

The term "optionally substituted" used in this application indicates that the group thus designated is either unsubstituted or mono- or polysubstituted by the substituents specified. If the group in question is polysubstituted, the substituents may be identical or different.

The style used hereinbefore and hereinafter, according to which in a cyclic group a bond of a substituent is shown towards the centre of this cyclic group, unless otherwise stated, indicates that this substituent may be bound to any free position of the cyclic group carrying an H atom.

Thus in the example

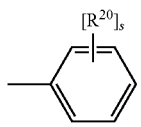

the substituent $R^{20}$ where s=1 may be bound to any of the free positions of the phenyl ring; where s=2 selected substituents $R^{20}$ may differently from one another be bound to different free positions of the phenyl ring.

The H atom of any carboxy group present or an H atom bound to an N atom (imino or amino group) may in each case be replaced by a group which can be cleaved in vivo. By a group which can be cleaved in vivo from an N atom is meant, for example, a hydroxy group, an acyl group such as the benzoyl or pyridinoyl group or a $C_{1-16}$-alkanoyl group such as the formyl, acetyl, propionyl, butanoyl, pentanoyl, or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert-butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, or hexadecyloxycarbonyl group, a phenyl-$C_{1-6}$-alkoxycarbonyl group such as the benzyloxycarbonyl, phenylethoxycarbonyl, or phenylpropoxycarbonyl group, a $C_{1-3}$-alkylsulfonyl-$C_{2-4}$-alkoxycarbonyl, $C_{1-3}$-alkoxy-$C_{2-4}$-alkoxy-$C_{2-4}$-alkoxycarbonyl, or $R_eCO$—O—$(R_fCR_g)$—O—CO— group wherein Re denotes a $C_{1-8}$-alkyl, $C_{5-7}$-cycloalkyl, phenyl, or phenyl-$C_{1-3}$-alkyl group, $R_f$ denotes a hydrogen atom, a $C_{1-3}$-alkyl, $C_{5-7}$-cycloalkyl, or phenyl group, and $R_g$ denotes a hydrogen atom, a $C_{1-3}$-alkyl or $R_eCO$—O—$(R_fCR_g)$—O group wherein $R_e$ to $R_g$ are as hereinbefore defined, while the phthalimido group is an additionally possibility for an amino group, and the abovementioned ester groups may also be used as a group which can be converted in vivo into a carboxy group.

The residues and substituents described above may be mono- or polysubstituted by fluorine as described. Preferred fluorinated alkyl groups are fluoromethyl, difluoromethyl, and trifluoromethyl. Preferred fluorinated alkoxy groups are fluoromethoxy, difluoromethoxy, and trifluoromethoxy. Preferred fluorinated alkylsulfinyl and alkylsulfonyl groups are trifluoromethylsulfinyl and trifluoromethylsulfonyl.

The compounds of general formula I according to the invention may have acid groups, predominantly carboxyl groups, and/or basic groups such as, e.g., amino functions. Compounds of general formula I may therefore be present as internal salts, as salts with pharmaceutically useable inorganic acids such as hydrochloric acid, sulfuric acid, phosphoric acid, sulfonic acid, or organic acids (such as, for example, maleic acid, fumaric acid, citric acid, tartaric acid, or acetic acid) or as salts with pharmaceutically useable bases such as alkali or alkaline earth metal hydroxides or carbonates, zinc or ammonium hydroxides, or organic amines such as, e.g., diethylamine, triethylamine, and triethanolamine.

The compounds according to the invention may be obtained using methods of synthesis which are known in principle. Preferably the compounds are obtained analogously to the methods of preparation explained more fully hereinafter, which are also an object of this invention. The abbreviations used hereinafter are defined in the introduction to the experimental section or are already familiar to those skilled in the art.

If the starting materials or intermediate products listed below contain groups $R^1$, $R^2$, $R^3$, X, Y, Z, A, or B with amine functions, these are preferably used in protected form, for example, with a Boc, Fmoc, or Cbz protective group, and liberated at the end of the reactions using standard methods.

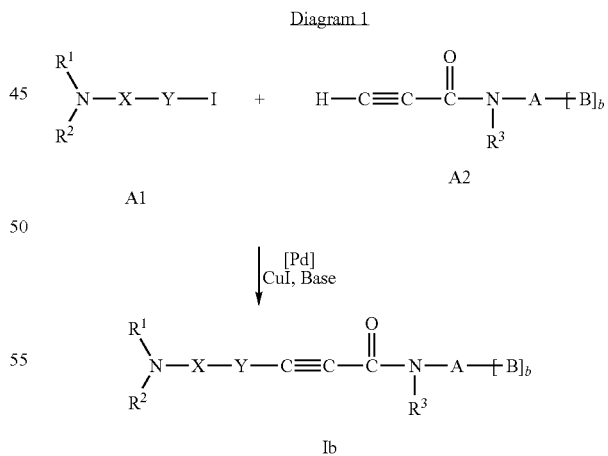

Diagram 1

To obtain a compound of general formula Ib, a compound of general formula A1 is reacted with a compound of general formula A2 in a Sonogashira coupling in the presence of a catalyst such as, for example, palladium with or without ligands and copper iodide in a solvent such as, for example, dioxane, DMF, toluene, acetonitrile, or THF, or a mixture of solvents, using an amine base such as, for example, triethylamine, or an inorganic base such as cesium carbonate at temperatures between −20° C. and 200° C.

Instead of the arylboric acid derivatives it is also possible to use organometallic aryl compounds such as, for example, tin

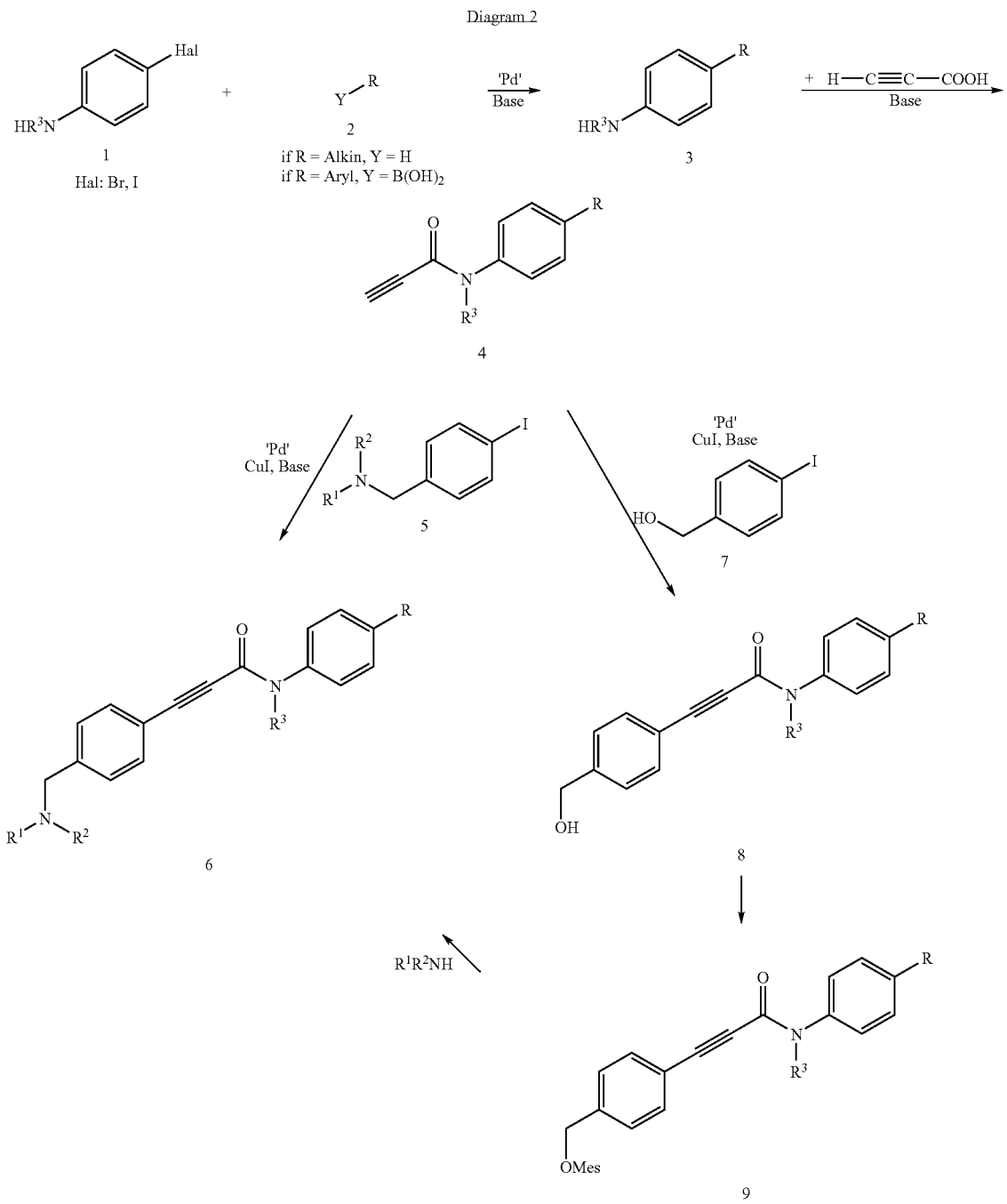

Diagram 2

In order to obtain compounds of formula 6, an aniline derivative of formula I is reacted with a compound of formula 2. If the compound 2 is an arylboric acid derivative, the reaction to the compound 3 is carried out in the presence of a catalyst such as, for example, palladium with or without ligands in a solvent or mixture of solvents comprising, for example, dioxane, DMF, toluene, THF, or water, using a base such as, for example, triethylamine or potassium carbonate, at temperatures between ambient temperature and 200° C. or zinc compounds. If the compound 2 is an alkyne derivative, the reaction to obtain the compound 3 is carried out as a Sonogashira coupling in the presence of a catalyst such as, for example, palladium with or without ligands and copper iodide in a solvent or mixture of solvents comprising, for example, dioxane, DMF, toluene, acetonitrile, or THF using a base such as, for example, triethylamine at temperatures between −20° C. and 200° C. A compound of formula 4 is obtained by reacting a compound of formula 3 with propynecarboxylic acid in the presence of a base and activating reagents such as, for example, CDI, TBTU, or DCC. Instead of the propynecarboxylic acid it is also possible to use propynecarboxylic acid chloride. Compounds of formula 4 may be reacted to compounds of formula 6 by a Sonogashira coupling as hereinbefore described. Alternatively, a compound of formula 4 may be reacted with compound 7 in a Sonogashira coupling as described. The resulting compound of formula 8 is converted into the sulfonic acid derivative 9 by reacting with methanesulfonic acid chloride in the presence of a base such as triethylamine in an inert solvent such as, for example, dichloromethane, at a temperature between 0° C. and 50° C. For the reaction to a compound of formula 6 it is possible to use an analogous tosylate or a corresponding halogen compound instead of the mesylate 9. A compound of formula 9 is then reacted with the corresponding amine in a solvent such as, for example, THF, at a temperature between 0° C. and 150° C., producing a compound of formula 6.

Diagram 3a

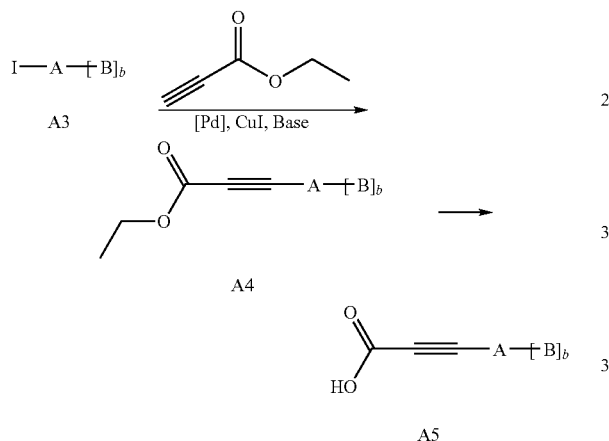

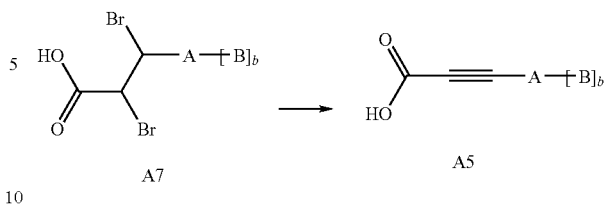

A compound of general formula A5 may also be prepared by reacting a compound of general formula A7 in an organic solvent such as, for example, dioxane, ethanol, or THF with or without the addition of water with a base such as potassium tert-butoxide, sodium hydroxide, or sodium ethoxide at temperatures from 0° C. to 150° C. However, it is also possible in this reaction to react a compound of general formula A7 with pyridine or quinoline at temperatures from 0° C. to 150° C. A compound of general formula A7 is obtained by brominating a compound of general formula A6 in a solvent such as, for example, carbon tetrachloride, at temperatures between −20° C. to 100° C., preferably at temperatures between 0° C. and ambient temperature.

Diagram 3c

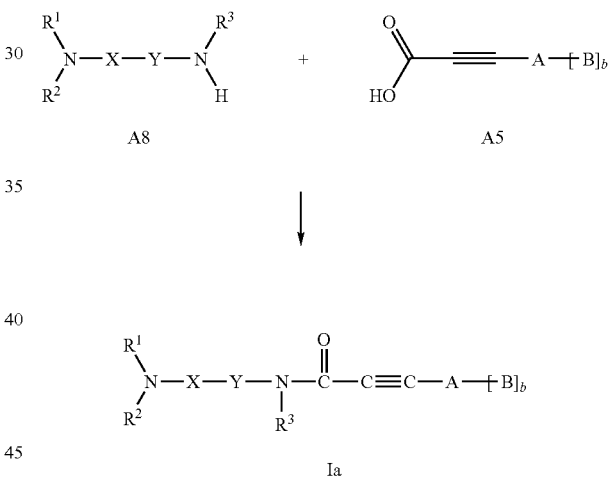

In order to obtain a compound of general formula A4, a compound of general formula A3 is reacted with an ester of propynoic acid, preferably with ethyl propynoate, in a Sonogashira coupling in the presence of a catalyst such as, for example, palladium with or without ligands and copper iodide, in a solvent such as, for example, dioxane, DMF, toluene, acetonitrile, or THF, or a solvent mixture, using an amine base such as, for example, triethylamine, or an inorganic base such as cesium carbonate, at temperatures between −20° C. and 200° C. The compound of general formula A4 is converted into a compound of general formula A5 in the course of an ester splitting. The ester splitting may take place in a solvent such as ethanol, dioxane, or THF with or without the addition of water in the presence of an inorganic base such as sodium hydroxide, lithium hydroxide, potassium hydroxide, or potassium carbonate at temperatures from 0° C. to 150° C. Ester splitting is also possible in an organic solvent such as THF or dioxane in the presence of acid, for example, aqueous hydrochloric acid or sulfuric acid.

A compound of general formula Ia is obtained by reacting a compound of general formula A8 with a compound of general formula A5 in an organic solvent such as, for example, DMF, THF, dioxane, acetonitrile, or toluene in the presence of a base such as, for example, triethylamine, and activating reagents such as, for example, CDI, TBTU, or DCC. Instead of the compound A5, it is also possible to use carboxylic acid chloride or a mixed anhydride of the compound A5.

Diagram 3b

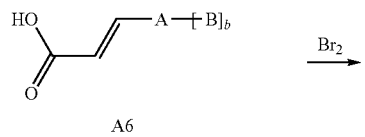

Diagram 4

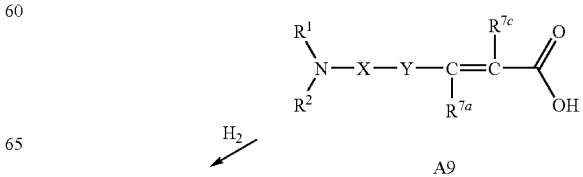

-continued

A10

A11

A12

↓ H₂

Ic

A compound of general formula Ic is advantageously obtained by hydrogenation of a compound of general formula A12 in an organic solvent such as, for example, methanol, ethanol, THF, or dioxane in the presence of a catalyst such as Raney nickel, palladium, or platinum at temperatures between 0° C. and 150° C. The reaction of the compound A12 to the compound Ic may however also take place in the presence of other hydrogen-transferring reagents. A compound of general formula A12 is obtained by reacting a compound of general formula A9 with a compound of general formula A11 in an organic solvent such as, for example, DMF, THF, dioxane, acetonitrile, or toluene in the presence of a base such as, for example, triethylamine, and activating reagents such as, for example, CDI, TBTU, or DCC. Instead of the compound A9 it is also possible to use the carboxylic acid chloride of the compound A9. Compound Ic may also be obtained by reacting a compound of general formula A10 with a compound of general formula A11 under conditions as described above for the reaction of A9 and A11 to A12. The compound of general formula A10 may be obtained by reduction of a compound of general formula A9 analogously to the reaction of A12 to Ic.

A13
$\xrightarrow{HC(OMe)_3}$

-continued

A14
$\xrightarrow[NEt_3, TBTU]{A11}$

A15
$\xrightarrow{H^+}$

A16
$\xrightarrow{NaB(O_2CCH_3)_3H}$

A17

A18
T = Cl, MeSO₂O⁻
$\xrightarrow[H]{A19}$

A20
$\xrightarrow[H_2]{Raney-Ni}$

A21

A compound of general formula A21 may be obtained as follows. The cinnamic acid derivative A13 is converted by reaction with orthomethyl formate with or without an organic solvent such as, for example, methanol, THF, or dioxane at temperatures between ambient temperature and 200° C. into the protected cinnamic acid derivative A14. This is reacted in the course of an amide linking with the amine of general formula A11 in the presence of TBTU and triethylamine in an organic solvent such as, for example, DMF or THF at a temperature between 0° C. and ambient temperature, to obtain a compound of general formula A15. A compound of general formula A16 is obtained by the action of acid such as, for example, trifluoroacetic acid on the compound A15 in a solvent such as, for example, dichloromethane, chloroform, or water, or combinations thereof at temperatures between 0° C. and 100° C. Reduction of the compound A16 by the action of a hydride transfer agent such as sodium triacetoxyborohydride or sodium borohydride in an organic solvent such as, for example, THF in the presence of an acid such as acetic acid at temperatures between 0° C. and 100° C. yields a compound of general formula A17. Reacting A17 with methanesulfonic acid chloride in an organic solvent such as dichloromethane in the presence of a base such as triethylamine at temperatures between 0° C. and 100° C. yields a compound of general formula A18. To convert A17 into A18 it is also possible to react A17 with thionyl chloride. Compound A20 is obtained by reacting A18 with a compound of general formula A19 in an organic solvent such as DMF, acetonitrile, or THF, at temperatures of 0° C. and 100° C. A compound of general formula A21 is obtained by hydrogenation of a compound of general formula A20 in an organic solvent such as, for example, methanol, ethanol, THF, or dioxane, in the presence of a catalyst such as Raney nickel, palladium, or platinum, at temperatures between 0° C. and 150° C. The reaction of compound A20 to compound A21 may however also be carried out in the presence of other hydrogen-transferring reagents.

The compounds according to the invention may advantageously also be obtained by the processes described in the Examples that follow, and these may also be combined with processes known to the skilled man from the literature, for example, from WO 04/024702, WO 04/039780, and WO 04/039764, which are each hereby incorporated by reference in their entireties.

Stereoisomeric compounds of formula (I) may chiefly be separated by conventional methods. The diastereomers are separated on the basis of their different physico-chemical properties, e.g., by fractional crystallization from suitable solvents, by high pressure liquid or column chromatography, using chiral or preferably non-chiral stationary phases.

Racemates covered by general formula (I) may be separated, for example, by HPLC on suitable chiral stationary phases (e.g., Chiral AGP, CHIRALPAK® AD). Racemates which contain a basic or acidic function can also be separated via the diastereomeric, optically active salts which are produced on reacting with an optically active acid, for example, (+)- or (−)-tartaric acid, (+)- or (−)-diacetyltartaric acid, (+)- or (−)-monomethyl tartrate or (+)-camphorsulfonic acid, or an optically active base, for example, with (R)-(+)-1-phenylethylamine, (S)-(−)-1-phenylethylamine, or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol, or mixtures thereof, for example, in a ratio by volume of 50:50, are used. Then each of the optically active salts is dissolved in water, carefully neutralized with a base such as sodium carbonate or potassium carbonate, or with a suitable acid, e.g., with dilute hydrochloric acid or aqueous methanesulfonic acid and in this way the corresponding free compound is obtained in the (+)- or (−)-form.

The (R)- or (S)-enantiomer alone or a mixture of two optically active diastereomeric compounds covered by general formula I may also be obtained by performing the syntheses described above with a suitable reaction component in the (R)- or (S)-configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion.

The acid addition salts may be prepared, for example, using hydrochloric acid, hydrobromic acid, sulfuric acid, phosphoric acid, methanesulfonic acid, ethanesulfonic acid, toluenesulfonic acid, benzenesulfonic acid, acetic acid, fumaric acid, succinic acid, lactic acid, citric acid, tartaric acid, or maleic acid. Moreover, mixtures of the above mentioned acids may be used. To prepare the alkali and alkaline earth metal salts of the compound of formula (I) with acidically bound hydrogen the alkali and alkaline earth metal hydroxides and hydrides are preferably used, while the hydroxides and hydrides of the alkali metals, particularly of sodium and potassium, are preferred and sodium and potassium hydroxide are most preferred.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, such as, for example, rats, mice, guinea pigs, hares, dogs, cats, sheep, horses, pigs, cattle, monkeys, and particularly humans, for the treatment and/or prevention of symptoms and/or diseases which are caused by MCH or are otherwise causally connected with MCH.

Diseases caused by MCH or otherwise causally connected with MCH are particularly metabolic disorders, such as, for example, obesity, and eating disorders, such as, for example, bulimia, including bulimia nervosa. The indication obesity includes in particular exogenic obesity, hyperinsulinemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, and central obesity. This range of indications also includes cachexia, anorexia, and hyperphagia.

Compounds according to the invention may be particularly suitable for reducing hunger, reining in appetite, controlling eating behavior, and/or inducing a feeling of satiation.

In addition, the diseases caused by MCH or otherwise causally connected with MCH also include hyperlipidemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia, and hormonal disorders.

Compounds according to the invention are also suitable as active substances for the prevention and/or treatment of other illnesses and/or disorders, particularly those which accompany obesity, such as, for example, diabetes, diabetes mellitus, particularly type II diabetes, hyperglycemia, particularly chronic hyperglycemia, complications of diabetes including diabetic retinopathy, diabetic neuropathy, diabetic nephropathy, etc., insulin resistance, pathological glucose tolerance, encephalorrhagia, cardiac insufficiency, and cardiovascular diseases, particularly arteriosclerosis and high blood pressure, arthritis, and gonitis.

MCH antagonists and formulations according to the invention may advantageously be used in combination with a dietary therapy, such as, for example, a dietary diabetes treatment, and exercise.

Another range of indications for which the compounds according to the invention are advantageously suitable is the prevention and/or treatment of micturition disorders, such as, for example, urinary incontinence, hyperactive bladder, nycturia, and enuresis, while the hyperactive bladder and urinary incontinence may or may not be connected with benign prostatic hyperplasia.

The dosage required to achieve such an effect is conveniently, by intravenous or subcutaneous route, 0.001 to 30 mg/kg of bodyweight, preferably 0.01 to 5 mg/kg of bodyweight, and by oral or nasal route or by inhalation, 0.01 to 50 mg/kg of bodyweight, preferably 0.1 to 30 mg/kg of bodyweight, in each case 1× to 3× daily.

For this purpose, the compounds of formula I prepared according to the invention may be formulated, optionally together with other active substances as described hereinafter, together with one or more physiologically acceptable excipients, inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat or suitable mixtures thereof, to produce conventional galenic preparations such as plain or coated tablets, capsules, powders, granules, solutions, emulsions, syrups, aerosols for inhalation, ointments, or suppositories.

In addition to pharmaceutical compositions, the invention also includes compositions containing at least one amide compound according to the invention and/or a salt according to the invention optionally together with one or more physiologically acceptable excipients. Such compositions may also be, for example, foodstuffs which may be solid or liquid, in which the compound according to the invention is incorporated.

For the abovementioned combinations it is possible to use as additional active substances particularly those which, for example, potentiate the therapeutic effect of an MCH antagonist according to the invention in terms of one of the indications mentioned above and/or which make it possible to reduce the dosage of an MCH antagonist according to the invention. Preferably one or more additional active substances are selected from among: active substances for the treatment of diabetes, active substances for the treatment of diabetic complications, active substances for the treatment of obesity, preferably other than MCH antagonists, active substances for the treatment of high blood pressure, active substances for the treatment of hyperlipidemia, including arteriosclerosis, active substances for the treatment of arthritis, active substances for the treatment of anxiety states, and active substances for the treatment of depression. The abovementioned categories of active substances will now be explained in more detail by means of examples.

Examples of active substances for the treatment of diabetes are insulin sensitizers, insulin secretion accelerators, biguanides, insulins, α-glucosidase inhibitors, and $\beta_3$ adreno-receptor agonists. Insulin sensitizers include pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, and GW-1929. Insulin secretion accelerators include sulfonylureas, such as, for example, tolbutamide, chloropropamide, tolazamide, acetohexamide, glyclopyramide and its ammonium salts, glibenclamide, gliclazide, and glimepiride. Further examples of insulin secretion accelerators are repaglinide, nateglinide, mitiglinide (KAD-1229), and JTT-608. Biguanides include metformin, buformin and phenformin. Insulins include those obtained from animals, particularly cattle or pigs, semisynthetic human insulins which are synthesized enzymatically from insulin obtained from animals, human insulin obtained by genetic engineering, e.g., from *Escherichia coli* or yeasts. Moreover, the term insulin also includes insulin-zinc (containing 0.45 to 0.9 percent by weight of zinc) and protamine-insulin-zinc obtainable from zinc chloride, protamine sulfate, and insulin. Insulin may also be obtained from insulin fragments or derivatives (for example, INS-1, etc.). Insulin may also include different kinds, e.g., with regard to the onset time and duration of effect ("ultra immediate action type", "immediate action type", "two phase type", "intermediate type", "prolonged action type", etc.), which are selected depending on the pathological condition of the patient. α-Glucosidase inhibitors include acarbose, voglibose, miglitol, and emiglitate. $\beta_3$ adreno-receptor agonists include AJ-9677, BMS-196085, SB-226552, and AZ40140. Active substances for the treatment of diabetes other than those mentioned above include ergoset, pramlintide, leptin, and BAY-27-9955, as well as glycogen phosphorylase inhibitors, sorbitol dehydrogenase inhibitors, protein tyrosine phosphatase 1B inhibitors, dipeptidyl protease inhibitors, glipazide, and glyburide.

Active substances for the treatment of diabetic complications include, for example, aldose reductase inhibitors, glycation inhibitors and protein kinase C inhibitors, DPP-IV blockers, GLP-1 or GLP-2 analogues, and SGLT-2 inhibitors. Aldose reductase inhibitors are, for example, tolrestat, epalrestat, imirestat, zenarestat, SNK-860, zopolrestat, ARI-50i, and AS-3201. An example of a glycation inhibitor is pimagedine. Protein Kinase C inhibitors are, for example, NGF and LY-333531. DPP-IV blockers are, for example, LAF237 (Novartis) and MK431 (Merck), as well as 815541, 823093, and 825964 (all GlaxoSmithKline). GLP-1 analogues are, for example, liraglutide (NN2211) (NovoNordisk), CJC1131 (Conjuchem), and exenatide (Amylin). SGLT-2 inhibitors are, for example, AVE-2268 (Aventis) and T-1095 (Tanabe, Johnson & Johnson). Active substances other than those mentioned above for the treatment of diabetic complications include alprostadil, thiapride hydrochloride, cilostazol, mexiletine hydrochloride, ethyl eicosapentate, memantine, and pimagedine (ALT-711).

Active substances for the treatment of obesity, preferably other than MCH antagonists, include lipase inhibitors and anorectics. A preferred example of a lipase inhibitor is orlistat. Examples of preferred anorectics are phentermine, mazindol, fluoxetine, sibutramine, baiamine, (S)-sibutramine, SR-141716, and NGD-95-1.

Active substances other than those mentioned above for the treatment of obesity include lipstatin.

Moreover, for the purposes of this application, the active substance group of anti-obesity active substances also includes the anorectics, of which the 3 agonists, thyromimetic active substances, and NPY antagonists should be emphasized. The range of substances which may be considered as preferred anti-obesity or anorectic active substances is indicated by the following additional list, by way of example: phenylpropanolamine, ephedrine, pseudoephedrine, phentermnine, a cholecystokinin-A (hereinafter referred to as CCK-A) agonist, a monoamine reuptake inhibitor (such as, for example, sibutramine), a sympathomimetic active substance, a serotonergic active substance (such as, for example, dexfenfluramine, fenfluramine, or a 5-HT2C agonist such as BVT.933 or APD356), a dopamine antagonist (such as, for example, bromocriptine or pramipexole), a melanocyte-stimulating hormone receptor agonist or mimetic, an analogue of melanocyte-stimulating hormone, a cannabinoid receptor antagonist (ACOMPLIA™ (rimonabant)), an MCH antagonist, the OB protein (hereinafter referred to as leptin), a leptin analogue, a leptin receptor agonist, a galanine antagonist, and a GI lipase inhibitor or reducer (such as, for example, orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as, for example, exendin and ciliary neurotrophic factors, such as, for example, axokines. In this context mention should also be made of the forms of therapy which produce weight loss by increasing the fatty acid oxidation in the peripheral tissue, such as, for example, inhibitors of acetyl-CoA carboxylase.

Active substances for the treatment of high blood pressure include inhibitors of angiotensin converting enzyme, calcium antagonists, potassium channel openers, and angiotensin II antagonists. Inhibitors of angiotensin converting enzyme include captopril, enalapril, alacepril, delapril (hydrochloride), lisinopril, imidapril, benazepril, cilazapril, temocapril, trandolapril, and manidipine (hydrochloride). Examples of calcium antagonists are nifedipine, amlodipine, efonidipine, and nicardipine. Potassium channel openers include levcromakalim, L-27152, AL0671, and NIP-121. Angiotensin II antagonists include telmisartan, losartan, candesartan cilexetil, valsartan, irbesartan, CS-866, and E4177.

Active substances for the treatment of hyperlipidemia, including arteriosclerosis, include HMG-CoA reductase inhibitors and fibrate compounds. HMG-CoA reductase inhibitors include pravastatin, simvastatin, lovastatin, atorvastatin, fluvastatin, lipantil, cerivastatin, itavastatin, ZD-4522, and their salts. Fibrate compounds include bezafibrate, clinofibrate, clofibrate and simfibrate.

Active substances for the treatment of arthritis include NSAIDs (non-steroidal anti-inflammatory drugs), particularly COX2 inhibitors, such as, for example, meloxicam or ibuprofen.

Active substances for the treatment of anxiety states include chlordiazepoxide, diazepam, oxozolam, medazepam, cloxazolam, bromazepam, lorazepam, alprazolam, and fludiazepam.

Active substances for the treatment of depression include fluoxetine, fluvoxamine, imipramine, paroxetine, and sertraline.

The dosage for these active substances is conveniently ⅕ of the lowest normal recommended dose up to ¼ of the normal recommended dose.

In another embodiment, the invention also relates to the use of at least one alkyne compound according to the invention and/or a salt according to the invention for influencing the eating behavior of a mammal. This use is particularly based on the fact that compounds according to the invention may be suitable for reducing hunger, restricting appetite, controlling eating behavior, and/or inducing a feeling of satiety. The eating behavior is advantageously influenced so as to reduce food intake. Therefore, compounds according to the invention are advantageously used for reducing bodyweight. Another use according to the invention is the prevention of increases in bodyweight, for example, in people who had previously taken steps to lose weight and are interested in maintaining their lower bodyweight. According to this embodiment it is preferably a non-therapeutic use. Such a non-therapeutic use might be a cosmetic use, for example, to alter the external appearance, or an application to improve general health. The compounds according to the invention are preferably used non-therapeutically for mammals, particularly humans, not suffering from any diagnosed eating disorders, no diagnosed obesity, bulimia, diabetes, and/or no diagnosed micturition disorders, particularly urinary incontinence. Preferably, the compounds according to the invention are suitable for non-therapeutic use in people whose BMI (body mass index), defined as their bodyweight in kilograms divided by their height (in meters) squared, is below a level of 30, particularly below 25.

The Examples that follow are intended to illustrate the invention.

Preliminary Remarks

As a rule, IR, $^1$H-NMR and/or mass spectra have been obtained for the compounds prepared. Unless otherwise stated the $R_f$ values were determined using ready-made silica gel 60 TLC plates $F_{254}$ (E. Merck, Darmstadt, Item No. 1.05714) without chamber saturation. The $R_f$ values obtained under the heading Alox were determined using ready-made aluminum oxide 60 TLC plates $F_{254}$ (E. Merck, Darmstadt, Item No. 1.05713) without chamber saturation. The ratios specified for the eluants are based on units by volume of the solvents in question. The units by volume specified in the case of $NH_3$ relate to a concentrated solution of $NH_3$ in water. For chromatographic purification, silica gel made by Messrs Millipore (MATREX™, 35-70 my) is used. For chromatographic purification, Alox (E. Merck, Darmstadt, standardized aluminum oxide 90, 63-200 Am, Item No.: 1.01097.9050) is used.

The HPLC data specified were measured under the parameters indicated below:

Analytical columns: Zorbax column (Agilent Technologies), SB (Stable Bond)-C18; 3.5 µm; 4.6×75 mm; column temperature: 30° C.; flow: 0.8 mL/min; injection volume: 5 µL; detection at 254 nm (methods A and B).

Symmetry 300 (Waters), 3.5 µm; 4.6×75 mm; column temperature: 30° C.; flow: 0.8 mL/min; injection volume: 5 µL; detection at 254 nm (method C)

Method A: water:acetonitrile:formic acid (9:1:0.01) towards (1:9:0.01) over 9 minutes Method B: water:acetonitrile:formic acid (9:1:0.01) towards (1:9:0.01) over 4 minutes, then 6 minutes (1:9:0.01)

method C: water:acetonitrile:formic acid (9:1:0.01) after (1:9:0.01) over 4 minutes, then 6 minutes (1:9:0.01)

Preparative column: Zorbax column (Agilent Technologies), SB (Stable Bond)-C18; 3.5 µm; 30×100 mm; column temperature: ambient temperature; flow: 30 mL/min; detection at 254 nm.

In preparative HPLC purification, as a rule the same gradients are used which were used when obtaining the analytical HPLC data. The products are collected under mass control, the fractions containing the product are combined and freeze-dried. If there is no specific information as to the configuration, it is not clear whether there are pure enantiomers or whether partial or even total racemization has taken place.

The following abbreviations are used above and hereinafter:

| | |
|---|---|
| Boc | tert-butoxycarbonyl |
| Cbz | benzyloxycarbonyl |
| CDI | N,N'-carbonyldiimidazole |
| CDT | 1,1'-carbonyldi(1,2,4-triazole) |
| DMF | N,N-dimethylformamide |
| Et | ethyl |
| ether | diethyl ether |
| EtOAc | ethyl acetate |
| EtOH | ethanol |
| Fmoc | 9-fluorenylmethoxycarbonyl |
| HCl | hydrochloric acid |
| HOAc | acetic acid |
| HOBt | 1-hydroxybenzotriazole-hydrate |
| Hunig base | N-ethyldiisopropylamine |
| HV | high vacuum |
| in vacuo | under vacuum |
| KOH | potassium hydroxide |
| Me | methyl |
| MeOH | methanol |
| MTBE | methyl-tert-butylether |
| NaCl | sodium chloride |
| NaOH | sodium hydroxide |
| org. | organic |
| Ph | phenyl |
| RT | ambient temperature (approx. 20° C.) |
| TBTU | 2-(1H-benzotriazol-1-yl)-1,1,3,3-tetramethyluronium-tetrafluoroborate |
| TEBAC | triethylbenzylammonium chloride |
| TFA | trifluoroacetic acid |
| THF | tetrahydrofuran |
| →* | denotes the binding site of a group |

In the structural formulae shown previously and hereinafter, as well as the H atoms at C atoms, the H atoms at O and N atoms, as in hydroxyl or amino groups, for example, are generally not specifically shown for reasons of clarity.

EXAMPLE 1.1

3-(4-pyrrolidin-1-ylmethylphenyl)propynoic acid-(4-prop-1-ynylphenyl)amide

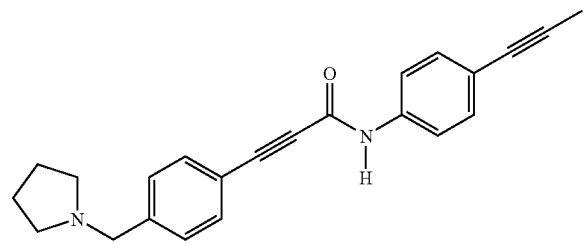

1.1.a. 4-prop-1-ynylphenylamine 5.47 g (25 mmol) of 4-iodoaniline, 0.878 g (1.25 mmol) of bis-triphenylphosphine palladium dichloride, 0.47 g (2.5 mmol) of copper (I) iodide, and 20 mL of piperidine are placed in a pressure apparatus. Then 6.1 bar gaseous propyne are piped into the pressure apparatus, while the temperature rises to 39° C. It is therefore cooled with water. The mixture is stirred for 2 hours at ambient temperature and the reaction mixture is then extracted with ethyl acetate and water. The organic phase is dried over sodium sulfate, evaporated down, and the residue purified by column chromatography on silica gel (eluant: cyclohexane/ethyl acetate (4:1)). Yield: 2.1 g (64% of theory); $C_9H_9N$ (M=131.17); calc.: molecular ion peak $(M+H)^+$: 132; found: molecular ion peak $(M+H)^+$: 132.

1.1.b. Propynoic acid-(4-prop-1-ynylphenyl)amide 1.2 g (5.86 mmol) of DCC is added to a solution of 375 mg (5.35 mmol) of propynoic acid in 10 mL of dichloromethane at 0° C. and the mixture is stirred for 30 minutes. Then 0.7 g (5.35 mmol) of 4-prop-1-ynylphenylamine dissolved in dichloromethane is slowly added dropwise and the mixture is stirred for 2 hours again at 0° C. The reaction mixture is then filtered through CELITE® filter aid and the filtrate is evaporated down. The purification is carried out by column chromatography on silica gel (eluant: dichloromethane/ethanol (40:1)). Yield: 0.7 g (71.4% of theory); $C_{12}H_9NO$ (M=183.21); calc.: molecular ion peak $(M+H)^+$: 184; found: molecular ion peak $(M+H)^+$: 184; $R_f$ value: 0.65 (silica gel, dichloromethane/ethanol/acetic acid 20:1).

1.1.c. 1-(4-iodobenzyl)pyrrolidine

A solution of 5 g (16.83 mmol) of 4-iodobenzyl bromide, 1.41 mL (17 mmol) of pyrrolidine, and 4.8 mL (34.43 mmol) of triethylamine in 50 mL of dichloromethane is stirred for 14 hours at ambient temperature. The reaction mixture is combined with water, and the organic phase is separated off and dried over sodium sulfate. Yield: 4 g (82.7% of theory); $C_{11}H_{14}IN$ (M=287.14); calc.: molecular ion peak $(M+H)^+$: 288; found: molecular ion peak $(M+H)^+$: 288.

1.1.d. 3-(4-pyrrolidin-1-ylmethylphenyl)propynoic acid-(4-prop-1-ynylphenyl)amide 10 mL of acetonitrile is degassed and combined with 0.35 mL (2 mmol) of ethyldiisopropylamine and 0.2 g (0.69 mmol) of 1-(4-iodobenzyl)pyrrolidine. Then the mixture is again degassed and 13 mg of copper (I) iodide, 34 mg of tetrakistriphenylphosphine palladium, and 137 mg (0.75 mmol) of propynoic acid-(4-prop-1-ynylphenyl)amide are then added in succession. The reaction mixture is stirred for 24 hours at ambient temperature and then combined with 60 mg of propynoic acid-(4-prop-1-ynylphenyl)amide. After 24 hours, the mixture is evaporated down. The purification is carried out by column chromatography on silica gel (dichloromethane/methanol/ammonia (30:1:0.1 to 20:1:0.1)). Yield: 24 mg (10% of theory); $C_{23}H_{22}N_2O$ (M=342.44); calc.: molecular ion peak $(M+H)^+$: 343; found: molecular ion peak $(M+H)^+$: 343; $R_f$ value: 0.2 (silica gel, dichloromethane/methanol/ammonia=10:1:0.1).

EXAMPLE 1.2

3-(4-piperidin-1-ylemthylphenyl)propynoic acid-(4-prop-1-ynylphenyl)amide

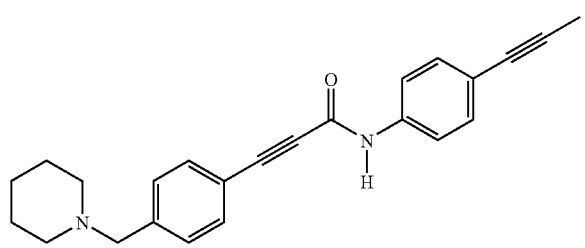

1.2.a. 3-(4-hydroxymethylphenyl)propynoic acid-(4-prop-1-ynylphenyl)amide 40 mL of THF are degassed, combined with 2.62 g (8.03 mmol) of cesium carbonate and 4-iodobenzyl alcohol and again degassed. To this reaction mixture is added successively 138 mg (0.12 mmol) of tetrakistriphenylphosphine palladium, 53 mg (0.28 mmol) of copper (I) iodide, and 0.7 g (3.2 mmol) of propynoic acid-(4-prop-1-ynylphenyl)amide. The mixture is stirred for 24 hours at ambient temperature and the reaction mixture is then evaporated down. The purification of the residues is carried out by column chromatography on silica gel (eluant: dichloromethane/ethanol (60:1)). Yield: 0.5 g (57.8% of theory); $C_{19}H_{15}NO_2$ (M=289.33); calc.: molecular ion peak (M+H)$^+$: 290; found: molecular ion peak (M+H)$^+$: 290; $R_f$ value: 0.21 (silica gel, dichloromethane/ethanol (50:1)).

1.2.b. 4-[(4-prop-1-ynylphenylcarbamoyl)ethynyl]benzyl methanesulfonate 0.14 mL (1.8 mmol) of methanesulfonic acid chloride is slowly added dropwise at ambient temperature to a solution of 0.5 g (1.72 mmol) of 3-(4-hydroxymethylphenyl)propynoic acid (4-prop-1-ynylphenyl)amide and 0.49 mL (3.6 mmol) of triethylamine in 20 mL of dichloromethane and the reaction mixture is stirred for 2 hours at ambient temperature. It is extracted three times with water and the organic phase is dried over sodium sulfate. The solvent is distilled off and the residue is stirred with diisopropyl ether. Yield: 0.48 g (75.6% of theory); $C_{20}H_{17}NO_4S$ (M=367.42); calc.: molecular ion peak (M+H)$^+$: 368; found: molecular ion peak (M+H)$^+$: 368; $R_f$ value: 0.48 (silica gel, dichloromethane/ethanol (20:1)).

1.2.c. 3-(4-piperidin-1-ylmethylphenyl)propynoic acid-(4-prop-1-ynylphenyl)amide A reaction mixture of 0.5 mg (0.13 mmol) of 4-[(4-prop-1-ynylphenylcarbamoyl)ethynyl]benzyl methanesulfonate, 0.028 mL (0.28 mmol) of piperidine in 5 mL of THF is stirred for 14 hours at ambient temperature. The reaction mixture is evaporated down. The purification is carried out by column chromatography on silica gel (eluant: dichloromethane/ethanol (25:1 to 15:1)). Yield: 13 mg (26.8% of theory); melting point: 180° C.-181° C.; $C_{24}H_{24}N_2O$ (M=356.47); calc.: molecular ion peak (M+H)$^+$: 357; found: molecular ion peak (M+H)$^+$: 357; $R_f$ value: 0.21 (silica gel, dichloromethane/ethanol (20:1)).

The following compounds are prepared analogously to Example 1.2.c.:

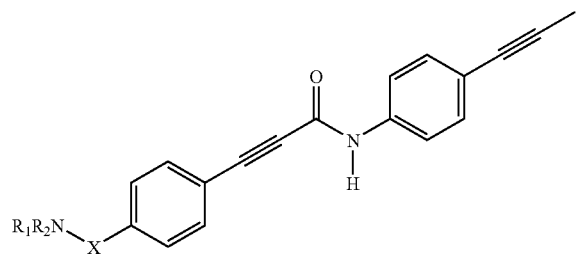

| Example | $R_1R_2N-X$ | educt | empirical formula | mass spectrum | mp [° C.] | $R_f$ value |
|---|---|---|---|---|---|---|
| 1.3 | 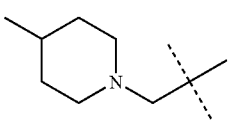 | 1.2.b | $C_{25}H_{26}N_2O$ | 371 [M + H]$^+$ | 158-159 | 0.21 (A) |
| 1.4 | 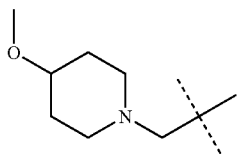 | 1.2.b | $C_{25}H_{26}N_2O_2$ | 387 [M + H]$^+$ | 176–177 | 0.3 (A) |

-continued

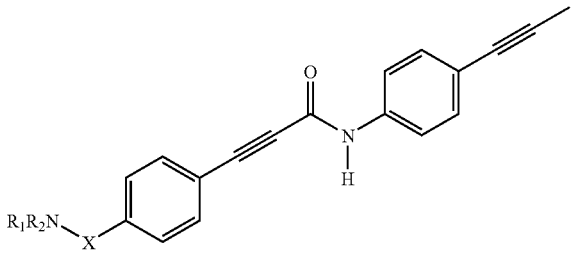

| Example | R₁R₂N-X | educt | empirical formula | mass spectrum | mp [° C.] | $R_f$ value |
|---|---|---|---|---|---|---|
| 1.5 | (2-pyridylamino-piperidinyl-methyl) | 1.2.b | $C_{29}H_{28}N_4O$ | 449 [M + H]⁺ | 141 | 0.18 (A) |
| 1.6 | (4-hydroxy-4-phenylpiperidinyl-methyl) | 1.2.b | $C_{30}H_{28}N_2O_2$ | 449 [M + H]⁺ | 161.5 | 0.3 (A) |
| 1.7 | (4-(2-hydroxypropan-2-yl)piperidinyl-methyl) | 1.2.b | $C_{27}H_{30}N_2O_2$ | 415 [M + H]⁺ | 120 | 0.1 (A) |

$R_f$ value: A = silica gel, dichloromethane/ethanol (20:1)

EXAMPLE 1.8

3-(4-piperidin-1-ylmethylphenyl)propynoic acid-(4'-methoxybiphenyl-4-yl)amide

1.8.a. Propynoic acid-(4'-methoxybiphenyl-4-yl)amide

Prepared analogously to Example 1.1.b. from propynoic acid and 4'-methoxybiphenyl-4-ylamine. Yield: 1.3 g (17.2% of theory); $C_{16}H_{13}NO_2$ (M=251.28); calc.: molecular ion peak (M+H)⁺: 252; found: molecular ion peak (M+H)⁺: 252; $R_f$ value: 0.6 (silica gel, dichloromethane/ethanol (20:1)).

1.8.b. 3-(4-hydroxymethylphenyl)propynoic acid-(4'-methoxybiphenyl-4-yl)amide Prepared analogously to Example 1.2.a. from iodobenzyl alcohol and propynoic acid-(4'-methoxybiphenyl-4-yl) amide. Yield: 0.21 g (22.9% of theory); $C_{23}H_{19}NO_3$ (M=357.41); calc.: molecular ion peak (M+H)⁺: 358; found: molecular ion peak (M+H)⁺: 358; $R_f$ value: 0.35 (silica gel, dichloromethane/ethanol (20:1)).

1.8.c. 4-[(4'-methoxybipheny-4-ylcarbamoyl)ethynyl]benzyl methanesulfonate

Prepared analogously to Example 1.2.b. from 3-(4-hydroxymethylphenyl)propynoic acid-(4'-methoxybiphenyl-4-yl)amide and methanesulfonic acid chloride. Yield: 0.18 g (70.3% of theory); $C_{24}H_{21}NO_5S$ (M=435.50); $R_f$ value: 0.58 (silica gel, dichloromethane/ethanol (20:1)).

1.8.d. 3-(4-piperidin-1-ylmethylphenyl)propynoic acid-(4'-methoxyphenyl)amide Prepared analogously to Example 1.2.c. from 4-[(4'-methoxybipheny-4-ylcarbamoyl)ethynyl]benzyl methanesulfonate and piperidine. Yield: 5 mg (18.8% of theory); melting point: 170° C.; $C_{28}H_{28}N_2O_2$ (M=424.54); calc.: molecular ion peak (M+H)⁺: 425; found: molecular ion peak (M+H)⁺: 425; $R_f$ value: 0.28 (silica gel, dichloromethane/ethanol (20:1)).

The following compounds are prepared analogously to Example 1.8.d.:
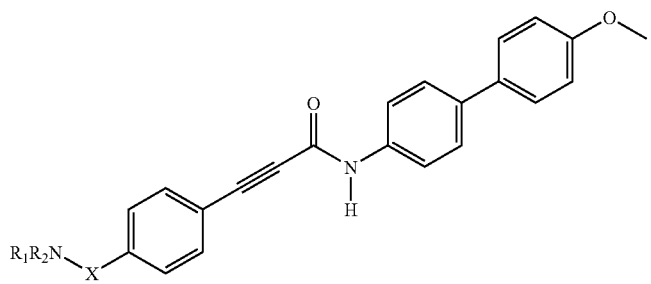
| Example | R₁R₂N-X | educt | empirical formula | mass spectrum | mp [° C.] | R$_f$ value |
|---|---|---|---|---|---|---|
| 1.9 | | 1.8.c | $C_{29}H_{30}N_2O_2$ | 439 [M + H]⁺ | 168-169 | 0.2 (A) |
| 1.10 | | 1.8.c | $C_{29}H_{30}N_2O_3$ | 455 [M + H]⁺ | 190.5 | 0.22 (A) |
| 1.11 | | 1.8.c | $C_{33}H_{32}N_4O_2$ | 517 [M + H]⁺ | 196-197 | 0.15 (A) |
| 1.12 | | 1.8.c | $C_{34}H_{32}N_2O_3$ | 517 [M + H]⁺ | 167.5 | 0.2 (A) |
| 1.13 | | 1.8.c | $C_{29}H_{30}N_2O_3$ | 455 [M + H]⁺ | 156 | 0.35 (B) |
| 1.14 | | 1.8.c | $C_{31}H_{34}N_2O_3$ | 483 [M + H]⁺ | 192-193 | 0.45 (B) |
| 1.15 | | 1.8.c | $C_{32}H_{35}N_3O_2$ | 494 [M + H]⁺ | 181-182 | 0.05 (B) |

-continued

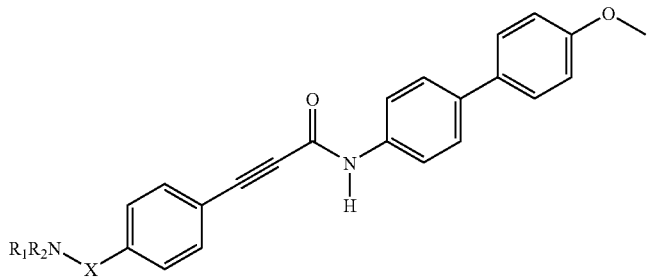

| Example | R₁R₂N-X | educt | empirical formula | mass spectrum | mp [° C.] | $R_f$-value |
|---|---|---|---|---|---|---|
| 1.16 | (2-pyridyloxy-piperidinyl-methyl group) | 1.8.c | $C_{33}H_{31}N_3O_3$ | 518 [M + H]⁺ | 196-197 | |

$R_f$-value:
A = silica gel, dichloromethane/ethanol/ammonia (20:1)
B = silica gel, dichloromethane/ethanol/ammonia (5:1)

EXAMPLE 1.17

3-(4-pyrrolidin-1-ylmethylphenyl)propynoic acid-(4'-chloro-3-fluorobiphenyl-4-yl)amide

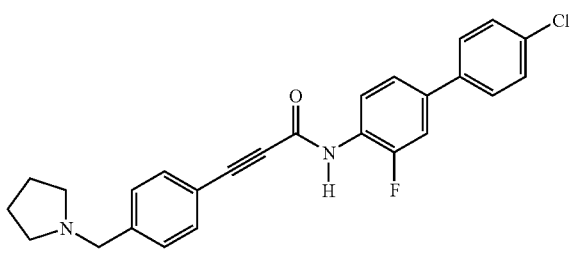

1.17.a. 4'-chloro-3-fluorobiphenyl-4-ylamine 1.95 g (12.47 mmol) of 4-chlorophenylboric acid, dissolved in 10 mL of methanol, and 3.9 g (36.79 mmol) of sodium carbonate, dissolved in 10 mL of water, are added successively to a reaction mixture of 2.28 g (12 mmol) of 4-bromo-2-fluoroaniline and 0.6 g (0.51 mmol) of tetrakistriphenylphosphine palladium in 90 mL of dioxane and stirred for 14 hours at 80° C. Then ethyl acetate is added and the reaction mixture is filtered. The filtrate is evaporated down and extracted with ethyl acetate and water. The organic phase is dried over sodium sulfate. The purification is carried out by column chromatography on silica gel (eluant: cyclohexane/ethyl acetate (3:1)). Yield: 2 g (75.2% of theory); $C_{12}H_9FN$ (M=221.66); calc.: molecular ion peak (M+H)⁺: 222; found: molecular ion peak (M+H)⁺: 222; $R_f$-value: 0.41 (silica gel, cyclohexane/ethyl acetate (3:1)).

1.17.b. Propynoic acid-(4'-chloro-3-fluorobiphenyl-4-yl)amide

Prepared analogously to Example 1.1.b. from 4'-chloro-3-fluorobiphenyl-4-ylamine and propynoic acid. Yield: 0.16 g (43.7% of theory); $C_{15}H_9ClFNO$ (M=273.69); calc.: molecular ion peak (M+H)⁺: 274/276; found: molecular ion peak (M+H)⁺: 274/276; $R_f$-value: 0.3 (silica gel, cyclohexane/ethyl acetate (3:1)).

1.17.c. 3-(4-pyrrolidin-1-ylmethylphenyl)propynoic acid-(4'-chloro-3-fluorobiphenyl-4-yl)amide Prepared analogously to Example 1.1.d. from 1-(4-iodobenzyl)pyrrolidine and propynoic acid-(4'-chloro-3-fluorobiphenyl-4-yl)amide. Yield: 20 mg (13% of theory); melting point: 136° C.; $C_{26}H_{22}ClFN_2O$ (M=432.92); calc.: molecular ion peak (M+H)⁺: 433/435/437; found: molecular ion peak (M+H)⁺: 433/435/437; $R_f$ value: 0.3 (silica gel, dichloromethane/methanol/ammonia (10:1:0.1)).

EXAMPLE 1.18

3-[4-(4-methylpiperidin-1-ylmethyl)phenyl]propynoic acid-(4'-chloro-2'-fluorobiphenyl-4-yl)amide

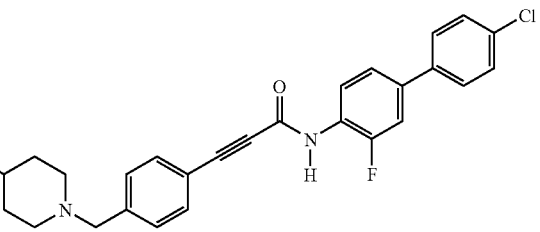

1.18.a. 3-(4-hydroxymethylphenyl)propynoic acid-(4'-chloro-2'-fluorobiphenyl-4-yl)amide Prepared analogously to Example 1.2.a. from propynoic acid-(4'-chloro-3-fluorobiphenyl-4-yl)amide and 4-iodobenzyl alcohol. Yield: 0.4 g (41% of theory); $C_{22}H_{15}ClFNO_2$ (M=379.82); calc.: molecular ion peak (M+H)⁺: 380/382;

found: molecular ion peak (M+H)⁺: 380/382; $R_f$ value: 0.5 (silica gel, dichloromethane/methanol/ammonia (20:1:0.1)).

1.18.b. 4-[(4'-chloro-2'-fluorobiphenyl-4-ylcarbamoyl)ethynyl]benzyl methanesulfonate Prepared analogously to Example 1.2.b. from 3-(4-hydroxymethylphenyl)propynoic acid-(4'-chloro-2'-fluorobiphenyl-4-yl)amide and methanesulfonic acid chloride. Yield: 0.23 g (50% of theory); $C_{23}H_{17}ClFN_2O_2S$ (M=457.91); calc.: molecular ion peak (M+H)⁺: 456/458; found: molecular ion peak (M+H)⁺: 456/458; $R_f$ value: 0.5 (silica gel, dichloromethane/methanol/ammonia (20:1:0.1)).

1.18.c. 3-[4-(4-methylpiperidin-1-ylmethyl)phenyl] propynoic acid-(4'-chloro-2'-fluorobiphenyl-4-yl) amide Prepared analogously to Example 1.2.c. from 4-[(4'-chloro-2'-fluorobiphenyl-4-ylcarbamoyl)ethynyl]benzyl methanesulfonate and 4-methylpiperidine. Yield: 13 mg (21% of theory); melting point: 149° C.-150° C.; $C_{28}H_{26}ClFN_2O$ (M=460.98); calc.: molecular ion peak (M+H)⁺: 461/463; found: molecular ion peak (M+H)⁺: 461/463; $R_f$ value: 0.3 (silica gel, dichloromethane/methanol/ammonia (20:1:0.1)).

The following compounds were prepared analogously to Example 1.2.c.:

| Example | $R_1R_2N$-X | educt | empirical formula | mass spectrum | mp [° C.] | $R_f$ value |
|---|---|---|---|---|---|---|
| 1.19 | (piperidine-4-carboxamide-N-CH₂C(CH₃)₂-) | 1.18.b | $C_{28}H_{25}ClFN_3O_2$ | 488/490 [M + H]⁺ | 222-223 | 0.1 (A) |
| 1.20 | (2-(methoxymethyl)pyrrolidine) | 1.18.b | $C_{27}H_{24}ClFN_2O_2$ | 463/465 [M + H]⁺ | 146-148 | 0.25 (A) |
| 1.21 | (4-methoxypiperidine) | 1.18.b | $C_{27}H_{24}ClFN_2O_2$ | 463/465 [M + H]⁺ | 164-165 | 0.3 (B) |
| 1.22 | (morpholine) | 1.18.b | $C_{26}H_{22}ClFN_2O_2$ | 449/451 [M + H]⁺ |  | 0.3 (A) |

$R_f$ value:
A = silica gel, dichloromethane/ethanol/ammonia (20:1:0.1)
B = silica gel, dichloromethane/methanol/ammonia (10:1:0.1)

EXAMPLE 1.23

3-(4-pyrrolidin-1-ylmethylphenyl)propynoic acid-(4'-chlorobiphenyl-4-yl)methylamide

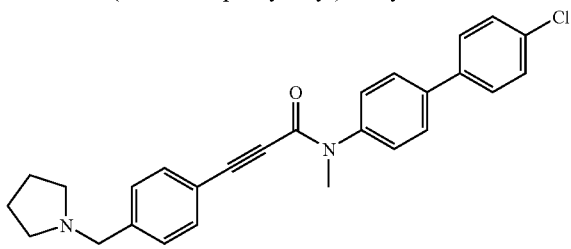

1.23.a. Propynoic acid-(4'-chlorobiphenyl-4-yl)amide

Prepared analogously to Example 1.1.b. from 4'-chlorobiphenyl-4-ylamine and propynoic acid. Yield: 0.4 g (29.2% of theory); $C_{15}H_{10}ClNO$ (M=255.70); calc.: molecular ion peak $(M+H)^+$: 256/258; found: molecular ion peak $(M+H)^+$: 256/258; $R_f$ value: 0.35 (silica gel, dichloromethane/ethanol 20:1).

1.23.b. Propynoic acid-(4'-chlorobiphenyl-4-yl)methylamide 75 mg (1.72 mmol) of sodium hydride (55%) is added to a solution of 0.4 g (1.56 mmol) of propynoic acid-(4'-chlorobiphenyl-4-yl)amide in 10 mL of THF at 0° C. and stirred for 1 hour at this temperature. Then 0.098 mL (1.56 mmol) of methyl iodide is added dropwise and the mixture is stirred for 14 hours, while the reaction mixture is allowed to come up to ambient temperature. Then the reaction mixture is extracted with water and ethyl acetate and the organic phase is dried over sodium sulfate. The purification is carried out by column chromatography on silica gel (eluant: cyclohexane/ethyl acetate (3:1)). Yield: 0.15 g (35.6% of theory); $C_{16}H_{12}ClNO$ (M=269.73); calc.: molecular ion peak $(M+H)^+$: 270/272; found: molecular ion peak $(M+H)^+$: 270/272; $R_f$ value: 0.61 (silica gel, cyclohexane/ethyl acetate (1:1)).

1.23.c. 3-(4-pyrrolidin-1-ylmethylphenyl)propynoic acid-(4'-chlorobiphenyl-4-yl)methylamide Prepared analogously to Example 1.1.d. from 1-(4-iodobenzyl)pyrrolidine and propynoic acid-(4'-chlorobiphenyl-4-yl)methylamide. Yield: 38 mg (25.4% of theory); melting point: 161° C.-164° C.; $C_{27}H_{25}ClN_2O$ (M=428.96); calc.: molecular ion peak $(M+H)^+$: 429/431; found: molecular ion peak $(M+H)^+$: 429/431; $R_f$ value: 0.41 (silica gel, dichloromethane/methanol/ammonia (10:1:0.1)).

EXAMPLE 1.24
3-[4-(4-pyrrolidin-1-ylpiperidin-1-ylmethyl)phenyl]propynoic acid-(4'-chlorobiphenyl-4-yl)methylamideditrifluoroacetate

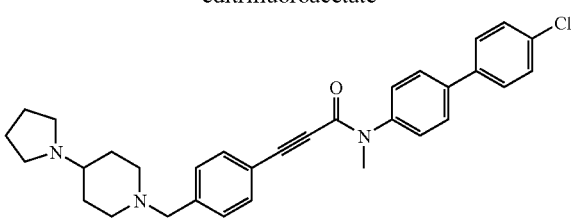

1.24.a. 1-(4-iodobenzyl)-4-pyrrolidin-1-ylpiperidine

Prepared analogously to Example 1.1.c. from 4-iodobenzyl bromide and 4-pyrrolidin-1-ylpiperidine. Yield: 0.57 g (51% of theory); $C_{16}H_{23}IN_2$ (M=370.28); calc.: molecular ion peak $(M+H)^+$: 371; found: molecular ion peak $(M+H)^+$: 371; $R_f$ value: 0.3 (silica gel, dichloromethane/ethanol (20:1)).

1.24.b. 3-[4-(4-pyrrolidin-1-ylpiperidin-1-ylmethyl)phenyl]propynoic acid-(4'-chlorobiphenyl-4-yl)methylamideditrifluoroacetate Prepared analogously to Example 1.1.d. from 1-(4-iodobenzyl)-4-pyrrolidin-1-ylpiperidine and propynoic acid-(4'-chlorobiphenyl-4-yl)methylamide. Yield: 5 mg (4% of theory); melting point: 161° C.-164° C.; $C_{32}H_{34}ClN_3O*2CF_3CO_2H$ (M=740.14); calc.: molecular ion peak $(M+H)^+$: 512/514; found: molecular ion peak $(M+H)^+$: 512/514; $R_f$ value: 0.41 (silica gel, dichloromethane/methanol/ammonia (10:1:0.1)).

EXAMPLE 1.25

3-[4-(4-methylpiperidin-1-ylmethyl)phenyl]propynoic acid-(4'-chlorobiphenyl-4-yl)methylamide

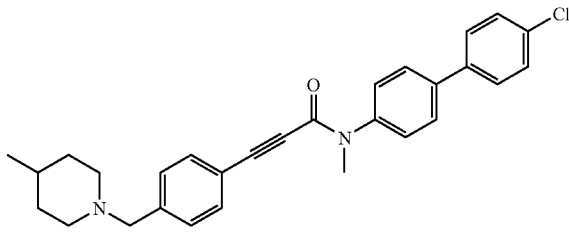

1.25.a. 3-(4-hydroxymethylphenyl)propynoic acid-(4'-chlorobiphenyl-4-yl)methylamide Prepared analogously to Example 1.2.a. from 4-iodobenzyl alcohol and propynoic acid-(4'-chlorobiphenyl-4-yl)methylamide. Yield: 0.52 g (90% of theory); $C_{23}H_{18}ClNO_2$ (M=375.85); calc.: molecular ion peak $(M+H)^+$: 376/378; found: molecular ion peak $(M+H)^+$: 376/378; $R_f$ value: 0.4 (silica gel, dichloromethane/methanol/ammonia (10:1:0.1)).

1.25.b. 4-{[(4'-chlorobiphenyl-4-yl)methylcarbamoyl]ethynyl}benzyl methanesulfonate Prepared analogously to Example 1.2.b. from 3-(4-hydroxymethylphenyl)propynoic acid-(4'-chlorobiphenyl-4-yl)methylamide. Yield: 0.54 g (100% of theory); $C_{24}H_{20}ClNO_4S$ (M=453.94); calc.: molecular ion peak $(M+H)^+$: 454/456; found: molecular ion peak $(M+H)^+$: 454/456.

1.25.c. 3-[4-(4-methylpiperidin-1-ylmethyl)phenyl]Propynoic acid-(4'-chlorobiphenyl-4-yl)methylamide Prepared analogously to Example 1.2.c. from 4-{[(4'-chlorobiphenyl-4-yl)methyl-carbamoyl]ethynyl}benzyl methanesulfonate and 4-methylpiperidine. Yield: 8 mg (16% of theory); $C_{29}H_{29}ClN_2O$ (M=457.02); calc.: molecular ion peak $(M+H)^+$: 457/459; found: molecular ion peak $(M+H)^+$: 457/459; $R_f$ value: 0.41 (silica gel, dichloromethane/methanol/ammonia (10:1:0.1)).

The following compounds are prepared analogously to Example 1.2.c.:

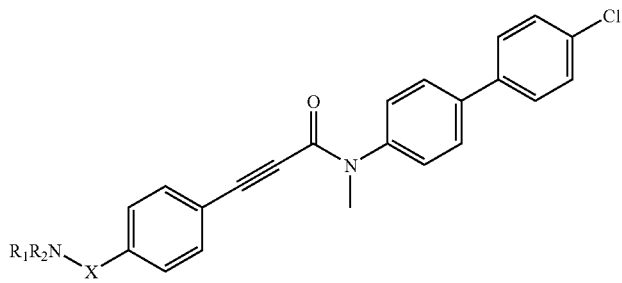
| Example | R₁R₂N-X | educt | empirical formula | mass spectrum | mp [° C.] | $R_f$-value |
|---|---|---|---|---|---|---|
| 1.26 | 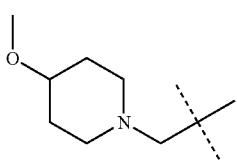 | 1.25.c | $C_{29}H_{29}ClN_2O_2$ | 473/475 $[M + H]^+$ | 163.5 | |
| 1.27 | 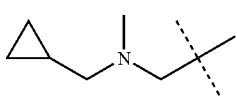 | 1.25.c | $C_{28}H_{27}ClN_2O$ | 443/445 $[M + H]^+$ | 131.5 | |
| 1.28 | 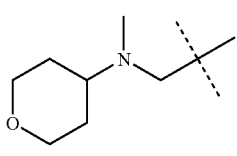 | 1.25.c | $C_{29}H_{29}ClN_2O_2$ | 473/475 $[M + H]^+$ | 147-148 | |
| 1.29 | 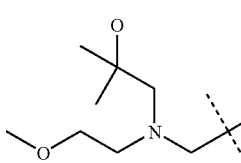 | 1.25.c | $C_{30}H_{33}ClN_2O_3$ | 505/507 $[M + H]^+$ | 134 | |
| 1.30 | 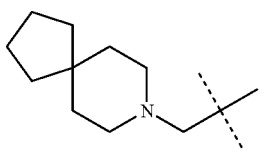 | 1.25.c | $C_{32}H_{33}ClN_2O$ | 497/499 $[M + H]^+$ | 190 | |
| 1.31 | 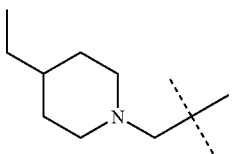 | 1.25.c | $C_{30}H_{31}ClN_2O$ | 471/473 $[M + H]^+$ | 166 | |
| 1.32 | 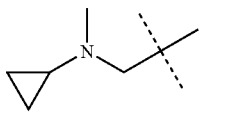 | 1.25.c | $C_{27}H_{25}ClN_2O$ | 429/431 $[M + H]^+$ | 148-149 | |
$R_f$-value: A = silica gel, dichloromethane/methanol/ammonia (10:1:0.1)

EXAMPLE 1.33

3-(4-pyrrolidin-1-ylmethylphenyl)propynoic acid-(4'-chlorobiphenyl-4-yl)amide

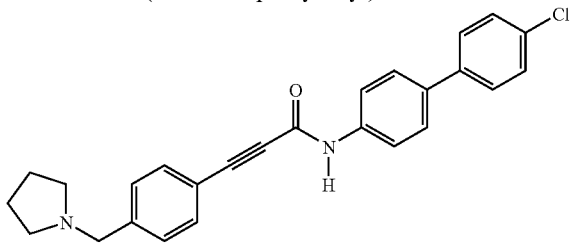

1.33.a. 1-(4-trimethylsilanylethynylbenzyl)pyrrolidine

A reaction mixture of 1 g (3.48 mmol) of 1-(4-iodobenzyl)pyrrolidine, 5 mL of piperidine, 105 mg (0.091 mmol) of tetrakistriphenylphosphine palladium, and 10 mg (0.053 mmol) of copper (I) iodide is cooled to 0° C. At this temperature, 0.59 mL (4.18 mmol) of trimethylsilylacetylene is added dropwise and then the cooling bath is removed. It is stirred for 3 hours at ambient temperature, then combined with a saturated aqueous ammonium chloride solution, and extracted with dichloromethane. The organic phase is dried over sodium sulfate. The purification is carried out by column chromatography on silica gel (eluant: cyclohexane/ethyl acetate (1:1)). Yield: 0.75 g (83.6% of theory); $C_{16}H_{23}NSi$ (M=257.45); calc.: molecular ion peak $(M+H)^+$: 258; found: molecular ion peak $(M+H)^+$: 258.

1.33.b. 1-(4-ethynylbenzyl)pyrrolidine

A solution of 0.75 g (2.91 mmol) of 1-(4-trimethylsilanylethynylbenzyl)pyrrolidine in 10 mL of dichloromethane and 10 mL of methanol is combined with 2.4 mL of a 1M sodium hydroxide solution and stirred for 3 hours at ambient temperature. The reaction mixture is evaporated down and the residue is extracted with water and ethyl acetate. The organic phase is stirred with activated charcoal, filtered, and then dried over sodium sulfate. Yield: 0.4 g (74.1% of theory); $C_{13}H_{15}N$ (M=185.27); calc.: molecular ion peak $(M+H)^+$: 186; found: molecular ion peak $(M+H)^+$: 186.

1.33.c. (4-pyrrolidin-1-ylmethylphenyl)propynoic acid 5.98 mL (14.85 mmol) of a 1.6M butyllithium solution in n-hexane is added dropwise to a solution of 2.3 g (12.41 mmol) of 1-(4-ethynylbenzyl)pyrrolidine in 50 mL of THF at −78° C. and stirred for 1 hour at this temperature. Then dry ice is added to the reaction mixture. Then the reaction mixture is allowed to come up to ambient temperature and stirred for 14 hours. The reaction mixture is combined with dilute hydrochloric acid and extracted with dichloromethane. The organic phase is separated off and dried over sodium sulfate. The sodium sulfate is separated off and the solvent is removed. Yield: 0.3 g (10.5% of theory); $C_{14}H_{15}NO_2$ (M=229.28); calc.: molecular ion peak $(M+H)^+$: 230; found: molecular ion peak $(M+H)^+$: 230; $R_f$ value: 0.15 (silica gel, dichloromethane/methanol/ammonia (9:1:0.1)).

1.33.d. 3-(4-pyrrolidin-1-ylmethylphenyl)propynoic acid-(4'-chlorobiphenyl-4-yl)amide A solution of 0.3 g (1.30 mmol) of (4-pyrrolidin-1-ylmethylphenyl)propynoic acid, 0.27 g (1.32 mmol) of 4'-chlorobiphenyl-4-ylamine, 0.42 g (1.32 mmol) of TBTU, and 0.18 mL (1.32 mmol) of triethylamine in 30 mL of DMF is stirred for 14 hours at ambient temperature. The reaction mixture is evaporated down and the residue is extracted with water and dichloromethane. The organic phase is dried over sodium sulfate. The purification is carried out by column chromatography on silica gel (eluant: dichloromethane/ethanol (10:1)). Yield: 0.095 g (17.5% of theory); melting point: from 180° C.; $C_{26}H_{23}ClN_2O$ (M=414.93); calc.: molecular ion peak $(M+H)^+$: 415/417; found: molecular ion peak $(M+H)^+$: 415/417; $R_f$ value: 0.3 (silica gel, dichloromethane/ethanol (5:1)).

EXAMPLE 1.34

3-{4-[4-(1-hydroxy-1-methylethyl)piperidin-1-ylmethyl]phenyl}propynoic acid-(4'-chlorobiphenyl-4-yl)amide

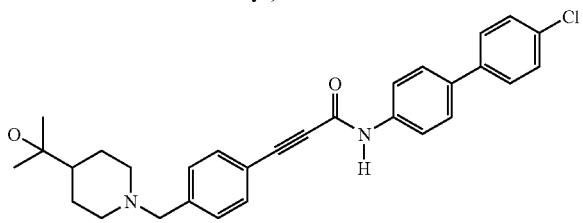

1.34.a. 2-[1-(4-iodobenzyl)piperidin-4-yl]propan-2-ol

Prepared analogously to Example 1.1.c. from 4-iodobenzyl bromide and 2-piperidin-4-ylpropan-2-ol. Yield: 1.01 g (67% of theory); $C_{15}H_{22}INO$ (M=359.25); calc.: molecular ion peak $(M+H)^+$: 360; found: molecular ion peak $(M+H)^+$: 360; $R_f$ value: 0.4 (silica gel, dichloromethane/ethanol (20:1)).

1.34.b. 3-{4-[4-(1-hydroxy-1-methylethyl)piperidin-1-ylmethyl]phenyl}propynoic acid-(4'-chlorobiphenyl-4-yl)amide Prepared analogously to Example 1.1.d. from 2-[1-(4-iodobenzyl)piperidin-4-yl]propan-2-ol and propynoic acid-(4'-chlorobiphenyl-4-yl)amide. Yield: 45 mg (30% of theory); melting point: 194-195° C.; $C_{30}H_{31}ClN_2O_2$ (M=487.04); calc.: molecular ion peak $(M+H)^+$: 487/489; found: molecular ion peak $(M+H)^+$: 487/489; $R_f$ value: 0.3 (silica gel, dichloromethane/methanol/ammonia (10:1:0.1)).

EXAMPLE 1.35

3-[4-(4-methylpiperidin-1-ylmethyl)phenyl]propynoic acid-(4'-chlorobiphenyl-4-yl)amide

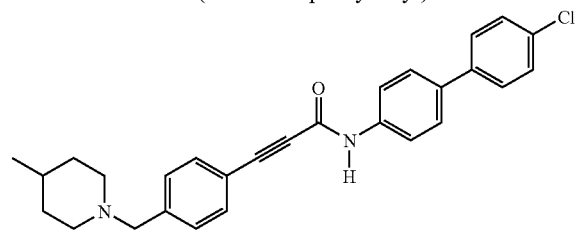

1.35.a. 1-(4-iodobenzyl)-4-methylpiperidine

Prepared analogously to Example 1.1.c. from 4-iodobenzyl bromide and 4-methylpipiridine. Yield: 0.95 g (71.6% of

1.35.b. 3-[4-(4-methylpiperidin-1-ylmethyl)phenyl]propynoic acid-(4'-chlorobiphenyl-4-yl)amide Prepared analogously to Example 1.1.d. from 1-(4-iodobenzyl)₄-methylpiperidine and propynoic acid-(4'-chlorobiphenyl-4-yl)amide. Yield: 50 mg (27% of theory); $C_{28}H_{27}ClN_2O$ (M=442.99); calc.: molecular ion peak (M+H)⁺: 443/445; found: molecular ion peak (M+H)⁺: 443/445; $R_f$ value: 0.45 (silica gel, dichloromethane/methanol (10:1)).

EXAMPLE 1.36

3-[4-(4-methoxypiperidin-1-ylmethyl)phenyl]propynoic acid-(4'-chlorobiphenyl-4-yl)amide

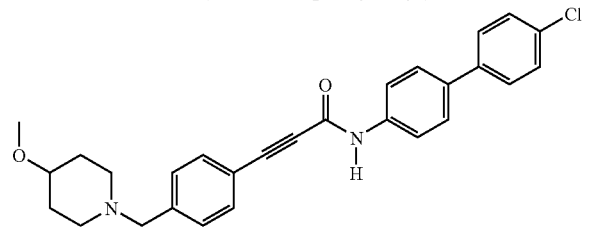

1.36.a. 1-(4-iodobenzyl)-4-methoxypiperidine

Prepared analogously to Example 1.1.c. from 4-iodobenzyl bromide and 4-methoxypiperidine. Yield: 0.93 g (66.7% of theory); $C_{13}H_{18}INO$ (M=331.19); calc.: molecular ion peak (M+H)⁺: 332; found: molecular ion peak (M+H)⁺: 332; $R_f$ value: 0.55 (silica gel, dichloromethane/ethanol (20:1)).

1.36.b. 3-[4-(4-methoxypiperidin-1-ylmethyl)phenyl]propynoic acid-(4'-chlorobiphenyl-4-yl)amide Prepared analogously to Example 1.1.d. from 1-(4-iodobenzyl)-4-methoxypiperidine and propynoic acid-(4'-chlorobiphenyl-4-yl)amide. Yield: 25 mg (13% of theory); melting point: 145° C.-146° C.; $C_{28}H_{27}ClN_2O_2$ (M=458.99); calc.: molecular ion peak (M+H)⁺: 459/461; found: molecular ion peak (M+H)⁺: 459/461; $R_f$ value: 0.4 (silica gel, dichloromethane/methanol (10:1)).

EXAMPLE 1.37

3-[4-(4-hydroxy-4-methylpiperidin-1-ylmethyl)phenyl]propynoic acid-(4'-chlorobiphenyl-4-yl)amide

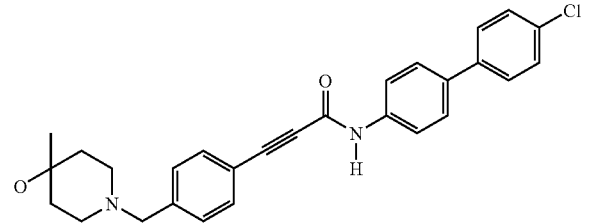

1.37.a. 1-(4-iodobenzyl)-4-methylpiperidin-4-ol

Prepared analogously to Example 1.1.c. from 4-iodobenzyl bromide and 4-methylpiperidin-4-ol. Yield: 0.22 g (30% of theory); $C_{13}H_{18}INO$ (M=331.19); calc.: molecular ion peak (M+H)⁺: 332; found: molecular ion peak (M+H)⁺: 332; $R_f$ value: 0.45 (silica gel, dichloromethane/ethanol (20:1)).

1.37.b. 3-[4-(4-hydroxy-4-methylpiperidin-1-ylmethyl)phenyl]propynoic acid-(4'-chlorobiphenyl-4-yl)amide Prepared analogously to Example 1.1.d. from 1-(4-iodobenzyl)-4-methylpiperidin-4-ol and propynoic acid-(4'-chlorobiphenyl-4-yl)amide. Yield: 25 mg (13% of theory); melting point: 192° C.-193° C.; $C_{28}H_{27}ClN_2O_2$ (M=458.99); calc.: molecular ion peak (M+H)⁺: 459/461; found: molecular ion peak (M+H)⁺: 459/461; $R_f$ value: 0.2 (silica gel, dichloromethane/methanol (10:1)).

EXAMPLE 1.38

3-[4-(4-pyrrolidin-1-ylpiperidin-1-ylmethyl)phenyl]propynoic acid-(4'-chlorobiphenyl-4-yl)amide

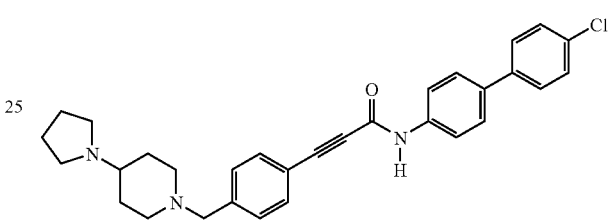

1.38.a. 3-[4-(4-pyrrolidin-1-ylpiperidin-1-ylmethyl)phenyl]propynoic acid-(4'-chlorobiphenyl-4-yl)amide Prepared analogously to Example 1.1.d. from 1-(4-iodobenzyl)-4-pyrrolidin-1-ylpiperidine and propynoic acid-(4'-chlorobiphenyl-4-yl)amide. Yield: 15 mg (7% of theory); melting point: 191° C.-192° C.; $C_{31}H_{32}ClN_3O$ (M=498.07); calc.: molecular ion peak (M+H)⁺: 498/500; found: molecular ion peak (M+H)⁺: 498/500; $R_f$ value: 0.45 (silica gel, dichloromethane/methanol/ammonia (10:1:0.1)).

EXAMPLE 1.39

3-(4-piperidin-1-ylemthylphenyl)propynoic acid-(4'-chlorobiphenyl-4-yl)amide

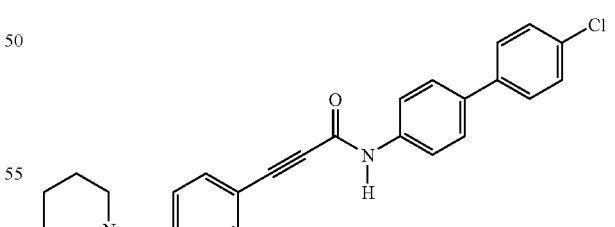

1.39.a. 1-(4-iodobenzyl)piperidine

Prepared analogously to Example 1.1 c. from 4-iodobenzyl bromide and piperidine. Yield: 0.85 g (67% of theory); $C_{12}H_{16}IN$ (M=301.17); calc.: molecular ion peak (M+H)⁺: 322; found: molecular ion peak (M+H)⁺: 302; $R_f$ value: 0.55 (silica gel, dichloromethane/ethanol (20:1)).

1.39.b. 3-(4-piperidin-1-ylmethylphenyl)propynoic acid-(4'-chlorobiphenyl-4-yl)amide Prepared analogously to Example 1.1.d. from 1-(4-iodobenzyl)piperidine and propynoic acid-(4'-chlorobiphenyl-4-yl)amide. Yield: 6 mg (4% of theory); melting point: 179.5° C.; $C_{27}H_{25}ClN_2O$ (M=428.96); calc.: molecular ion peak (H+ H)$^+$: 429/431; found: molecular ion peak (M+H)$^+$: 429/431; $R_f$ value: 0.5 (silica gel, dichloromethane/methanol/ammonia (10:1:0.1)).

EXAMPLE 1.40

3-{4-[cyclopropylmethylmethylamino)methyl]phenyl}propynoic acid-(4'-chlorobiphenyl-4-yl)amide

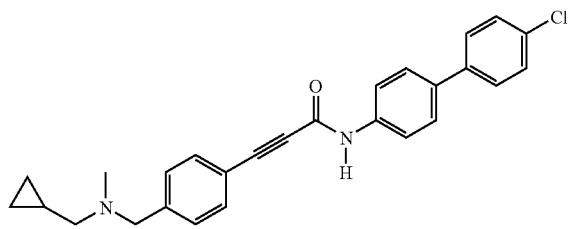

1.40.a. Propynoic acid-(4'-chlorobiphenyl-4-yl)amide 36 mL of a 1 molar DCC solution in dichloromethane is added dropwise at −10° C. to a solution of 4.9 g (70 mmol) of propynoic acid in 120 mL of dichloromethane and the mixture is stirred for 30 minutes. Then 7 g (34.37 mmol) 4'-chlorobiphenyl-4-ylamine, dissolved in dichloromethane, is slowly added dropwise and the mixture is stirred for 2 hours at −8° C. The reaction mixture is then filtered through CELITE®E filter aid, washed again with methanol, and the filtrate is evaporated down. The purification is carried out by column chromatography on silica gel (eluant: cyclohexane/ethyl acetate (6:1 to 2:1)). Yield: 7.6 g (95% of theory); $C_{15}H_{10}ClN_O$ (M=255.70); calc.: molecular ion peak (M+H)$^+$: 256/8 (Cl); found: molecular ion peak (M+H)$^+$: 256/8 (Cl); $R_f$ value: 0.2 (silica gel, cyclohexane/ethyl acetate (1:1)).

1.40.b 3-(4-hydroxymethylphenyl)propynoic acid-4'-chlorobiphenyl-4-yl)amide 10 g (30.69 mmol) of cesium carbonate and 2.4 g (10.26 mmol) of 4-iodobenzyl alcohol are placed in 120 mL of THF and cooled to −15° C. in the ice/methanol bath, rinsed with argon and degassed. To this reaction mixture are added successively 660 mg (0.57 mmol) of tetrakistriphenylphosphine palladium and 240 mg (1.26 mmol) of copper (I) iodide and the mixture is again degassed. 3.2 g (12.52 mmol) of propynoic acid-(4'-chlorobiphenyl-4-yl)amide are finally added. The mixture is stirred for 24 hours at ambient temperature and the reaction mixture is then evaporated down. The residue is extracted with water and ethyl acetate. The organic phase is dried over sodium sulfate, evaporated down and the residue is purified by column chromatography on silica gel (eluant: dichloromethane/methanol (30:1)). Yield: 2 g (54% of theory); $C_{22}H_{16}ClNO_2$ (M=361.82); calc.: molecular ion peak (M+H)$^+$: 362/4 (Cl); found: molecular ion peak (M+H)$^+$: 362/4 (Cl); $R_f$ value: 0.35 (silica gel, dichloromethane/ethanol/ammonia (20:1:0.1)).

1.40.c. 3-(4-chloromethylphenyl)propynoic acid-(4'-chlorobiphenyl-4-yl)amide 0.45 mL (5.81 mmol) of methanesulfonic acid chloride is slowly added dropwise at ambient temperature to a solution of 2 g (3.87 mmol) of 3-(4-hydroxymethylphenyl)propynoic acid-4'-chlorobiphenyl-4-yl)amide and 1.56 mL (11.2 mmol) of triethylamine in 100 mL dichloromethane and the reaction mixture is stirred for 24 hours at ambient temperature. It is extracted three times with water and the organic phase is dried over sodium sulfate. The solvent is distilled off and the residue is stirred with diisopropyl ether and suction filtered. Yield: 0.8 g (54% of theory); $C_{22}H_{15}Cl_2NO$ (M=380.27); calc.: molecular ion peak (M+H)$^+$: 380/2/4 (Cl$_2$); found: molecular ion peak (M+H)$^+$: 380/2/4 (Cl$_2$); $R_f$ value: 0.7 (silica gel, dichloromethane/ethanol (50:1)).

1.40.d. 3-{4-[cyclopropylmethylmethylamino)methyl]phenyl}propynoic acid-(4'-chlorobiphenyl-4-yl)amide A reaction mixture of 70 mg (0.18 mmol) of 3-(4-chloromethylphenyl)propynoic acid-(4'-chlorobiphenyl-4-yl)amide, 19 mg (0.19 mmol) of cyclopropylmethylmethylamine, and 51 mg (0.37 mmol) of potassium carbonate in 5 mL of acetone is agitated for 24 hours at reflux temperature. The reaction mixture is evaporated down. The residue is extracted between water and ethyl acetate. The organic phase is dried over sodium sulfate, evaporated down, and the residue is purified by column chromatography on silica gel (eluant: dichloromethane/methanol (100:0 to 50:50)). Yield: 30 mg (38% of theory); melting point: 181° C.; $C_{27}H_{25}ClN_2O$ (M=428.95); calc.: molecular ion peak (M+H)$^+$: 429/31(Cl); found: molecular ion peak (M+H)$^+$: 429/31(Cl); $R_f$ value: 0.5 (silica gel, dichloromethane/ethanol/ammonia (20:1:0.1)).

The following compounds are prepared analogously to Example 1.40.d.:

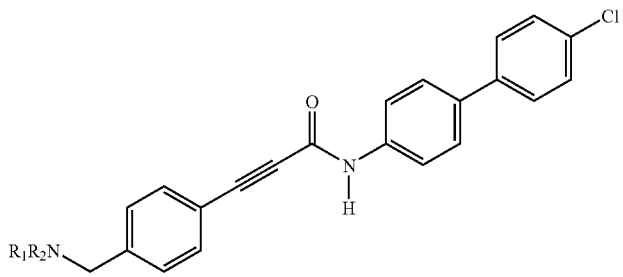
| Example | R₁R₂N-X | educt | empirical formula | mass spectrum | mp [° C.] | $R_f$ value |
|---|---|---|---|---|---|---|
| 1.41 | | 1.40.c | $C_{28}H_{27}ClN_2O_2$ | 459/61 (Cl) [M + H]⁺ | 196 | 0.35 (A) |
| 1.42 | | 1.40.c | $C_{29}H_{29}ClN_2O$ | 457/9 (Cl) [M + H]⁺ | 215 | 0.4 (A) |
| 1.43 | | 1.40.c | $C_{29}H_{29}ClN_2O_2$ | 473/5 (Cl) [M + H]⁺ | 181-182 | 0.5 (A) |
| 1.44 | Chiral | 1.40.c | $C_{26}H_{23}ClN_2O_2$ | 431/3 (Cl) [M + H]⁺ | 175 | 0.15 (A) |
| 1.45 | Chiral | 1.40.c | $C_{26}H_{23}ClN_2O_2$ | 431/3 (Cl) [M + H]⁺ | 135-136 | 0.15 (A) |
| 1.46 | | 1.40.c | $C_{26}H_{25}ClN_2O_2$ | 433/5 (Cl) [M + H]⁺ | 149 | 0.3 (A) |
| 1.47 | Chiral | 1.40.c | $C_{31}H_{27}ClN_2O$ | 479/81 (Cl) [M + H]⁺ | 162-164 | 0.3 (B) |
| 1.48 | Chiral | 1.40.c | $C_{31}H_{27}ClN_2O$ | 479/81 (Cl) [M + H]⁺ | 165-166 | 0.3 (B) |

-continued

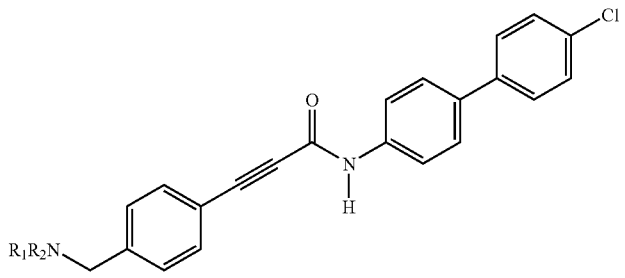

| Example | R₁R₂N-X | educt | empirical formula | mass spectrum | mp [° C.] | R$_f$ value |
|---|---|---|---|---|---|---|
| 1.49 | | 1.40.c | $C_{29}H_{23}ClN_2O$ | 451/3 (Cl) [M + H]⁺ | 150-154 | 0.2 (B) |
| 1.50 | | 1.40.c | $C_{29}H_{24}ClN_3O$ | 466/68 (Cl) | 186 | 0.1 (B) |
| 1.51 | | 1.40.c | $C_{28}H_{27}ClN_2O$ | 443/5 (Cl) | 223.5-224 | 0.2 (B) |
| 1.52 | | 1.40.c | $C_{30}H_{31}ClN_2O$ | 471/3 (Cl) | 156-157 | 0.2 (B) |
| 1.53 | | 1.40.c | $C_{29}H_{24}ClN_3O$ | 466/68 (Cl) | 175-176 | |

R$_f$ value:
A = silica gel, dichloromethane/ethanol/ammonia (20:1:0.1)
B = silica gel, dichloromethane/ethanol/ammonia (50:1:0.1)

EXAMPLE 1.54

3-(4-{[(2-hydroxy-2-methylpropyl)-(2-methoxyethyl)amino]methyl}phenyl)propionic acid-(4'-chlorobiphenyl-4-yl) amide trifluoroacetate

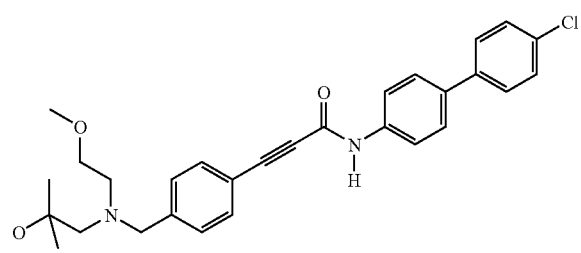

A reaction mixture of 70 mg (0.18 mmol) of 3-(4-chloromethylphenyl)propynoic acid-(4'-chlorobiphenyl-4-yl)amide, 19 mg (0.19 mmol) of 1-(2-methoxyethylamino)-2-methyl-propan-2-ol, and 51 mg (0.37 mmol) of potassium carbonate in 5 mL of acetone is agitated for 24 hours at reflux temperature. The reaction mixture is evaporated down. The residue is extracted between water and ethyl acetate. The organic phase is dried over sodium sulfate, evaporated down, and the residue is purified by column chromatography first of all on silica gel (eluant: dichloromethane/methanol (100:0 to 50:50)) and then on RP-18 (eluant: water+0.1% trifluoroacetic acid/acetonitrile+0.1% trifluoroacetic acid (100:0 to 50:50)). Yield: 11 mg (11% of theory); $C_{29}H_{31}ClN_2O_3$*$C_2HF_3O_2$ (M=605.04); calc.: molecular ion peak (M+H)⁺: 491/93 (Cl); found: molecular ion peak (M+H)⁺: 491/93 (Cl).

The following compounds are prepared analogously to Example 1.54:

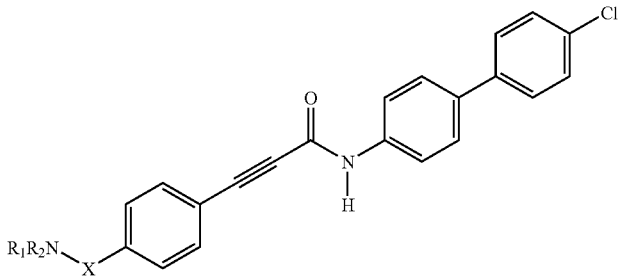

| Example | R₁R₂N-X | educt | empirical formula | mass spectrum | mp [° C.] |
|---|---|---|---|---|---|
| 1.55 | [structure] | 1.40.c | $C_{28}H_{24}ClF_3N_2O_2$ | 513/15 (Cl) | 70-78 |
| 1.56 | [structure] | 1.40.c | $C_{28}H_{29}ClN_2O_2$ | 461/63 (Cl) | |
| 1.57 | [structure] | 1.40.c | $C_{25}H_{21}ClN_2O_2$ | 401/3 (Cl) | 224-225 |

EXAMPLE 1.58
3-{4-[(methylpyridin-2-ylmethylamino)methylphenyl}propynoic acid-(4'-chlorobiphenyl-4-yl)amide

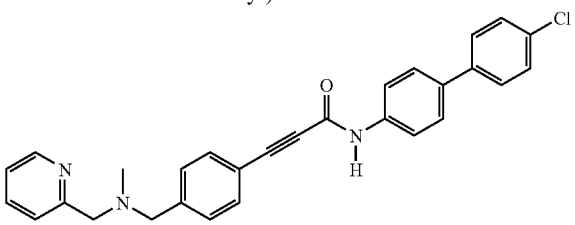

A reaction mixture of 55 mg (0.15 mmol) of 3-(4-chloromethylphenyl)propynoic acid-(4'-chlorobiphenyl-4-yl)amide, 18.3 mg (0.159 mmol) of methylpyridin-2-ylmethylamine, and 51 mg (0.37 mmol) of potassium carbonate in 5 mL of acetone is agitated for 24 hours at reflux temperature. The reaction mixture is evaporated down. The residue is triturated with water and diisopropyl ether and the product is suction filtered and dried in the air. Yield: 20 mg (30% of theory); melting point: 217° C.-218° C.; $C_{29}H_{24}ClN_3O$ (M=465.97); calc.: molecular ion peak (M+H)⁺: 466/468 (Cl); found: molecular ion peak (M+H)⁺: 466/468 (Cl).

The following compound is prepared analogously to Example 1.58:

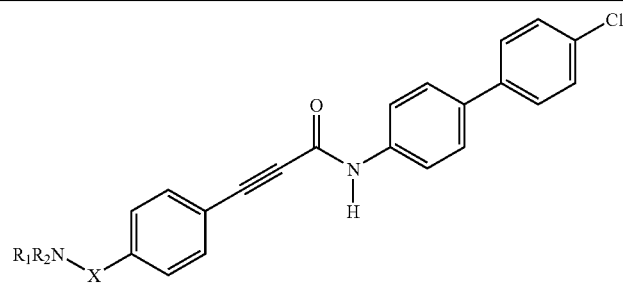

| Example | R₁R₂N-X | educt | empirical formula | mass spectrum | mp [° C.] |
|---|---|---|---|---|---|
| 1.59 | [structure] | 1.40.c | $C_{27}H_{25}ClN_2O$ | 429/31/33 (Cl) | 195-196 |

The following compounds are prepared analogously to Example 1.2.c.:
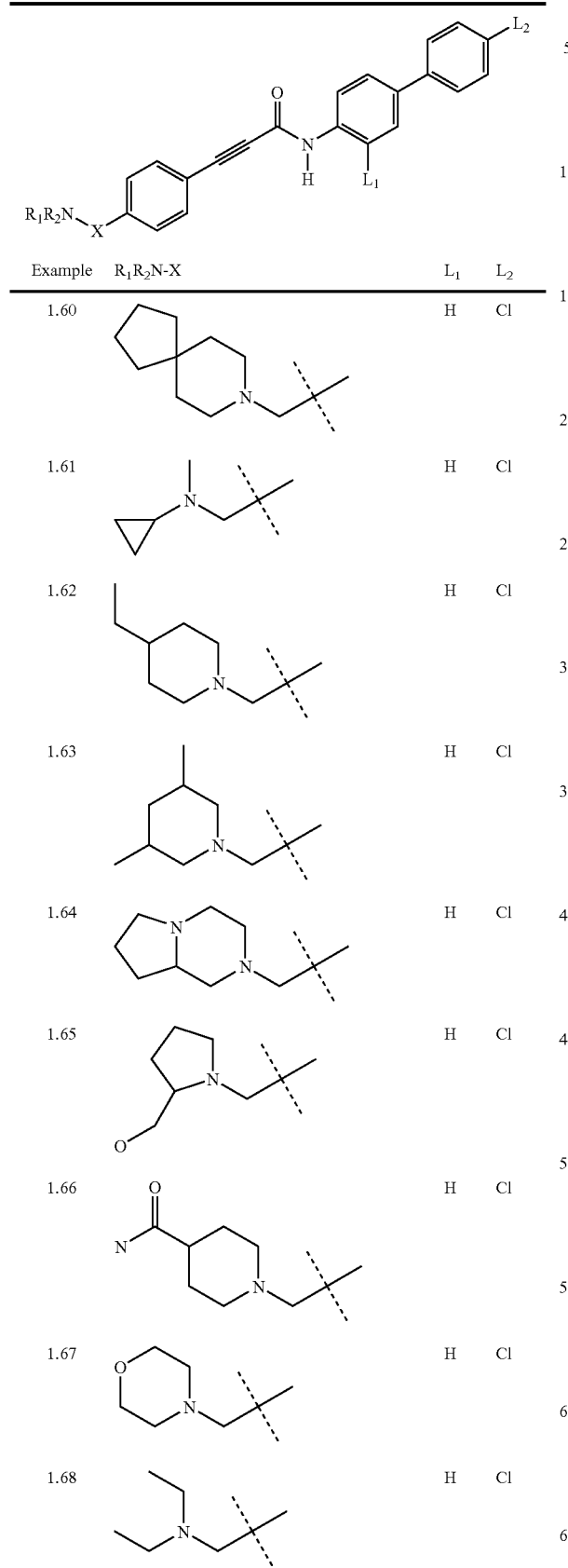
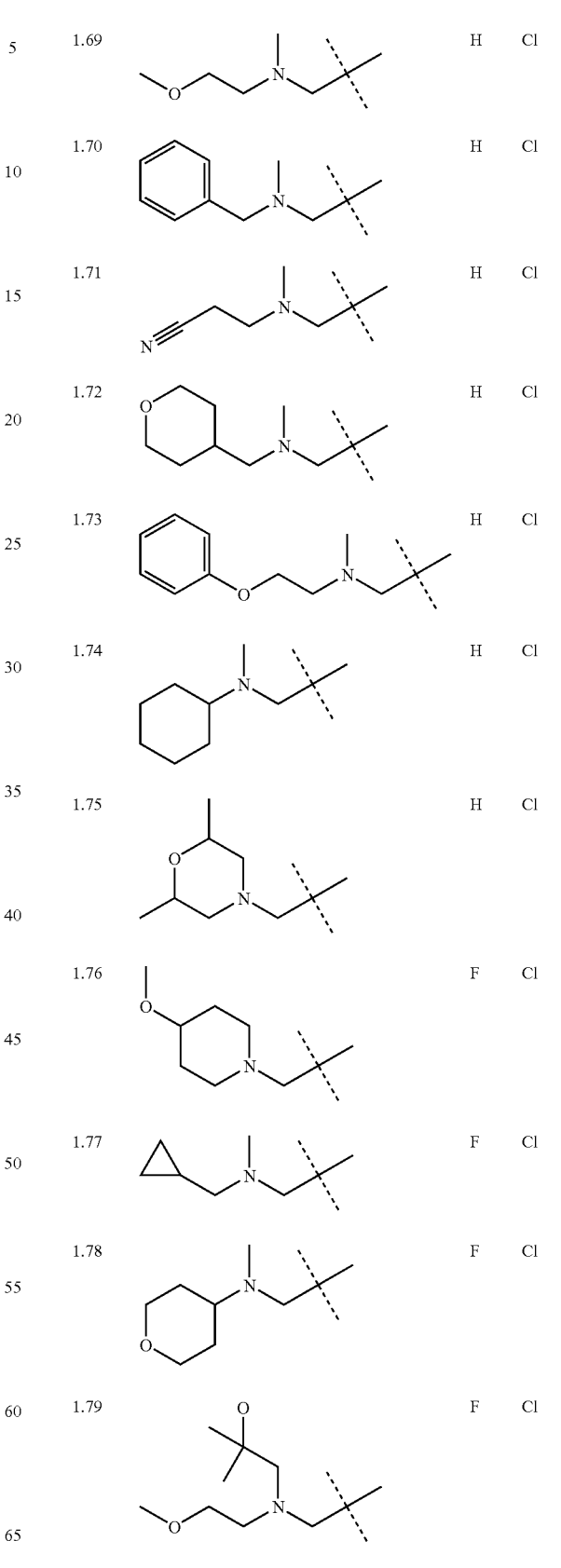

-continued
| | | | |
|---|---|---|---|
| 1.80 | 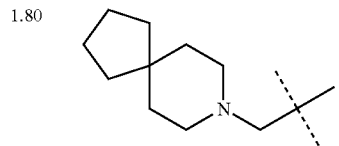 | F | Cl |
| 1.81 | 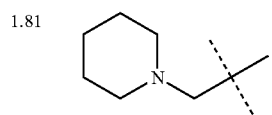 | F | Cl |
| 1.82 | 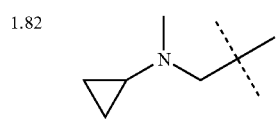 | F | Cl |
| 1.83 | 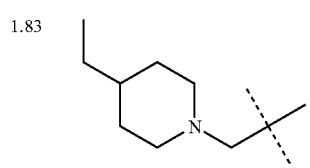 | F | Cl |
| 1.84 | 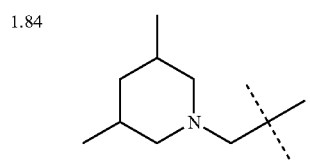 | F | Cl |
| 1.85 | 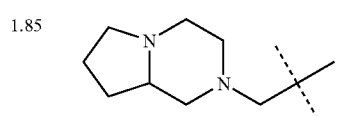 | F | Cl |
| 1.86 | 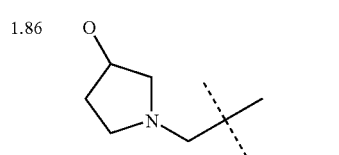 | F | Cl |
| 1.87 | 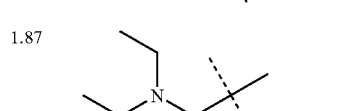 | F | Cl |
| 1.88 | 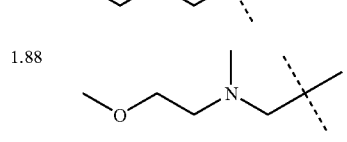 | F | Cl |
| 1.89 | 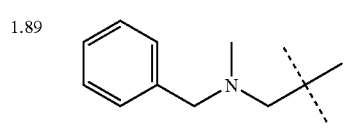 | F | Cl |
| 1.90 | 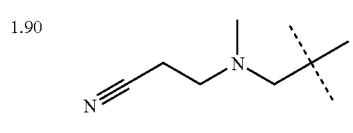 | F | Cl |
| 1.91 | 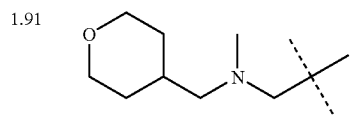 | F | Cl |
-continued
| | | | |
|---|---|---|---|
| 1.92 | 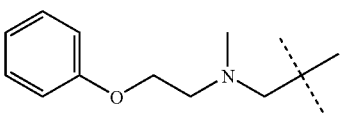 | F | Cl |
| 1.93 | 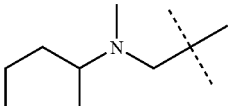 | F | Cl |
| 1.94 | 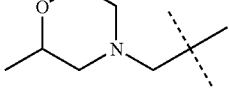 | F | Cl |
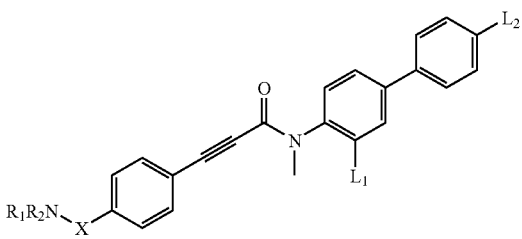
| Example | R₁R₂N-X | L₁ | L₂ |
|---|---|---|---|
| 1.95 | 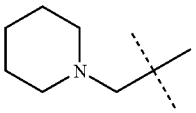 | H | Cl |
| 1.96 | 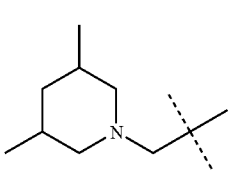 | H | Cl |
| 1.97 | 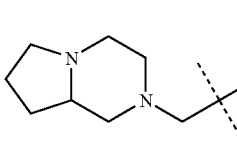 | H | Cl |
| 1.98 | 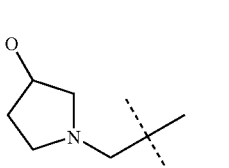 | H | Cl |
| 1.99 | 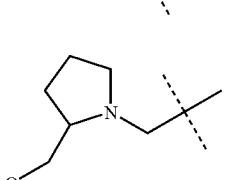 | H | Cl |

-continued

| | | | |
|---|---|---|---|
| 1.100 | [piperidine-4-carboxamide with N-CH2-] | H | Cl |
| 1.101 | [morpholine-N-CH2-] | H | Cl |
| 1.102 | [diethylamino-CH2-] | H | Cl |
| 1.103 | [methoxyethyl(methyl)amino-CH2-] | H | Cl |
| 1.104 | [benzyl(methyl)amino-CH2-] | H | Cl |
| 1.105 | [(2-cyanoethyl)(methyl)amino-CH2-] | H | Cl |
| 1.106 | [(tetrahydropyran-4-ylmethyl)(methyl)amino-CH2-] | H | Cl |
| 1.107 | [(2-phenoxyethyl)(methyl)amino-CH2-] | H | Cl |
| 1.108 | [cyclohexyl(methyl)amino-CH2-] | H | Cl |
| 1.109 | [2,6-dimethylmorpholine-N-CH2-] | H | Cl |
| 1.110 | [4-methoxypiperidine-N-CH2-] | F | Cl |
| 1.111 | [(cyclopropylmethyl)(methyl)amino-CH2-] | F | Cl |
| 1.112 | [(tetrahydropyran-4-yl)(methyl)amino-CH2-] | F | Cl |
| 1.113 | [(2-methoxyethyl)(2-hydroxy-2-methylpropyl)amino-CH2-] | F | Cl |
| 1.114 | [2-azaspiro[4.5]decane-CH2-] | F | Cl |
| 1.115 | [piperidine-N-CH2-] | F | Cl |
| 1.116 | [cyclopropyl(methyl)amino-CH2-] | F | Cl |
| 1.117 | [4-methylpiperidine-N-CH2-] | F | Cl |
| 1.118 | [4-ethylpiperidine-N-CH2-] | F | Cl |
| 1.119 | [3,5-dimethylpiperidine-N-CH2-] | F | Cl |
| 1.120 | [octahydropyrrolo[1,2-a]pyrazine-N-CH2-] | F | Cl |
| 1.121 | [3-oxopyrrolidine-N-CH2-] | F | Cl |

-continued
| | | | |
|---|---|---|---|
| 1.122 | 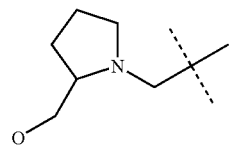 | F | Cl |
| 1.123 | 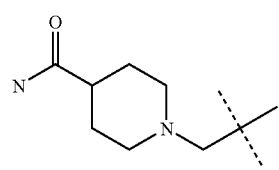 | F | Cl |
| 1.124 | 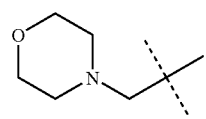 | F | Cl |
| 1.125 | 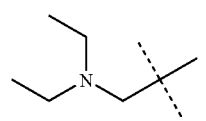 | F | Cl |
| 1.126 | 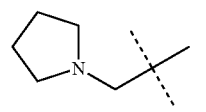 | F | Cl |
| 1.127 | 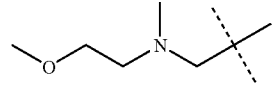 | F | Cl |
| 1.128 | 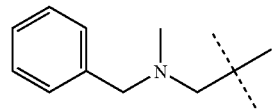 | F | Cl |
| 1.129 | 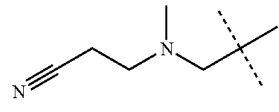 | F | Cl |
| 1.130 | 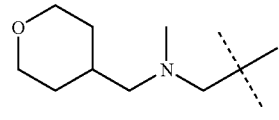 | F | Cl |
| 1.131 | 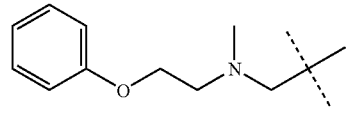 | F | Cl |
| 1.132 | 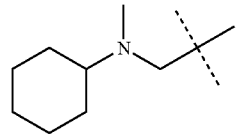 | F | Cl |
| 1.133 | 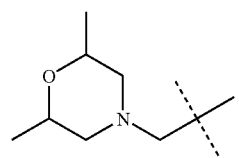 | F | Cl |
-continued
| Example | $R_1R_2N-X$ | $L_1$ | $L_2$ |
|---|---|---|---|
| 1.134 |  | H | $CF_3$ |
| 1.135 |  | H | $CF_3$ |
| 1.136 | 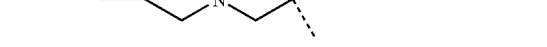 | H | $CF_3$ |
| 1.137 | 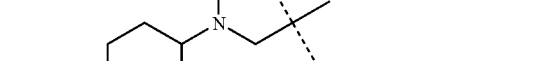 | H | $CF_3$ |
| 1.138 |  | H | $CF_3$ |
| 1.139 |  | H | $CF_3$ |
| 1.140 |  | H | $CF_3$ |
| 1.141 |  | H | $CF_3$ |
| 1.142 |  | H | $CF_3$ |

| | | | | | | | |
|---|---|---|---|---|---|---|---|
| 1.143 | [3,5-dimethylpiperidinyl-CH2-] | H | CF3 | | 1.155 | [PhO-CH2CH2-N(Me)-CH2-] | H | CF3 |
| 1.144 | [hexahydropyrrolo[1,2-a]pyrazinyl-CH2-] | H | CF3 | | 1.156 | [cyclohexyl-N(Me)-CH2-] | H | CF3 |
| 1.145 | [3-hydroxypyrrolidinyl-CH2-] | H | CF3 | | 1.157 | [2,6-dimethylmorpholinyl-CH2-] | H | CF3 |
| 1.146 | [2-(hydroxymethyl)pyrrolidinyl-CH2-] | H | CF3 | | 1.158 | [4-methoxypiperidinyl-CH2-] | H | Me |
| 1.147 | [4-carbamoylpiperidinyl-CH2-] | H | CF3 | | 1.159 | [cyclopropylmethyl-N(Me)-CH2-] | H | Me |
| 1.148 | [morpholinyl-CH2-] | H | CF3 | | 1.160 | [tetrahydropyran-4-yl-N(Me)-CH2-] | H | Me |
| 1.149 | [Et2N-CH2-] | H | CF3 | | 1.161 | [MeOCH2CH2-N(CH2C(Me)2OH)-CH2-] | H | Me |
| 1.150 | [pyrrolidinyl-CH2-] | H | CF3 | | 1.162 | [2-azaspiro[4.5]decan-8-yl-CH2-] | H | Me |
| 1.151 | [MeOCH2CH2-N(Me)-CH2-] | H | CF3 | | 1.163 | [piperidinyl-CH2-] | H | Me |
| 1.152 | [PhCH2-N(Me)-CH2-] | H | CF3 | | 1.164 | [cyclopropyl-N(Me)-CH2-] | H | Me |
| 1.153 | [NC-CH2CH2-N(Me)-CH2-] | H | CF3 | | 1.165 | [4-methylpiperidinyl-CH2-] | H | Me |
| 1.154 | [(tetrahydropyran-3-yl)methyl-N(Me)-CH2-] | H | CF3 | | | | | |

-continued

| | | | H | Me |
|---|---|---|---|---|
| 1.166 | (4-ethylpiperidin-1-yl)methyl | | H | Me |
| 1.167 | (3,5-dimethylpiperidin-1-yl)methyl | | H | Me |
| 1.168 | hexahydropyrrolo[1,2-a]pyrazin-2(1H)-yl methyl | | H | Me |
| 1.169 | (3-hydroxypyrrolidin-1-yl)methyl | | H | Me |
| 1.170 | (2-(hydroxymethyl)pyrrolidin-1-yl)methyl | | H | Me |
| 1.171 | (4-carbamoylpiperidin-1-yl)methyl | | H | Me |
| 1.172 | morpholinomethyl | | H | Me |
| 1.173 | (diethylamino)methyl | | H | Me |
| 1.174 | pyrrolidin-1-ylmethyl | | H | Me |
| 1.175 | ((2-methoxyethyl)(methyl)amino)methyl | | H | Me |
| 1.176 | (benzyl(methyl)amino)methyl | | H | Me |

-continued

| | | | H | Me |
|---|---|---|---|---|
| 1.177 | ((2-cyanoethyl)(methyl)amino)methyl | | H | Me |
| 1.178 | (((tetrahydro-2H-pyran-4-yl)methyl)(methyl)amino)methyl | | H | Me |
| 1.179 | (methyl(2-phenoxyethyl)amino)methyl | | H | Me |
| 1.180 | (cyclohexyl(methyl)amino)methyl | | H | Me |
| 1.181 | (2,6-dimethylmorpholino)methyl | | H | Me |
| 1.182 | (4-methoxypiperidin-1-yl)methyl | | H | F |
| 1.183 | ((cyclopropylmethyl)(methyl)amino)methyl | | H | F |
| 1.184 | methyl(tetrahydro-2H-pyran-4-yl)amino)methyl | | H | F |
| 1.185 | ((2-methoxyethyl)(2,2-dimethyl-2-hydroxyethyl)amino)methyl | | H | F |
| 1.186 | 2-azaspiro[4.5]decan-8-yl methyl | | H | F |
| 1.187 | piperidin-1-ylmethyl | | H | F |

| | | | | | | | | |
|---|---|---|---|---|---|---|---|---|
| | | -continued | | | | | -continued | |
| 1.188 | [structure] | H | F | | 1.199 | [structure] | H | F |
| 1.189 | [structure] | H | F | | 1.200 | [structure] | H | F |
| 1.190 | [structure] | H | F | | 1.201 | [structure] | H | F |
| 1.191 | [structure] | H | F | | 1.202 | [structure] | H | F |
| 1.192 | [structure] | H | F | | 1.203 | [structure] | H | F |
| 1.193 | [structure] | H | F | | 1.204 | [structure] | H | F |
| 1.194 | [structure] | H | F | | 1.205 | [structure] | H | F |
| 1.195 | [structure] | H | F | | 1.206 | [structure] | F | $CF_3$ |
| 1.196 | [structure] | H | F | | 1.207 | [structure] | F | $CF_3$ |
| 1.197 | [structure] | H | F | | 1.208 | [structure] | F | $CF_3$ |
| 1.198 | [structure] | H | F | | 1.209 | [structure] | F | $CF_3$ |

| | | | F | CF₃ |
|---|---|---|---|---|
| 1.210 | (spiro cyclopentane-piperidine-CH₂) | | F | CF₃ |
| 1.211 | (piperidine-CH₂) | | F | CF₃ |
| 1.212 | (N-methyl-N-cyclopropyl-CH₂) | | F | CF₃ |
| 1.213 | (4-methylpiperidine-CH₂) | | F | CF₃ |
| 1.214 | (4-ethylpiperidine-CH₂) | | F | CF₃ |
| 1.215 | (3,5-dimethylpiperidine-CH₂) | | F | CF₃ |
| 1.216 | (octahydropyrrolo[1,2-a]pyrazine-CH₂) | | F | CF₃ |
| 1.217 | (3-hydroxypyrrolidine-CH₂) | | F | CF₃ |
| 1.218 | (2-hydroxymethylpyrrolidine-CH₂) | | F | CF₃ |
| 1.219 | (4-carbamoylpiperidine-CH₂) | | F | CF₃ |
| 1.220 | (morpholine-CH₂) | | F | CF₃ |
| 1.221 | (N,N-diethyl-CH₂) | | F | CF₃ |
| 1.222 | (pyrrolidine-CH₂) | | F | CF₃ |
| 1.223 | (N-methyl-N-(2-methoxyethyl)-CH₂) | | F | CF₃ |
| 1.224 | (N-methyl-N-benzyl-CH₂) | | F | CF₃ |
| 1.225 | (N-methyl-N-(2-cyanoethyl)-CH₂) | | F | CF₃ |
| 1.226 | (N-methyl-N-(tetrahydropyran-4-ylmethyl)-CH₂) | | F | CF₃ |
| 1.227 | (N-methyl-N-(2-phenoxyethyl)-CH₂) | | F | CF₃ |
| 1.228 | (N-methyl-N-cyclohexyl-CH₂) | | F | CF₃ |
| 1.229 | (2,6-dimethylmorpholine-CH₂) | | F | CF₃ |
| 1.230 | (4-methoxypiperidine-CH₂) | | F | Me |
| 1.231 | (N-methyl-N-cyclopropylmethyl-CH₂) | | F | Me |
| 1.232 | (N-methyl-N-(tetrahydropyran-4-yl)-CH₂) | | F | Me |

-continued
| | | | | |
|---|---|---|---|---|
| 1.233 | 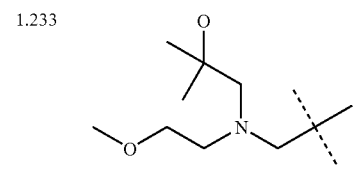 | F | Me | |
| 1.234 | 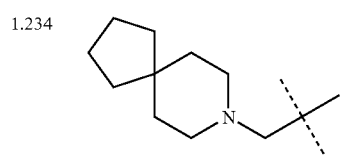 | F | Me | |
| 1.235 | 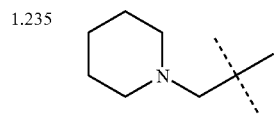 | F | Me | |
| 1.236 | 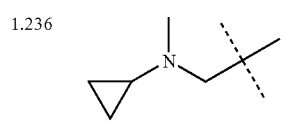 | F | Me | |
| 1.237 | 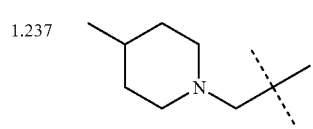 | F | Me | |
| 1.238 | 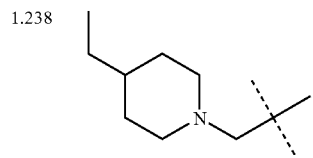 | F | Me | |
| 1.239 | 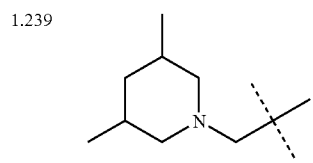 | F | Me | |
| 1.240 | 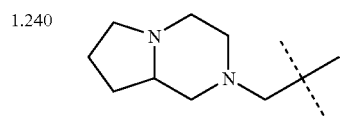 | F | Me | |
| 1.241 | 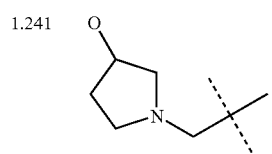 | F | Me | |
| 1.242 | 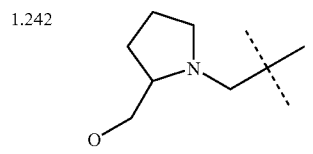 | F | Me | |
-continued
| | | | | |
|---|---|---|---|---|
| 1.243 | 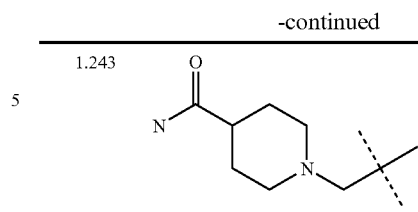 | F | Me | |
| 1.244 | 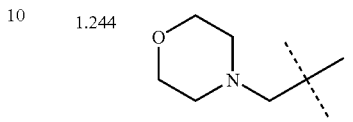 | F | Me | |
| 1.245 | 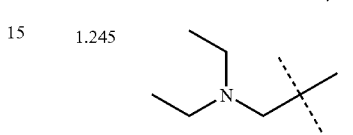 | F | Me | |
| 1.246 | 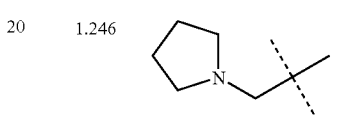 | F | Me | |
| 1.247 | 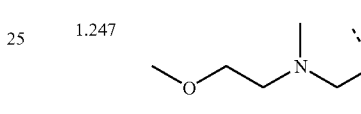 | F | Me | |
| 1.248 | 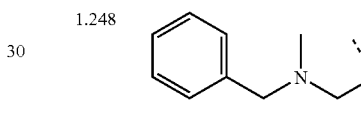 | F | Me | |
| 1.249 | 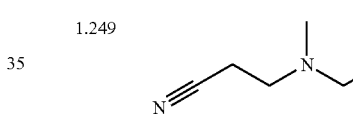 | F | Me | |
| 1.250 | 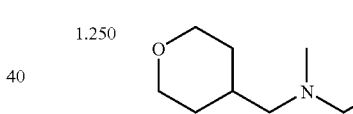 | F | Me | |
| 1.251 | 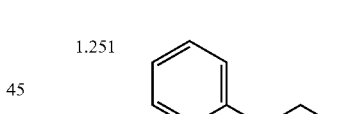 | F | Me | |
| 1.252 | 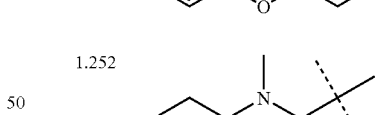 | F | Me | |
| 1.253 | 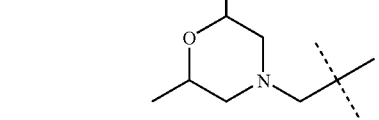 | F | Me | |
| 1.254 | 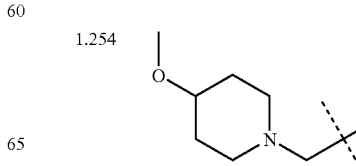 | F | F | |

| | | | | |
|---|---|---|---|---|
| 1.255 | 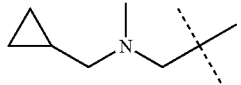 | F | F | |
| 1.256 | 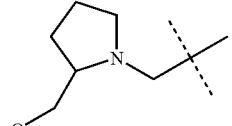 | F | F | |
| 1.257 | 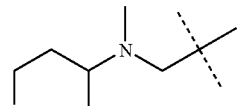 | F | F | |
| 1.258 | 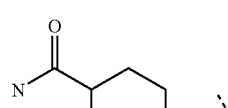 | F | F | |
| 1.259 | 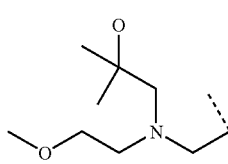 | F | F | |
| 1.260 | 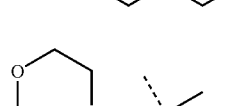 | F | F | |
| 1.261 | 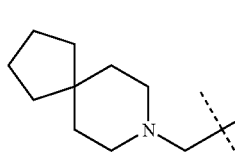 | F | F | |
| 1.262 | 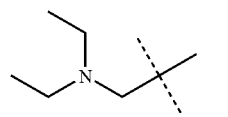 | F | F | |
| 1.263 | 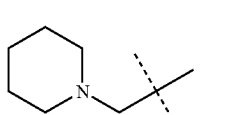 | F | F | |
| 1.264 | 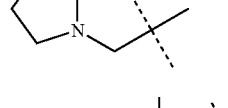 | F | F | |
| 1.265 | 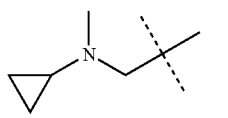 | F | F | |
| 1.266 | 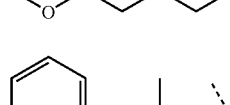 | F | F | |
| 1.267 | 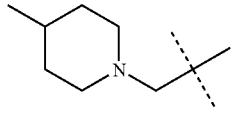 | F | F | |
| 1.268 | 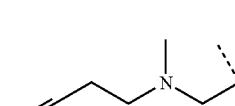 | F | F | |
| 1.269 | 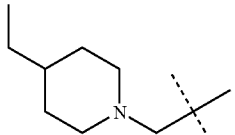 | F | F | |
| 1.270 | 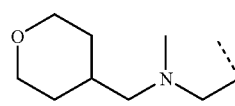 | F | F | |
| 1.271 | 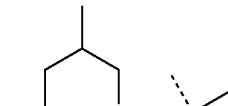 | F | F | |
| 1.272 | 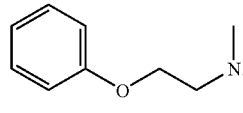 | F | F | |
| 1.273 | 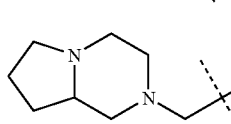 | F | F | |
| 1.274 | 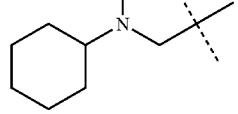 | F | F | |
| 1.275 | 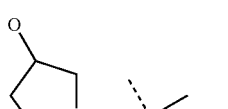 | F | F | |
| 1.276 | 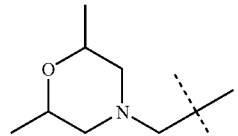 | F | F | |
| 1.277 | 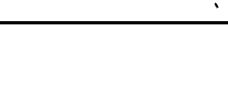 | F | F | |

-continued
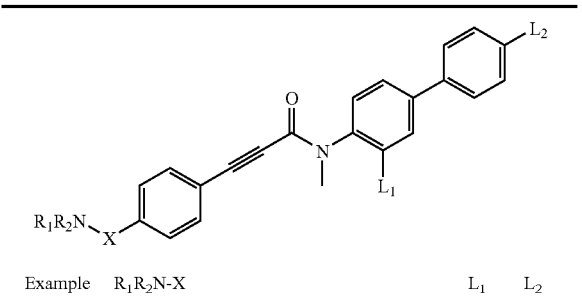
| Example | R₁R₂N-X | L₁ | L₂ |
|---|---|---|---|
| 1.278 | | H | CF₃ |
| 1.279 | | H | CF₃ |
| 1.280 | | H | CF₃ |
| 1.281 | | H | CF₃ |
| 1.282 | | H | CF₃ |
| 1.283 | | H | CF₃ |
| 1.284 | | H | CF₃ |
| 1.285 | | H | CF₃ |
| 1.286 | | H | CF₃ |
| 1.287 | | H | CF₃ |
| 1.288 | | H | CF₃ |
| 1.289 | | H | CF₃ |
| 1.290 | | H | CF₃ |
| 1.291 | | H | CF₃ |
| 1.292 | | H | CF₃ |
| 1.293 | | H | CF₃ |
| 1.294 | | H | CF₃ |
| 1.295 | | H | CF₃ |
| 1.296 | | H | CF₃ |
| 1.297 | | H | CF₃ |
| 1.298 | | H | CF₃ |

| | | | |
|---|---|---|---|
| 1.299 | [phenoxyethyl-N-methyl structure] | H | CF₃ |
| 1.300 | [N-cyclohexyl-N-methyl structure] | H | CF₃ |
| 1.301 | [2,6-dimethylmorpholine structure] | H | CF₃ |
| 1.302 | [4-methoxypiperidine structure] | H | Me |
| 1.303 | [cyclopropylmethyl-N-methyl structure] | H | Me |
| 1.304 | [N-(tetrahydropyran-4-yl)-N-methyl structure] | H | Me |
| 1.305 | [N-(2-methoxyethyl)-N-(2-hydroxy-2-methylpropyl) structure] | H | Me |
| 1.306 | [spiro[4.5]decane structure] | H | Me |
| 1.307 | [piperidine structure] | H | Me |
| 1.308 | [N-cyclopropyl-N-methyl structure] | H | Me |
| 1.309 | [4-methylpiperidine structure] | H | Me |
| 1.310 | [4-ethylpiperidine structure] | H | Me |
| 1.311 | [3,5-dimethylpiperidine structure] | H | Me |
| 1.312 | [octahydropyrrolo[1,2-a]pyrazine structure] | H | Me |
| 1.313 | [3-hydroxypyrrolidine structure] | H | Me |
| 1.314 | [2-(hydroxymethyl)pyrrolidine structure] | H | Me |
| 1.315 | [piperidine-4-carboxamide structure] | H | Me |
| 1.316 | [morpholine structure] | H | Me |
| 1.317 | [N,N-diethyl structure] | H | Me |
| 1.318 | [pyrrolidine structure] | H | Me |
| 1.319 | [N-(2-methoxyethyl)-N-methyl structure] | H | Me |
| 1.320 | [N-benzyl-N-methyl structure] | H | Me |

-continued

| | | | | | | | | |
|---|---|---|---|---|---|---|---|---|
| 1.321 | (structure) | H | Me | | 1.332 | (structure) | H | F |
| 1.322 | (structure) | H | Me | | 1.333 | (structure) | H | F |
| 1.323 | (structure) | H | Me | | 1.334 | (structure) | H | F |
| 1.324 | (structure) | H | Me | | 1.335 | (structure) | H | F |
| 1.325 | (structure) | H | Me | | 1.336 | (structure) | H | F |
| 1.326 | (structure) | H | F | | 1.337 | (structure) | H | F |
| 1.327 | (structure) | H | F | | 1.338 | (structure) | H | F |
| 1.328 | (structure) | H | F | | 1.339 | (structure) | H | F |
| 1.329 | (structure) | H | F | | 1.340 | (structure) | H | F |
| 1.330 | (structure) | H | F | | 1.341 | (structure) | H | F |
| 1.331 | (structure) | H | F | | 1.342 | (structure) | H | F |

-continued

| | | | |
|---|---|---|---|
| 1.343 | [structure: MeO-CH2CH2-N(Me)-CH2-C(Me)2-] | H | F |
| 1.344 | [structure: PhCH2-N(Me)-CH2-C(Me)2-] | H | F |
| 1.345 | [structure: N≡C-CH2CH2-N(Me)-CH2-C(Me)2-] | H | F |
| 1.346 | [structure: tetrahydropyran-4-yl-CH2-N(Me)-CH2-C(Me)2-] | H | F |
| 1.347 | [structure: PhO-CH2CH2-N(Me)-CH2-C(Me)2-] | H | F |
| 1.348 | [structure: cyclohexyl-N(Me)-CH2-C(Me)2-] | H | F |
| 1.349 | [structure: 2,6-dimethylmorpholin-4-yl-CH2-C(Me)2-] | H | F |
| 1.350 | [structure: 4-methoxypiperidin-1-yl-CH2-C(Me)2-] | F | CF3 |
| 1.351 | [structure: cyclopropyl-CH2-N(Me)-CH2-C(Me)2-] | F | CF3 |
| 1.352 | [structure: tetrahydropyran-4-yl-N(Me)-CH2-C(Me)2-] | F | CF3 |
| 1.353 | [structure: MeO-CH2CH2-N(CH2-C(Me)2-OMe)-CH2-C(Me)2-] | F | CF3 |
| 1.354 | [structure: 2-azaspiro[4.5] containing N-CH2-C(Me)2-] | F | CF3 |
| 1.355 | [structure: piperidin-1-yl-CH2-C(Me)2-] | F | CF3 |
| 1.356 | [structure: cyclopropyl-N(Me)-CH2-C(Me)2-] | F | CF3 |
| 1.357 | [structure: 4-methylpiperidin-1-yl-CH2-C(Me)2-] | F | CF3 |
| 1.358 | [structure: 4-ethylpiperidin-1-yl-CH2-C(Me)2-] | F | CF3 |
| 1.359 | [structure: 3,5-dimethylpiperidin-1-yl-CH2-C(Me)2-] | F | CF3 |
| 1.360 | [structure: hexahydropyrrolo[1,2-a]pyrazin-2-yl-CH2-C(Me)2-] | F | CF3 |
| 1.361 | [structure: 3-hydroxypyrrolidin-1-yl-CH2-C(Me)2-] | F | CF3 |
| 1.362 | [structure: 2-(hydroxymethyl)pyrrolidin-1-yl-CH2-C(Me)2-] | F | CF3 |
| 1.363 | [structure: 4-carbamoylpiperidin-1-yl-CH2-C(Me)2-] | F | CF3 |
| 1.364 | [structure: morpholin-4-yl-CH2-C(Me)2-] | F | CF3 |

-continued

| | | | | |
|---|---|---|---|---|
| 1.365 | [diethylaminomethyl group] | | F | CF₃ |
| 1.366 | [pyrrolidin-1-ylmethyl] | | F | CF₃ |
| 1.367 | [(2-methoxyethyl)(methyl)aminomethyl] | | F | CF₃ |
| 1.368 | [benzyl(methyl)aminomethyl] | | F | CF₃ |
| 1.369 | [(2-cyanoethyl)(methyl)aminomethyl] | | F | CF₃ |
| 1.370 | [((tetrahydropyran-4-yl)methyl)(methyl)aminomethyl] | | F | CF₃ |
| 1.371 | [(2-phenoxyethyl)(methyl)aminomethyl] | | F | CF₃ |
| 1.372 | [cyclohexyl(methyl)aminomethyl] | | F | CF₃ |
| 1.373 | [(2,6-dimethylmorpholin-4-yl)methyl] | | F | CF₃ |
| 1.374 | [(4-methoxypiperidin-1-yl)methyl] | | F | CF₃ |
| 1.375 | [(cyclopropylmethyl)(methyl)aminomethyl] | | F | CF₃ |
| 1.376 | [(tetrahydropyran-4-yl)(methyl)aminomethyl] | | F | Me |

-continued

| | | | | |
|---|---|---|---|---|
| 1.377 | [(2-methoxyethyl)(2-hydroxy-2-methylpropyl)aminomethyl] | | F | Me |
| 1.378 | [2-azaspiro[4.5]decan-2-ylmethyl] | | F | Me |
| 1.379 | [piperidin-1-ylmethyl] | | F | Me |
| 1.380 | [cyclopropyl(methyl)aminomethyl] | | F | Me |
| 1.381 | [(4-methylpiperidin-1-yl)methyl] | | F | Me |
| 1.382 | [(4-ethylpiperidin-1-yl)methyl] | | F | Me |
| 1.383 | [(3,5-dimethylpiperidin-1-yl)methyl] | | F | Me |
| 1.384 | [hexahydropyrrolo[1,2-a]pyrazin-2-ylmethyl] | | F | Me |
| 1.385 | [(3-hydroxypyrrolidin-1-yl)methyl] | | F | Me |
| 1.386 | [(2-(hydroxymethyl)pyrrolidin-1-yl)methyl] | | F | Me |

| | | | | | | | | |
|---|---|---|---|---|---|---|---|---|
| 1.387 | 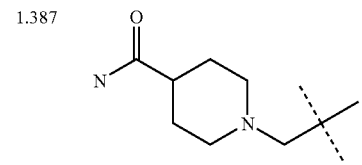 | F | Me | | 1.399 | 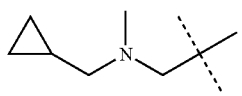 | F | F |
| 1.388 | 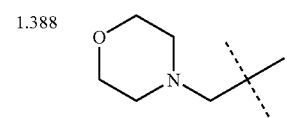 | F | Me | | 1.400 | 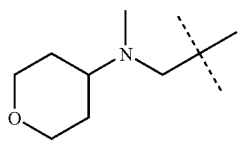 | F | F |
| 1.389 | 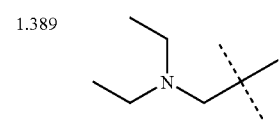 | F | Me | | 1.401 | 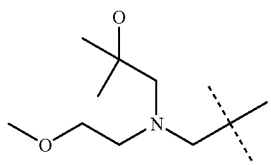 | F | F |
| 1.390 | 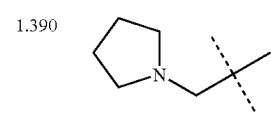 | F | Me | | 1.402 | 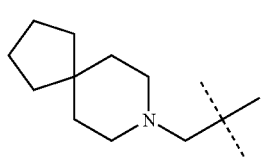 | F | F |
| 1.391 | 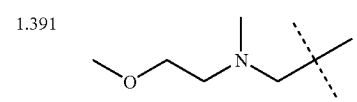 | F | Me | | 1.403 | 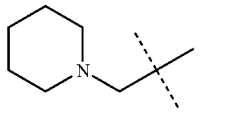 | F | F |
| 1.392 | 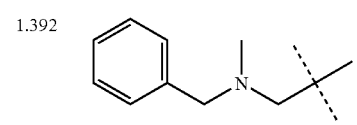 | F | Me | | 1.404 | 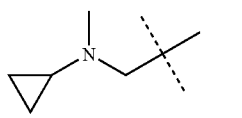 | F | F |
| 1.393 | 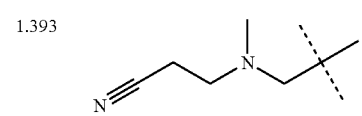 | F | Me | | 1.405 | 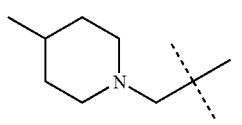 | F | F |
| 1.394 | 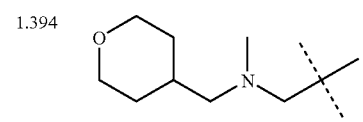 | F | Me | | 1.406 | 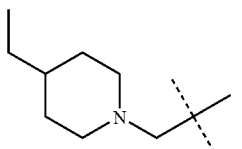 | F | F |
| 1.395 | 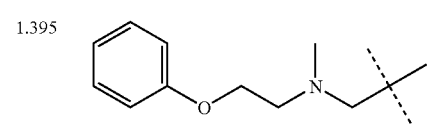 | F | Me | | 1.407 | 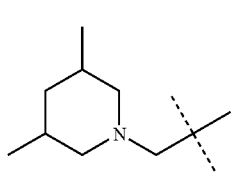 | F | F |
| 1.396 | 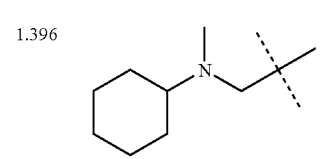 | F | Me | | 1.408 | 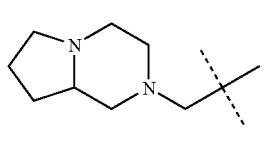 | F | F |
| 1.397 | 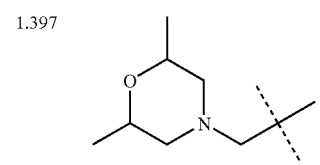 | F | Me | | 1.409 | 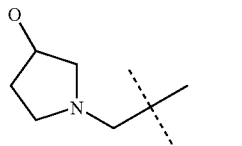 | F | F |
| 1.398 | 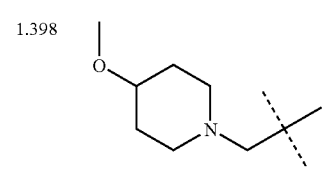 | F | F | | | | | |

| | | | |
|---|---|---|---|
| 1.410 | (pyrrolidinyl-CH2O-CH2-) | F | F |
| 1.411 | (piperidine-4-carboxamide-N-CH2-) | F | F |
| 1.412 | (morpholine-N-CH2-) | F | F |
| 1.413 | (Et2N-CH2-) | F | F |
| 1.414 | (pyrrolidine-N-CH2-) | F | F |
| 1.415 | (MeO-CH2CH2-N(Me)-CH2-) | F | F |
| 1.416 | (PhCH2-N(Me)-CH2-) | F | F |
| 1.417 | (NC-CH2CH2-N(Me)-CH2-) | F | F |
| 1.418 | (tetrahydropyran-3-yl-CH2-N(Me)-CH2-) | F | F |
| 1.419 | (PhO-CH2CH2-N(Me)-CH2-) | F | F |
| 1.420 | (cyclohexyl-N(Me)-CH2-) | F | F |
| 1.421 | (2-methylmorpholine-N-CH2-) | F | F |

EXAMPLE 1.422

3-[4-(1-aminocyclopropyl)phenyl]propynoic acid-(4'-chlorobiphenyl-4-yl)amide trifluoroacetate

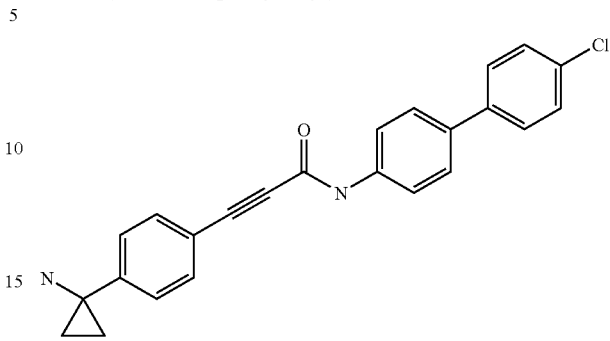

1.422.a: tert-butyl 1-(4-bromophenyl)cyclopropyl]carbamate 10 g (29.04 mmol) of 1-(4-bromobenzene)-1-cyclopropanecarboxylic acid and 6.07 mL (43.55 mmol) of triethylamine are dissolved in 63 mL of tert-butanol. At RT, 9.68 mL (43.55 mmol) of diphenylphosphorylazide (DPPA) are added dropwise and refluxed for 15 hours. Then 14.69 g (65.27 mmol) of di-tert-butyl pyrocarbonate is added and the mixture is refluxed for another 15 hours. The solvent is distilled off and the residue is taken up in ethyl acetate and washed successively with 5% citric acid, saturated sodium hydrogen carbonate solution, and saturated sodium chloride solution. The organic phase is dried with magnesium sulfate, filtered, and the solvent is distilled off. Yield: 6.00 g (66% of theory); $C_{14}H_{18}BrNO_2$ (M=312.20); calc.: molecular ion peak $(M+H)^+$: 312/14 (Br); found: molecular ion peak $(M+H)^+$: 312/14 (Br); $R_f$-value: 0.8 (silica gel, dichloromethane/ethanol (20:1)).

1.422.b. tert-butyl[1-(4-iodophenyl)cyclopropyl]carbamate 0.43 mL (4 mmol) of N,N'-dimethylethylenediamine is added to a reaction mixture of 0.4 g (2 mmol) of copper (I) iodide, 6.2 g (19.86 mmol) of tert-butyl [1-(4-bromophenyl)-cyclopropyl]carbamate, and 6 g (40 mmol) of sodium iodide in 15 mL of 1,4-dioxane and refluxed for 24 hours under nitrogen. Then the cooled suspension is combined with 30% ammonia solution, poured onto distilled water, and extracted with dichloromethane. The organic phase is dried over sodium sulfate, filtered, and the solvent is distilled off. Yield: 6.60 g (93% of theory); $C_{14}H_{18}INO_2$ (M=359.20); calc.: molecular ion peak $(M+H)^+$: 360; found: molecular ion peak $(M+H)^+$: 360; $R_f$-value: 0.8 (silica gel, dichloromethane/ethanol (50:1)).

1.422.c. 3-[4-(1-tert-butoxycarbonylaminocyclopropyl)phenyl]propynoic acid-(4'-chlorobiphenyl-4-yl) amide 1.4 g (4.2 mmol) of cesium carbonate and 0.5 g (1.4 mmol) of tert-butyl [1-(4-iodophenyl)cyclopropyl]carbamate are placed in 20 mL of THF and cooled to −15° C. in the ice/methanol bath, rinsed with argon, and degassed. To this reaction mixture is added successively 160 mg (0.14 mmol) of tetrakistriphenylphosphine palladium and 30 mg (0.158 mmol) of copper (I) iodide and the mixture is again degassed.

0.5 g (1.4 mmol) of propynoic acid-(4'-chlorobiphenyl-4-yl) amide is finally added. The mixture is stirred for 24 hours at ambient temperature and the reaction mixture is then evaporated down. The residue is triturated with water and ethyl acetate, suction filtered, washed with ethyl acetate, and dried in the air. Yield: 0.4 g (59% of theory); $C_{29}H_{27}ClN_2O_3$ (M=486.99); calc.: molecular ion peak (M+H)$^+$: 487/89 (Cl); found: molecular ion peak (M+H)$^+$: 487/89 (Cl); $R_f$ value: 0.62 (silica gel, cyclohexane/ethyl acetate (1:1)).

1.422.d. 3-[4-(1-aminocyclopropyl)phenyl]propynoic acid-(4'-chlorobiphenyl-4-yl)amide trifluoroacetate 1 mL (12.92 mmol) of trifluoroacetic acid is added to a solution of 0.24 g (0.49 mmol) of 3-[4-(1-tert-butoxycarbonylaminocyclopropyl)phenyl]propynoic acid-(4'-chlorobiphenyl-4-yl)amide in 20 mL dichloromethane and stirred for 24 hours. Then the solvent is eliminated by rotary evaporation and the residue is combined with toluene and again subjected to rotary evaporation. This residue is then triturated with dichloromethane, suction filtered and dried in the air. Yield: 0.22 g (89% of theory); $C_{24}H_{19}ClN_2O*C_2HF_3O_2$ (M=500.90); calc.: molecular ion peak (M+H)$^+$: 387 (Cl); found: molecular ion peak (M+H)$^+$: 387 (Cl); melting point: 160° C.-164° C.

EXAMPLE 1.423

3-[4-(1-methylaminocyclopropyl)phenyl]propynoic acid-(4'-chlorobiphenyl-4-yl)amide trifluoroacetate

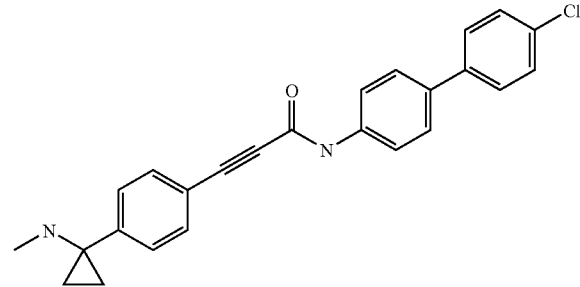

1.423.a: tert-butyl [1-(4-iodophenyl)cyclopropyl]methylcarbamate 131 mg (3 mmol) of sodium hydride (55%) is added at RT to a solution of 1 g (2.78 mmol) of tert-butyl [1-(4-iodophenyl)cyclopropyl]carbamate in 20 mL of DMF and the mixture is stirred for 30 minutes at RT. Then 0.287 mL (4.4 mmol) of methyl iodide is added dropwise and the mixture is stirred for 24 hours. The solvent is eliminated by rotary evaporation. The residue is extracted between water and ethyl acetate and the organic phase is dried over sodium sulfate. The solvent is again eliminated by rotary evaporation. Yield: 1 g (96% of theory); $C_{15}H_{20}INO_2$ (M=373.23); calc.: molecular ion peak (M+H)$^+$: 374; found: molecular ion peak (M+H)$^+$: 374; $R_f$ value: 0.68 (silica gel, cyclohexane/ethyl acetate (3:1)).

1.423.b: 3-[4-(1-tert-butoxycarbonylmethylaminocyclopropyl)phenyl]propynoic acid-(4'-chlorobiphenyl-4-yl)amide 2.28 g (7 mmol) of cesium carbonate and 1 g (2.68 mmol) of tert-butyl [1-(4-iodophenyl)cyclopropyl]methylcarbamate are placed in 20 mL of THF and cooled to −15° C. in the ice/methanol bath, rinsed with argon, and degassed. To this reaction mixture is added successively 180 mg (0.16 mmol) of tetrakistriphenylphosphine palladium and 50 mg (0.263 mmol) of copper (I) iodide and the mixture is again degassed. 0.75 g (2.9 mmol) of propynoic acid-(4'-chlorobiphenyl-4-yl) amide is finally added. The mixture is stirred for 24 hours at ambient temperature and the reaction mixture is then evaporated down. The residue is extracted between water and ethyl acetate, the organic phase is dried with sodium sulfate, and the solvent is eliminated by rotary evaporation. The purification is carried out by column chromatography on silica gel (eluant: cyclohexane/ethyl acetate (2:1)). Yield: 0.75 g (56% of theory); $C_{30}H_{29}ClN_2O_3$ (M=501.02); calc.: molecular ion peak (M+H)$^+$: 501/3 (Cl); found: molecular ion peak (M+H)$^+$: 501/3 (Cl); $R_f$ value: 0.75 (silica gel, cyclohexane/ethyl acetate (1:1)).

1.423.c: 3-[4-(1-methylaminocyclopropyl)phenyl] propynoic acid-(4'-chlorobiphenyl-4-yl)amide Prepared analogously to Example 1.422.d. from 3-[4-(1-tert-butoxycarbonylmethylaminocyclopropyl)phenyl]propynoic acid-(4'-chlorobiphenyl-4-yl)amide. Yield: 0.43 g (56% of theory); $C_{25}H_{21}ClN_2O*C_2HF_3O_2$ (M=514.92); calc.: molecular ion peak (M+H)$^+$: 401/3 (Cl); found: molecular ion peak (M+H)$^+$: 401/3 (Cl); melting point: 217.3° C.

EXAMPLE 1.424

3-{4-[1-(4-methylpiperidin-1-yl)cyclopropyl] phenyl}propynoic acid(4'-chlorobiphenyl-4-yl)amide

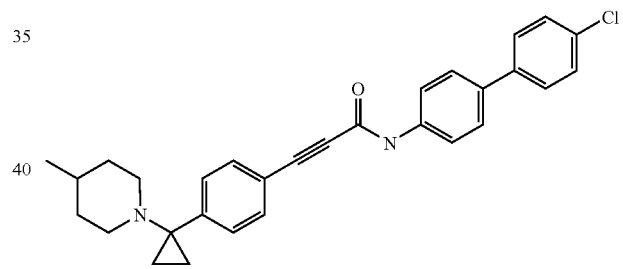

1.424.a. 1-(4-iodophenyl)cyclopropylamine 3 mL (38.76 mmol) of trifluoroacetic acid are added to a solution of 1 g (2.78 mmol) of tert-butyl [1-(4-iodophenyl) cyclopropyl]carbamate in 40 mL dichloromethane and stirred for 24 h. Then the solvent is eliminated by rotary evaporation and the residue is combined with toluene and then again eliminated by rotary evaporation. This residue is then added to a solution of 0.39 g (2.8 mmol) of potassium carbonate in 20 mL of water and stirred for 30 minutes at RT. The aqueous phase is extracted with dichloromethane, the organic phase is dried with sodium sulfate and the solvent is eliminated by rotary evaporation. Yield: 0.7 g (97% of theory); $C_9H_{10}IN$ (M=259.09); calc.: molecular ion peak (M+H)$^+$: 260; found: molecular ion peak (M+H)$^+$: 260.

1.424.b. 1-[1-1-(4-iodophenyl)cyclopropyl]-4-methylpiperidine 0.55 g (4 mmol) of potassium carbonate are added to a reaction mixture of 0.5 g (1.93 mmol) of 1-(4-iodophenyl)

cyclopropylamine and 0.89 g (2 mmol) of 1,5-dibromo-3-methylpentane in 20 mL of DMF stirred at 80° C. for 24 hours. Then the solvent is evaporated down and the residue is extracted between ethyl acetate and water. The organic phase is dried over sodium sulfate. The purification is carried out by column chromatography (eluant: cyclohexane/ethyl acetate 3:1). Yield: 0.065 g (10% of theory); $C_{15}H_{20}IN$ (M=341.23); calc.: molecular ion peak $(M+H)^+$: 342; found: molecular ion peak $(M+H)^+$: 342; $R_f$ value: 0.65 (silica gel, cyclohexane/ethyl acetate (3:1)).

1.424.c. 3-{4-[1-(4-methylpiperidin-1-yl)cyclopropyl]phenyl}propynoic acid(4'-chlorobiphenyl-4-yl)amide Prepared analogously to Example 1.424.b. from 1[1-1-(4-iodophenyl)cyclopropyl]-4-methylpiperidine and propynoic acid-(4'-chlorobiphenyl-4-yl)amide. Yield: 20 mg (24% of theory); $C_{30}H_{29}ClN_2O$ (M=469.02); calc.: molecular ion peak $(M+H)^+$: 469/71 (Cl); found: molecular ion peak $(M+H)^+$: 469/71 (Cl); $R_f$ value: 0.3 (silica gel, cyclohexane/ethyl acetate (3:1)); melting point: 128° C.-129° C.

EXAMPLE 1.425

3-{4-[cyclopentylmethylamino)methyl]phenyl}propynoic acid-(4'-chlorobiphenyl-4-yl)amide

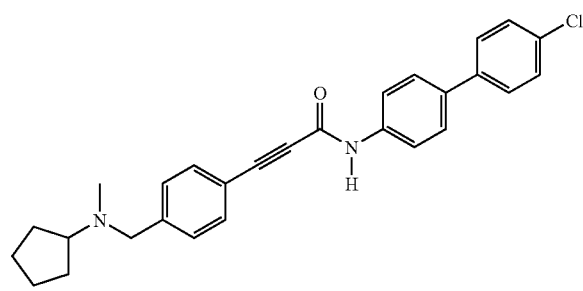

Prepared analogously to Example 1.40.d. from 3-(4-chloromethylphenyl)propynoic acid-(4'-chlorobiphenyl-4-yl)amide and methylcyclopentylamine. Yield: 10 mg (316% of theory); melting point: 217° C.-219° C.; $C_{28}H_{27}ClN_2O$ (M=442.98); calc.: molecular ion peak $(M+H)^+$: 443/45 (Cl); found: molecular ion peak $(M+H)^+$: 443/45 (Cl).

EXAMPLE 2.1

3-[4-(2-pyrrolidin-1-ylethyl)phenyl]propynoic Acid biphenyl-4-ylamide

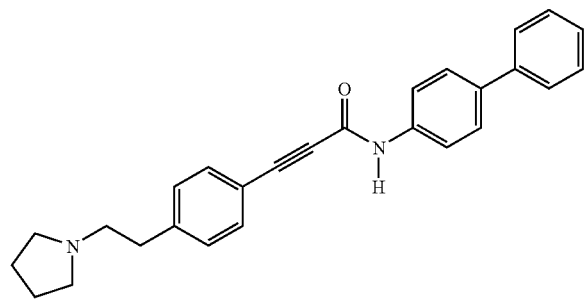

2.1.a. 2-(4-iodophenyl)ethanol 0.474 g (2.48 mmol) of copper (I) iodide, 5 g (24.86 mmol) 2-(4-bromophenyl)ethanol and 7.45 g (49.73 mmol) of sodium iodide are successively added to a flask under an argon atmosphere. Then 0.438 g (4.97 mmol) of dimethylenediamine and 25 mL dioxane are added and the reaction mixture is refluxed for 14 hours. Then the reaction mixture is combined with 20 mL concentrated ammonia solution at ambient temperature, with 100 mL of water diluted and extracted with dichloromethane. The organic phase is extracted three times with water and dried over sodium sulfate. Yield: 5.4 g (87.5% of theory); $C_8H_9IO$ (M=248.06); calc.: molecular ion peak $(M)^+$: 248; found: molecular ion peak $(M)^+$: 248; $R_f$ value: 0.6 (silica gel, dichloromethane/ethanol (10:1)).

2.1.b. 2-(4-iodophenyl)ethyl methanesulfonate

Prepared analogously to Example 1.2.b. from 2-(4-iodophenyl)ethanol and methanesulfonic acid chloride. Yield: 5.7 g (77.4% of theory); $C_9H_{11}IO_3S$ (M=326.15); calc.: molecular ion peak $(M)^+$: 326; found: molecular ion peak $(M)^+$: 326.

2.1.c. 1-[2-(4-iodophenyl)ethyl]pyrrolidine 1 mL (12.26 mmol) of pyrrolidine are added to a solution of 2 g (6.13 mmol) of 2-(4-iodophenyl)ethyl methanesulfonate in 30 mL DMF and the reaction solution is stirred for 6 hours at 70° C. The reaction mixture is poured onto water and extracted with ethyl acetate. The organic phase is extracted three times with water and dried over sodium sulfate. The sodium sulfate is separated off and the solvent removed. Yield: 1.28 g (69.3% of theory); $C_{12}H_{16}IN$ (M=301.17); calc.: molecular ion peak $(M+H)^+$: 302; found: molecular ion peak $(M+H)^+$: 302; $R_f$ value: 0.4 (silica gel, dichloromethane/methanol=10:1)).

2.1.d. Propynoic acid-biphenyl-4-ylamide 9.38 g (45.5 mmol) of DCC are added batchwise to a solution of 2.89 g (41.36 mmol) of propynoic acid in 100 mL dichloromethane at −15° C. and stirred for 1 hour. Then a solution of 7 g (41.36 mmol) of biphenyl-4-ylamine-15° C. is added dropwise to 30 mL dichloromethane and stirred for 2 hours. After this time, the cooling bath is removed and the reaction mixture is allowed to come up to ambient temperature. 20 g of CELITE® filter aid is added to the reaction mixture and it is then filtered. The filtrate is evaporated down in vacuo. The residue is combined with acetonitrile and stirred. The suspension is filtered, the filtrate is evaporated down and the residue is stirred with petroleum ether and pentane. The solid is isolated by filtration. Yield: 5.5 g (60.1% of theory); $C_{15}H_{11}NO$ (M=221.26); calc.: molecular ion peak $(M+H)^+$: 222; found: molecular ion peak $(M+H)^+$: 222; $R_f$ value: 0.7 (silica gel, dichloromethane/methanol (10:1)).

2.1.e. 3-[4-(2-pyrrolidin-1-ylethyl)phenyl]propynoic acid-biphenyl-4-ylamide 25 mL of THF are degassed and combined with 0.25 g (0.83 mmol) of 1-[2-(4-iodophenyl)ethyl]pyrrolidine, 0.81 g (2.49 mmol) of cesium carbonate, 16 mg (0.083 mmol) of copper (I) iodide and 38 mg (0.033 mmol) of tetrakistriphenylphosphine palladium. Then the mixture is again degassed, and 184 mg (0.83 mmol) of propynoic acid-biphenyl-4-ylamide are added. The reaction mixture is stirred for 3 hours at ambient temperature, poured onto water and extracted with ethyl acetate. The organic phase is extracted three times with water and dried over sodium sulfate. The purification is carried out by column chromatography on silica gel (dichloromethane/methanol/ammonia=10:1:0.1)). Yield: 90 mg (27.5% of theory); melting point: 180-189° C.; $C_{27}H_{26}N_2O$ (M=394.52); calc.: molecular ion peak $(M+H)^+$: 395; found: molecular ion peak $(M+H)^+$: 395.

EXAMPLE 2.2

3-[4-(2-pyrrolidin-1-ylethyl)phenyl]propynoic acid-4-chlorophenylamide

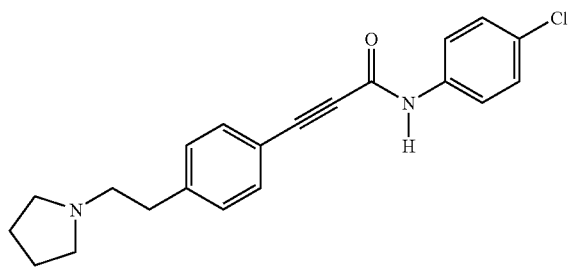

2.2.a. Propynoic acid-(4-chlorophenyl)amide

Prepared analogously to Example 1.1.b. from propynoic acid and 4-chloroaniline. Yield: 0.56 g (31.2% of theory); $C_9H_6ClNO$ (M=179.60); calc.: molecular ion peak $(M-H)^-$: 178/180; found: molecular ion peak $(M-H)^-$: 178/180; $R_f$ value: 0.53 (silica gel, dichloromethane/methanol/ammonia (90:10:1)).

2.2.b. 3-[4-(2-pyrrolidin-1-ylethyl)phenyl]propynoic acid-4-chlorophenylamide Prepared analogously to Example 2.1.e. from propynoic acid-(4-chlorophenyl)amide and 1-[2-(4-iodophenyl)ethyl] pyrrolidine. Yield: 80 mg (34.1% of theory); melting point: 153° C.-154° C.; $C_{21}H_{21}ClN_2O$ (M=352.86); calc.: molecular ion peak $(M+H)^+$: 353/355; found: molecular ion peak $(M+H)^+$: 353/355.

EXAMPLE 2.3

3-(1-pyrrolidin-1-ylindan-5-yl)propynoic acid-(4'-chlorobiphenyl-4-yl)amide

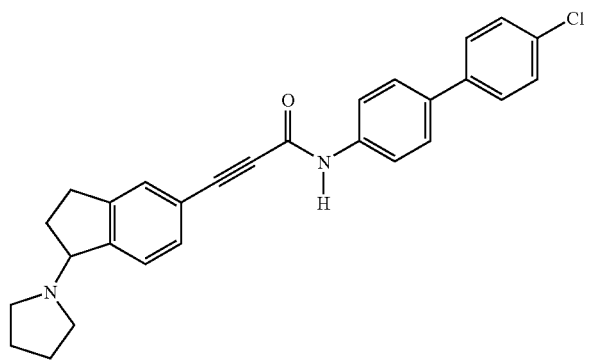

2.3.a. 5-bromoindan-1-ol 0.987 g (23 mmol) of sodium borohydride are added to a solution of 5 g (22.98 mmol) of 5-bromo-1-indanone in 100 mL isopropanol at ambient temperature and the reaction mixture is stirred for 5 hours. Then an acidic pH is obtained by the careful addition of potassium hydrogen sulfate solution and the reaction mixture is extracted with tert-butylmethylether. The organic phase is extracted with saturated sodium chloride solution and then dried with magnesium sulfate. The filtrate is evaporated down in vacuo after removal of the magnesium sulfate. The residue is dissolved in tert-butylmethylether and extracted successively with dilute sodium hydrogen carbonate solution and water. Then it is dried over magnesium sulfate and filtered through activated charcoal. The filtrate is evaporated down in vacuo. Yield: 3.6 g (73.5% of theory); $C_9H_9BrO$ (M=213.07); $R_f$ value: 0.6 (silica gel, petroleum ether/ethyl acetate (6:4)).

2.3.b. 5-bromo-1-chloroindane 3.09 mL (37.45 mmol) of thionyl chloride, dissolved in cooled dichloromethane, are added dropwise at −10° C. to a solution of 3.8 g (17.83 mmol) of 5-bromoindan-1-ol in 200 mL dichloromethane. The reaction mixture is allowed to come up slowly to ambient temperature and stirred for 14 hours at ambient temperature. Then ice and 100 mL of dilute sodium hydrogen carbonate solution are added successively. The organic phase is extracted twice with 50 mL of water. The combined organic phases are dried over magnesium sulfate, filtered and the solvent is distilled off. Yield: 3.7 g (90% of theory); $C_9H_8BrCl$ (M=231.52); $R_f$ value: 0.91 (silica gel, petroleum ether/ethyl acetate (6:4)).

2.3.c. 1-(5-bromoindan-1-yl)pyrrolidine 7 mL (85.23 mmol) of pyrrolidine are added at 0° C. to a solution of 3.71 g (16.92 mmol) of 5-bromo-1-chloroindane in 250 mL of dichloromethane. The reaction mixture is allowed to come up to ambient temperature and stirred for 24 hours. Then it is extracted once with water and the organic phase is extracted with potassium hydrogen sulfate solution. The aqueous phase is extracted once with dichloromethane. Then the aqueous phase is made basic with sodium carbonate solution, in order to liberate the product. This solution is extracted with dichloromethane, the organic phase is extracted with water and dried over magnesium sulfate. Yield: 1.81 g (42.4% of theory); $C_{13}H_{16}BrN$ (M=266.18); calc.: molecular ion peak $(M+H)^+$: 266/268; found: molecular ion peak $(M+H)^+$: 266/268.

2.3.d. 1-(5-iodoindan-1-yl)pyrrolidine

Prepared analogously to Example 2.1.a. from 1-(5-bromoindan-1-yl)pyrrolidine. Yield: 1.42 g (83.5% of theory); $C_{13}H_{16}IN$ (M=313.18); calc.: molecular ion peak $(M+H)^+$: 314; found: molecular ion peak $(M+H)^+$: 314.

2.3.e. (1-pyrrolidin-1-ylindan-5-yl)propynoic Acid

Under an argon atmosphere at 0° C., 0.5 g (1.59 mmol) of 1-(5-iodoindan-1-yl)pyrrolidine and 123 mL (2 mmol) of propynoic acid are dissolved in 25 mL of acetonitrile. 0.66 mL (4.79 mmol) of triethylamine, 30 mg (0.16 mmol) of copper (I) iodide, and 80 mg (0.11 mmol) of ditriphenylphosphine palladium dichloride are added to this solution and the mixture is stirred for 2 hours, while the solution is allowed to come up to ambient temperature. The purification is carried out by preparative HPLC (eluant: dichloromethane/methanol/ammonia (8:2:0.2)). Yield 0.1 g (24.5% of theory); $C_{16}H_{17}NO_2$ (M=255.31); calc.: molecular ion peak (M+H)+: 256; found: molecular ion peak (M+H)+: 256.

2.3.f. 3-(1-pyrrolidin-1-ylindan-5-yl)propynoic acid-(4'-chlorobiphenyl-4-yl)amide A solution of 0.1 g (0.39 mmol) of (1-pyrrolidin-1-ylindan-5-yl)propynoic acid and 47 mL (0.43 mmol) of N-methylmorpholine in 5 mL of absolute THF is combined with 56 mL (0.43 mmol) of isobutyl chloroformate at −15° C. and stirred for ten minutes. Then 87 mg (0.43 mmol) of 4'-chlorobiphenyl-4-ylamine are added at ambient temperature and the reaction mixture is stirred for 14 hours. Then 3 mL of dichloromethane are added to the reaction mixture and this is stirred for 48 hours. Then the reaction mixture is filtered, the filtrate is evaporated down, combined with water and extracted with dichloromethane. The organic phase is evaporated down. The purification is carried out by preparative HPLC (eluant: dichloromethane/methanol/ammonia=8:2:0.2). Yield: 9 mg (5.7% of theory); $C_{28}H_{25}ClN_2O$ (M=440.97); calc.: molecular ion peak (M+H)+: 441/443; found: molecular ion peak (M+H)+: 441/443.

EXAMPLE 2.4

3-[4-(2-pyrrolidin-1-ylethyl)phenyl]propynoic acid-(4'-chlorobiphenyl-4-yl)amide

2.3.a. 3-[4-(2-pyrrolidin-1-ylethyl)phenyl]propynoic acid-(4'-chlorobiphenyl-4-yl)amide Prepared analogously to Example 2.1.e. from propynoic acid-(4'-chlorobiphenyl-4-yl)amide and 1-[2-(4-iodophenyl)ethyl]pyrrolidine. Yield: 70 mg (32.8% of theory); melting point: 217-218 C; $C_{27}H_{25}ClN_2O$ (M=428.96); calc.: molecular ion peak (M+H)+: 429/431; found: molecular ion peak (M+H)+: 429/431; $R_f$ value: 0.3 (silica gel, dichloromethane/methanol (10:1)).

EXAMPLE 2.5

3-[4-(2-pyrrolidin-1-ylethyl)phenyl]propynoic acid-(4-prop-1-ynylphenyl)amide

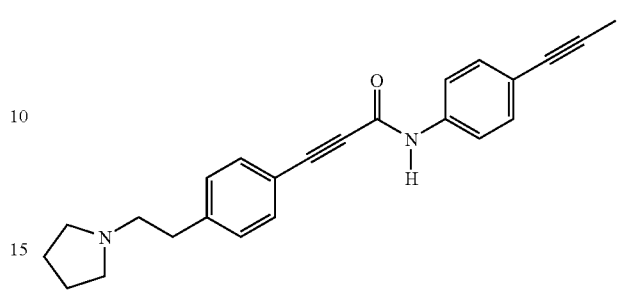

2.4.a. 3-[4-(2-pyrrolidin-1-ylethyl)phenyl]propynoic acid-(4-prop-1-ynylphenyl)amide Prepared analogously to Example 2.1.e. from propynoic acid-(4-prop-1-ynylphenyl)amide and 1-[2-(4-iodophenyl)ethyl]pyrrolidine. Yield: 20 mg (11% of theory); melting point: 198° C.-199° C.; $C_{24}H_{24}N_2O$ (M=356.47); $R_f$ value: 0.1 (silica gel, dichloromethane/methanol (10:1))

EXAMPLE 3.1

3-phenylpropynoic acid-[4-(2-diethylaminoethoxy)phenyl]methylamide

3.1.a. diethyl-[2-(4-nitrophenoxy)ethyl]amine 88.7 g (515.41 mmol) of (2-chloroethyl)diethylamine hydrochloride are added at ambient temperature to a suspension of 71.7 g (515.41 mmol) of p-nitrophenol and 284.94 g (2.061 mol) of potassium carbonate in 600 mL DMF and the reaction mixture is heated to 80° C. for 8 hours. The reaction mixture is evaporated down and the residue poured onto water and extracted with ethyl acetate. The organic phase is extracted three times with water and dried over sodium sulfate. The desiccant is filtered off and the filtrate is evaporated down. Yield: 110.52 g (90% of theory); $C_{12}H_{18}N_2O_3$ (M=238.28); $R_f$ value: 0.52 (silica gel, dichloromethane/methanol (10:1)).

3.1.b. 4-(2-diethylaminoethoxy)phenylamine

A reaction mixture of 110.52 g (0.464 mol) of diethyl-[2-(4-nitrophenoxy)ethyl]amine and 17 g of Raney nickel in 700 mL of methanol is hydrogenated for 30 hours at 20° C. and 3 bar hydrogen. The catalyst is filtered off and the filtrate is evaporated down. Yield: 93 g (96.2% of theory); $C_{12}H_{20}N_2O$ (M=208.30); calc.: molecular ion peak $(M)^+$: 209; found: molecular ion peak $(M)^+$: 209.

3.1.c. methyl [4-(2-diethylaminoethoxy)phenyl]carbamate 76.38 g (366.66 mmol) of 4-(2-diethylaminoethoxy)phenylamine and 101.65 mL (733.33 mmol) of triethylamine are dissolved in 400 mL of THF. A solution of 49.16 g (366.66 mmol) of dimethylpyrocarbonate in 200 mL of THF is added dropwise to this solution within 45 minutes at 25° C. and the mixture is stirred for 2 hours at ambient temperature. The reaction mixture is evaporated down, the residue is added to water and extracted with ethyl acetate. The combined organic phases are extracted twice with water. The organic phase is evaporated down, during which time a precipitate forms, which is filtered off. The filtrate is evaporated down further. The purification is carried out by column chromatography on aluminum oxide (eluant: ethyl acetate/petroleum ether (3:1)). Yield: 63.3 g (64.8% of theory); $C_{14}H_{22}N_2O_3$ (M=266.34); calc.: molecular ion peak $(M+H)^+$: 267; found: molecular ion peak $(M+H)^+$: 267; $R_f$ value: 0.62 (aluminum oxide, ethyl acetate/petroleum ether (3:1)).

3.1.d. [4-(2-diethylaminoethoxy)phenyl]methylamine 30 g (112.63 mmol) of methyl [4-(2-diethylaminoethoxy)phenyl]carbamate, dissolved in 300 mL of absolute THF, is slowly added dropwise to a suspension of 10.68 g (281.59 mmol) of lithium aluminum hydride in 600 mL of absolute THF while cooling with ice under a nitrogen atmosphere. Then the mixture is stirred for 14 hours, while the reaction mixture is allowed to come up to ambient temperature. Then, after the reaction has been monitored, 7 g of lithium aluminum hydride is added and the mixture is stirred for 14 hours. The reaction is stopped by the addition of 60 mL of 20% sodium hydroxide solution. The precipitate is filtered off and rinsed with diisopropyl ether. The filtrate is dried over sodium sulfate and the solvent is distilled off. Yield: 24.7 g (98.6% of theory); $C_{13}H_{22}N_2O$ (M=222.33); calc.: molecular ion peak $(M+H)^+$: 223; found: molecular ion peak $(M+H)^+$: 223; $R_f$ value: 0.44 (silica gel, dichloromethane/methanol/ammonia (10:1)).

3.1.e. 3-phenylpropynoic acid-[4-(2-diethylaminoethoxy)phenyl]methylamide

A solution of 0.29 g (2 mmol) of phenylpropynoic acid, 0.44 g (2 mmol) of [4-(2-diethylaminoethoxy)phenyl]methylamine, 0.7 g (2.2 mmol) of TBTU, 0.29 g (2.2 mmol) of HOBT and 0.51 mL (3 mmol) of Hünig base in 30 mL of THF and 2 mL of DMF is stirred for 14 hours at ambient temperature. The reaction mixture is evaporated down. The purification is carried out by column chromatography on silica gel (dichloromethane/methanol (80:20)). Yield: 130 mg (18.5% of theory); $C_{22}H_{26}N_2O_2$ (M=350.46); calc.: molecular ion peak $(M+H)^+$: 351; found: molecular ion peak $(M+H)^+$: 351; $R_f$ value: 0.39 (silica gel, dichloromethane/methanol (80:20)).

EXAMPLE 3.2

3-(4-methoxyphenyl)propynoic acid-[4-(2-diethylaminoethoxy)phenyl]methylamide

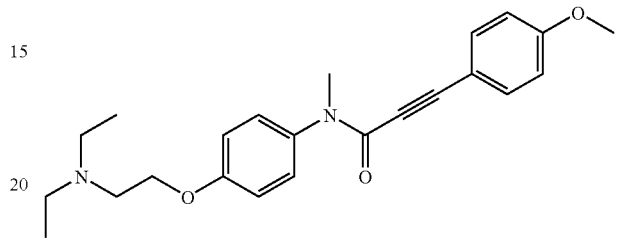

3.2.a. 3-(4-methoxyphenyl)propynoic acid-[4-(2-diethylaminoethoxy)phenyl]methylamide Prepared analogously to Example 3.1.e. from [4-(2-diethylaminoethoxy)phenyl]methylamine and (4-methoxyphenyl)propynoic acid in dichloromethane as solvent. Yield: 300 mg (46.3% of theory); $C_{23}H_{28}N_2O_3$ (M=380.49); calc.: molecular ion peak $(M+H)^+$: 381; found: molecular ion peak $(M+H)^+$: 381; $R_f$ value: 0.42 (silica gel, dichloromethane/methanol (80:20)).

EXAMPLE 3.3

3-(4-chlorophenyl)propynoic acid-[4-(2-diethylaminoethoxy)phenyl]methylamide

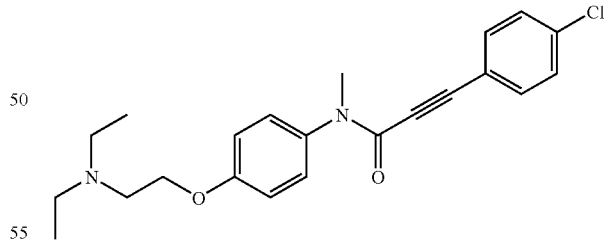

3.3.a. 3-(4-chlorophenyl)propynoic acid-[4-(2-diethylaminoethoxy)phenyl]methylamide Prepared analogously to Example 3.1.e. from [4-(2-diethylaminoethoxy)phenyl]methylamine and (4-chlorophenyl)propynoic acid in dichloromethane as solvent. Yield: 36 mg (5% of theory); $C_{22}H_{25}ClN_2O_2$ (M=384.91); calc.: molecular ion peak $(M+H)^+$: 385/387; found: molecular ion peak (M+H)⁺: 385/387; $R_f$ value: 0.4 (silica gel, dichloromethane/methanol/ammonia (90:10:1)).

EXAMPLE 3.4

3-(2,4-dichlorophenyl)propynoic acid-[4-(2-diethylaminoethoxy)phenyl]amide

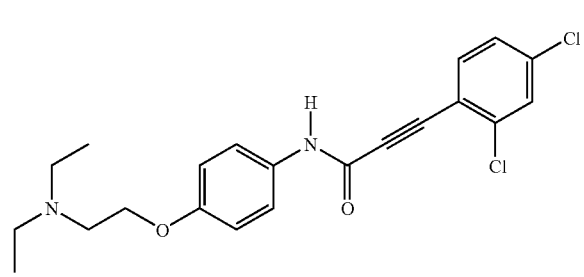

3.4.a. 2,3-dibromo-3-(2,4-dichlorophenyl)propanecarboxylic Acid 9.45 g (59.14 mmol) of bromine dissolved in 20 mL of carbon tetrachloride, is added dropwise at 0° C. to a suspension of 11.67 g (53.76 mmol) of 2,6-dichlorocinnamic acid in 500 mL of carbon tetrachloride and the mixture is stirred for 3 hours at ambient temperature. Then the solvent is distilled off and the residue is combined with petroleum ether. The solid is filtered off and dried in the circulating air dryer at 50° C. Yield: 19.22 g (94.9% of theory); melting point: 184° C.-185° C.; $C_9H_6Br_2Cl_2O_2$ (M=376.86).

3.4.b. (2,4-dichlorophenyl)propynoic Acid

A solution of 19.2 g (50.94 mmol) of 2,3-dibromo-3-(2,4-dichlorophenyl)propanecarboxylic acid in 130 mL of tert-butanol is combined batchwise with a total of 22.86 (203.78 mmol) of potassium tert-butoxide, so that the temperature does not exceed 40° C. Then the mixture is stirred for another 90 minutes at this temperature. The reaction mixture is poured into 2N hydrochloric acid and the precipitate is taken up in ethyl acetate. The organic phase is extracted three times with water and dried over sodium sulfate. The desiccant is filtered off and the solvent is distilled off. The residue is dried in the circulating air dryer at 80° C. Yield: 9.73 g (88.8% of theory); melting point: 168° C.-171° C.; $C_9H_4Cl_2O_2$ (M=215.03); $R_f$ value: 0.5 (silica gel, dichloromethane/ethanol/glacial acetic acid (10:1:0.1)).

3.4.c. 3-(2,4-dichlorophenyl)propynoic acid-[4-(2-diethylaminoethoxy)phenyl]amide Prepared analogously to Example 2.3.f. from 4-(2-diethylaminoethoxy)phenylamine and (2,4-dichlorophenyl)propynoic acid. Yield: 0.62 g (85% of theory); melting point: 107° C.-109° C.; $C_{21}H_{22}Cl_2N_2O_2$ (M=405.32); calc.: molecular ion peak (M+H)⁺: 405/407/409; found: molecular ion peak (M+H)⁺: 405/407/409; $R_f$ value: 0.6 (silica gel, dichloromethane/methanol/ammonia (5:1:0.1)).

EXAMPLE 3.5

3-(2,4-dichlorophenyl)propynoic acid-[4-(2-diethylaminopropoxy)phenyl]amide

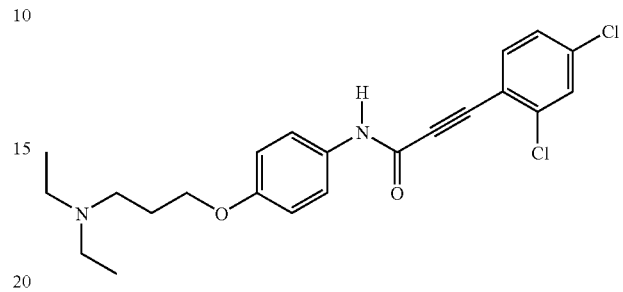

3.5.a; 3-(2,4-dichlorophenyl)propynoic acid-[4-(2-diethylaminopropoxy)phenyl]amide Prepared analogously to Example 3.4.c. from 4-(2-diethylaminopropoxy)phenylamine and (2,4-dichlorophenyl)propynoic acid. Yield: 0.41 g (65.2% of theory); melting point: 70° C.-72° C.; $C_{22}H_{24}Cl_2N_2O_2$ (M=419.35); calc.: molecular ion peak (M+H)⁺: 419/421/423; found: molecular ion peak (M+H)⁺: 419/421/423; $R_f$ value: 0.4 (silica gel, dichloromethane/ethanol/ammonia (5:1:0.01)).

EXAMPLE 3.6

3-(4'-chlorobiphenyl-4-yl)propynoic acid-(4-piperidin-1-ylmethylphenyl)amide

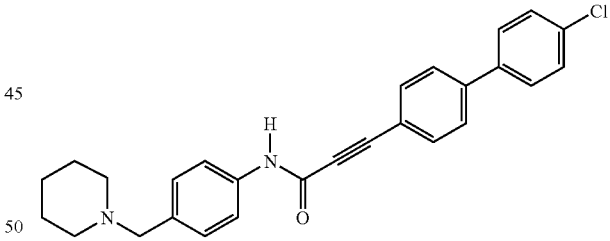

3.6.a. ethyl(E)-3-(4'-chlorobiphenyl-4-yl)acrylate 173 mg (0.15 mmol) of tetrakistriphenylphosphine palladium and 4.4 mL (8.8 mmol) of a 2M sodium carbonate solution is added at ambient temperature to a solution of 1.124 g (4.04 mmol) of ethyl (E)-3-(4-bromophenyl)acrylate in 50 mL of dioxane. 0.689 g (4.404 mmol) of 4-chlorophenylboric acid dissolved in 10 mL of methanol is added to this reaction mixture and refluxed for 5 hours. The reaction mixture is evaporated down, the residue is taken up in dichloromethane, and extracted with water. The organic phase is dried over sodium sulfate. The purification is carried out by column chromatography on silica gel (eluant: petroleum ether/ethyl acetate (9:1)). Yield: 0.94 g (74.4% of theory); $C_{17}H_{15}ClO_2$ (M=286.76); calc.: molecular ion peak (M+H)$^+$: 287/289; found: molecular ion peak (M+H)$^+$: 287/289; $R_f$ value: 0.44 (silica gel, petroleum ether/ethyl acetate (40:10)).

3.6.b. [(E)-3-(4'-chlorobiphenyl-4-yl)acrylic Acid 6.27 mL of a 1M sodium hydroxide solution is added to a solution of 0.9 g (3.13 mmol) of ethyl (E)-3-(4'-chlorobiphenyl-4-yl)acrylate in 30 mL of ethanol and stirred for 3 hours at ambient temperature. The reaction is stopped by the addition of 6.27 mL of 1N hydrochloric acid and the reaction mixture is stirred for 2 hours. Then the mixture is evaporated down, the residue is combined with water, and the precipitate is filtered off. The precipitate is repeatedly rinsed with water and dried at 80° C. in the vacuum drying chamber. Yield: 0.68 g (67% of theory); $C_{15}H_{11}ClO_2$ (M=258.70); calc.: molecular ion peak (M−H)$^-$: 257/259; found: molecular ion peak (M−H)$^-$: 257/259; $R_f$ value: 0.5 (silica gel, dichloromethane/methanol (90:10)).

3.6.c. (E)-3-(4'-chlorobiphenyl-4-yl)-N-(4-piperidin-1-ylmethylphenyl)acrylamide Prepared analogously to Example 3.1.e. from [(E)-3-(4'-chlorobiphenyl-4-yl)acrylic acid and 4-piperidin-1-ylmethylphenylamine. Yield: 0.57 g (62.9% of theory); melting point: 265° C.-270° C.; $C_{27}H_{27}ClN_2O$ (M=430.98); calc.: molecular ion peak (M+H)$^+$: 431/433; found: molecular ion peak (M+H)$^+$: 431/433; $R_f$ value: 0.31 (silica gel, dichloromethane/methanol (90:10)).

3.6.d. 2,3-dibromo-3-(4'-chlorobiphenyl-4-yl)-N-(4-piperidin-1-ylmethylphenyl)propionamide A suspension of 150 mg (0.348 mmol) of (E)-3-(4'-chlorobiphenyl-4-yl)-N-(4-piperidin-1-ylmethylphenyl)acrylamide in 15 mL of dichloromethane is combined with 0.02 mL (0.383 mmol) of bromine and stirred for 3 hours at ambient temperature. Then the reaction mixture is evaporated down, the residue is recrystallized from petroleum ether and dried at 70° C. in the vacuum drying chamber. Yield: 0.19 g (92.4% of theory); melting point: 145° C.-150° C.; $C_{27}H_{27}Br_2ClN_2O$ (M=590.79); calc.: molecular ion peak (M+H)$^+$: 589/591/593/595; found: molecular ion peak (M+H)$^+$: 589/591/593/595; $R_f$ value: 0.47 (silica gel, dichloromethane/methanol/ammonia (90:10:1)).

3.6.e. 3-(4'-chlorobiphenyl-4-yl)propynoic acid-(4-piperidin-1-ylmethylphenyl)amide Prepared analogously to Example 3.4.b. from 2.3-dibromo-3-(4'-chlorobiphenyl-4-yl)-N-(4-piperidin-1-ylmethylphenyl)propionamide. Yield: 26 mg (23.9% of theory); $C_{27}H_{25}ClN_2O$ (M=428.96); calc.: molecular ion peak (M+H)$^+$: 429/431; found: molecular ion peak (M+H)$^+$: 429/431; $R_f$ value: 0.42 (silica gel, dichloromethane/methanol/ammonia (90:10:1)).

EXAMPLE 3.7

3-(4'-chlorobiphenyl-4-yl)propynoic acid-(4-piperidin-1-ylmethylphenyl)methylamide

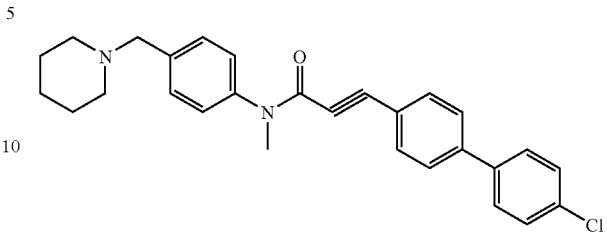

3.7.a. 2,3 dibromo-3-(4'-chlorobiphenyl-4-yl)propynoic Acid 3.3 mL (64.22 mmol) of bromine is added dropwise at ambient temperature to a suspension of 15 g (58 mmol) of 3-(4'-chlorobiphenyl-4-yl) acrylic acid in 370 mL of carbon tetrachloride and stirred for 3 hours at ambient temperature. The precipitate obtained is suction filtered, washed with petroleum ether and dried in the circulating air dryer at 70° C. Yield: 24 g (99% of theory); melting point: 230° C.-234° C.; $C_{15}H_{11}Br_2ClO_2$ (M=418.51); $R_f$ value: 0.2 (silica gel, dichloromethane/methanol (90:10)).

3.7.b. (4'-chlorobiphenyl-4-yl)propynoic Acid

A solution of 24 g (57.35 mmol) of 2,3-dibromo-3-(4'-chlorobiphenyl-4-yl) propynoic acid in 270 mL of THF is combined batchwise with 25.74 g (229.39 mmol) of potassium tert-butoxide so that the temperature does not exceed 40° C. Then the mixture is stirred for another 3.5 hours at this temperature. The reaction mixture is poured onto ice water/concentrated hydrochloric acid and the precipitate is taken up in ethyl acetate. The organic phase is washed with water and dried over sodium sulfate. The desiccant is filtered off and the solvent is distilled off. The residue is stirred with petroleum ether and suction filtered. Yield: 14.2 g (97% of theory); $C_{15}H_9ClO_2$ (M=256.68); $R_f$ value: 0.45 (silica gel, dichloromethane/methanol/glacial acetic acid (90:10:0.1)).

3.7.c. 3-(4'-chlorobiphenyl-4-yl)propynoic acid-(4-piperidin-1-ylmethylphenyl)methylamide A solution of 0.26 g (1 mmol) of (4'-chlorobiphenyl-4-yl) propynoic acid and 0.12 mL (1.1 mmol) of N-methylmorpholine in 20 mL of absolute THF is combined at −15° C. with 0.14 mL (1.1 mmol) of isobutyl chloroformate and stirred for ten minutes. Then 0.225 g (1.1 mmol) of methyl-(4-piperidin-1-ylmethylphenyl)amine dissolved in 10 mL of THF is added and the reaction mixture is stirred for 2 hours until it reaches ambient temperature. The reaction mixture is evaporated down and the residue is dissolved in dichloromethane. The organic phase is washed twice with water and then dried over sodium sulfate. The desiccant is filtered off and the solvent is distilled off. The residue is triturated with ether, suction filtered, and dried at 80° C. in the vacuum drying chamber. Yield: 220 mg (50% of theory); melting point: 237° C.-239° C.; $C_{28}H_{27}ClN_2O$ (M=442.98); calc.: molecular ion peak (M+H)⁺: 443/445 (Cl); found: molecular ion peak (M+H)⁺: 443/445 (Cl); R_f value: 0.5 (silica gel, dichloromethane/methanol (90:10)).

EXAMPLE 3.8

3-(4'-chlorobiphenyl-4-yl)propynoic acid-[4-(4-methylpiperazin-1-ylmethyl)phenyl]amide

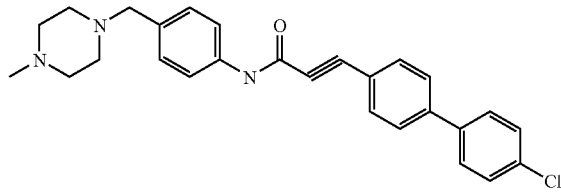

A solution of 0.26 g (1 mmol) of (4'-chlorobiphenyl-4-yl)propynoic acid and 0.12 mL (1.1 mmol) of N-methylmorpholine in 20 mL of absolute THF is combined at −15° C. with 0.14 mL (1.1 mmol) of isobutyl chloroformate and stirred for ten minutes. Then 0.226 g (1.1 mmol) of 4-(4-methylpiperazin-1-ylmethyl)phenylamine dissolved in 7 mL of THF is added and the reaction mixture is stirred for 2 hours until ambient temperature is reached. The reaction mixture is evaporated down and the residue is dissolved in dichloromethane. The organic phase is washed twice with water and then dried over sodium sulfate. The desiccant is filtered off and the solvent is distilled off. The residue is triturated with ether and suction filtered. The purification is carried out by column chromatography on silica gel (dichloromethane/methanol/ammonia (90:10:0.1)). Yield: 60 mg (14% of theory); melting point: 182° C.-185° C.; $C_{27}H_{26}ClN_3O$ (M=443.97); calc.: molecular ion peak (M+H)⁺: 444/446 (Cl); found: molecular ion peak (M+H)⁺: 444/446 (Cl); R_f value: 0.4 (silica gel, dichloromethane/methanolic ammonia (90:10:0.1)).

EXAMPLE 3.9

3-(4'-chlorobiphenyl-4-yl)propynoic acid-[4-(2,6-dimethylpiperidin-1-ylmethyl)phenyl]amide

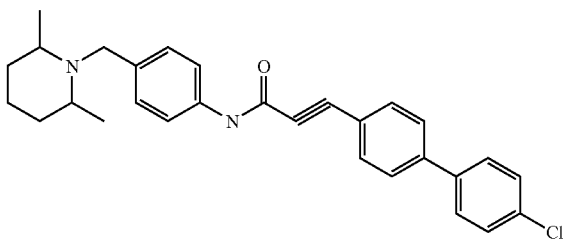

Prepared analogously to Example 3.8. from (4'-chlorobiphenyl-4-yl)propynoic acid and 4-(2,6-dimethylpiperidin-1-ylmethyl)phenylamine. Yield: 100 mg (22% of theory); melting point: 158° C.-163° C.; $C_{29}H_{29}ClN_2O$ (M=457.01); calc.: molecular ion peak (M+H)⁺: 458/460 (Cl); found: molecular ion peak (M+H)⁺: 458/460 (Cl); R_f value: 0.50 (silica gel, dichloromethane/methanolic ammonia (90:10:0.1)).

EXAMPLE 3.10

3-(4'-chlorobiphenyl-4-yl)propynoic acid-{4-[(cyclohexylmethylamino)methyl]phenyl}amide

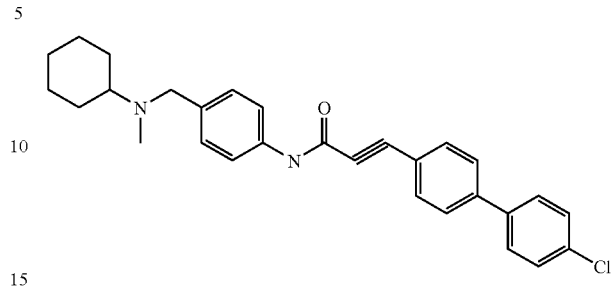

Prepared analogously to Example 3.8. from (4'-chlorobiphenyl-4-yl)propynoic acid and 4-[(cyclohexylmethylamino)methyl]phenylamine hydrochloride. Yield: 60 mg (13% of theory); melting point: 205° C.-210° C.; $C_{29}H_{29}ClN_2O$ (M=457.01); calc.: molecular ion peak (M+H)⁺: 457/459 (Cl); found: molecular ion peak (M+H)⁺: 457/459 (Cl); R_f value: 0.60 (silica gel, dichloromethane/methanol (90:10)).

EXAMPLE 3.11

3-(4'-chlorobiphenyl-4-yl)propynoic acid-(4-{[(2-methoxyethyl)methylamino]methyl}phenyl)amide

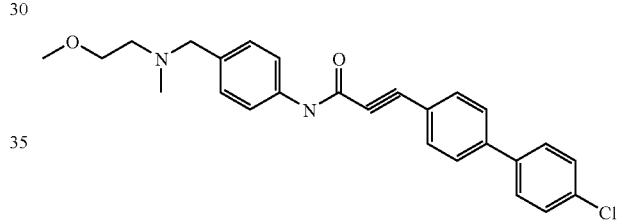

Prepared analogously to Example 3.8. from (4'-chlorobiphenyl-4-yl)propynoic acid and 4-{[(2-methoxyethyl)methylamino]methyl}phenylamine. Yield: 150 mg (35% of theory); melting point: 130° C.-133° C.; $C_{26}H_{25}ClN_2O_2$ (M=432.94); calc.: molecular ion peak (M+H)⁺: 433/435 (Cl); found: molecular ion peak (M+H)⁺: 433/435 (Cl); R_f value: 0.50 (silica gel, dichloromethane/methanol/ammonia (90:10:1)).

EXAMPLE 3.12

3-(4'-chlorobiphenyl-4-yl)propynoic acid-[4-(3,5-dimethylpiperidin-1-ylmethyl)phenyl]amide

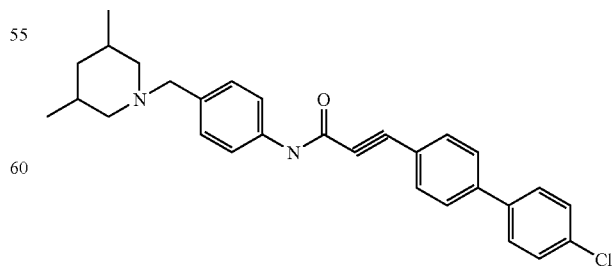

A solution of 0.26 g (1 mmol) of (4'-chlorobiphenyl-4-yl)propynoic acid and 0.12 mL (1.1 mmol) of N-methylmorpholine in 20 mL of absolute THF is combined with 0.14 mL (1.1 mmol) of isobutyl chloroformate at −15° C. and stirred for ten minutes. Then 0.240 mg (1.1 mmol) of 4-[(3,5-dimethylcyclohexylamino)methyl]phenylamine dissolved in 7 mL of THF is added and the reaction mixture is stirred for 16 hours. The reaction mixture is evaporated down. The purification is carried out by column chromatography on silica gel (dichloromethane/methanol=90/10). Yield: 300 mg (66% of theory); melting point: 209° C.-214° C.; $C_{29}H_{29}ClN_2O$ (M=457.01); calc.: molecular ion peak $(M+H)^+$: 457/459 (Cl); found: molecular ion peak $(M+H)^+$: 457/459 (Cl); $R_f$ value: 0.60 (silica gel, dichloromethane/methanol (90:10)).

The following compounds are prepared analogously to Example 3.12:

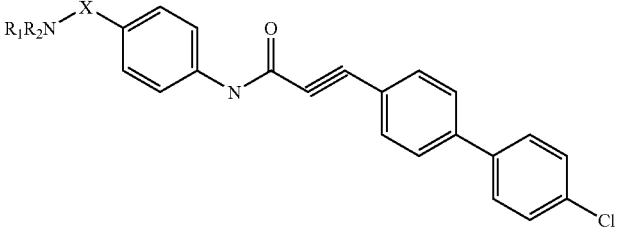

| Example | $R_1R_2N$-X | educt | empirical formula | mass spectrum | mp [° C.] | $R_f$ value |
|---|---|---|---|---|---|---|
| 3.13 | 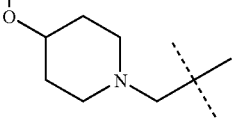 | 3.7.b | $C_{28}H_{27}ClN_2O_2$ | 459/461 (Cl) $[M + H]^+$ | 227-234 | 0.6 (B) |
| 3.14 | 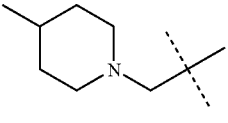 | 3.7.b | $C_{28}H_{27}ClN_2O$ | 443/445 (Cl) $[M + H]^+$ | 263-268 | 0.5 (B) |
| 3.15 | 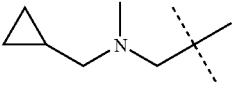 | 3.7.b | $C_{27}H_{25}ClN_2O$ | 429/431 (Cl) $[M + H]^+$ | 164-167 | 0.5 (A) |
| 3.16 | 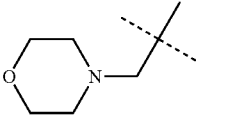 | 3.7.b | $C_{26}H_{23}ClN_2O_2$ | 431/433 (Cl) $[M + H]^+$ | 180-184 | 0.4 (B) |
| 3.17 | 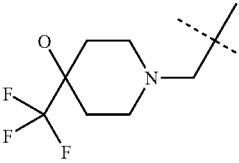 | 3.7.b | $C_{28}H_{24}ClF_3N_2O_2$ | 513/515 (Cl) $[M + H]^+$ | 194-200 | 0.5 (B) |

$R_f$ value:
A = silica gel, dichloromethane/methanol/ammonia (90:10:0.1)
B = silica gel, dichloromethane/methanol (90:10)

EXAMPLE 3.18

3-(4'-chlorobiphenyl-4-yl)propynoic acid-[4-(4-hydroxypiperidin-1-ylmethyl)phenyl]amide

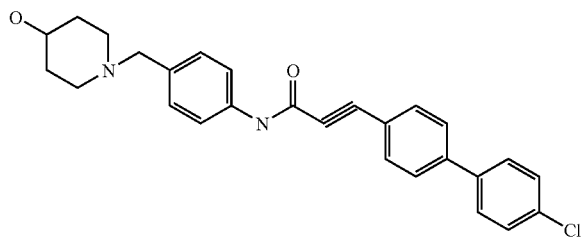

3.18.a 4-(4-nitrobenzyl)piperidin-4-ol 137 mL (0.983 mol) of triethylamine is added to a solution of 41.5 g (0.410 mol) of 4-hydroxypiperidine in 500 mL of dichloromethane. Then 56.28 g (0.328 mol) of 4-nitrobenzylchloride is slowly added. The reaction mixture is boiled for 12 hours. The solid formed is suction filtered, the filtrate is washed twice with water and dried over magnesium sulfate. The solvent is evaporated down. Yield: 66.45 g (86% of theory); $C_{12}H_{16}N_2O_3$ (M=236.27); calc.: molecular ion peak $(M+H)^+$: 237; found: molecular ion peak $(M+H)^+$: 237.

3.18.b. 4-(4-aminobenzyl)piperidin-4-ol 6.6 g of Raney nickel is added to a solution of 66.45 g (0.281 mol) of 4-(4-nitrobenzyl)piperidin-4-ol in 660 mL of methanol. The reaction mixture is hydrogenated for 13 hours at ambient temperature and 3 bar hydrogen. The catalyst is filtered off and the filtrate is evaporated down. Yield: 64.5 g (111% of theory); $C_{12}H_{18}N_2O$ (M=206.28); calc.: molecular ion peak $(M+H)^+$: 207; found: molecular ion peak $(M+H)^+$: 207.

3.18.c. 4-[4-(tert-butyldimethylsilanyloxy)piperidin-1-ylmethyl]phenylamine 3.3 g (22 mmol) of tert-butyldimethylchlorosilane is added to a solution of 4.13 g (20 mmol) of 4-(4-aminobenzyl)piperidin-4-ol and 3.4 g (50 mmol) of imidazole in 30 mL of DMF. The reaction mixture is stirred for 16 hours at ambient temperature. Then the solvent is evaporated down and extracted between ether and water. The organic phase is dried over sodium sulfate and evaporated down. The purification is carried out by column chromatography on aluminum oxide (eluant: petroleum ether/ethyl acetate (90:10)). Yield: 1.65 g (26% of theory); $C_{18}H_{32}N_2OSi$ (M=320.55); calc.: molecular ion peak $(M+H)^+$: 321; found: molecular ion peak $(M+H)^+$: 321; $R_f$ value: 0.80 (aluminum oxide, petroleum ether/ethyl acetate (1:1)).

3.18.d. 3-(4'-chlorobiphenyl-4-yl)propynoic acid-{4-[(4-hydroxycyclohexylamine)methyl]phenyl}amide A solution of 0.26 g (1 mmol) of (4'-chlorobiphenyl-4-yl)propynoic acid and 0.12 mL (1.1 mmol) of N-methylmorpholine in 20 mL of absolute THF is combined with 0.14 mL (1.1 mmol) of isobutyl chloroformate at −15° C. and stirred for ten minutes. Then 0.350 g (1.1 mmol) of 4-[4-(tert-butyldimethylsilanyloxy)piperidin-1-ylmethyl]phenylamine dissolved in 7 mL of THF is added and the reaction mixture is stirred for 4 hours. The reaction mixture is evaporated down. The residue is dissolved in 30 mL of THF and combined with 0.95 g (3 mmol) of tetrabutylammonium fluoride hydrate. The reaction mixture is stirred for 16 hours at ambient temperature. Then another 0.5 g (1.5 mmol) of tetrabutylammonium fluoride hydrate is added and the mixture is stirred for another 16 hours at ambient temperature. The last step is repeated twice more. Then the solvent is evaporated down and the residue is extracted between dichloromethane and water. The organic phase is dried over sodium sulfate, the desiccant is filtered off and the filtrate is evaporated down. The purification is carried out by column chromatography on silica gel (dichloromethane/methanol (90/10)). Yield: 100 mg (23% of theory); melting point: 243° C.-247° C.; $C_{27}H_{25}ClN_2O_2$ (M=444.95); calc.: molecular ion peak $(M+H)^+$: 445/447 (Cl); found: molecular ion peak $(M+H)^+$: 445/447 (Cl); $R_f$ value: 0.40 (silica gel, dichloromethane/methanol/ammonia (90:10:1)).

EXAMPLE 3.19

3-(4'-chlorobiphenyl-4-yl)propynoic acid-[1-(2-pyrrolidin-1-ylethyl)-1H-indol-5-yl]amide

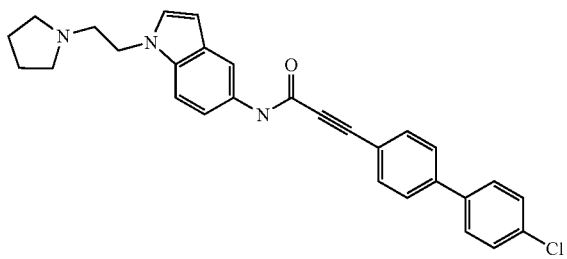

3.19.a. 5-nitro-1-(2-pyrrolidin-1-ylethyl)-1H-indole

A reaction mixture of 16.22 g (0.1 mol) of 5-nitroindole, 35 g (0.205 mol) of 1-(2-chloroethyl)pyrrolidine hydrochloride, and 51 g (0.369 mol) of potassium carbonate in 500 mL of DMF is stirred for 48 hours at ambient temperature and then filtered. The filtrate is evaporated down, the residue dissolved in dichloromethane and dried over sodium sulfate. The desiccant is filtered off and the filtrate is evaporated down. Yield: 25 g (96.3% of theory); $C_{14}H_{17}N_3O_2$ (M=259.31); calc.: molecular ion peak $(M+H)^+$: 260; found: molecular ion peak $(M+H)^+$: 260; $R_f$ value: 0.65 (silica gel, dichloromethane/methanol/ammonia (90:10:1)).

3.19.b. 5-amino-1-(2-pyrrolidin-1-ylethyl)-1H-indole

Prepared analogously to Example 3.1.b. from 5-nitro-1-(2-pyrrolidin-1-ylethyl)-1H-indole in THF as solvent. Yield: 0.83 g (93.9% of theory); $C_{14}H_{19}N_3$ (M=229.32); calc.: molecular ion peak (M+H)$^+$: 230; found: molecular ion peak (M+H)$^+$: 230; $R_f$ value: 0.37 (silica gel, dichloromethane/methanol/ammonia (90:10:1)).

3.19.c. 3-(4'-chlorobiphenyl-4-yl)propynoic acid-[1-(2-pyrrolidin-1-ylethyl)-1H-indol-5-yl]amide Prepared analogously to Example 3.7.c. from 5-amino-1-(2-pyrrolidin-1-ylethyl)-1H-indole and (4'-chlorobiphenyl-4-yl)propynoic acid in THF as solvent. Yield: 230 mg (49% of theory); $C_{29}H_{26}ClN_3O$ (M=467.99); melting point: 224° C.-227° C.; calc.: molecular ion peak (M+H)$^+$: 468/470 (Cl); found: molecular ion peak (M+H)$^+$: 468/470 (Cl); $R_f$ value: 0.4 (silica gel, dichloromethane/methanol (90:10)).

EXAMPLE 3.20

3-(4'-chlorobiphenyl-4-yl)propynoic acid-(3-chloro-4-piperidin-1-ylmethylphenyl)amide

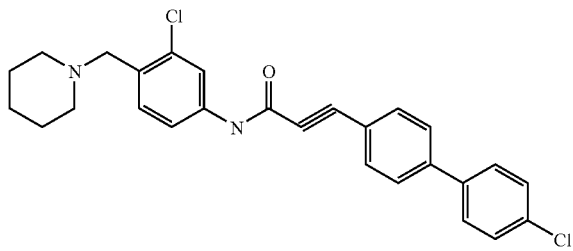

3.20.a. (2-chloro-4-nitrophenyl)methanol 35.9 g (0.22 mol) of 1,1'-carbonyldiimidazole is slowly added to a solution of 41.1 g (0.2 mol) of 2-chloro-4-nitrobenzoic acid in 400 mL of THF. The reaction mixture is stirred for 1.5 hours at 35° C. Then the green reaction mixture is cooled down using ice and at maximum 20° C. combined dropwise with a solution of 26.5 g (0.7 mol) of sodium borohydride in 400 mL of water. After 1.5 hours stirring, the reaction mixture is diluted with 200 mL of water and then neutralized with 250 mL of semiconcentrated hydrochloric acid. It is stirred for 1 hour, then extracted twice with ethyl acetate and the organic phase is dried over sodium sulfate. The desiccant is filtered off and the solvent is evaporated down. The residue is crystallized with petroleum ether, suction filtered, and dried at 50° C. in the drying chamber. Yield: 37.66 g (100% of theory); melting point: 62° C.-64° C.; $C_7H_6ClNO_3$ (M=187.58); calc.: molecular ion peak (M+H)$^+$: 187/189 (Cl); found: molecular ion peak (M+H)$^+$: 187/189 (Cl); $R_f$ value: 0.70 (silica gel, dichloromethane/methanol (90:10)).

3.20.b. 2-chloro-1-chloromethyl-4-nitrobenzene 11.6 mL (160 mmol) of thionyl chloride and 1 mL of DMF are added to a solution of 15 g (80 mmol) of 2-chloro-4-nitrophenyl)methanol in 300 mL of dichloromethane and the whole lot is refluxed for 2 hours. Then the solvent is evaporated down and the residue is dissolved in ethyl acetate and washed with water. The organic phase is dried over sodium sulfate, the desiccant is filtered off, and the filtrate is evaporated down. Oily product. Yield: 16.8 g (102% of theory); $C_7H_5Cl_2NO_2$ (M=206.03); calc.: molecular ion peak (M+H)$^+$: 205/7/9 (Cl$_2$); found: molecular ion peak (M+H)$^+$: 205/7/9 (Cl$_2$); $R_f$ value: 0.90 (silica gel, dichloromethane/methanol (90:10)).

3.20.c. 1-(2-chloro-4-nitrobenzyl)piperidine 2 g (9.71 mmol) of 2-chloro-1-chloromethyl-4-nitrobenzene is slowly added to 4 mL (40.04 mmol) of piperidine at ambient temperature. After 15 minutes, the reaction mixture is combined with ethyl acetate and washed twice with water. The organic phase is dried over sodium sulfate, the desiccant is filtered off, and the filtrate is evaporated down. Oily product. Yield: 2.39 g (97% of theory); $C_{12}H_{15}ClN_2O_2$ (M=254.71); $R_f$ value: 0.30 (silica gel, petroleum ether/ethyl acetate (6:1)).

3.20.d. 3-chloro-4-piperidin-1-ylmethylphenylamine 0.4 g of Raney nickel is added to a solution of 2.37 g (9.31 mmol) of 1-(2-chloro-4-nitrobenzyl)piperidine in 100 mL of THF and hydrogenated at ambient temperature and 3 bar hydrogen. After hydrogen uptake has ended, the catalyst is filtered off and the filtrate is evaporated down. Yield: 1.88 g (90% of theory); $C_{12}H_{17}ClN_2$ (M=224.73); calc.: molecular ion peak (M+H)$^+$: 255/7 (Cl); found: molecular ion peak (M+H)$^+$: 255/7 (Cl); $R_f$ value: 0.20 (silica gel, dichloromethane/methanol (90:10)).

3.20.e. 3-(4'-chlorobiphenyl-4-yl)propynoic acid(3-chloro-4-piperidin-1-ylmethylphenyl)amide Prepared analogously to Example 3.7.c. from (4'-chlorobiphenyl-4-yl)propynoic acid and 3-chloro-4-piperidin-1-ylmethylphenylamine. Yield: 0.1 g (22% of theory); melting point: 277° C.-281° C.; $C_{27}H_{24}Cl_2N_2O$ (M=463.4); calc.: molecular ion peak (M+H)$^+$: 463/5/7 (Cl$_2$); found: molecular ion peak (M+H)$^+$: 463/5/7 (Cl$_2$); $R_f$ value: 0.50 (silica gel, dichloromethane/methanol (90:10)).

The following compounds are prepared analogously to Example 3.20:

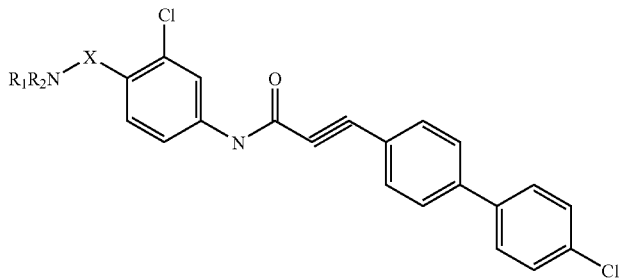

| Example | R₁R₂N-X | educt | empirical formula | mass spectrum | mp [° C.] | $R_f$ value |
|---|---|---|---|---|---|---|
| 3.21 | | 3.7.b | $C_{29}H_{28}Cl_2N_2O$ | 491/3/5 (Cl₂) [M + H]⁺ | 282-286 | 0.5 (A) |
| 3.22 | | 3.7.b | $C_{27}H_{24}Cl_2N_2O_2$ | 479/81/83 (Cl₂) [M + H]⁺ | 197-203 | 0.5 (B) |
| 3.23 | | 3.7.b | $C_{27}H_{24}Cl_2O_2$ | 479/81/83 (Cl₂) [M + H]⁺ | 204-209 | 0.45 (B) |

$R_f$ value:
A = (silica gel, dichloromethane/methanol (90:10)
B = (silica gel, dichloromethane/methanol/ammonia (90:10:0.1)

EXAMPLE 3.24

3-(4'-chlorobiphenyl-4-yl)propynoic acid-[3-chloro-4-(2-dimethylaminoethoxy)phenyl]amide hydrochloride

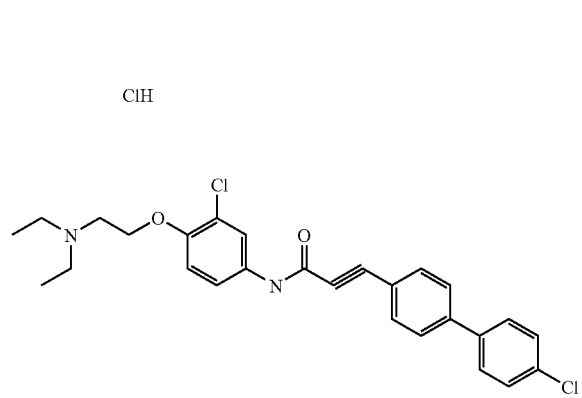

Prepared analogously to Example 3.7.c. from (4'-chlorobiphenyl-4-yl)propynoic acid and 3-chloro-4-(2-diethylaminoethoxy)phenylamine. Yield: 0.28 g (58% of theory); melting point: 226° C.-233° C.; $C_{27}H_{26}Cl_2N_2O_2$ (M=481.41)*HCl; calc.: molecular ion peak (M+H)⁺: 481/3/5 (Cl₂); found: molecular ion peak (M+H)⁺: 481/3/5 (Cl₂); $R_f$ value: 0.45 (silica gel, dichloromethane/methanol (90:10)).

EXAMPLE 3.25

3-[5-(4-chlorophenyl)pyridin-2-yl]propynoic acid-(4-piperidin-1-ylmethylphenyl)amide

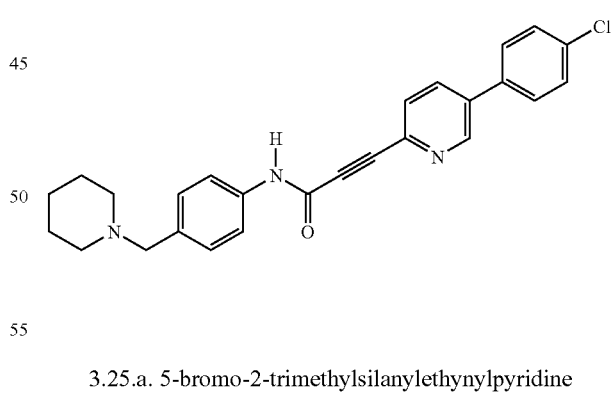

3.25.a. 5-bromo-2-trimethylsilanylethynylpyridine 1.15 g (1.63 mmol) of tetrakistriphenylphosphine palladium, 0.311 g (1.63 mmol) of copper (1) iodide, and 50 mL of triethylamine are added to a solution of 20 g (81.89 mmol) of 2,5-dibromopyridine in 250 mL of absolute THF under an argon atmosphere. At 17° C., a solution of 13 mL (90.14 mmol) of trimethylsilylacetylene in 20 mL of THF is immediately added dropwise to this reaction mixture. After ten minutes, the cooling is removed. After 20 minutes, the temperature is 30° C. The mixture is then cooled to 20° C. and briefly stirred. The reaction mixture is evaporated down, the residue is taken up in ethyl acetate and extracted twice with sodium hydrogen carbonate solution. The combined organic phases are dried over magnesium sulfate. The purification is carried out by column chromatography on silica gel (eluant: petroleum ether). Yield: 20.4 g (98% of theory); $C_{10}H_{12}BrNSi$ (M=254.20); calc.: molecular ion peak $(M+H)^+$: 254/256; found: molecular ion peak $(M+H)^+$: 254/256; $R_f$ value: 0.72 (silica gel, petroleum ether).

3.25.b. 5-(4-chlorophenyl)-2-trimethylsilanylethynylpyridine

In an argon atmosphere, 6.93 g (6 mmol) of tetrakistriphenylphosphine palladium and 17 mL of a 2M sodium carbonate solution are added to a solution of 20.4 g (80.25 mmol) of 5-bromo-2-trimethylsilanylethynylpyridine and 26.33 g (160 mmol) of 4-chlorophenylboric acid in 350 mL of dioxane and the reaction mixture is stirred for 5 hours at 90° C., while every 30 minutes 7 mL of 2M sodium carbonate solution is added. Then at ambient temperature, 1000 mL of ethyl acetate is added, and the mixture is extracted twice with 400 mL of sodium hydrogen carbonate solution. The organic phase is dried over magnesium sulfate. The purification is carried out by column chromatography on silica gel (eluant: petroleum ether to petroleum ether/ethyl acetate (9:1)). Yield: 7.9 g (34.4% of theory); $C_{16}H_{16}ClNSi$ (M=285.85); calc.: molecular ion peak $(M-H)^-$: 286/288; found: molecular ion peak $(M-H)^-$: 286/288; $R_f$ value: 0.6 (silica gel, petroleum ether/ethyl acetate (8:2)).

3.25.c. 5-(4-chlorophenyl)-2-ethynylpyridine

A reaction mixture of 7.4 g (25.88 mmol) of 5-(4-chlorophenyl)-2-trimethylsilanylethynylpyridine and 7.18 g (52 mmol) of potassium carbonate in 80 mL of methanol is stirred for 30 minutes at ambient temperature. 500 mL of dichloromethane is added and the reaction mixture is extracted with water and sodium hydrogen carbonate solution. The combined organic phases are dried over magnesium sulfate. The purification is carried out by column chromatography on silica gel (eluant: petroleum ether to petroleum ether/ethyl acetate (8:2)). Yield: 2 g (36.2% of theory); $C_{13}H_8ClN$ (M=213.66); calc.: molecular ion peak $(M+H)^+$: 214/216; found: molecular ion peak $(M+H)^+$: 214/216.

3.25.d. [5-(4-chlorophenyl)pyridin-2-yl]propynoic acid 1.6 mL (2.46 mmol) of butyllithium solution (1.6M in hexane) are added dropwise at −10° C. to a solution of 0.5 g (2.34 mmol) of 5-(4-chlorophenyl)-2-ethynylpyridine in 30 mL of absolute THF and the mixture is stirred for five minutes at −8° C. stirred. The reaction mixture is combined with dry ice batchwise at −70° C., stirred for 1 hour at ambient temperature, and evaporated down. The residue is suspended in 5 mL of water and combined with 1.6 mL of 1N hydrochloric acid, whereupon a precipitate is formed. Then ethyl acetate is added and the suspension is filtered. The solid is dried in the vacuum drying chamber at 70° C. Yield: 0.25 g (41.5% of theory); melting point: 210° C.; $C_{14}H_8ClNO_2$ (M=257.67); calc.: molecular ion peak $(M+H)^+$: 258/260; found: molecular ion peak $(M+H)^+$: 258/260.

3.25.e. 3-[5-(4-chlorophenyl)pyridin-2-yl]propynoic acid-(4-piperidin-1-ylmethylphenyl)amide Prepared analogously to Example 2.3.f. from [5-(4-chlorophenyl)pyridin-2-yl]propynoic acid and 4-piperidin-1-ylmethylphenylamine. Yield: 0.2 g (48% of theory); $C_{26}H_{24}ClN_3O$ (M=429.95); calc.: molecular ion peak $(M+H)^+$: 430/432; found: molecular ion peak $(M+H)^+$: 430/432; $R_f$ value: 0.4 (silica gel, dichloromethane/methanol/ammonia (90:10:0.1)).

The following compounds are prepared analogously to Example 3.25:

| Example | $R_1R_2N$-X | educt | empirical formula | mass spectrum | mp [° C.] | $R_f$ value |
|---|---|---|---|---|---|---|
| 3.26 | 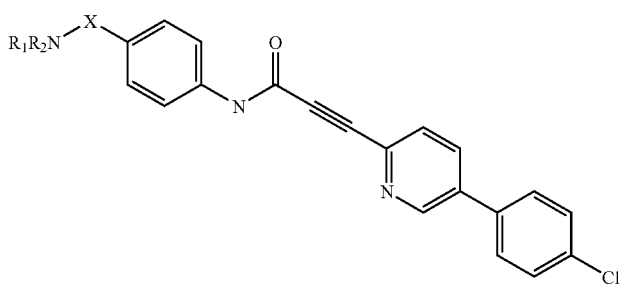 | 3.24.d | $C_{27}H_{26}ClN_3O_2$ | 460/462 (Cl) $[M+H]^+$ | 155-159 | 0.6 (A) |

-continued

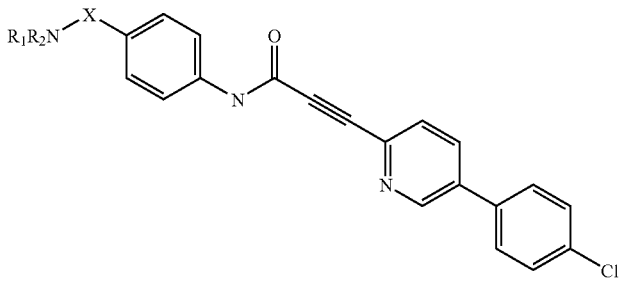

| Example | R₁R₂N-X | educt | empirical formula | mass spectrum | mp [° C.] | Rf-value |
|---|---|---|---|---|---|---|
| 3.27 | | 3.24.d | $C_{27}H_{26}ClN_3O$ | 444/446 (Cl) [M + H]⁺ | 183-185 | 0.7 (B) |
| 3.28 | | 3.24.d | $C_{26}H_{24}ClN_3O$ | 430/432 (Cl) [M + H]⁺ | 158-161 | 0.6 (B) |
| 3.29 | | 3.24.d | $C_{28}H_{28}ClN_3O$ | 458/460 (Cl) [M + H]⁺ | 195-197 | 0.7 (B) |
| 3.30 | | 3.24.d | $C_{26}H_{23}Cl_2N_3O$ | 464/66/68 (Cl₂) [M + H]⁺ | 150-153 | 0.6 (B) |
| 3.31 | | 3.24.d | $C_{28}H_{27}Cl_2N_3O$ | 492/94/96 (Cl₂) [M + H]⁺ | 180-185 | 0.8 (B) |

Rf-value:
A = (silica gel, dichloromethane/methanol (90:10))
B = (silica gel, dichloromethane/methanol/ammonia (90:10:0.1))

EXAMPLE 3.32

3-(3-chlorobiphenyl-4-yl)propynoic acid-[3-chloro-4-(2-diethylaminoethoxy)phenyl]amide hydrochloride

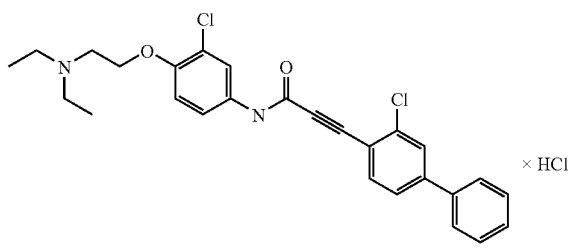

3.32.a. trifluoromethanesulfonic acid 3-chlorobiphenyl-4-yl ester 6.7 mL (40.32 mmol) of trifluoromethanesulfonic acid anhydride dissolved in 5 mL dichloromethane is added dropwise between −10° C. to −5° C. to a solution of 7.5 g (36.65 mmol) of 3-chlorobiphenyl-4-ol and 6.1 mL (44 mmol) of triethylamine in 100 mL of dichloromethane. Then the mixture is stirred for 30 minutes. The reaction solution is then extracted with water, the organic phase is separated off and filtered through an Alox frit. The filtrate is concentrated by evaporation. Yield: 12 g (97% of theory); $C_{13}H_8ClF_3O_3S$ (M=336.72); calc.: molecular ion peak (M+H)⁺: 336/338 (Cl); found: molecular ion peak (M+H)⁺: 336/338 (Cl); Rf value: 0.7 (silica gel, petroleum ether/ethyl acetate (5:1)).

3.32.b. tert-butyl-(3-chlorobiphenyl-4-ylethynyl) dimethylsilane 0.84 g (1.2 mmol) of bis-(triphenylphosphine)palladium (II) chloride, 0.23 g (1.2 mmol) of copper (I) iodide, and 6.28 mL (33.6 mmol) of (tert-butyldimethylsilyl)acetylene is added under an argon atmosphere to a solution of 8.1 g (24 mmol) of 3-chlorobiphenyl-4-yl trifluoromethanesulfonate in 50 mL of absolute DMF and 13.31 mL (96 mmol) of triethylamine.

At ambient temperature, the reaction mixture is stirred for 24 hours. Then the reaction mixture is evaporated down, the residue is taken up in ethyl acetate and extracted with water. The organic phase is dried. The purification is carried out by column chromatography on silica gel (eluant: petroleum ether/ethyl acetate (4:1)). Yield: 8.4 g (107% of theory); $C_{20}H_{23}ClSi$ (M=326.94); calc.: molecular ion peak (M+H)$^+$: 327/329 (Cl); found: molecular ion peak (M+H)$^+$: 327/329 (Cl); R$_f$ value: 0.7 (silica gel, petroleum ether/toluene (9:1)).

3.32.c. 3-chloro-4-ethynylbiphenyl 7.85 g (24 mmol) of tert-butyl-(3-chlorobiphenyl-4-ylethynyl)dimethylsilane is dissolved in 150 mL of absolute THF and at 5° C. combined batchwise with 11.4 g (36 mmol) of tetrabutylammonium fluoride*3H$_2$O. The reaction mixture reaches ambient temperature after 30 minutes. Then the solvent is evaporated down and the residue is extracted between ether and water. The organic phase is dried, combined with activated charcoal and filtered through CELITE® filter aid. The filtrate is evaporated down. The purification is carried out by column chromatography on silica gel (eluant: petroleum ether/ethyl acetate (20:1)). Yield: 4.7 g (92% of theory); $C_{14}H_9Cl$ (M=212.67); R$_f$ value: 0.6 (silica gel, petroleum ether/toluene (5:1)).

3.32.d. (3-chlorobiphenyl-4-yl)propynoic acid 13.8 mL (22.1 mmol) of butyllithium solution (1.6M in hexane) are added dropwise to a solution of 4.7 g (22.1 mmol) of 3-chloro-4-ethynylbiphenyl in 100 mL of absolute THF at −10° C. to −20° C. and after five minutes cooled to −60° C. At this temperature dry ice is added batchwise to the reaction mixture and it is slowly allowed to come up to ambient temperature. Then the solvent is evaporated down and the residue is extracted between ethyl acetate and 1M hydrochloric acid. The organic phase is dried, the desiccant filtered off, and the solvent concentrated by evaporation. The residue is stirred with petroleum ether, suction filtered, and dried at 80° C. in the circulating air dryer. Yield: 4.8 g (85% of theory); $C_{15}H_9ClO_2$ (M=256.68); calc.: molecular ion peak (M+H)$^+$: 257/259 (Cl); found: molecular ion peak (M+H)$^+$: 257/259 (Cl); R$_f$ value: 0.2 (silica gel, dichloromethane/methanol/glacial acetic acid (90:10:0.1)).

3.32.e. 3-(3-chlorobiphenyl-4-yl)propynoic acid-[3-chloro-4-(2-diethylaminoethoxy)phenyl]amide hydrochloride Prepared analogously to Example 3.8.a. from (3-chlorobiphenyl-4-yl)propynoic acid and 3-chloro-4-(2-diethylaminoethoxy)phenylamine. Yield: 0.35 g (68% of theory); melting point: 195° C.-200° C.; $C_{27}H_{26}Cl_2N_2O_2$*HCl (M=517.87); calc.: molecular ion peak (M+H)$^+$: 481/3/5 (Cl$_2$); found: molecular ion peak (M+H)$^+$: 481/3/5 (Cl$_2$); R$_f$ value: 0.6 (silica gel, dichloromethane/methanol/ammonia (90:10:0.1)).

EXAMPLE 3.33

3-(3-chlorobiphenyl-4-yl)propynoic acid-(4-piperidin-1-ylmethylphenyl)amide hydrochloride

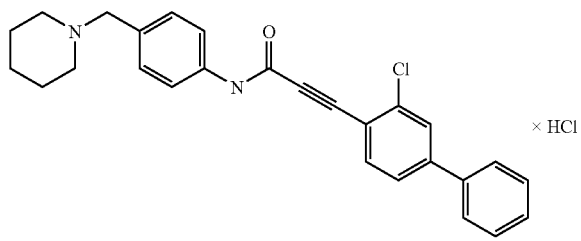

Prepared analogously to Example 3.8 from (3-chlorobiphenyl-4-yl)propynoic acid and 4-piperidin-1-ylmethylphenylamine. Yield: 0.35 g (75% of theory); melting point: 260° C.-265° C.; $C_{27}H_{25}ClN_2O$*HCl (M=465.41); calc.: molecular ion peak (M+H)$^+$: 429/31 (Cl); found: molecular ion peak (M+H)$^+$: 429/31 (Cl); R$_f$ value: 0.6 (silica gel, dichloromethane/methanol/ammonia (90:10:0.1)).

EXAMPLE 3.34

3-(2,4-dichlorophenyl)propynoic acid-[4-(2-diethylaminoethyl)phenyl]amide hydrochloride

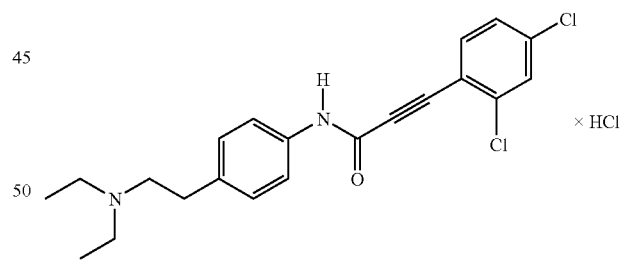

3.34.a. 3-(2,4-dichlorophenyl)propynoic acid-[4-(2-diethylaminoethyl)phenyl]amide hydrochloride Prepared analogously to Example 2.3.f. from 4-(2-diethylaminoethyl)phenylamine and (2,4-dichlorophenyl)propynoic acid. Yield: 0.3 g (47% of theory); melting point: 204° C.-208° C.; $C_{21}H_{22}Cl_2N_2O$ (M=425.78); calc.: molecular ion peak (M+H)$^+$: 389/391/393; found: molecular ion peak (M+H)$^+$: 389/391/393; R$_f$ value: 0.6 (silica gel, dichloromethane/ethanol/ammonia (5:1:0.01)).

EXAMPLE 3.35

3-(2-chloro-4-trifluoromethylphenyl)propynoic acid-[4-(2-diethylaminoethyl)phenyl]amide

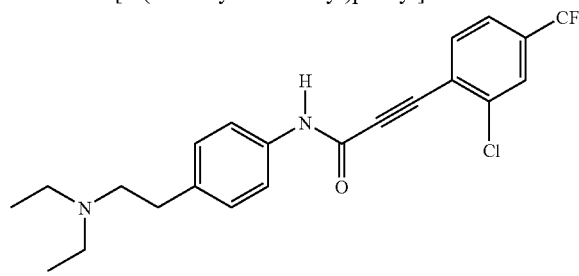

Prepared analogously to Example 2.3.f. from 90 mg (0.44 mmol) of 4-(2-diethylaminoethyl)phenylamine and 99 mg (0.40 mmol) of 2-chloro-4-trifluoromethylphenyl)propynoic acid. Yield: 71 mg (42% of theory); melting point: 145° C.-150° C.; $C_{22}H_{22}ClF_3N_2O$ (M=422.88); calc.: molecular ion peak $(M+H)^+$: 423/425; found: molecular ion peak $(M+H)^+$: 423/425; $R_f$ value: 0.30 (silica gel, dichloromethane/methanol (9:1)).

EXAMPLE 3.36

3-(2-chloro-4-trifluoromethylphenyl)propynoic acid-{4-[N-(2-dimethylaminoethyl)methylamino]phenyl}amide formate

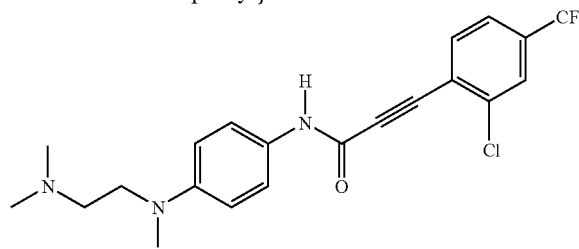

Prepared analogously to Example 2.3.f. from 90 mg (0.44 mmol) of 4-[N-(2-dimethylaminoethyl)methylamino]phenylamine (for preparation see International Patent Application WO 01/27081) and 99 mg (0.40 mmol) of 2-chloro-4-trifluoromethylphenyl)propynoic acid. Yield: 64 mg (38% of theory); $C_{21}H_{21}ClF_3N_3O*CH_2O_2$ (M=469.89); calc.: molecular ion peak $(M+H)^+$: 424/426; found: molecular ion peak $(M+H)^+$: 424/426; $R_f$ value: 0.35 (silica gel, dichloromethane/methanol (9:1)).

EXAMPLE 3.37

3-(2-chloro-4-trifluoromethylphenyl)propynoic acid-[4-(2-diethylaminopropoxy)phenyl]amide

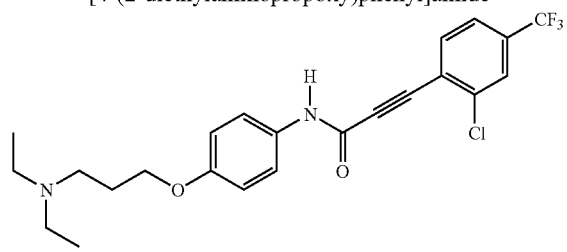

Prepared analogously to Example 2.3.f. from 67 mg (0.3 mmol) of 4-(2-diethylaminopropoxy)phenylamine and 75 mg (0.3 mmol) of (2-chloro-4-trifluoromethylphenyl)propynoic acid. Yield: 71 mg (52% of theory); melting point: 172° C.-176° C.; $C_{23}H_{24}ClF_3N_2O_2$ (M=452.90); calc.: molecular ion peak $(M+H)^+$: 453/455; found: molecular ion peak $(M+H)^+$: 453/455; $R_f$ value: 0.30 (silica gel, dichloromethane/methanol (9:1)).

EXAMPLE 3.38

3-(2-chloro-4-trifluoromethylphenyl)propynoic acid-[4-(2-diethylaminoethoxy)phenyl]amide

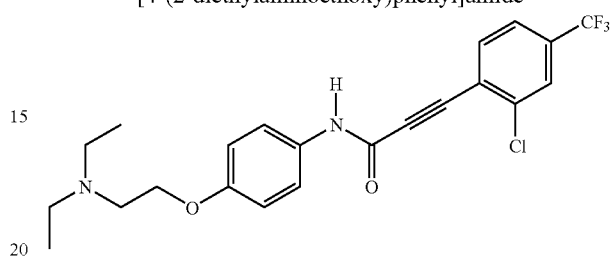

Prepared analogously to Example 2.3.f. from 69 mg (0.33 mmol) of 4-(2-diethylaminoethoxy)phenylamine and 75 mg (0.30 mmol) of (2-chloro-4-trifluoromethylphenyl)propynoic acid. Yield: 70 mg (53% of theory); melting point: 194° C.-197° C.; $C_{22}H_{22}ClF_3N_2O_2$ (M=438.88); calc.: molecular ion peak $(M+H)^+$: 439/441; found: molecular ion peak $(M+H)^+$: 439/441; $R_f$ value: 0.35 (silica gel, dichloromethane/methanol=(9:1)).

EXAMPLE 3.39

3-(2-chloro-4-methylphenyl)propynoic acid-[4-(2-diethylaminoethoxy)phenyl]methylamide

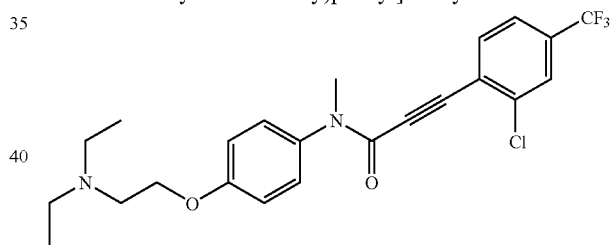

Prepared analogously to Example 2.3.f. from [4-(2-diethylaminoethoxy)phenyl]methylamine and (2-chloro-4-trifluoromethylphenyl)propynoic acid. Yield: 60 mg (22% of theory); melting point: 135° C.-138° C.; $C_{23}H_{24}ClF_3N_2O_2$ (M=452.90); calc.: molecular ion peak $(M+H)^+$: 453/455; found: molecular ion peak $(M+H)^+$: 453/455; $R_f$ value: 0.4 (silica gel, dichloromethane/methanol (9:1)).

EXAMPLE 3.40

3-(2-chloro-4-trifluoromethylphenyl)propynoic acid-(4-diethylaminomethylphenyl)amide

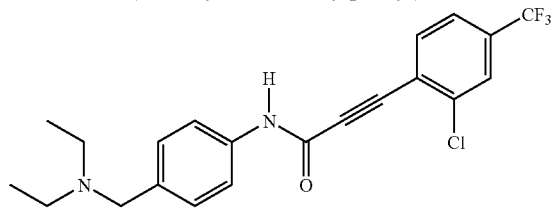

Prepared analogously to Example 2.3.f. from 4-diethylaminomethylphenylamine and (2-chloro-4-trifluoromethylphenyl)propynoic acid. Yield: 72 mg (59% of theory);

$C_{21}H_{20}ClF_3N_2O$ (M=408.85); calc.: molecular ion peak $(M+H)^+$: 409/411; found: molecular ion peak $(M+H)^+$: 409/411; $R_f$ value: 0.35 (silica gel, dichloromethane/methanol (9:1)).

EXAMPLE 3.41

3-(2-chloro-4-trifluoromethylphenyl)propynoic acid (4-piperidin-1-ylmethylphenyl)amide hydrochloride

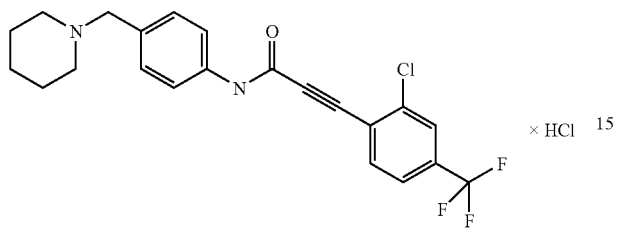

Prepared analogously to Example 2.3.f. from 4-piperidin-1-ylmethylphenylamine and (2-chloro-4-trifluoromethylphenyl)propynoic acid. Yield: 170 mg (40% of theory); $C_{22}H_{20}ClF_3N_2O$ (M=420.86); melting point: 193° C.-195° C.; calc.: molecular ion peak $(M-H)^-$: 419/421(Cl); found: molecular ion peak $(M-H)^-$: 419/421 (Cl); $R_f$ value: 0.5 (silica gel, dichloromethane/methanol (9:1)).

EXAMPLE 3.42

3-(2-chloro-4-trifluoromethylphenyl)propynoic acid-[4-(2-pyrazol-1-ylethoxy)phenyl]amide

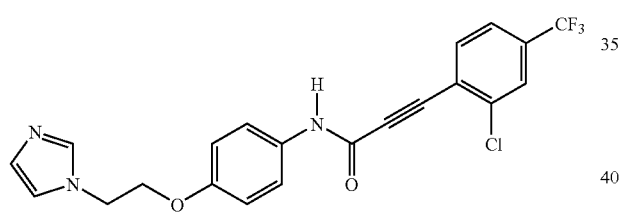

Prepared analogously to Example 2.3.f from 4-(2-imidazol-1-ylethoxy)phenylamine and (2-chloro-4-trifluoromethylphenyl)propynoic acid. Yield: 78 mg (60% of theory); melting point: 182° C.-186° C.; $C_{21}H_{15}ClF_3N_3O_2$ (M=433.82); calc.: molecular ion peak $(M+H)^+$: 434/436; found: molecular ion peak $(M+H)^+$: 434/436; $R_f$ value: 0.33 (silica gel, dichloromethane/methanol (9:1)).

EXAMPLE 3.43

3-(2-chloro-4-trifluoromethylphenyl)propynoic acid-[4-(2-pyrazol-1-ylethoxy)phenyl]amide

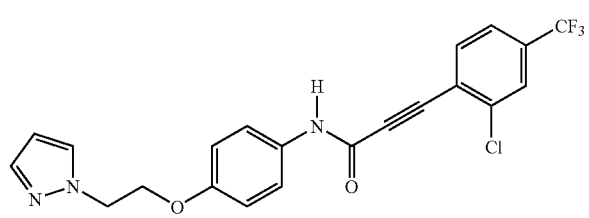

Prepared analogously to Example 2.3.f. from 4-(2-pyrazol-1-ylethoxy)phenylamine and (2-chloro-4-trifluorometh-ylphenyl)propynoic acid. Yield: 56 mg (43% of theory); melting point: 120° C.-125° C.; $C_{21}H_{15}ClF_3N_3O_2$ (M=433.82); calc.: molecular ion peak $(M+H)^+$: 434/436; found: molecular ion peak $(M+H)^+$: 434/436; $R_f$ value: 0.6 (silica gel, dichloromethane/methanol (9:1)).

EXAMPLE 3.44

3-(2-chloro-4-trifluoromethylphenyl)propynoic acid-[4-(2-[1.2.4]triazol-4-ylethoxy)phenyl]amide

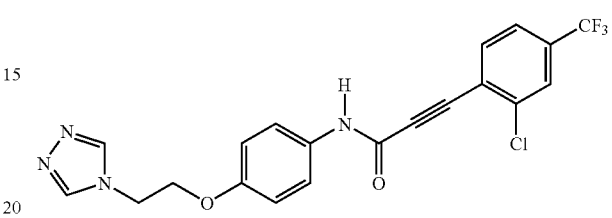

Prepared analogously to Example 2.3.f. from 4-(2-[1.2.4]triazol-4-ylethoxy)phenylamine and (2-chloro-4-trifluoromethylphenyl)propynoic acid. Yield: 51 mg (39.4% of theory); melting point: 223° C.-227° C.; $C_{20}H_{14}ClF_3N_4O_2$ (M=434.80); calc.: molecular ion peak $(M+H)^+$: 435/437; found: molecular ion peak $(M+H)^+$: 435/437; $R_f$ value: 0.31 (silica gel, dichloromethane/methanol (9:1)).

EXAMPLE 3.45

3-(2-chloro-4-trifluoromethylphenyl)propynoic acid {4-[2-(4-methylpiperidin-1-yl)ethoxy]phenyl}amide hydrochloride

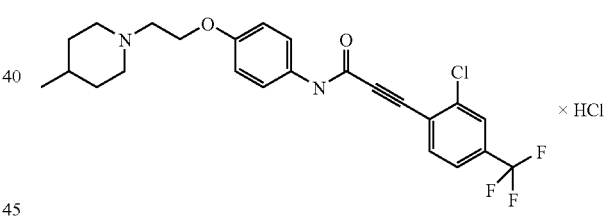

3.45.a.
4-methyl-1-[2-(4-nitrophenoxy)ethyl]piperidine 200 mg (4.2 mmol) of sodium hydride (55%) is added at 0° C. to a solution of 0.54 g (3.83 mmol) of 1-fluoro-4-nitrobenzene and 0.6 g (4.2 mmol) of 2-(4-methylpiperidin-1-yl)ethanol in 10 mL of DMF under an argon atmosphere. The reaction mixture is stirred for 2 hours at 0° C. and then stirred for a further 1.5 hours at ambient temperature. The reaction mixture is evaporated down and the residue is extracted between water and ethyl acetate. The organic phase is dried, the desiccant is filtered off and the filtrate is evaporated down. The purification is carried out by column chromatography on silica gel (eluant: dichloromethane/methanol (9:1)). Yield: 700 mg (69% of theory); $C_{14}H_{20}N_2O_3$ (M=264.32); calc.: molecular ion peak $(M+H)^+$: 265; found: molecular ion peak $(M+H)^+$: 265; $R_f$ value: 0.7 (silica gel, dichloromethane/methanol (9:1)).

3.45.b.
4-[2-(4-methylpiperidin-1-yl)ethoxy]phenylamine

A reaction mixture of 680 mg (2.57 mmol) of 4-methyl-1-[2-(4-nitrophenoxy)ethyl]piperidine and 80 mg palladium (10% on charcoal) in 10 mL of methanol is hydrogenated at ambient temperature and 3 bar hydrogen for 4.5 hours. The catalyst is suction filtered and the filtrate is evaporated down. Yield: 540 mg (90% of theory); $C_{14}H_{22}N_2O$ (M=234.34); calc.: molecular ion peak (M+H)$^+$: 235; found: molecular ion peak (M+H)$^+$: 235; $R_f$ value: 0.33 (silica gel, dichloromethane/methanol/ammonia (90:10:0.1)).

3.45.c. 3-(2-chloro-4-trifluoromethylphenyl)propynoic acid {4-[2-(4-methylpiperidin-1-yl)ethoxy]phenyl}amide hydrochloride Prepared analogously to Example 3.7.c. from 4-[2-(4-methylpiperidin-1-yl)ethoxy]phenylamine and (2-chloro-4-trifluoromethylphenyl)propynoic acid. Yield: 230 mg (49% of theory); $C_{24}H_{24}ClF_3N_2O_2$ (M=464.91)*HCl; melting point: 240° C.-245° C.; calc.: molecular ion peak (M+H)$^+$: 465/467 (Cl); found: molecular ion peak (M+H)$^+$: 465/467 (Cl); $R_f$ value: 0.6 (silica gel, dichloromethane/methanol (9:1)).

The following compounds are prepared analogously to the Examples mentioned above:

| Example | R₁R₂N-X | L1 | L2 | B | Q |
|---|---|---|---|---|---|
| 3.52 | (CH₃)(H₃C)N-CH₂-C(CH₃)₂- | —H | —H | 4-Cl-C₆H₄- | CH |
| 3.53 | (H₃C-CH₂)₂N-CH₂-C(CH₃)₂- | —H | —H | 4-Cl-C₆H₄- | CH |
| 3.54 | pyrrolidin-1-yl-CH₂-C(CH₃)₂- | —H | —H | 4-Cl-C₆H₄- | CH |
| 3.55 | 2,5-dihydro-1H-pyrrol-1-yl-CH₂-C(CH₃)₂- | —H | —H | 4-Cl-C₆H₄- | CH |
| 3.56 | (2-hydroxymethyl)pyrrolidin-1-yl-CH₂-C(CH₃)₂- | —H | —H | 4-Cl-C₆H₄- | CH |
| 3.57 | thiomorpholin-4-yl-CH₂-C(CH₃)₂- | —H | —H | 4-Cl-C₆H₄- | CH |

-continued

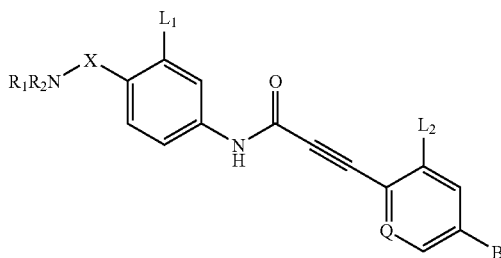

| Example | R₁R₂N-X | L1 | L2 | B | Q |
|---|---|---|---|---|---|
| 3.58 | 4-hydroxy-4-methylpiperidin-1-yl-CH₂C(CH₃)₂- | —H | —H | 4-chlorophenyl | CH |
| 3.59 | 3-hydroxypiperidin-1-yl-CH₂C(CH₃)₂- | —H | —H | 4-chlorophenyl | CH |
| 3.60 | (3R,4R)-3,4-dihydroxy-4-methylpiperidin-1-yl-CH₂C(CH₃)₂- | —H | —H | 4-chlorophenyl | CH |
| 3.61 | 4-carbamoylpiperidin-1-yl-CH₂C(CH₃)₂- | —H | —H | 4-chlorophenyl | CH |
| 3.62 | 1,2,3,4-tetrahydroisoquinolin-2-yl-CH₂C(CH₃)₂- | —H | —H | 4-chlorophenyl | CH |
| 3.63 | N-benzyl-N-ethylamino-CH₂C(CH₃)₂- | —H | —H | 4-chlorophenyl | CH |
| 3.64 | azetidin-1-yl-CH₂C(CH₃)₂- | —H | —H | 4-chlorophenyl | CH |
| 3.65 | azepan-1-yl-CH₂C(CH₃)₂- | —H | —H | 4-chlorophenyl | CH |

-continued
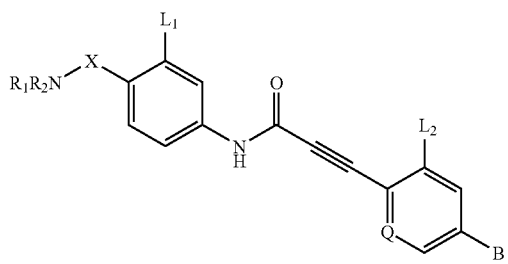
| Example | R₁R₂N-X | L1 | L2 | B | Q |
|---|---|---|---|---|---|
| 3.66 | (CH₃)₂CHCH₂-NH- (isobutyl-NH) | —H | —H | 4-Cl-phenyl | CH |
| 3.67 | (isobutyl)₂N- | —H | —H | 4-Cl-phenyl | CH |
| 3.68 | cyclopropylmethyl-NH- | —H | —H | 4-Cl-phenyl | CH |
| 3.69 | cyclopropylmethyl(n-propyl)N- | —H | —H | 4-Cl-phenyl | CH |
| 3.70 | cyclopropylmethyl(cyclopentyl)N- | —H | —H | 4-Cl-phenyl | CH |
| 3.71 | bis(cyclopropylmethyl)N- | —H | —H | 4-Cl-phenyl | CH |
| 3.72 | (CH₃)₂N- | —Cl | —H | 4-Cl-phenyl | CH |
| 3.73 | (C₂H₅)₂N- | —Cl | —H | 4-Cl-phenyl | CH |

-continued

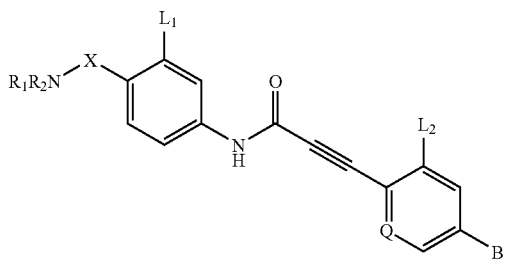

| Example | R₁R₂N-X | L1 | L2 | B | Q |
|---|---|---|---|---|---|
| 3.74 | pyrrolidine-CH₂C(CH₃)₂- | —Cl | —H | 4-chlorophenyl | CH |
| 3.75 | 2,5-dihydropyrrole-CH₂C(CH₃)₂- | —Cl | —H | 4-chlorophenyl | CH |
| 3.76 | 2-(hydroxymethyl)pyrrolidine-CH₂C(CH₃)₂- | —Cl | —H | 4-chlorophenyl | CH |
| 3.78 | 3,5-dimethylpiperidine-CH₂C(CH₃)₂- | —Cl | —H | 4-chlorophenyl | CH |
| 3.79 | 2,6-dimethylpiperidine-CH₂C(CH₃)₂- | —Cl | —H | 4-chlorophenyl | CH |
| 3.80 | morpholine-CH₂C(CH₃)₂- | —Cl | —H | 4-chlorophenyl | CH |
| 3.81 | thiomorpholine-CH₂C(CH₃)₂- | —Cl | —H | 4-chlorophenyl | CH |
| 3.82 | 4-methoxypiperidine-CH₂C(CH₃)₂- | —Cl | —H | 4-chlorophenyl | CH |

-continued

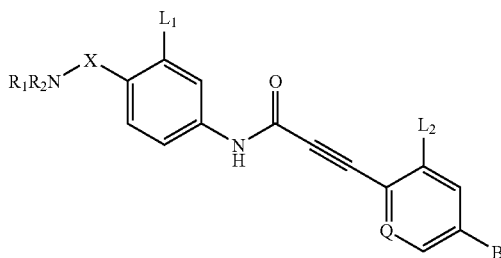

| Example | R₁R₂N-X | L1 | L2 | B | Q |
|---|---|---|---|---|---|
| 3.83 | 4-hydroxy-4-methylpiperidin-1-yl-CH₂C(CH₃)₂– | —Cl | —H | 4-chlorophenyl | CH |
| 3.84 | (3R,4R)-3,4-dihydroxy-4-methylpiperidin-1-yl-CH₂C(CH₃)₂– | —Cl | —H | 4-chlorophenyl | CH |
| 3.85 | 4-carbamoylpiperidin-1-yl-CH₂C(CH₃)₂– | —Cl | —H | 4-chlorophenyl | CH |
| 3.86 | 1,2,3,4-tetrahydroisoquinolin-2-yl-CH₂C(CH₃)₂– | —Cl | —H | 4-chlorophenyl | CH |
| 3.87 | N-benzyl-N-ethylamino-CH₂C(CH₃)₂– | —Cl | —H | 4-chlorophenyl | CH |
| 3.88 | 4-methylpiperazin-1-yl-CH₂C(CH₃)₂– | —Cl | —H | 4-chlorophenyl | CH |
| 3.89 | azetidin-1-yl-CH₂C(CH₃)₂– | —Cl | —H | 4-chlorophenyl | CH |
| 3.90 | azepan-1-yl-CH₂C(CH₃)₂– | —Cl | —H | 4-chlorophenyl | CH |

-continued
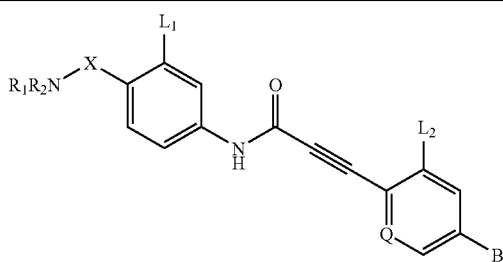
| Example | R₁R₂N-X | L1 | L2 | B | Q |
|---|---|---|---|---|---|
| 3.91 | isobutyl-NH- (neopentyl) | —Cl | —H | 4-Cl-phenyl | CH |
| 3.92 | diisobutyl-N- | —Cl | —H | 4-Cl-phenyl | CH |
| 3.93 | cyclopropylmethyl-NH- | —Cl | —H | 4-Cl-phenyl | CH |
| 3.94 | cyclopropylmethyl-N(CH₃)- | —Cl | —H | 4-Cl-phenyl | CH |
| 3.95 | cyclopropylmethyl-N(propyl)- | —Cl | —H | 4-Cl-phenyl | CH |
| 3.96 | cyclopropylmethyl-N(cyclopentyl)- | —Cl | —H | 4-Cl-phenyl | CH |
| 3.97 | bis(cyclopropylmethyl)-N- | —Cl | —H | 4-Cl-phenyl | CH |
| 3.98 | (CH₃)₂N- | —H | —H | 4-Cl-phenyl | N |

-continued

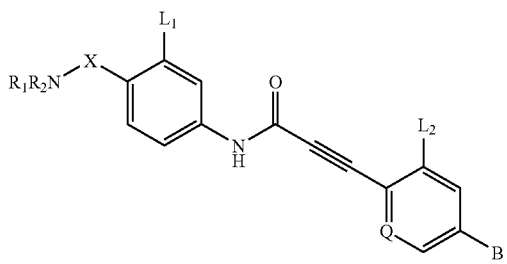

| Example | R₁R₂N-X | L1 | L2 | B | Q |
|---|---|---|---|---|---|
| 3.99 | H₃C\N(CH₂CH₃)CH₂- (N,N-diethylaminomethyl) | —H | —H | 4-Cl-phenyl | N |
| 3.100 | pyrrolidin-1-ylmethyl | —H | —H | 4-Cl-phenyl | N |
| 3.101 | 2,5-dihydro-1H-pyrrol-1-ylmethyl | —H | —H | 4-Cl-phenyl | N |
| 3.102 | (2-(hydroxymethyl)pyrrolidin-1-yl)methyl | —H | —H | 4-Cl-phenyl | N |
| 3.103 | (2,6-dimethylpiperidin-1-yl)methyl | —H | —H | 4-Cl-phenyl | N |
| 3.104 | morpholin-4-ylmethyl | —H | —H | 4-Cl-phenyl | N |
| 3.105 | thiomorpholin-4-ylmethyl | —H | —H | 4-Cl-phenyl | N |
| 3.106 | (4-hydroxy-4-methylpiperidin-1-yl)methyl | —H | —H | 4-Cl-phenyl | N |

-continued

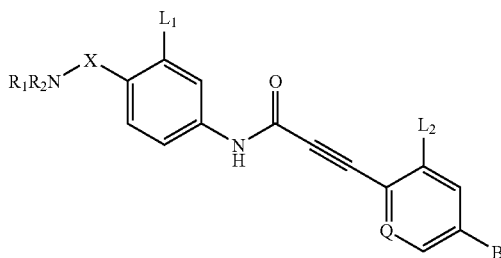

| Example | R₁R₂N-X | L1 | L2 | B | Q |
|---|---|---|---|---|---|
| 3.108 | 3-hydroxypiperidin-1-yl (HO on piperidine) | —H | —H | 4-chlorophenyl | N |
| 3.109 | 3,4-dihydroxy-4-methylpiperidin-1-yl | —H | —H | 4-chlorophenyl | N |
| 3.110 | 4-carbamoylpiperidin-1-yl | —H | —H | 4-chlorophenyl | N |
| 3.111 | 1,2,3,4-tetrahydroisoquinolin-2-yl | —H | —H | 4-chlorophenyl | N |
| 3.112 | N-benzyl-N-ethylamino | —H | —H | 4-chlorophenyl | N |
| 3.113 | 4-methylpiperazin-1-yl | —H | —H | 4-chlorophenyl | N |
| 3.114 | azetidin-1-yl | —H | —H | 4-chlorophenyl | N |
| 3.115 | azepan-1-yl | —H | —H | 4-chlorophenyl | N |

-continued
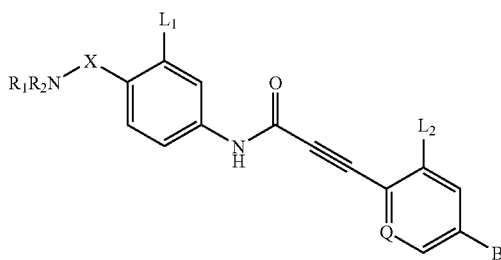
| Example | R₁R₂N-X | L1 | L2 | B | Q |
|---|---|---|---|---|---|
| 3.116 | (CH₃)₂CHCH₂-NH- (isobutylamino) | —H | —H | 4-Cl-phenyl | N |
| 3.117 | (iBu)₂N- (diisobutylamino) | —H | —H | 4-Cl-phenyl | N |
| 3.118 | cyclopropylmethyl-NH- | —H | —H | 4-Cl-phenyl | N |
| 3.119 | cyclopropylmethyl(propyl)N- | —H | —H | 4-Cl-phenyl | N |
| 3.120 | cyclopropylmethyl(cyclopentyl)N- | —H | —H | 4-Cl-phenyl | N |
| 3.121 | bis(cyclopropylmethyl)N- | —H | —H | 4-Cl-phenyl | N |
| 3.122 | (CH₃)₂N- | —Cl | —H | 4-Cl-phenyl | N |
| 3.123 | (Et)₂N- | —Cl | —H | 4-Cl-phenyl | N |

-continued

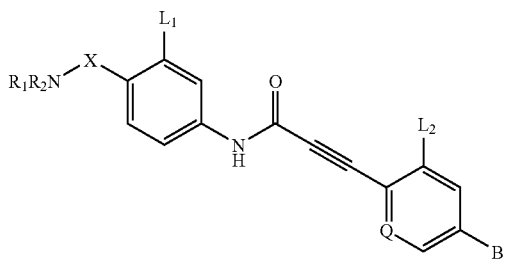

| Example | R₁R₂N-X | L1 | L2 | B | Q |
|---|---|---|---|---|---|
| 3.124 | pyrrolidine-CH₂- | —Cl | —H | 4-chlorophenyl | N |
| 3.125 | 2,5-dihydropyrrole-CH₂- | —Cl | —H | 4-chlorophenyl | N |
| 3.126 | 2-(hydroxymethyl)pyrrolidine-CH₂- | —Cl | —H | 4-chlorophenyl | N |
| 3.127 | 4-methylpiperazine-CH₂- | —Cl | —H | 4-chlorophenyl | N |
| 3.128 | 3,5-dimethylpiperidine-CH₂- | —Cl | —H | 4-chlorophenyl | N |
| 3.129 | 2,6-dimethylpiperidine-CH₂- | —Cl | —H | 4-chlorophenyl | N |
| 3.130 | morpholine-CH₂- | —Cl | —H | 4-chlorophenyl | N |
| 3.131 | thiomorpholine-CH₂- | —Cl | —H | 4-chlorophenyl | N |

-continued

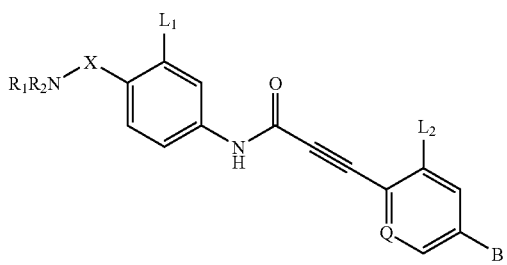

| Example | R₁R₂N-X | L1 | L2 | B | Q |
|---|---|---|---|---|---|
| 3.132 | 4-MeO-piperidin-1-ylmethyl | —Cl | —H | 4-chlorophenyl | N |
| 3.133 | 4-hydroxy-4-methyl-piperidin-1-ylmethyl | —Cl | —H | 4-chlorophenyl | N |
| 3.134 | 4-hydroxy-piperidin-1-ylmethyl | —Cl | —H | 4-chlorophenyl | N |
| 3.135 | 3-hydroxy-piperidin-1-ylmethyl | —Cl | —H | 4-chlorophenyl | N |
| 3.136 | 3,4-dihydroxy-4-methyl-piperidin-1-ylmethyl | —Cl | —H | 4-chlorophenyl | N |
| 3.137 | 4-carbamoyl-piperidin-1-ylmethyl | —Cl | —H | 4-chlorophenyl | N |
| 3.138 | 1,2,3,4-tetrahydroisoquinolin-2-ylmethyl | —Cl | —H | 4-chlorophenyl | N |
| 3.139 | N-benzyl-N-ethylaminomethyl | —Cl | —H | 4-chlorophenyl | N |

-continued
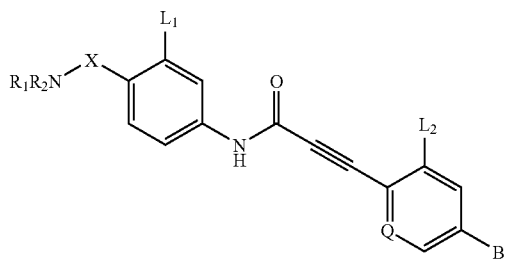
| Example | R₁R₂N-X | L1 | L2 | B | Q |
|---|---|---|---|---|---|
| 3.140 | 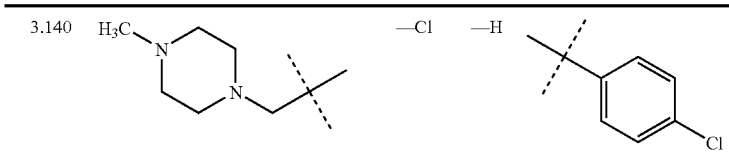 | —Cl | —H | 4-Cl-phenyl | N |
| 3.141 |  | —Cl | —H | 4-Cl-phenyl | N |
| 3.142 |  | —Cl | —H | 4-Cl-phenyl | N |
| 3.143 | 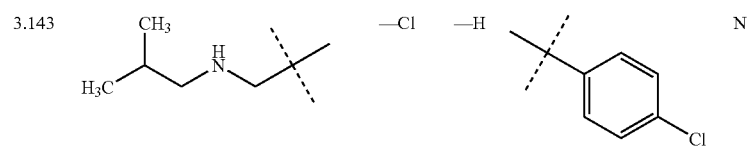 | —Cl | —H | 4-Cl-phenyl | N |
| 3.144 | 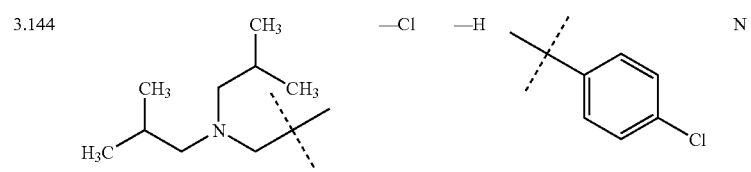 | —Cl | —H | 4-Cl-phenyl | N |
| 3.145 | 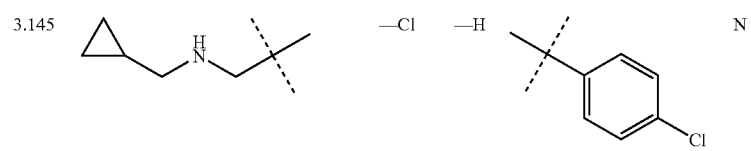 | —Cl | —H | 4-Cl-phenyl | N |
| 3.146 | 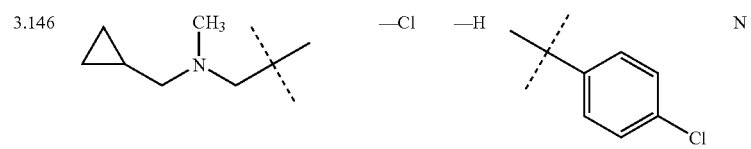 | —Cl | —H | 4-Cl-phenyl | N |
| 3.147 | 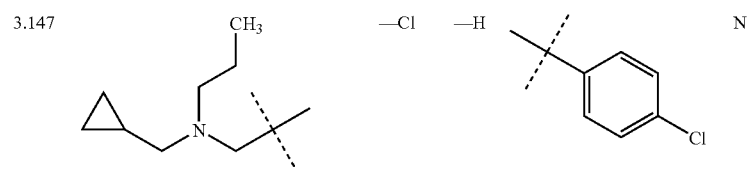 | —Cl | —H | 4-Cl-phenyl | N |

-continued
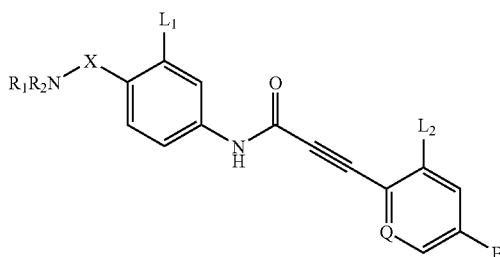
| Example | R₁R₂N-X | L1 | L2 | B | Q |
|---|---|---|---|---|---|
| 3.148 | 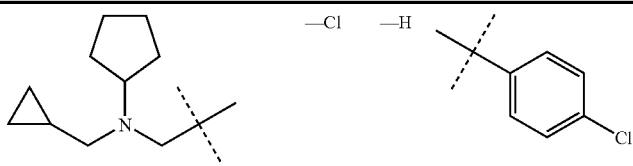 | —Cl | —H | 4-Cl-phenyl | N |
| 3.149 | 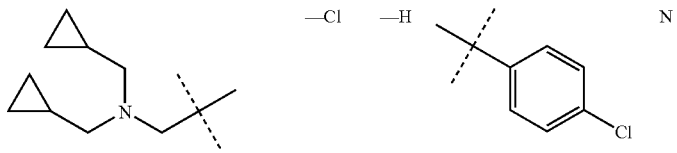 | —Cl | —H | 4-Cl-phenyl | N |
The following compounds are prepared analogously to Example 3.20:
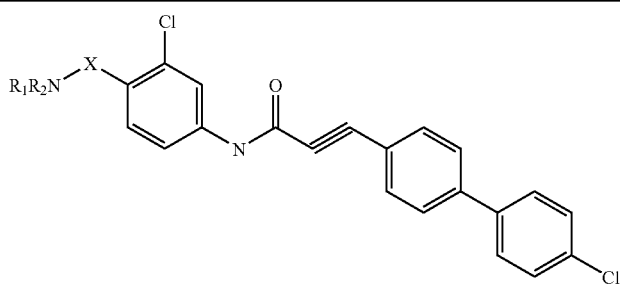
| Example | R₁R₂N-X | educt | empirical formula | mass spectrum | mp [° C.] | $R_f$ value |
|---|---|---|---|---|---|---|
| 3.166 | 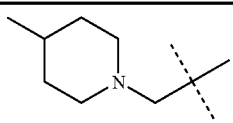 | 3.7.b | $C_{28}H_{26}Cl_2N_2O$ | 477/79/81 (Cl$_2$) [M + H]⁺ | 160-164 | 0.8 (B) |
| 3.167 | 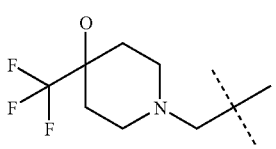 | 3.7.b | $C_{28}H_{23}Cl_2F_3N_2O_2$ | 547/49/51 (Cl$_2$) [M + H]⁺ | 128-132 | 0.5 (A) |
$R_f$ value:
A = (silica gel, dichloromethane/methanol (90:10))
B = (silica gel, dichloromethane/methanol/ammonia (90:10:0.1))

EXAMPLE 3.168

3-[5-(4-chlorophenyl)pyridin-2-yl]propynoic acid-[4-(4-hydroxypiperidin-1-ylmethyl)phenyl]amide

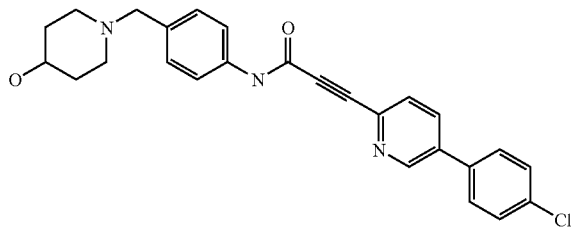

Prepared analogously to Example 2.3.f. from [5-(4-chlorophenyl)pyridin-2-yl]propynoic acid and 4-[4-(tert-butyldimethylsilanyloxy)piperidin-1-ylmethyl]phenylamine. The cleaving of the silyl group is carried out by adding tetrabutylammonium fluoride to a solution of the silylether in THF. Yield: 0.25 g (43% of theory); melting point: 186° C.-190° C.; $C_{26}H_{24}ClN_3O_2$ (M=445.94); calc.: molecular ion peak (M+H)$^+$: 446/448; found: molecular ion peak (M+H)$^+$: 446/448; $R_f$ value: 0.6 (silica gel, dichloromethane/methanol/ammonia (90:10:0.1)).

EXAMPLE 4.1

3-(2,4-dichlorophenyl)propynoic acid-[3-chloro-4-(2-diethylaminoethoxy)phenyl]amide

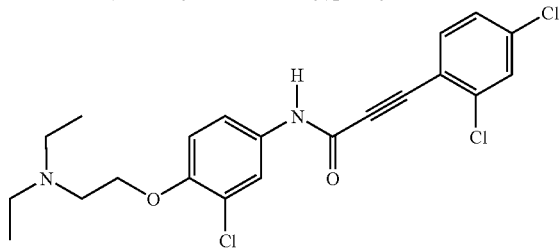

4.1.a. [2-(2-chloro-4-nitrophenoxy)ethyl]diethylamine 112 g (0.81 mol) of potassium carbonate are added to a solution of 35 g (0.202 mol) of 2-chloro-4-nitrophenol in 350 mL of DMF. Then the reaction mixture is combined with 35 g (0.203 mol) of (2-chloroethyl)diethylamine hydrochloride and stirred for 3 hours at 80° C. and 14 hours at ambient temperature. The reaction mixture is evaporated down and the residue is poured onto 1000 mL of water and this mixture is extracted three times with ethyl acetate. The combined organic phases are dried over sodium sulfate, the desiccant is filtered off and the filtrate is evaporated down. Yield: 49.6 g (90% of theory); $C_{12}H_{17}ClN_2O_3$ (M=272.73); calc.: molecular ion peak (M+H)$^+$: 273; found: molecular ion peak (M+H)$^+$: 273; $R_f$ value: 0.36 (silica gel, dichloromethane/methanol (90:10)).

4.1.b. [2-(2-chloro-4-aminophenoxy)ethyl]diethylamine

Prepared analogously to Example 3.1.b. from [2-(2-chloro-4-nitrophenoxy)ethyl]diethylamine in methanol in a reaction time of 4.5 hours. Yield: 36.12 g (81.8% of theory); $C_{12}H_{19}ClN_2O$ (M=242.75); calc.: molecular ion peak (M+H)$^+$: 243/245; found: molecular ion peak (M+H)$^+$: 243/245; $R_f$ value: 0.36 (silica gel, dichloromethane/methanol (90:10)).

4.1.c. (2,4-dichlorophenyl)propynoic acid chloride

A reaction mixture of 0.34 g (1.58 mmol) of (2,4-dichlorophenyl)propynoic acid and 0.14 mL (1.9 mmol) of thionyl chloride in 15 mL of absolute toluene is stirred for 3 hours at 70° C. and then evaporated down. The residue is taken up in absolute toluene and the solution is evaporated to dryness. This procedure is then repeated once more and the residue is further reacted in its crude state.

4.1.d. 3-(2,4-dichlorophenyl)propynoic acid-[3-chloro-4-(2-diethylaminoethoxy)phenyl]amide 0.37 g (1.58 mmol) of (2,4-dichlorophenyl)propynoic acid chloride is dissolved in 15 mL of absolute toluene and while cooling with ice combined with 0.77 g (3.16 mmol) of [2-(2-chloro-4-aminophenoxy)ethyl]diethylamine, dissolved in 10 mL of absolute toluene, and stirred for 4 hours at ambient temperature. Then the reaction mixture is extracted with ethyl acetate and dilute aqueous ammonia solution. The organic phase is extracted with water and dried over sodium sulfate. The purification is carried out by column chromatography on silica gel (eluant: dichloromethane/methanol (9:1)). The product obtained is recrystallized from petroleum ether and dried in the vacuum drying chamber at 50° C. Yield: 0.21 g (30.2% of theory); melting point: 98° C.-100° C.; $C_{21}H_{21}Cl_3N_2O_2$ (M=439.77); calc.: molecular ion peak (M+H)$^+$: 439/441/443; found: molecular ion peak (M+H)$^+$: 439/441/443; $R_f$ value: 0.5 (silica gel, dichloromethane/methanol/ammonia (9:1:0.1)).

EXAMPLE 4.2

3-(2-chloro-4-trifluoromethylphenyl)propynoic acid-[3-chloro-4-(2-diethylaminoethoxy)phenyl]amide

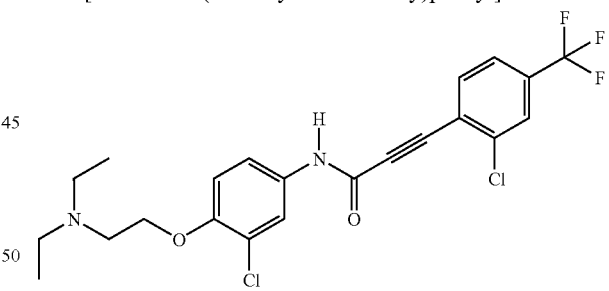

4.2.a. (2-chloro-4-trifluoromethylphenyl)propynoic acid chloride

Prepared analogously to Example 4.1.c. from (2-chloro-4-trifluoromethylphenyl)propynoic acid. The compound is further reacted in its crude state.

4.2.b. 3-(2-chloro-4-trifluoromethylphenyl)propynoic acid-[3-chloro-4-(2-diethylaminoethoxy)phenyl]amide Prepared analogously to Example 4.1.d. from (2-chloro-4-trifluoromethylphenyl)propynoic acid chloride and [2-(2-chloro-4-aminophenoxy)ethyl]diethylamine. Yield: 0.26 g (27.5% of theory); $C_{22}H_{21}Cl_2F_3N_2O_2$ (M=473.32); calc.:

molecular ion peak (M+H)⁺: 473/475; found: molecular ion peak (M+H)⁺: 473/475; $R_f$ value: 0.5 (silica gel, dichloromethane/methanol/ammonia (9:1:0.1)).

EXAMPLE 4.3

3-pyridin-2-ylpropynoic acid-[3-chloro-4-(2-diethylaminoethoxy)phenyl]amide hydrochloride

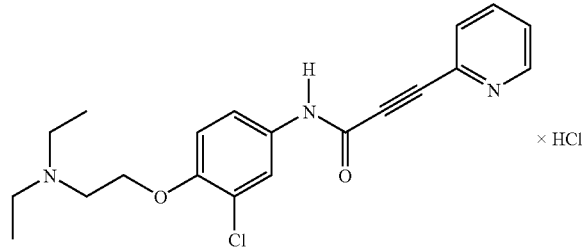

4.3.a. pyridin-2-ylpropynoic Acid 6.3 mL of n-butyllithium solution (1.6M in hexane) is added dropwise at −10° C. to a solution of 1 g (9.7 mmol) of 2-ethynylpyridine in 30 mL of absolute THF and stirred for 30 minutes. At −78° C., dry ice is added batchwise and the reaction mixture is allowed to heat up to ambient temperature. After about 1 hour, the reaction mixture is evaporated down and the residue is taken up in 10 mL of 1N hydrochloric acid while cooling with ice. The precipitate is filtered off, rinsed with isopropanol and diethyl ether, and dried in the vacuum drying chamber at 70° C. Yield: 0.6 g (42% of theory); melting point: 130° C.; $C_8H_5NO_2$ (M=147.13); calc.: molecular ion peak (M+H)⁺: 148; found: molecular ion peak (M+H)⁺: 148.

4.3.b. 3-pyridin-2-ylpropynoic acid-[3-chloro-4-(2-diethylaminoethoxy)phenyl]amide hydrochloride Prepared analogously to Example 2.3.f. from pyridin-2-ylpropynoic acid and [2-(2-chloro-4-aminophenoxy)ethyl]diethylamine. Yield: 0.37 g (53.3% of theory); $C_{20}H_{22}ClN_3O_2$*HCl (M=408.33); calc.: molecular ion peak (M+H)⁺: 372/374; found: molecular ion peak (M+H)⁺: 372/374; $R_f$ value: 0.5 (silica gel, dichloromethane/methanol/ammonia (9:1:0.1)).

EXAMPLE 4.4

3-biphenyl-4-ylpropynoic acid-[3-chloro-4-(2-diethylaminoethoxy)phenyl]amide

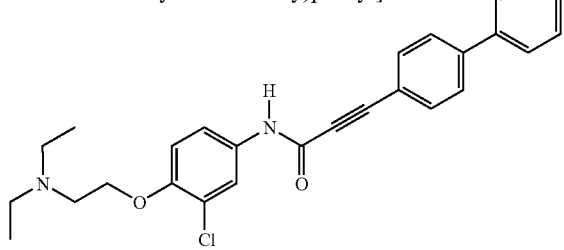

4.4.a.
3-biphenyl-4-yl-2,3-dibromopropanecarboxylic acid

Prepared analogously to Example 3.4.a. from 3-biphenyl-4-ylacrylic acid. Yield: 5 g (91.2% of theory); melting point: 200° C.-203° C.; $C_{15}H_{12}Br_2O_2$ (M=384.07); $R_f$ value: 0.4 (silica gel, dichloromethane/methanol/acetic acid (90:10:1)).

4.4.b. biphenyl-4-ylpropynoic acid

Prepared analogously to Example 3.4.b. from 3-biphenyl-4-yl-2,3-dibromopropanecarboxylic acid. Yield: 2.8 g (96.8% of theory); $C_{15}H_{10}O_2$ (M=222.24); melting point: 170° C.; calc.: molecular ion peak (M+H)⁺: 223; found: molecular ion peak (M+H)⁺: 223; $R_f$ value: 0.4 (silica gel, dichloromethane/methanol/acetic acid (90:10:1)).

4.4.c. biphenyl-4-ylpropynoic acid chloride

Prepared analogously to Example 4.1.c. from biphenyl-4-ylpropynoic acid. The compound is further reacted in its crude state.

4.4.d. 3-biphenyl-4-ylpropynoic acid-[3-chloro-4-(2-diethylaminoethoxy)phenyl]amide Prepared analogously to Example 4.1.d. from biphenyl-4-ylpropynoic acid chloride and [2-(2-chloro-4-aminophenoxy)ethyl]diethylamine. Yield: 0.28 g (31.3% of theory); melting point: 105° C.-108° C.; $C_{27}H_{27}ClN_2O_2$ (M=446.98); calc.: molecular ion peak (M+H)⁺: 447/449; found: molecular ion peak (M+H)⁺: 447/449; $R_f$ value: 0.5 (silica gel, dichloromethane/methanol/ammonia (9:1:0.1)).

EXAMPLE 4.5

3-(2,4,6-trichlorophenyl)propynoic acid-[3-chloro-4-(2-diethylaminoethoxy)phenyl]amide hydrochloride

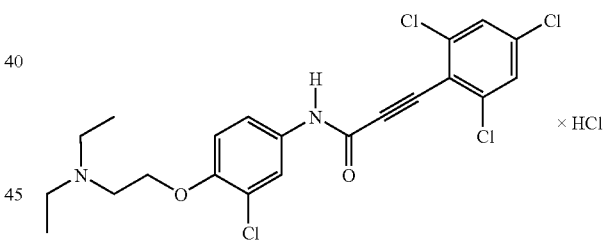

4.5.a. triphenyl-(2,4,6-trichlorophenylethynyl)silane

In an argon atmosphere, 9 g (34.6 mmol) of 1-bromo-2,4,6-trichlorobenzene, 9.8 g (34.45 mmol) of triphenylsilylacetylene, and 15 mL of triethylamine are dissolved in 100 mL of absolute dioxane and at 90° C. combined with 0.2 g (1.04 mmol) of copper (I) iodide and 1.2 g (1.04 mmol) of tetrakistriphenylphosphine palladium and stirred for 20 hours. The reaction mixture is filtered through CELITE® filter aid and the filtrate is evaporated down. The residue is taken up in ethyl acetate and extracted with water. The organic phase is dried over sodium sulfate. The purification is carried out by column chromatography on silica gel (eluant: petroleum ether/toluene (5:1)). The product is recrystallized from petroleum ether and dried in the vacuum drying chamber at 70° C. Yield: 6.9 g (43% of theory); melting point: 115° C.-120° C.; $C_{26}H_{17}Cl_3Si$ (M=463.87); calc.: molecular ion peak (M+H)⁺: 463/465/467/469; found: molecular ion peak (M+H)⁺: 463/465/467/469; $R_f$ value: 0.6 (silica gel, petroleum ether/toluene (4:1)).

4.5.b. 1,3,5-trichloro-2-ethynylbenzene

A reaction mixture of 5 g (10.8 mmol) of triphenyl-(2,4,6-trichlorophenylethynyl)silane and 4.2 g (16.2 mmol) of tetrabutylammonium fluoride in 50 mL of absolute THF is stirred for half an hour at ambient temperature and then evaporated down. The residue is taken up in diethyl ether and water and extracted. The organic phase is dried over sodium sulfate. The purification is carried out by column chromatography on silica gel (eluant: petroleum ether/toluene (9:1)). Yield: 0.46 g (20.7% of theory); $R_f$ value: 0.6 (silica gel, petroleum ether/toluene (9:1)).

4.5.c. (2,4,6-trichlorophenyl)propynoic acid

Prepared analogously to Example 4.3.a. from triphenyl-(2,4,6-trichlorophenylethynyl)silane and dry ice. Yield: 3.3 g (77.7% of theory); melting point: 170° C.-175° C.; $C_9H_3Cl_3O_2$ (M=249.48); calc.: molecular ion peak (M+H)⁺: 249/251/253; found: molecular ion peak (M+H)⁺: 249/251/253; $R_f$ value: 0.4 (silica gel, dichloromethane/methanol/acetic acid (50:10:1)).

4.5.d. 3-(2,4,6-trichlorophenyl)propynoic acid-[3-chloro-4-(2-diethylaminoethoxy)phenyl]amide hydrochloride Prepared analogously to Example 2.3.f. from (2,4,6-trichlorophenyl)propynoic acid and [2-(2-chloro-4-aminophenoxy)ethyl]diethylamine. Yield: 0.72 g (82.9% of theory); melting point: 188° C.-191° C.; $C_{21}H_{20}Cl_4N_2O_2$*HCl (M=510.67); calc.: molecular ion peak (M+H)⁺: 473/475/477/479/481; found: molecular ion peak (M+H)⁺: 473/475/477/479/481; $R_f$ value: 0.4 (silica gel, dichloromethane/methanol/ammonia (90:10:0.1)).

EXAMPLE 4.6

3-(2,4-dichlorophenyl)propynoic acid-[3-chloro-4-(2-diethylaminopropoxy)phenyl]amide hydrochloride

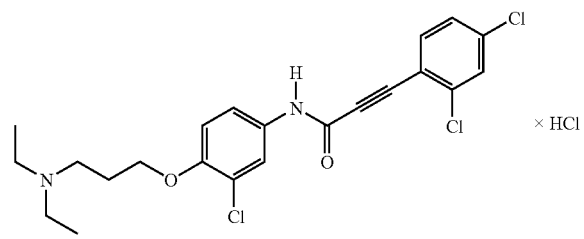

4.6.a. [2-(2-chloro-4-nitrophenoxy)propyl]diethylamine 1.6 g (33 mmol) of sodium hydride (50% in oil) are added at 0° C. to a solution of 5.3 g (30 mmol) of 3-chloro-4-fluoronitrobenzene and 4.3 g (33 mmol) of 3-diethylaminopropan-1-ol in 50 mL of DMF and stirred for 2 hours. Then the mixture is heated to ambient temperature and stirred for 1 hour. The reaction mixture is evaporated down, combined with water, and extracted with ethyl acetate. The organic phase is dried over sodium sulfate. The purification is carried out by column chromatography on silica gel (eluant: dichloromethane/methanol/ammonia (9:1:0.1)). Yield: 8 g (93% of theory); $C_{13}H_{19}ClN_2O_3$ (M=286.76); $R_f$ value: 0.3 (silica gel, dichloromethane/methanol/ammonia (90:10:0.1)).

4.6.b. [2-(2-chloro-4-aminophenoxy)propyl]diethylamine

Prepared analogously to Example 3.1.b. from [2-(2-chloro-4-nitrophenoxy)propyl]diethylamine in methanol in a reaction time of 8 hours. Yield: 6.7 g (93.5% of theory); $C_{13}H_{21}ClN_2O$ (M=256.77); calc.: molecular ion peak (M+H)⁺: 257/259; found: molecular ion peak (M+H)⁺: 257/259; $R_f$ value: 0.4 (silica gel, dichloromethane/methanol/ammonia (50:10:0.1)).

4.6.c. 3-(2,4-dichlorophenyl)propynoic acid-[3-chloro-4-(2-diethylaminopropoxy)phenyl]amide hydrochloride Prepared analogously to Example 3.4.c. from [2-(2-chloro-4-aminophenoxy)propyl]diethylamine and (2,4-dichlorophenyl)propynoic acid. Yield: 0.62 g (84.3% of theory); melting point: 180° C.-185° C.; $C_{22}H_{23}Cl_3N_2O_2$*HCl (M=490.26); calc.: molecular ion peak (M+H)⁺: 453/455/457/459; found: molecular ion peak (M+H)⁺: 453/455/457/459; $R_f$ value: 0.7 (silica gel, dichloromethane/methanol/ammonia (50:10:0.1)).

EXAMPLE 4.7

3-(2,4-dichlorophenyl)propynoic acid-[3-methoxy-4-(2-diethylaminoethoxy)phenyl]amide hydrochloride

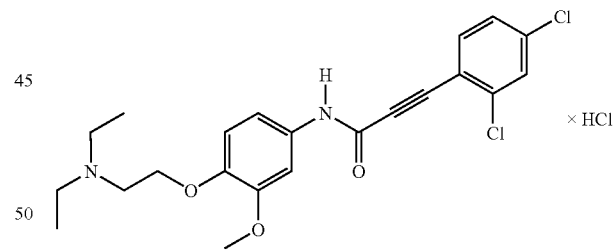

4.7.a. 3-(2,4-dichlorophenyl)propynoic acid-[3-methoxy-4-(2-diethylaminoethoxy)phenyl]amide hydrochloride Prepared analogously to Example 2.3.f. from (2,4-dichlorophenyl)propynoic acid chloride and [2-(2-methoxy-4-aminophenoxy)ethyl]diethylamine. Yield: 0.25 g (31.2% of theory); melting point: 205° C.-207° C.; $C_{22}H_{24}Cl_2N_2O_3$*HCl (M=471.81); calc.: molecular ion peak (M+H)⁺: 435/437/439; found: molecular ion peak (M+H)⁺: 435/437/439; $R_f$ value: 0.6 (silica gel, dichloromethane/methanol/ammonia (50:10:0.1)).

EXAMPLE 4.8

3-(2,4-dichlorophenyl)propynoic acid-[2-chloro-4-(2-diethylaminoethoxy)phenyl]amide

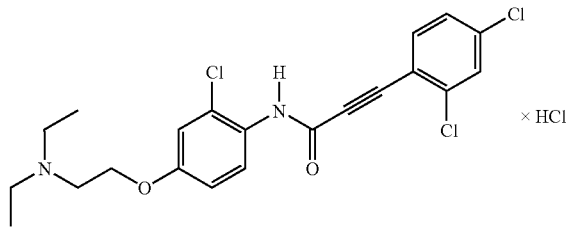

4.8.a.
[2-(3-chloro-4-nitrophenoxy)ethyl]diethylamine

Prepared analogously to Example 4.1.a. from 3-chloro-4-nitrophenol and (2-chloroethyl)diethylamine hydrochloride. Yield: 1.25 g (79.5% of theory); $C_{12}H_{17}ClN_2O_3$ (M=272.73); calc.: molecular ion peak (M+H)$^+$: 273/275; found: molecular ion peak (M+H)$^+$: 273/275; $R_f$ value: 0.44 (silica gel, dichloromethane/methanol (90:10)).

4.8.b.
[2-(3-chloro-4-aminophenoxy)ethyl]diethylamine

Prepared analogously to Example 3.1.b. from [2-(3-chloro-4-nitrophenoxy)ethyl]diethylamine in ethyl acetate. Yield: 1.05 g (95.4% of theory); $C_{12}H_{19}ClN_2O$ (M=242.75); calc.: molecular ion peak (M+H)$^+$: 243/245; found: molecular ion peak (M+H)$^+$: 243/245; $R_f$ value: 0.41 (silica gel, dichloromethane/methanol (90:10)).

4.8.c. 3-(2,4-dichlorophenyl)propynoic acid-[2-chloro-4-(2-diethylaminoethoxy)phenyl]amide hydrochloride Prepared analogously to Example 2.3.f. from (2,4-dichlorophenyl)propynoic acid chloride and [2-(3-chloro-4-aminophenoxy)ethyl]diethylamine. Yield: 0.53 g (65.5% of theory); melting point: 128° C.-130° C.; $C_{21}H_{21}Cl_3N_2O_2$*HCl (M=476.23); calc.: molecular ion peak (M+H)$^+$: 439/441/443; found: molecular ion peak (M+H)$^+$: 439/441/443; $R_f$ value: 0.7 (silica gel, dichloromethane/methanol/ammonia (50:10:0.1)).

EXAMPLE 4.9

3-(4-chlorophenyl)propynoic acid-[1-(2-pyrrolidin-1-ylethyl)-1H-indol-5-yl]amide

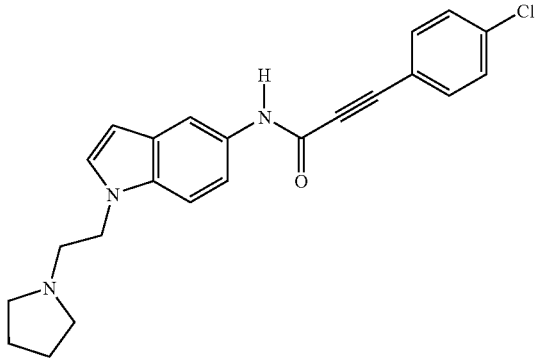

4.9.a. 5-nitro-1-(2-pyrrolidin-1-ylethyl)-1H-indole

A reaction mixture of 16.22 g (0.1 mol) of 5-nitroindole, 35 g (0.205 mol) of 1-(2-chloroethyl)pyrrolidine hydrochloride, and 51 g (0.369 mol) of potassium carbonate in 500 mL of DMF is stirred for 48 hours at ambient temperature and then filtered. The filtrate is evaporated down, the residue dissolved in dichloromethane, and dried over sodium sulfate. The desiccant is filtered off and the filtrate is evaporated down. Yield: 25 g (96.3% of theory); $C_{14}H_{17}N_3O_2$ (M=259.31); calc.: molecular ion peak (M+H)$^+$: 260; found: molecular ion peak (M+H)$^+$: 260; $R_f$ value: 0.65 (silica gel, dichloromethane/methanol/ammonia (90:10:1)).

4.9.b. 5-amino-1-(2-pyrrolidin-1-ylethyl)-1H-indole

Prepared analogously to Example 3.1.b. from 5-nitro-1-(2-pyrrolidin-1-ylethyl)-1H-indole in THF as solvent. Yield: 0.83 g (93.9% of theory); $C_{14}H_{19}N_3$ (M=229.32); calc.: molecular ion peak (M+H)$^+$: 230; found: molecular ion peak (M+H)$^+$: 230; $R_f$ value: 0.37 (silica gel, dichloromethane/methanol/ammonia (90:10:1)).

4.9.c. 3-(4-chlorophenyl)propynoic acid-[1-(2-pyrrolidin-1-ylethyl)-1H-indol-5-yl]amide Prepared analogously to Example 3.1.e. from 5-amino-1-(2-pyrrolidin-1-ylethyl)-1H-indole and (4-chlorophenyl)propynoic acid in THF as solvent. Yield: 186 mg (47.5% of theory); $C_{23}H_{22}ClN_3O$ (M=391.90); melting point: 135° C.-144° C.; calc.: molecular ion peak (M+H)$^+$: 393/394; found: molecular ion peak (M+H)$^+$: 393/394; $R_f$ value: 0.4 (silica gel, dichloromethane/methanol/ammonia (90:10:1)).

EXAMPLE 4.10

3-(4-chlorophenyl)propynoic acid-[1-(2-pyrrolidin-1-ylethyl)-1H-indol-5-yl]amide

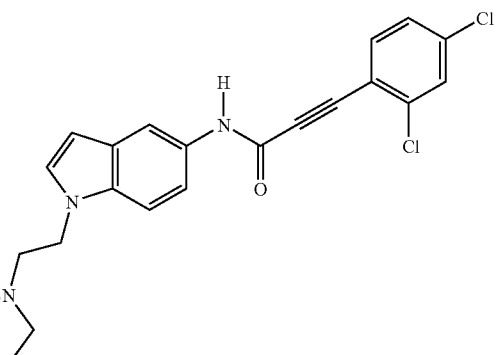

Prepared analogously to Example 3.1.e. from 5-amino-1-(2-pyrrolidin-1-ylethyl)-1H-indole and (2,4-dichlorophenyl)propynoic acid in THF as solvent. Yield: 133 mg (31.2% of theory); $C_{23}H_{21}Cl_2N_3O$ (M=426.34); melting point: 127° C.-129° C.; calc.: molecular ion peak (M+H)$^+$: 426/428/430; found: molecular ion peak (M+H)$^+$: 426/428/430; $R_f$ value: 0.4 (silica gel, dichloromethane/methanol/ammonia (90:10:1)).

EXAMPLE 4.11

3-(2-chloro-4-trifluoromethylphenyl)propynoic acid-[1-(2-pyrrolidin-1-ylethyl)-1H-indol-5-yl]amide

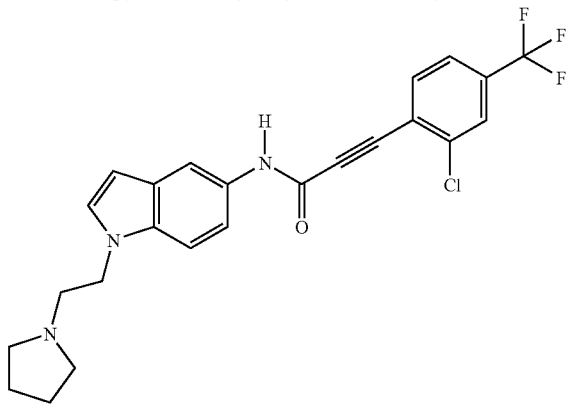

4.1.a. ethyl(2-chloro-4-trifluoromethylphenyl)propynoate

A reaction mixture of 0.556 mL (5.42 mmol) of ethyl propynoate, 875 mg (2.8 mmol) of 3-chloro-4-iodobenzotrifluoride, 214 mg (0.3 mmol) of bistriphenylphosphine palladium dichloride, 57.1 mg (0.3 mmol) of copper (I) iodide, and 1.17 g (3.6 mmol) of cesium carbonate in 50 mL of THF is degassed and stirred for 24 hours at ambient temperature under an argon atmosphere. The reaction mixture is combined with a saturated sodium hydrogen carbonate solution and twice extracted with ethyl acetate. The combined organic phases are extracted with saturated sodium chloride solution and dried over sodium sulfate. Yield: 0.65 g (43.3% of theory); $C_{12}H_8ClF_3O_2$ (M=276.64); calc.: molecular ion peak $(M+H)^+$: 277/279; found: molecular ion peak $(M+H)^+$: 277/279.

4.1.b. (2-chloro-4-trifluoromethylphenyl)propynoic acid 0.65 g (1.175 mmol) of ethyl (2-chloro-4-trifluoromethylphenyl)propynoate is dissolved in 20 mL of ethanol, combined with 2 mL of 2M sodium hydroxide solution, and stirred for 3 hours at ambient temperature. The reaction mixture is evaporated down, the residue is taken up in water, and extracted with ethyl acetate. The aqueous phase is combined with 2 mL of 1M hydrochloric acid and stirred for 1 hour at ambient temperature. Then it is extracted three times with ethyl acetate. The combined organic phases are dried over sodium sulfate. Yield: 0.14 g (48% of theory); $C_{10}H_4ClF_3O_2$ (M=248.59); calc.: molecular ion peak $(M-H)^-$: 247/249; found: molecular ion peak $(M-H)^-$: 247/249; $R_f$ value: 0.09 (silica gel, petroleum ether/ethyl acetate (4:1)).

4.11.c. 3-(2-chloro-4-trifluoromethylphenyl)propynoic acid-[1-(2-pyrrolidin-1-ylethyl)-1H-indol-5-yl]amide Prepared analogously to Example 2.3.f. from 5-amino-1-(2-pyrrolidin-1-ylethyl)-1H-indole and (2-chloro-4-trifluorophenyl)propynoic acid. Yield: 160 mg (66.5% of theory); $C_{24}H_{21}ClF_3N_3O$ (M=459.90); melting point: 200° C.-205° C.; calc.: molecular ion peak $(M+H)^+$: 460/462; found: molecular ion peak $(M+H)^+$: 460/462; $R_f$ value: 0.45 (silica gel, dichloromethane/methanol (90:10)).

EXAMPLE 4.12

3-(2,4-dichlorophenyl)propynoic acid-[2-(2-pyrrolidin-1-ylethyl)benzoxazol-5-yl]amide

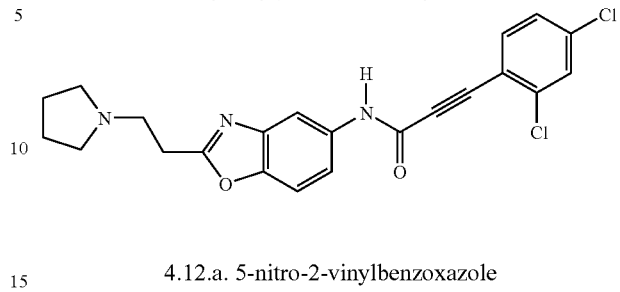

4.12.a. 5-nitro-2-vinylbenzoxazole

A reaction mixture of 1.54 g (10 mmol) of 2-amino-4-nitrophenol, 1.36 g (10 mmol) of ethyl 3-chloropropionate and 20 g polyphosphoric acid is stirred for 2 hours at 170° C. Then the mixture is neutralized by the addition of saturated sodium hydrogen carbonate solution at ambient temperature. The aqueous phase is extracted with dichloromethane. The organic phase is dried over sodium sulfate. The purification is carried out by column chromatography on silica gel (eluant: dichloromethane/ethanol (20:1)). Yield: 0.3 g (15.8% of theory); $C_9H_6N_2O_3$ (M=190.16); calc.: molecular ion peak $(M+H)^+$: 191; found: molecular ion peak $(M+H)^+$: 191; $R_f$ value: 0.8 (silica gel, dichloromethane/ethanol (20:1)).

4.12.b. 5-nitro-2-(2-pyrrolidin-1-ylethyl)benzoxazole

A solution of 1 g (5.25 mmol) of 5-nitro-2-vinylbenzoxazole and 0.66 mL (8 mmol) of pyrrolidine in 8 mL of ethanol is stirred for 2 hours at ambient temperature. Then the reaction solution is evaporated down. The purification is carried out by column chromatography on silica gel (eluant: dichloromethane/ethanol/ammonia (20:1:0.1)). Yield: 0.74 g (53.9% of theory); $C_{13}H_{15}N_3O_3$ (M=261.28); calc.: molecular ion peak $(M+H)^+$: 262; found: molecular ion peak $(M+H)^+$: 262; $R_f$ value: 0.2 (silica gel, dichloromethane/ethanol/ammonia (20:1:0.1)).

4.12.c. 5-amino-2-(2-pyrrolidin-1-ylethyl)benzoxazole

A reaction mixture of 0.74 g (2.83 mmol) of 5-nitro-2-(2-pyrrolidin-1-ylethyl)benzoxazole and 0.1 g of palladium (10% on activated charcoal) in 20 mL of ethanol is hydrogenated for 3 hours at 3 bar and 20° C. The catalyst is filtered off and the filtrate is evaporated down. Yield: 0.6 g (91.6% of theory); $C_{13}H_{17}N_3O$ (M=231.30); calc.: molecular ion peak $(M+H)^+$: 232; found: molecular ion peak $(M+H)^+$: 232; $R_f$ value: 0.3 (silica gel, dichloromethane/ethanol/ammonia (20:1:0.1)).

4.12.d. 3-(2,4-dichlorophenyl)propynoic acid-[2-(2-pyrrolidin-1-ylethyl)benzoxazol-5-yl]amide Prepared analogously to Example 3.1.e. from 5-amino-2-(2-pyrrolidin-1-ylethyl)benzoxazole and (2,4-dichlorophenyl)propynoic acid. Yield: 43 mg (33.1% of theory); $C_{22}H_{19}Cl_2N_3O_2$ (M=428.32); melting point: 130° C.; calc.: molecular ion peak $(M+H)^+$: 428/430/432; found: molecular ion peak $(M+H)^+$: 428/430/432; $C_{13}H_{17}N_3O$ (M=231.30); calc.: molecular ion peak $(M+H)^+$: 232; found: molecular ion peak $(M+H)^+$: 232; $R_f$ value: 0.21 (silica gel, dichloromethane/methanol/ammonia (10:1:0.1)).

EXAMPLE: 4.13

3-(2-chloro-4-trifluoromethylphenyl)propynoic acid-(2-pyrrolidin-1-ylmethylbenzoxazol-5-yl)amide

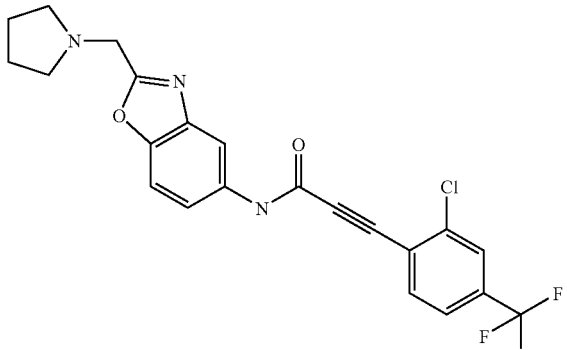

4.13.a 2-chloromethyl-5-nitrobenzoxazole 10.5 mL (77.87 mmol) of 2-chloro-orthoacetic acid is added to a solution of 12 g (77.86 mmol) of 2-amino-4-nitrophenol in 110 mL of ethanol and the whole lot is heated for 3 hours at 80° C. Then the reaction mixture is poured onto water, the precipitate formed is suction filtered, and washed several times with water. The product is dried at 80° C. in the circulating air dryer. Yield: 14.2 g (86% of theory); $C_8H_5ClN_2O_3$ (M=212.59); calc.: molecular ion peak $(M+H)^+$: 213/215 (Cl); found: molecular ion peak $(M+H)^+$: 213/215 (Cl).

4.13.b. 5-nitro-2-pyrrolidin-1-ylmethylbenzoxazole

A reaction mixture of 3 g (14.11 mmol) of 2-chloromethyl-5-nitrobenzoxazole, 1.5 mL (17.97 mmol) of pyrrolidine, and 3.9 g (28.22 mmol) of potassium carbonate in 30 mL of DMF is stirred for 4 hours at 50° C. Then the reaction mixture is diluted with water and covered with diisopropyl ether, The precipitated yellow solid is suction filtered, washed again, and dried in the circulating air dryer at 60° C. Yield: 1.8 g (52% of theory); $C_{12}H_{13}N_3O_3$ (M=247.25); calc.: molecular ion peak $(M+H)^+$: 248; found: molecular ion peak $(M+H)^+$: 248; $R_f$ value: 0.4 (silica gel, dichloromethane/ethanol (20:1)).

4.13.c. 2-pyrrolidin-1-ylmethylbenzoxazol-5-ylamine

Prepared analogously to Example 4.12.c. from 5-nitro-2-pyrrolidin-1-ylmethylbenzoxazole. Yield: 1.1 g (70% of theory); $C_{12}H_{15}N_3O$ (M=217.27); calc.: molecular ion peak $(M+H)^+$: 218; found: molecular ion peak $(M+H)^+$: 218; $R_f$ value: 0.6 (aluminum oxide, dichloromethane/ethanol (20:1)).

4.13.d. 3-(2-chloro-4-trifluoromethylphenyl)propynoic Acid (2-pyrrolidin-1-ylmethylbenzoxazol-5-yl)amide Prepared analogously to Example 2.3.f. from 0.2 g (0.92 mmol) of 2-pyrrolidin-1-ylmethylbenzoxazol-5-ylamine and 0.2 g (0.8 mmol) of (2-chloro-4-trifluoromethylphenyl)propynoic acid. Yield: 290 mg (81% of theory); $C_{22}H_{17}ClF_3N_3O_2$ (M=447.84); melting point: 218° C.-223° C.; calc.: molecular ion peak $(M+H)^+$: 448/450 (Cl); found: molecular ion peak $(M+H)^+$: 448/450 (Cl); $R_f$ value: 0.33 (silica gel, dichloromethane/methanol (19:1)).

EXAMPLE 4.14

3-(2-chloro-4-trifluoromethylphenyl)propynoic acid-[3-ethoxycarbonyl-4-(2-diethylaminoethoxy)phenyl]amide

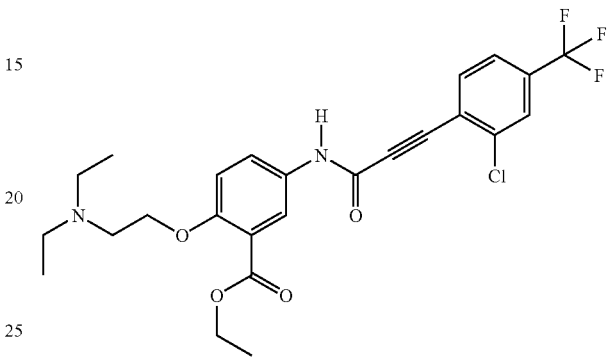

4.14.a. Ethyl 2-(2-diethylaminoethoxy)-5-nitrobenzoate 1.06 g (5.00 mmol) of ethyl 2-fluoro-5-nitrobenzoate and 0.58 mL (5.00 mmol) of 2-diethylaminoethanol are dissolved in 20 mL of DMF and at 0° C. 0.36 g (7.45 mmol) of sodium hydride (50%) is added. The mixture is stirred for 45 minutes at 0° C., poured onto ice water, and finally extracted three times with ethyl acetate. The organic phase is dried over sodium sulfate, the solvent is eliminated and the residue is purified through a silica gel column with petroleum ether/ethyl acetate (4:1) as eluant. Yield: 0.30 g (19% of theory); $C_{15}H_{22}N_2O_5$ (M=310.35); calc.: molecular ion peak $(M+H)^+$: 311; found: molecular ion peak $(M+H)^+$: 311; $R_f$ value: 0.1 (silica gel, petroleum ether/ethyl acetate (4:1)).

4.14.b. Ethyl 5-amino-2-(2-diethylaminoethoxy)benzoate

Prepared analogously to Example 3.1.b. from 0.30 g ethyl 2-(2-diethylaminoethoxy)-5-nitrobenzoate in ethyl acetate. Yield: 0.27 g (100% of theory); $C_{15}H_{24}N_2O_3$ (M=280.37); calc.: molecular ion peak $(M+H)^+$: 281; found: molecular ion peak $(M+H)^+$: 281; $R_f$ value: 0.40 (silica gel, dichloromethane/methanol/ammonia (39:1:0.1)).

4.14.c. 3-(2-chloro-4-trifluoromethylphenyl)propynoic acid-[3-ethoxycarbonyl-4-(2-diethylaminoethoxy)phenyl]amide Prepared analogously to Example 2.3.f. from 99 mg (0.40 mmol) of (2-chloro-4-trifluoromethylphenyl)propynoic acid and 120 mg (0.44 mmol) of ethyl 5-amino-2-(2-diethylaminoethoxy)benzoate. Yield: 44 mg (22% of theory); $C_{25}H_{26}ClF_3N_2O_4$ (M=510.94); calc.: molecular ion peak (M+H)+: 511/513; found: molecular ion peak (M+H)+: 511/513; $R_f$ value: 0.35 (silica gel, dichloromethane/methanol (9:1)).

EXAMPLE 4.15

3-(2-chloro-4-trifluoromethylphenyl)propynoic acid-[3-bromo-4-(2-diethylaminoethoxy)phenyl]amide

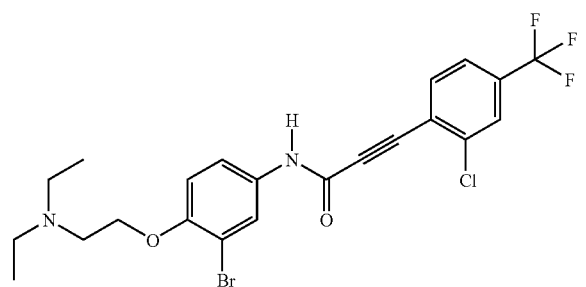

4.15.a.
[2-(2-bromo-4-nitrophenoxy)ethyl]diethylamine

Prepared analogously to Example 4.13.a. starting from 0.66 g (2.00 mmol) of 2-bromo-1-fluoro-4-nitrobenzene and 0.40 mL (3.00 mmol) of 2-diethylaminoethanol. Yield: 0.95 g (100% of theory); $C_{12}H_{17}BrN_2O_3$ (M=317.185); calc.: molecular ion peak (M+H)+: 317/319; found: molecular ion peak (M+H)+: 317/319; $R_f$ value: 0.50 (silica gel, dichloromethane/methanol (9:1)).

4.15.b.
3-bromo-4-(2-diethylaminoethoxy)phenylamine

Prepared analogously to Example 3.1.b. from 1.10 g (3.47 mmol) of [2-(2-bromo-4-nitrophenoxy)ethyl]diethylamine in ethyl acetate. Yield: 0.58 g (58% of theory); $C_{12}H_{19}BrN_2O$ (M=287.202); calc.: molecular ion peak (M+H)+: 287/289; found: molecular ion peak (M+H)+: 287/289; $R_f$ value: 0.30 (silica gel, dichloromethane/methanol (9:1)).

4.15.c. 3-(2-chloro-4-trifluoromethylphenyl)propynoic acid-[3-bromo-4-(2-diethylaminoethoxy)phenyl]amide Prepared analogously to Example 2.3.f. from 450 mg (1.80 mmol) of (2-chloro-4-trifluoromethylphenyl)propynoic acid and 550 mg (1.92 mmol) of 3-bromo-4-(2-diethylaminoethoxy)phenylamine. Yield: 370 mg (40% of theory); $C_{22}H_2BrClF_3N_2O_2$ (M=517.77); calc.: molecular ion peak (M+H)+: 517/519/521; found: molecular ion peak (M+H)+: 517/519/521; $R_f$ value: 0.45 (silica gel, dichloromethane/methanol (19:1)).

EXAMPLE 4.16

3-(2-chloro-4-trifluoromethylphenyl)propynoic acid-[3-bromo-4-(2-morpholin-4-ylethoxy)phenyl]amide

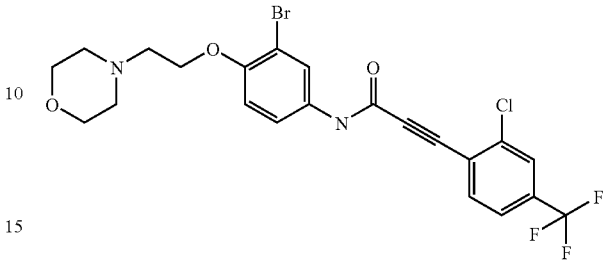

4.16.a.
4-[2-(2-bromo-4-nitrophenoxy)ethyl]morpholine 92 mg (1.9 mmol) of sodium hydride (55%) is added at 0° C. to a solution of 0.3 g (1.27 mmol) of 3-bromo-4-chloronitrobenzene and 0.15 mL (1.27 mmol) of in 20 mL of DMF under an argon atmosphere. The reaction mixture is stirred for 2 hours at 0° C. and then poured onto ice water. The aqueous phase is extracted three times with ethyl acetate. The organic phase is dried, the desiccant is filtered off, and the filtrate is evaporated down. The purification is carried out by column chromatography on silica gel (eluant: dichloromethane/methanol (19:1)). Yield: 230 mg (55% of theory); $C_{12}H_{15}BrN_2O_4$ (M=331.16); calc.: molecular ion peak (M+H)+: 331/333 (Br); found: molecular ion peak (M+H)+: 331/333 (Br).

4.16.b.
3-bromo-4-(2-morpholin-4-ylethoxy)phenylamine

A reaction mixture of 220 mg (0.66 mmol) of 4-[2-(2-bromo-4-nitrophenoxy)ethyl]morpholine and 100 mg Raney nickel in 50 mL of ethyl acetate is hydrogenated at ambient temperature and 3 bar hydrogen. The catalyst is suction filtered and the filtrate is evaporated down. The purification is carried out by column chromatography on aluminum oxide (eluant: petroleum ether/ethyl acetate (1:1)). Yield: 100 mg (50% of theory); $C_{12}H_{17}BrN_2O_2$ (M=301.18); calc.: molecular ion peak (M+H)+: 301/303 (Br); found: molecular ion peak (M+H)+: 301/303 (Br).

4.16.c. 3-(2-chloro-4-trifluoromethylphenyl)propynoic acid-[3-bromo-4-(2-morpholin-4-ylethoxy)phenyl]amide Prepared analogously to Example 2.3.f. from 100 mg (0.33 mmol) of 3-bromo-4-(2-morpholin-4-ylethoxy)phenylamine and 75 mg (0.3 mmol) of (2-chloro-4-trifluoromethylphenyl)propynoic acid. Yield: 130 mg (82% of theory); $C_{22}H_{19}BrClF_3N_2O_3$ (M=531.75); calc.: molecular ion peak (M+H)+: 529/531/533 (Br, Cl); found: molecular ion peak (M+H)+: 529/531/533 (Br, Cl); $R_f$ value: 0.33 (aluminum oxide, petroleum ether/ethyl acetate (1:1)).

EXAMPLE 4.17

3-(2-chloro-4-trifluoromethylphenyl)propynoic acid-[3-nitro-4-(2-diethylaminoethoxy)phenyl]amide

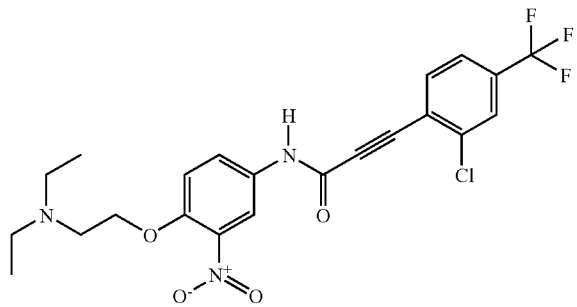

4.17.a. N-[4-(2-diethylaminoethoxy)-3-nitrophenyl]acetamide 0.74 g (7.29 mmol) of potassium nitrate are added batchwise at −10° C. to a solution of 1.52 g (6.07 mmol) of N-[4-(2-diethylaminoethoxy)phenyl]acetamide in 25 mL of concentrated sulfuric acid and the mixture is stirred for 1 hour at −10° C. The reaction mixture is poured onto a mixture of ice and concentrated aqueous ammonia and the aqueous phase is exhaustively extracted with ethyl acetate. The combined organic phases are dried over sodium sulfate and evaporated down. Yield: 1.8 g (100% of theory); $C_{14}H_{21}N_3O_4$ (M=295.34); calc.: molecular ion peak (M+H)$^+$: 296; found: molecular ion peak (M+H)$^+$: 296; $R_f$ value: 0.50 (Alox, dichloromethane/methanol (39:1)).

4.17.b. 4-(2-diethylaminoethoxy)-3-nitrophenylamine

A solution of 1.85 g (6.26 mmol) of N-[4-(2-diethylaminoethoxy)-3-nitrophenyl]acetamide in semiconcentrated aqueous hydrochloric acid is stirred for 2 hours at 100° C., cooled to ambient temperature, made basic with ice and concentrated aqueous ammonia and the aqueous phase is exhaustively extracted with ethyl acetate. The combined organic phases are washed with water and dried over sodium sulfate. Yield: 1.38 g (87% of theory); $C_{12}H_{19}N_3O_3$ (M=253.30); calc.: molecular ion peak (M+H)$^+$: 254; found: molecular ion peak (M+H)$^+$: 254; $R_f$ value: 0.68 (Alox, dichloromethane/methanol (39:1)).

4.17.c. 3-(2-chloro-4-trifluoromethylphenyl)propynoic acid-[3-nitro-4-(2-diethylaminoethoxy)phenyl]amide Prepared analogously to Example 2.3.f. from 450 mg (1.80 mmol) of (2-chloro-4-trifluoromethylphenyl)propynoic acid and 500 mg (1.98 mmol) of 4-(2-diethylaminoethoxy)-3-nitrophenylamine. Yield: 590 mg (68% of theory); $C_{22}H_{21}ClF_3N_3O_4$ (M=483.87); calc.: molecular ion peak (M+H)$^+$: 484/486; found: molecular ion peak (M+H)$^+$: 484/486; $R_f$ value: 0.40 (silica gel, dichloromethane/methanol (9:1)).

EXAMPLE 4.18

3-(2-chloro-4-trifluoromethylphenyl)propynoic acid-[3-chloro-4-(3-diethylaminopropoxy)phenyl]amide formate

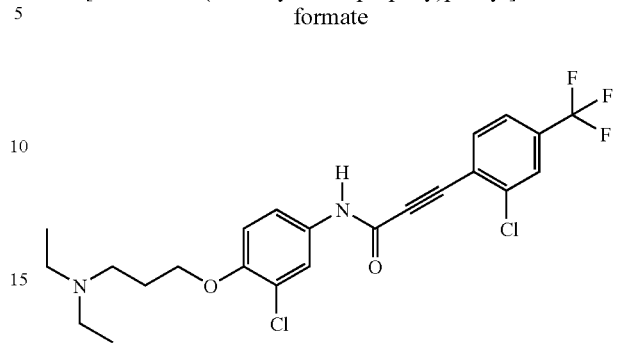

Prepared analogously to Example 2.3.f. from 99 mg (0.40 mmol) of (2-chloro-4-trifluoromethylphenyl)propynoic acid and 110 mg (0.44 mmol) of [2-(2-chloro-4-aminophenoxy)propyl]diethylamine. Yield: 49 mg (25% of theory); melting point: 112° C.-116° C.; $C_{23}H_{22}Cl_2F_3N_2O_2 * CH_2O_2$ (M=533.37); calc.: molecular ion peak (M+H)$^+$: 487/489/491; found: molecular ion peak (M+H)$^+$: 487/489/491; $R_f$ value: 0.35 (silica gel, dichloromethane/methanol (9:1)).

EXAMPLE 4.19

3-(2-chloro-4-trifluoromethylphenyl)propynoic acid-[3-chloro-4-(2-diethylaminoethoxy)phenyl]methylamide

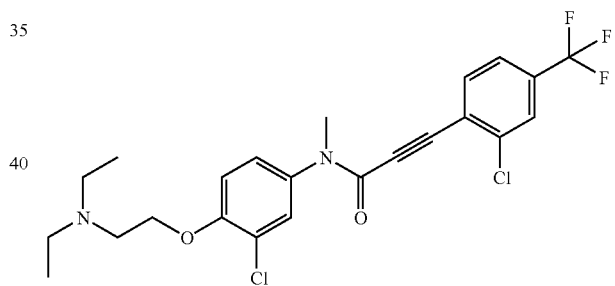

4.19.a. tert-butyl [3-chloro-4-(2-diethylaminoethoxy)phenyl]carbamate

Prepared analogously to Example 3.1.c. starting from 3.00 g (12.4 mmol) of 3-chloro-4-(2-diethylaminoethoxy)phenylamine and 2.97 g (13.6 mmol) of di-tert-butylpyrocarbonate in dichloromethane. Yield: 2.85 g (67% of theory); $C_{17}H_{27}ClN_2O_3$ (M=342.86); calc.: molecular ion peak (M+H)$^+$: 343/345; found: molecular ion peak (M+H)$^+$: 343/345.

4.19.b. [3-chloro-4-(2-diethylaminoethoxy)phenyl]methylamine

Prepared analogously to Example 3.1.d. from 2.85 g (8.31 mmol) of tert-butyl [3-chloro-4-(2-diethylaminoethoxy)phenyl]carbamate with 10.63 mL (24.9 mmol) of 10% lithium aluminum hydride solution in THF. Yield: 0.72 g (34% of theory); $C_{13}H_{21}ClN_2O$ (M=256.77); calc.: molecular ion peak (M+H)$^+$: 257/259; found: molecular ion peak (M+H)$^+$: 257/259; $R_f$ value: 0.80 (silica gel, ethyl acetate/methanol/ammonia (9:1:0.1)).

4.19.c. 3-(2-chloro-4-trifluoromethylphenyl)propynoic acid-[3-chloro-4-(2-diethylaminoethoxy)phenyl]methylamide Prepared analogously to Example 2.3.f. from 99 mg (0.40 mmol) of (2-chloro-4-trifluoromethylphenyl)propynoic acid and 110 mg (0.44 mmol) of [3-chloro-4-(2-diethylaminoethoxy)phenyl]methylamine. Yield: 54 mg (28% of theory); melting point: 97° C.-100° C.; $C_{23}H_{23}Cl_2F_3N_2O_2$ (M=487.35); calc.: molecular ion peak $(M+H)^+$: 487/489/491; found: molecular ion peak $(M+H)^+$: 487/489/491; $R_f$ value: 0.35 (silica gel, dichloromethane/methanol (9:1)).

EXAMPLE 4.20

3-(2-chloro-4-trifluoromethylphenyl)propynoic acid-[3-methoxy-4-(2-diethylaminoethoxy)phenyl]amide hydrochloride

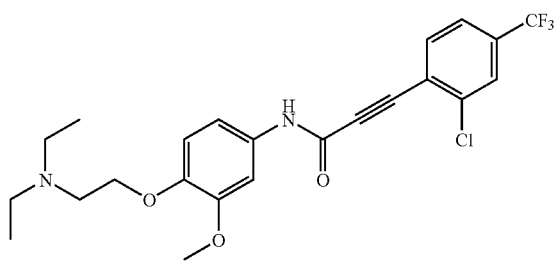

Prepared analogously to Example 2.3.f. from 75 mg (0.30 mmol) of (2-chloro-4-trifluoromethylphenyl)propynoic acid and 79 mg (0.33 mmol) of [2-(2-methoxy-4-aminophenoxy)ethyl]diethylamine. Yield: 14 mg (10% of theory); $C_{23}H_{24}ClF_3N_2O_3$ (M=468.90); calc.: molecular ion peak $(M+H)^+$: 469/471; found: molecular ion peak $(M+H)^+$: 469/471; $R_f$ value: 0.35 (silica gel, dichloromethane/methanol (9:1)).

EXAMPLE 4.21

3-(2-chloro-4-trifluoromethylphenyl)propynoic acid-[3-methyl-4-(2-diethylaminoethoxy)phenyl]amide

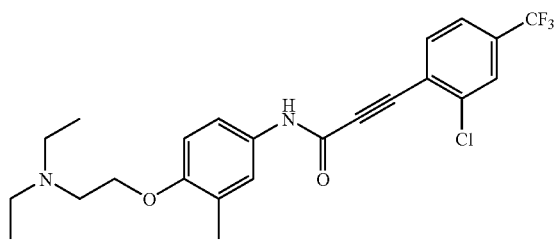

4.21.a. diethyl-[2-(2-methyl-4-nitrophenoxy)ethyl]amine 0.92 g (19.2 mmol) of sodium hydride (50% in oil) is added at 0° C. under an argon atmosphere to a solution of 2.70 g (17.4 mmol) of 2-fluoro-5-nitrotoluene and 2.54 mL (19.2 mmol) of 2-diethylaminoethanol in 50 mL of DMF and the mixture is stirred for 2 hours at 0° C. and for 1 hour at ambient temperature. The solvent is removed, the residue is taken up in ethyl acetate, and extracted with water. The organic phase is dried over sodium sulfate and evaporated down in vacuo.

Then it is purified by silica gel column chromatography with dichloromethane/methanol (9:1) as eluant. Yield: 3.1 g (71% of theory); $C_{13}H_{20}N_2O_3$ (M=252.31); calc.: molecular ion peak $(M+H)^+$: 253; found: molecular ion peak $(M+H)^+$: 253; $R_f$ value: 0.60 (silica gel, dichloromethane/methanol (9:1)).

4.21.b. 4-(2-diethylaminoethoxy)-3-methylphenylamine 3.10 g (12.3 mmol) of diethyl[2-(2-methyl-4-nitrophenoxy)ethyl]amine is dissolved in 250 mL of ethyl acetate, 0.55 g of Raney nickel is added, and the mixture is hydrogenated for 36 hours at 50 psi and ambient temperature. The catalyst is filtered off and the filtrate is evaporated down in vacuo. Yield: 2.70 g (99% of theory); $C_{13}H_{22}N_2O$ (M=222.33); calc.: molecular ion peak $(M+H)^+$: 223; found: molecular ion peak $(M+H)^+$: 223; $R_f$ value: 0.35 (silica gel, dichloromethane/methanol (9:1)).

4.21.c. 3-(2-chloro-4-trifluoromethylphenyl)propynoic acid-[3-methyl-4-(2-diethylaminoethoxy)phenyl]amide Prepared analogously to Example 2.3.f. from 75 mg (0.30 mmol) of (2-chloro-4-trifluoromethylphenyl)propynoic acid and 73 mg (0.33 mmol) of 4-(2-diethylaminoethoxy)-3-methylphenylamine. Yield: 134 mg (99% of theory); $C_{23}H_{24}ClF_3N_2O_2$ (M=452.90); calc.: molecular ion peak $(M+H)^+$: 453/455; found: molecular ion peak $(M+H)^+$: 453/455; $R_f$ value: 0.40 (silica gel, dichloromethane/methanol (9:1)).

EXAMPLE 4.22

3-(2-chloro-4-trifluoromethylphenyl)propynoic acid-[3-amino-4-(2-diethylaminoethoxy)phenyl]amide

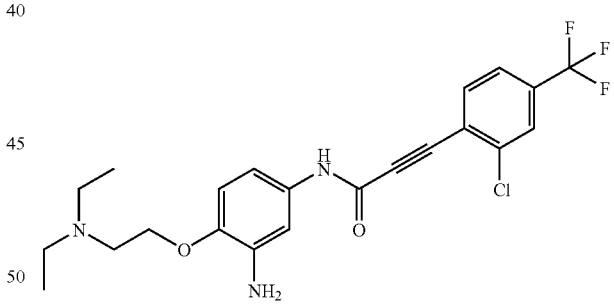

870 mg (10.3 mmol) of sodium hydrogen carbonate and 1.17 g (5.17 mmol) of tin (II) chloride dihydrate are added at ambient temperature to a solution of 250 mg (0.52 mmol) of 3-(2-chloro-4-trifluoromethylphenyl)propynoic acid-[3-nitro-4-(2-diethylaminoethoxy)phenyl]amide in 50 mL of ethyl acetate. The mixture is refluxed for 12 hours. After cooling, water is added and the organic phase is separated off. The aqueous phase is extracted twice more with ethyl acetate. The combined organic phases are dried over sodium sulfate and the solvent is eliminated. The purification of the residue is carried out by column chromatography on Alox (eluant: dichloromethane/methanol (39:1)). Yield: 100 mg (43% of theory); melting point: 127° C.-130° C.; $C_{22}H_{23}ClF_3N_3O_2$ (M=453.89); calc.: molecular ion peak $(M+H)^+$: 454/456;

EXAMPLE 4.23

3-(2-chloro-4-trifluoromethylphenyl)propynoic acid-[4-(3-diethylaminoethoxy)-3-methanesulfonylaminophenyl]amide

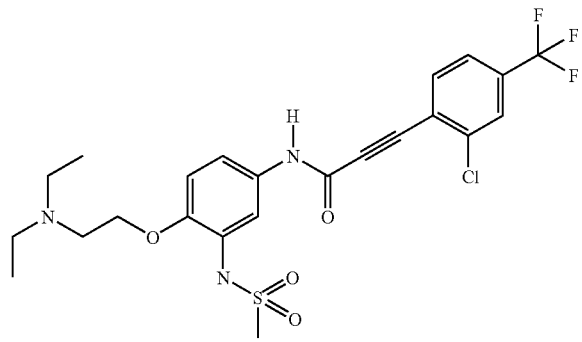

0.019 mL (0.242 mmol) of methanesulfonic acid chloride is added dropwise at 0° C. to a solution of 0.1 g (0.22 mmol) of 3-(2-chloro-4-trifluoromethylphenyl)propynoic acid-[3-amino-4-(2-diethylaminoethoxy)phenyl]amide in 5 mL of pyridine. The reaction mixture is slowly heated to ambient temperature and stirred for 3 hours. Then the reaction mixture is poured into ice water and extracted three times with ethyl acetate. The combined organic phases are dried over sodium sulfate and the solvent is distilled off. The residue is freeze-dried. Yield: 101 mg (86.3% of theory); melting point: 57° C.-60° C.; $C_{23}H_{25}ClF_3N_3O_4S$ (M=531.98); calc.: molecular ion peak (M+H)$^+$: 532/534; found: molecular ion peak (M+H)$^+$: 532/534; $R_f$ value: 0.32 (silica gel, dichloromethane/methanol (9:1)).

EXAMPLE 4.24

3-(2-chloro-4-trifluoromethylphenyl)propynoic acid-[4-(3-diethylaminoethoxy)-3-methoxyphenyl]methylamide

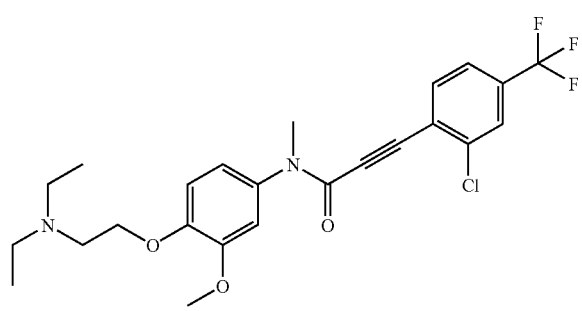

4.24.a. tert-butyl [4-(3-diethylaminoethoxy)-3-methoxyphenyl]carbamate

Prepared analogously to Example 3.1.c. from 4-(3-diethylaminoethoxy)-3-methoxyphenylamine. Yield: 0.26 g (91.6% of theory); $C_{18}H_{30}N_2O_4$ (M=338.45); calc.: molecular ion peak (M+H)$^+$: 339; found: molecular ion peak (M+H)$^+$: 339; $R_f$ value: 0.45 (silica gel, dichloromethane/methanol/ammonia (9:1:0.1)).

4.24.b. [4-(3-diethylaminoethoxy)-3-methoxyphenyl]methylamine

Prepared analogously to Example 3.1.d. from tert-butyl [4-(3-diethylaminopropoxy)-3-methoxyphenyl]carbamate. Yield: 0.08 g (44.7% of theory); $C_{14}H_{24}N_2O_2$ (M=252.36); calc.: molecular ion peak (M+H)$^+$: 253; found: molecular ion peak (M+H)$^+$: 253

4.24.c. 3-(2-chloro-4-trifluoromethylphenyl)propynoic acid-[4-(3-diethylaminoethoxy)-3-methoxyphenyl]methylamide Prepared analogously to Example 2.3.f. from (2-chloro-4-trifluoromethylphenyl)propynoic acid and [4-(3-diethylaminopropoxy)-3-methoxyphenyl]methylamine. Yield: 33 mg (30% of theory); $C_{24}H_{26}ClF_3N_2O_3$ (M=482.93); calc.: molecular ion peak (M+H)$^+$: 483/485; found: molecular ion peak (M+H)$^+$: 483/485; $R_f$ value: 0.43 (silica gel, dichloromethane/methanol (9:1)).

EXAMPLE 4.25

3-(2-chloro-4-trifluoromethylphenyl)propynoic acid-[4-(3-diethylaminoethoxy)-3-fluorophenyl]amide

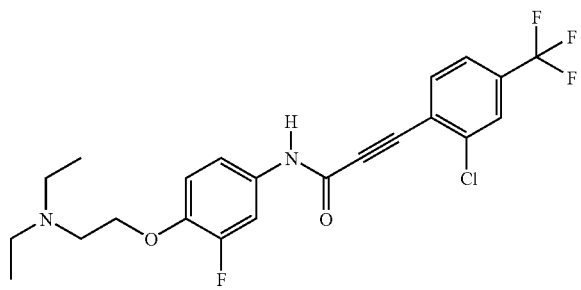

4.25.a. [diethyl-[3-(2-fluoro-4-nitrophenoxy)ethyl]amine

Prepared analogously to Example 4.6.a. from 3,4-difluoronitrobenzene and 2-diethylaminoethanol. Yield: 6.94 g (87.4% of theory); $C_{12}H_{17}FN_2O_3$ (M=256.27); calc.: molecular ion peak (M+H)$^+$: 257; found: molecular ion peak (M+H)$^+$: 257; $R_f$ value: 0.46 (silica gel, dichloromethane/methanol/ammonia (9:1:0.1)).

4.25.b. 4-(3-diethylaminoethoxy)-3-fluorophenylamine

Prepared analogously to Example 3.1.b. from [diethyl-[3-(2-fluoro-4-nitrophenoxy)ethyl]amine. Yield: 5.93 g (97.1% of theory); $C_{12}H_{19}FN_2O$ (M=226.29); calc.: molecular ion peak (M+H)$^+$: 229; found: molecular ion peak (M+H)$^+$: 227; $R_f$ value: 0.33 (silica gel, dichloromethane/methanol/ammonia (9:1:0.1)).

4.25.c. 3-(2-chloro-4-trifluoromethylphenyl)propynoic acid-[4-(3-diethylaminoethoxy)-3-fluorophenyl]amide Prepared analogously to Example 2.3.f. from (2-chloro-4-trifluoromethylphenyl)propynoic acid and 4-(3-diethylaminoethoxy)-3-fluorophenylamine. Yield: 0.14 g (33.5% of theory); melting point: 85° C.-88° C.; $C_{22}H_{21}ClF_4N_2O_2$

EXAMPLE 4.26

3-(2-chloro-4-trifluoromethylphenyl)propynoic acid-{3-chloro-4-[2-(4-methylpiperidin-1-yl)ethoxy]phenyl}amide

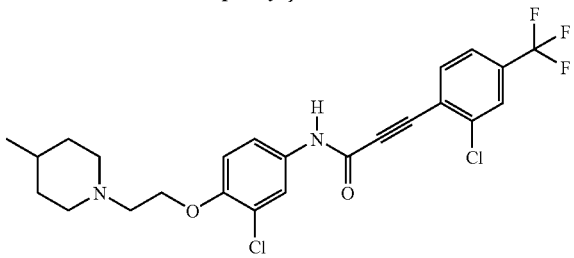

4.26.a. 1-[2-(2-chloro-4-nitrophenoxy)ethyl]4-methylpiperidine

A reaction mixture of 7.8 g (27.81 mmol) of 1-(2-bromoethoxy)-2-chloro-4-nitrobenzene and 10.14 mL (84 mmol) of 4-methylpiperidine in 100 mL of dichloromethane is stirred for 18 hours at ambient temperature. Then the solution is purified by column chromatography on 400 g of Alox act. II-III (eluant: dichloromethane/methanol (49:1)). Yield: 6.9 g (83% of theory); $C_{14}H_{19}ClN_2O_3$ (M=298.77); calc.: molecular ion peak (M+H)$^+$: 209/301; found: molecular ion peak (M+H)$^+$: 209/301; $R_f$ value: 0.48 (Alox, petroleum ether/ethyl acetate (3:1)).

4.26.b. 3-chloro-4-[2-(4-methylpiperidin-1-yl)ethoxy]phenylamine

Prepared analogously to Example 3.1.b. from 1-[2-(2-chloro-4-nitrophenoxy)ethyl]4-methylpiperidine. Yield: 3.66 g (59% of theory); $C_{14}H_{21}ClN_2O$ (M=268.78); calc.: molecular ion peak (M+H)$^+$: 269/271; found: molecular ion peak (M+H)$^+$: 269/271; $R_f$ value: 0.52 (silica gel, dichloromethane/methanol (9:1)).

4.26.c. 3-(2-chloro-4-trifluoromethylphenyl)propynoic acid-{3-chloro-4-[2-(4-methylpiperidin-1-yl)ethoxy]phenyl}amide Prepared analogously to Example 2.3.f. from (2-chloro-4-trifluoromethylphenyl)propynoic acid and 3-chloro-4-[2-(4-methylpiperidin-1-yl)ethoxy]phenylamine. Yield: 0.33 g (66% of theory); $C_{24}H_{23}Cl_2F_3N_2O_2$ (M=499.36); calc.: molecular ion peak (M+H)$^+$: 499/501/503; found: molecular ion peak (M+H)$^+$: 499/501/503; $R_f$ value: 0.68 (Alox, dichloromethane/methanol (49:1)).

EXAMPLE 4.27

3-(2-chloro-4-trifluoromethylphenyl)propynoic acid-{3-chloro-4-[2-(4-methylpiperidin-1-yl)ethylamino]phenyl}amide

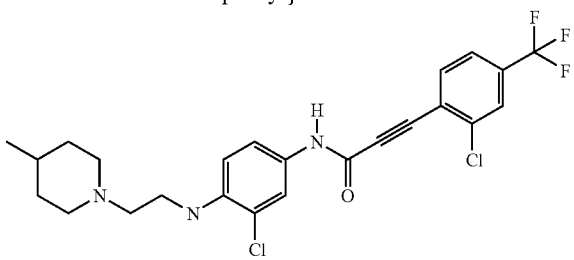

4.27.a. (2-chloro-4-nitrophenyl)-[2-(4-methylpiperidin-1-yl)ethyl]amine

A solution of 12.02 g (32.45 mmol) of 2-(4-methylpiperidin-1-yl)ethylamine in 100 mL of DMF is combined with 17.94 g (64.82 mmol) of potassium carbonate and stirred for 15 minutes at ambient temperature. Then 5.81 g (32.45 mmol) of 3-chloro-4-fluoronitrobenzene are added and the reaction mixture is stirred for 18 hours. Then the reaction mixture is poured into ice water and the crystalline residue is filtered off. Yield: 8.85 g (91.6% of theory); $C_{14}H_{20}ClN_3O_2$ (M=297.78); calc.: molecular ion peak (M+H)$^+$: 298/300; found: molecular ion peak (M+H)$^+$: 298/300.

4.27.b. 2-chloro-N'-[2-(4-methylpiperidin-1-yl)ethyl]benzene-1,4-diamine

Prepared analogously to Example 3.1.b. from (2-chloro-4-nitrophenyl)-[2-(4-methylpiperidin-1-yl)ethyl]amine. Yield: 7 g (89.3% of theory); $C_{14}H_{22}ClN_3$ (M=267.80); calc.: molecular ion peak (M+H)$^+$: 268/270; found: molecular ion peak (M+H)$^+$: 268/270; $R_f$ value: 0.6 (Alox, dichloromethane/methanol (49:1)).

4.27.c. 3-(2-chloro-4-trifluoromethylphenyl)propynoic acid-{3-chloro-4-[2-(4-methylpiperidin-1-yl)ethylamino]phenyl}amide Prepared analogously to Example 2.3.f. from (2-chloro-4-trifluoromethylphenyl)propynoic acid and 2-chloro-N-4-[2-(4-methylpiperidin-1-yl)ethyl]benzene-1,4-diamine. Yield: 0.35 g (70.2% of theory); $C_{24}H_{24}Cl_2F_3N_3O$ (M=498.38); calc.: molecular ion peak (M+H)$^+$: 455/457; found: molecular ion peak (M+H)$^+$: 455/457.

EXAMPLE 4.28

3-(2-chloro-4-trifluoromethylphenyl)propynoic acid-[3-chloro-4-(2-diethylaminoethylamino)phenyl]amide Formate

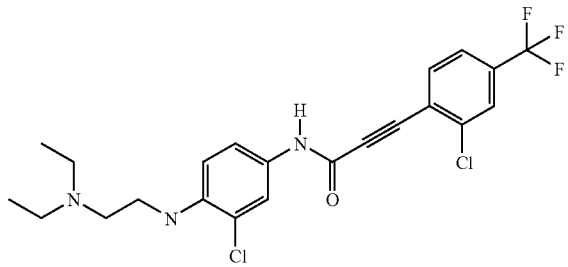

4.28.a. N'-(2-chloro-4-nitrophenyl)-N,N-diethylethane-1,2-diamine

Prepared analogously to Example 4.25.a. from $N^1,N^1$-diethylethane-1,2-diamine and 3-chloro-4-fluoronitrobenzene. Yield: 9.2 g (99.1% of theory); $C_{12}H_{18}ClN_3O_2$ (M=271.74); calc.: molecular ion peak (M+H)$^+$: 272/274; found: molecular ion peak (M+H)$^+$: 272/274; $R_f$ value: 0.72 (Alox, dichloromethane/methanol (49:1)).

4.28.b. 2-chloro-$N^1$-(2-diethylaminoethyl)benzene-1,4-diamine

Prepared analogously to Example 3.1.b. from N-(2-chloro-4-nitrophenyl)-N,N-diethylethane-1,2-diamine. Yield: 6.15 g (78% of theory); $C_{12}H_{20}ClN_3$ (M=241.76); calc.: molecular ion peak (M+H)$^+$: 242/244; found: molecular ion peak (M+H)$^+$: 242/244; $R_f$ value: 0.62 (Alox, dichloromethane/methanol (49:1)).

4.28.c. 3-(2-chloro-4-trifluoromethylphenyl)propynoic acid-[3-chloro-4-(2-diethylaminoethylamino)phenyl]amide Prepared analogously to Example 2.3.f. from (2-chloro-4-trifluoromethylphenyl)propynoic acid and 2-chloro-N'-(2-diethylaminoethyl)benzene-1,4-diamine. Yield: 0.17 g (32.8% of theory); $C_{22}H_{22}Cl_2F_3N_3O$*HCOOH (M=518.36); calc.: molecular ion peak (M+H)$^+$: 472/474/476; found: molecular ion peak (M+H)$^+$: 472/474/476

EXAMPLE 4.29

3-(2-chloro-4-trifluoromethylphenyl)propynoic acid-[3-chloro-4-(4-methylpiperidin-1-ylmethyl)phenyl]amide

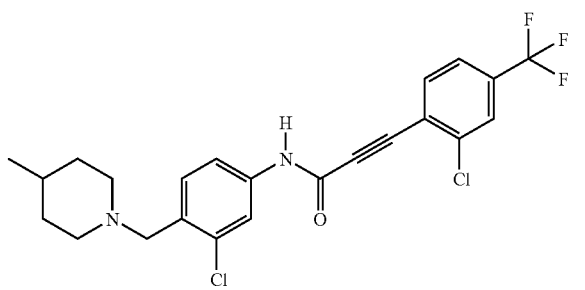

4.29.a. 1-(2-chloro-4-nitrobenzyl)-4-methylpiperidine 1 g (4.85 mmol) of 2-chloro-4-nitrobenzylchloride is slowly added dropwise to 2 mL (16.22 mmol) of 4-methylpiperidine at ambient temperature and the mixture is stirred for 15 minutes. The reaction mixture is diluted with ethyl acetate and extracted twice with water. The organic phase is dried over sodium sulfate and evaporated down. Yield: 1.3 g (99.7% of theory); $C_{13}H_{17}ClN_2O_2$ (M=268.74); calc.: molecular ion peak (M+H)$^+$: 269/271; found: molecular ion peak (M+H)$^+$: 269/271; $R_f$ value: 0.4 (Alox, petroleum ether).

4.29.b. 3-chloro-4-(4-methylpiperidin-1-ylmethyl)phenylamine

Prepared analogously to Example 3.1.b. from 1-(2-chloro-4-nitrobenzyl)$_4$-methylpiperidine. Yield: 0.93 g (80% of theory); $C_{12}H_{20}ClN_3$ (M=241.76); calc.: molecular ion peak (M+H)$^+$: 242/244; found: molecular ion peak (M+H)$^+$: 242/244; $R_f$ value: 0.59 (Alox, petroleum ether/ethyl acetate (3:1)).

4.29.c. 3-(2-chloro-4-trifluoromethylphenyl)propynoic acid-[3-chloro-4-(4-methylpiperidin-1-ylmethyl)phenyl]amide Prepared analogously to Example 2.3.f. from (2-chloro-4-trifluoromethylphenyl)propynoic acid and 3-chloro-4-(4-methylpiperidin-1-ylmethyl)phenylamine. Yield: 25 mg (5.3% of theory); $C_{23}H_{21}Cl_2F_3N_2O$ (M=469.33); calc.: molecular ion peak (M+H)$^+$: 469/471/473; found: molecular ion peak (M+H)$^+$: 469/471/473; $R_f$ value: 0.59 (Alox, petroleum ether/ethyl acetate (3:1)).

EXAMPLE 4.30

3-(2-chloro-4-trifluoromethylphenyl)propynoic acid-(3-chloro-4-piperidin-1-ylmethylphenyl)amide

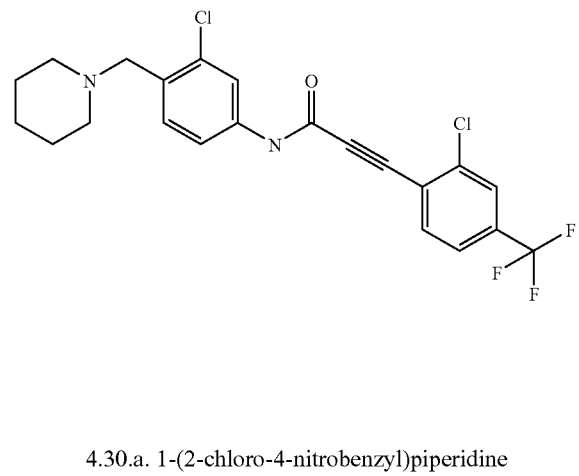

4.30.a. 1-(2-chloro-4-nitrobenzyl)piperidine

Prepared analogously to Example 4.29.a. from 4 mL (40 mmol) of piperidine and 2 g (9.71 mmol) of 2-chloro-4-nitrobenzylchloride. Yield: 2.39 g (97% of theory); $C_{12}H_{15}ClN_2O_2$ (M=254.71); calc.: molecular ion peak (M+H)$^+$: 255/257 (Cl); found: molecular ion peak (M+H)$^+$: 255/257 (Cl); $R_f$ value: 0.32 (silica gel, petroleum ether/ethyl acetate (6:1)).

4.30.b. 3-chloro-4-piperidin-1-ylmethylphenylamine

Prepared analogously to Example 3.1.b. from 1-(2-chloro-4-nitrobenzyl)piperidine. Yield: 1.88 g (90% of theory); $C_{12}H_{17}ClN_2$ (M=224.73); calc.: molecular ion peak (M+H)$^+$: 225/227 (Cl); found: molecular ion peak (M+H)$^+$: 225/227 (Cl); $R_f$ value: 0.2 (silica gel, dichloromethane/methanol (9:1)).

4.30.c. 3-(2-chloro-4-trifluoromethylphenyl)propynoic acid-(3-chloro-4-piperidin-1-ylmethylphenyl)amide Prepared analogously to Example 2.3.f. from (2-chloro-4-trifluoromethylphenyl)propynoic acid and 3-chloro-4-piperidin-1-ylmethylphenylamine. Yield: 200 mg (44% of theory); $C_{22}H_{19}Cl_2F_3N_2O$ (M=455.3)×HCl; calc.: molecular ion peak (M+H)$^+$: 455/457/459 (Cl) found: molecular ion peak (M+H)$^+$: 455/457/459 (Cl); $R_f$ value: 0.49 (silica gel, dichloromethane/methanol (9:1)).

EXAMPLE 4.31

3-(2-chloro-4-trifluoromethylphenyl)propynoic acid-[3-chloro-4-(2-diethylaminoethyl)phenyl]amide

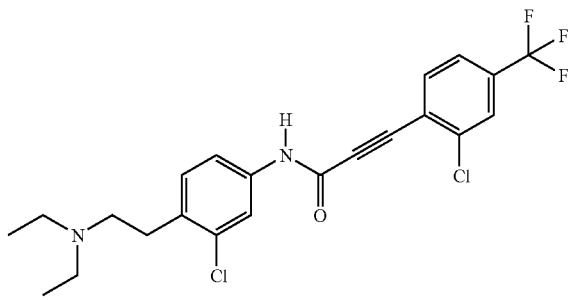

4.31.a. (2-chloro-4-nitrophenyl)acetic acid chloride

Prepared analogously to Example 4.1.c. from (2-chloro-4-nitrophenyl)acetic acid. The product is used in other reactions without further purification. Yield: 8.8 g (100% of theory); $C_8H_5Cl_2NO_3$ (M=234.04).

4.31.b. 2-(2-chloro-4-nitrophenyl)-N,N-diethylacetamide

Prepared analogously to Example 4.1.d. from (2-chloro-4-nitrophenyl)acetic acid chloride and diethylamine in ethyl acetate. Yield: 3.7 g (100% of theory); $C_{12}H_{15}ClN_2O_3$ (M=270.71); calc.: molecular ion peak (M+H)$^+$: 271/273; found: molecular ion peak (M+H)$^+$: 271/273; $R_f$ value: 0.45 (silica gel, petroleum ether/ethyl acetate (1:1)).

4.31.c. [2-(2-chloro-4-nitrophenyl)ethyl]diethylamine 65 mL (65 mmol) of a 1M borane-THF solution is added dropwise to a solution of 3.7 g (13.67 mmol) of 2-(2-chloro-4-nitrophenyl)-N,N-diethylacetamide in 130 mL of THF at ambient temperature and stirred for 4 hours. Then the reaction mixture is evaporated down and the residue is combined with 15 mL of methanol and 15 mL of dilute hydrochloric acid. The mixture is then stirred for 15 minutes at 100° C., cooled, and diluted with water. Then the mixture is made alkaline with sodium carbonate solution and extracted twice with ethyl acetate. The combined organic phases are extracted twice with water and once with saturated saline solution and dried over sodium sulfate. The purification is carried out by column chromatography on Alox, neutral, act. II-III (eluant: petroleum ether/ethyl acetate (4:1)). Yield: 2.1 g (59.8% of theory); $C_{12}H_{17}ClN_2O_2$ (M=256.73); $R_f$ value: 0.63 (Alox, petroleum ether/ethyl acetate (3:1)).

4.31.d. 3-chloro-4-(2-diethylaminoethyl)phenylamine

Prepared analogously to Example 3.1.b. from [2-(2-chloro-4-nitrophenyl)ethyl]diethylamine. Yield: 1.8 g (100% of theory); $C_{12}H_{19}ClN_2$ (M=226.75); calc.: molecular ion peak (M+H)$^+$: 227/229; found: molecular ion peak (M+H)$^+$: 227/229; $R_f$ value: 0.63 (Alox, petroleum ether/ethyl acetate (1:1)).

4.31.e. 3-(2-chloro-4-trifluoromethylphenyl)propynoic acid-[3-chloro-4-(2-diethylaminoethyl)phenyl]amide Prepared analogously to Example 2.3.f. from (2-chloro-4-trifluoromethylphenyl)propynoic acid and chloro-4-(2-diethylaminoethyl)phenylamine. Yield: 0.21 g (46.8% of theory); $C_{22}H_{21}Cl_2F_3N_2O$ (M=457.32); calc.: molecular ion peak (M+H)$^+$: 457/459/461; found: molecular ion peak (M+H)$^+$: 457/459/461; $R_f$ value: 0.63 (Alox, petroleum ether/ethyl acetate (1:1)).

EXAMPLE 4.32

3-(2-chloro-4-trifluoromethylphenyl)propynoic acid-{3-chloro-4-[2-(4-methylpiperidin-1-yl)ethyl]phenyl}amide

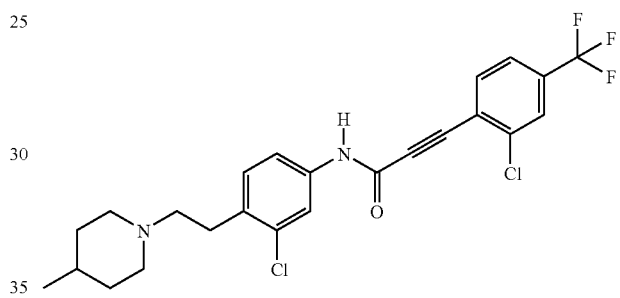

4.32.a. 3-chloro-4-[2-(4-methylpiperidin-1-yl)ethyl]phenylamine

Prepared analogously to Example 4.28.a. to c. from (2-chloro-4-nitrophenyl)acetic acid chloride. Yield: 0.71 g (99.3% of theory); $C_{14}H_{21}ClN_2$ (M=252.79); calc.: molecular ion peak (M+H)$^+$: 253/255; found: molecular ion peak (M+H)$^+$: 253/255.

4.32.b. 3-(2-chloro-4-trifluoromethylphenyl)propynoic acid-{3-chloro-4-[2-(4-methylpiperidin-1-yl)ethyl]phenyl}amide Prepared analogously to Example 2.3.f. from (2-chloro-4-trifluoromethylphenyl)propynoic acid and 3-chloro-4-[2-(4-methylpiperidin-1-yl)ethyl]phenylamine. Yield: 0.21 g (45.3% of theory); $C_{24}H_{23}Cl_2F_3N_2O$ (M=483.36); calc.: molecular ion peak (M+H)$^+$: 483/485/487; found: molecular ion peak (M+H)$^+$: 483/485/487; $R_f$ value: 0.65 (Alox, petroleum ether/ethyl acetate (1:1)).

EXAMPLE 4.33

3-(2-chloro-4-trifluoromethylphenyl)propynoic acid-{3-chloro-4-[2-(cyclopropylmethylamino)ethyl]phenyl}amide

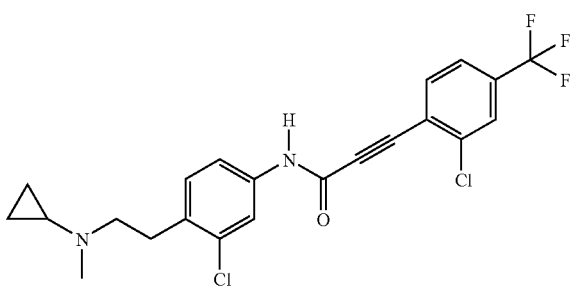

4.33.a.
[(E)-2-(2-chloro-4-nitrophenyl)vinyl]dimethylamine

A reaction mixture of 8.49 g (48 mmol) of 2-chloro-4-nitrotoluene and 15.03 mL (72.8 mmol) of tert-butoxybis(dimethylamino)methane in 200 mL of THF is refluxed for 8 hours. The reaction solution is evaporated down and the residue is combined with petroleum ether. The precipitate is filtered off, rinsed with petroleum ether and dried at ambient temperature under a high vacuum. The product is used in other reactions without further purification. Yield: 11 g, $C_{10}H_{11}ClN_2O_2$ (M=226.66); calc.: molecular ion peak $(M+H)^+$: 227/229; found: molecular ion peak $(M+H)^+$: 227/229; $R_f$ value: 0.55 (silica gel, petroleum ether/ethyl acetate (3:1)).

4.33.b. (2-chloro-4-nitrophenyl)acetaldehyde 50 mL of 1N hydrochloric acid is added dropwise to a solution of 10 g (30.88 mmol) of [(E)-2-(2-chloro-4-nitrophenyl)vinyl]dimethylamine in 200 mL of ethanol and the reaction mixture is then refluxed for 1 hour. Then the reaction mixture is evaporated down, diluted with water, and twice extracted with ethyl acetate. The combined organic phases are dried over sodium sulfate. The purification is carried out by column chromatography on silica gel (eluant: petroleum ether/ethyl acetate (3:1)). Yield: 4.5 g (73% of theory); $C_8H_6ClNO_3$ (M=199.59); $R_f$ value: 0.62 (silica gel, petroleum ether/ethyl acetate (1:1)).

4.33.c. [2-(2-chloro-4-nitrophenyl)ethyl]cyclopropylmethylamine 1.07 g (10 mmol) of N-methylcyclopropylamine is added to a solution of 1 g (5.01 mmol) of (2-chloro-4-nitrophenyl)acetaldehyde in 50 mL of THF and then 4.46 g (20 mmol) of sodium triacetoxyborohydride (95%) is added. The reaction mixture is stirred for 120 hours at ambient temperature and then poured into a saturated sodium hydrogen carbonate solution and twice extracted with ethyl acetate. The combined organic phases are dried over sodium sulfate. The purification is carried out by column chromatography on Alox, neutral, act. II-III (eluant: petroleum ether/ethyl acetate (5:1)). Yield: 0.75 g (58.8% of theory); $C_{12}H_{15}ClN_2O_2$ (M=254.71); calc.: molecular ion peak $(M+H)^+$: 255/257; found: molecular ion peak $(M+H)^+$: 255/257; $R_f$ value: 0.61 (Alox, petroleum ether/ethyl acetate (5:1)).

4.33.d. 3-chloro-4-[2-(cyclopropylmethylamino)ethyl]phenylamine

Prepared analogously to Example 3.1.b. from [2-(2-chloro-4-nitrophenyl)ethyl]cyclopropylmethylamine. Yield: 0.6 g (100% of theory); $C_{12}H_{17}ClN_2$ (M=224.73); calc.: molecular ion peak $(M+H)^+$: 225/227; found: molecular ion peak $(M+H)^+$: 225/227; $R_f$ value: 0.57 (Alox, petroleum ether/ethyl acetate (1:1)).

4.33.e. 3-(2-chloro-4-trifluoromethylphenyl)propynoic acid-{3-chloro-4-[2-(cyclopropylmethylamino)ethyl]phenyl}amide Prepared analogously to Example 2.3.f. from (2-chloro-4-trifluoromethylphenyl)propynoic acid and 3-chloro-4-[2-(cyclopropylmethylamino)ethyl]phenylamine. Yield: 15 mg (3.4% of theory); $C_{22}H_{19}Cl_2F_3N_2O$ (M=455.31); calc.: molecular ion peak $(M+H)^+$: 455/457/459; found: molecular ion peak $(M+H)^+$: 455/457/459; $R_f$ value: 0.3 (Alox, petroleum ether/ethyl acetate (3:1)).

EXAMPLE 4.34

3-(2-chloro-4-nitrophenyl)propynoic acid-[3-chloro-4-(2-diethylaminoethoxy)phenyl]amide

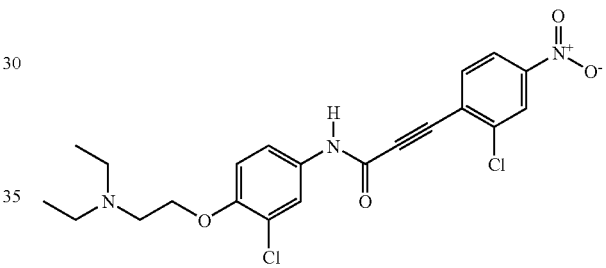

4.34.a. ethyl(2-chloro-4-nitrophenyl)propynoate

Prepared analogously to Example 4.11.a from 3-chloro-4-iodonitrobenzene and ethyl propynoate Yield: 1.6 g (46.5% of theory); $C_{11}H_8ClNO_4$ (M=253.64); calc.: molecular ion peak $(M+H)^+$: 254/256; found: molecular ion peak $(M+H)^+$: 254/256; $R_f$ value: 0.6 (silica gel, petroleum ether/ethyl acetate (6:1)).

4.34.b. (2-chloro-4-nitrophenyl)propynoic acid

Prepared analogously to Example 4.11.b. from ethyl (2-chloro-4-nitrophenyl)propynoate. Yield: 0.76 g (66.8% of theory); $C_9H_4ClNO_4$ (M=225.59); calc.: molecular ion peak $(M+H)^+$: 225/227; found: molecular ion peak $(M+H)^+$: 225/227.

4.34.c. 3-(2-chloro-4-nitrophenyl)propynoic acid-[3-chloro-4-(2-diethylaminoethoxy)phenyl]amide Prepared analogously to Example 2.3.f. from (2-chloro-4-nitrophenyl)propynoic acid and 3-chloro-4-(2-diethylaminoethoxy)phenylamine. Yield: 0.49 g (54.4% of theory); $C_{21}H_{21}Cl_2N_3O_4$ (M=450.32); calc.: molecular ion peak $(M+H)^+$: 448/450/452; found: molecular ion peak $(M+H)^+$: 448/450/452; $R_f$ value: 0.36 (silica gel, dichloromethane/methanol (9:1)).

EXAMPLE 4.35

3-(4-bromo-2-chlorophenyl)propynoic acid-[3-chloro-4-(2-diethylaminoethoxy)phenyl]amide

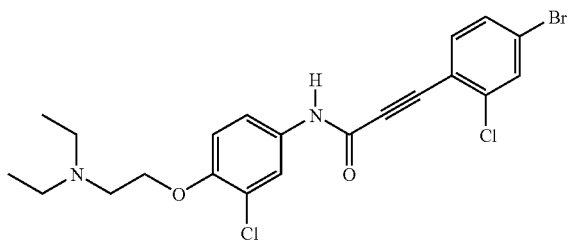

4.35.a. ethyl(4-bromo-2-chlorophenyl)propynoate

Prepared analogously to Example 4.11.a. from 3-chloro-4-iodobromobenzene and ethyl propynoate. Yield: 0.97 g (48.2% of theory); $C_{11}H_8BrClO_2$ (M=287.54); calc.: molecular ion peak (M+H)$^+$: 287/289/291; found: molecular ion peak (M+H)$^+$: 287/289/291; $R_f$ value: 0.62 (silica gel, petroleum ether/ethyl acetate (6:1)).

4.35.b. (4-bromo-2-chlorophenyl)propynoic acid

Prepared analogously to Example 4.11.b. from ethyl (4-bromo-2-chlorophenyl)propynoate. Yield: 0.8 g (93.4% of theory); $C_9H_4BrClO_2$ (M=259.48); calc.: molecular ion peak (M+H)$^+$: 258/260/262; found: molecular ion peak (M+H)$^+$: 258/260/262.

4.35.c. 3-(4-bromo-2-chlorophenyl)propynoic acid-[3-chloro-4-(2-diethylaminoethoxy)phenyl]amide Prepared analogously to Example 2.3.f. from (4-bromo-2-chlorophenyl)propynoic acid and 3-chloro-4-(2-diethylaminoethoxy)phenylanine. Yield: 0.25 g (64.5% of theory); $C_{21}H_{21}BrCl_2N_2O_2$ (M=484.22); calc.: molecular ion peak (M+H)$^+$: 483/485/487/489; found: molecular ion peak (M+H)$^+$: 483/485/487/489; $R_f$ value: 0.86 (silica gel, dichloromethane/methanol (49:1)).

The following compounds are prepared analogously to the abovementioned Examples:

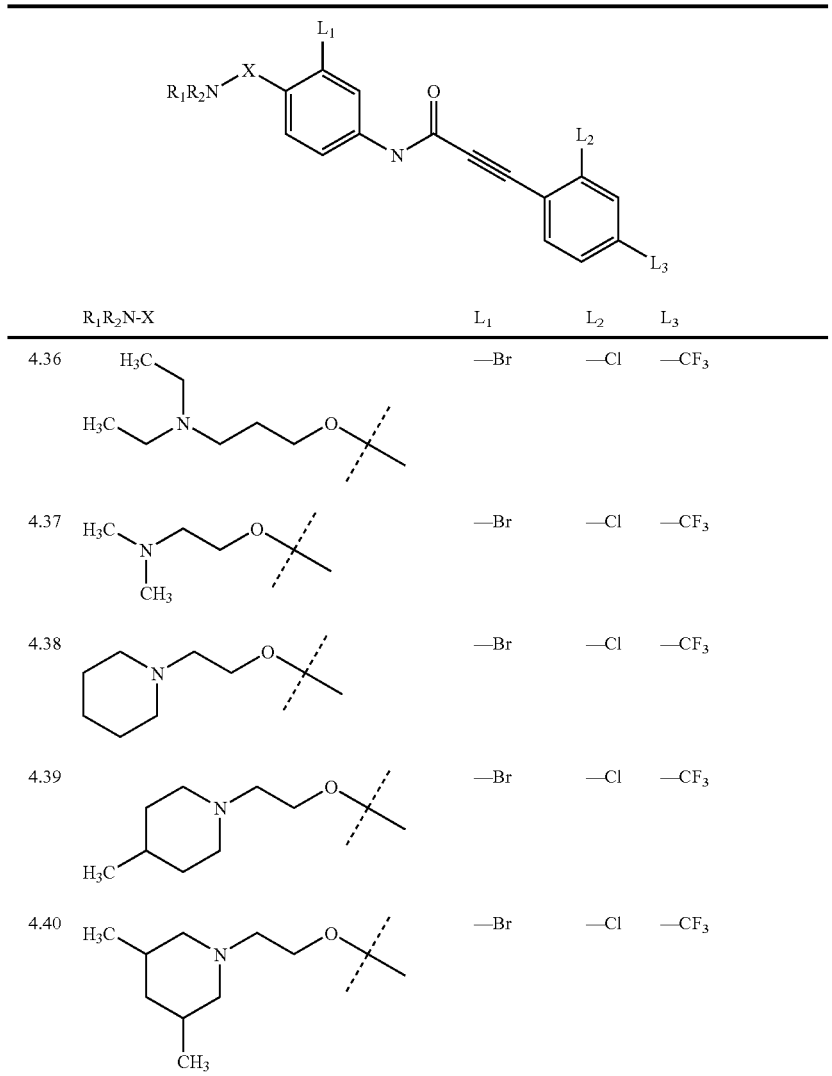

| | $R_1R_2N-X$ | $L_1$ | $L_2$ | $L_3$ |
|---|---|---|---|---|
| 4.36 | H₃C—CH₂—N(CH₂CH₃)—CH₂CH₂CH₂—O— | —Br | —Cl | —CF₃ |
| 4.37 | H₃C—N(CH₃)—CH₂CH₂—O— | —Br | —Cl | —CF₃ |
| 4.38 | piperidinyl—CH₂CH₂—O— | —Br | —Cl | —CF₃ |
| 4.39 | 4-methylpiperidinyl—CH₂CH₂—O— | —Br | —Cl | —CF₃ |
| 4.40 | 3,5-dimethylpiperidinyl—CH₂CH₂—O— | —Br | —Cl | —CF₃ |

-continued
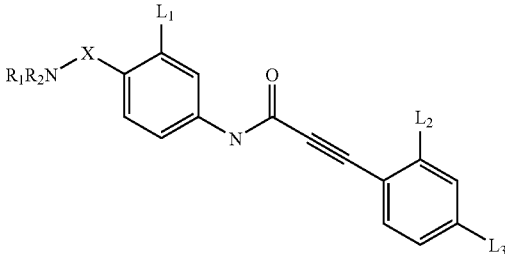
| | R₁R₂N-X | L₁ | L₂ | L₃ |
|---|---|---|---|---|
| 4.41 | 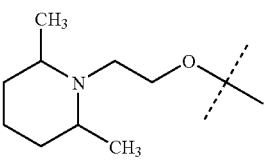 | —Br | —Cl | —CF₃ |
| 4.43 | 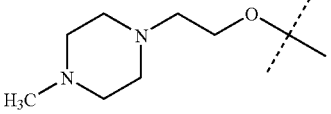 | —Br | —Cl | —CF₃ |
| 4.44 | 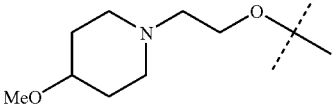 | —Br | —Cl | —CF₃ |
| 4.45 | 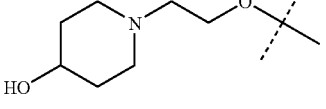 | —Br | —Cl | —CF₃ |
| 4.46 | 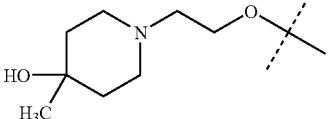 | —Br | —Cl | —CF₃ |
| 4.47 | 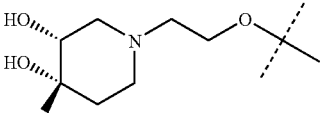 | —Br | —Cl | —CF₃ |
| 4.48 | 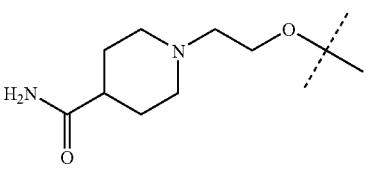 | —Br | —Cl | —CF₃ |
| 4.49 | 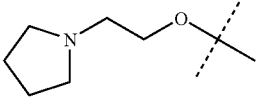 | —Br | —Cl | —CF₃ |
| 4.50 | 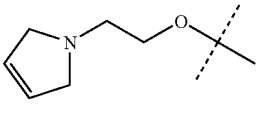 | —Br | —Cl | —CF₃ |

-continued
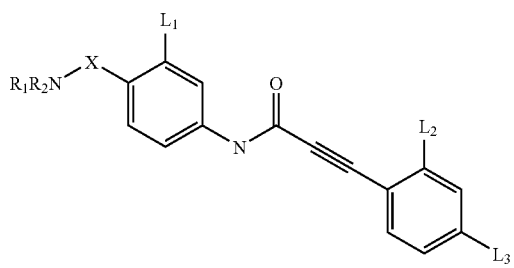
| | R₁R₂N-X | L₁ | L₂ | L₃ |
|---|---|---|---|---|
| 4.51 | | —Br | —Cl | —CF₃ |
| 4.52 | | —Br | —Cl | —CF₃ |
| 4.53 | | —Br | —Cl | —CF₃ |
| 4.54 | | —Br | —Cl | —CF₃ |
| 4.55 | | —Br | —Cl | —CF₃ |
| 4.56 | | —Br | —Cl | —CF₃ |
| 4.57 | | —Br | —Cl | —CF₃ |
| 4.58 | | —Br | —Cl | —CF₃ |

-continued
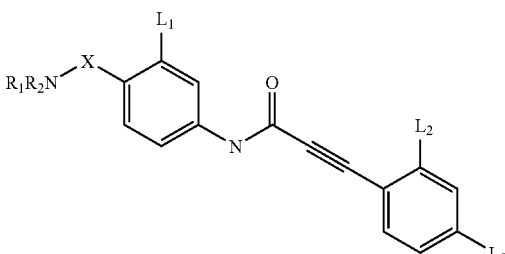
| | $R_1R_2N-X$ | $L_1$ | $L_2$ | $L_3$ |
|---|---|---|---|---|
| 4.59 | 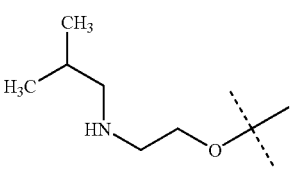 | —Br | —Cl | —$CF_3$ |
| 4.60 | 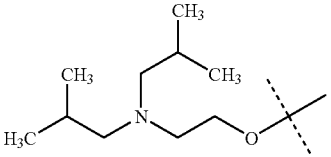 | —Br | —Cl | —$CF_3$ |
| 4.61 | 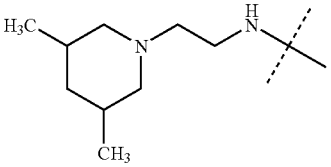 | —Br | —Cl | —$CF_3$ |
| 4.62 | 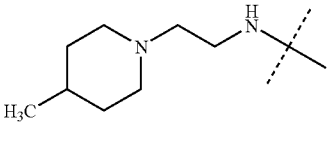 | —Br | —Cl | —$CF_3$ |
| 4.63 | 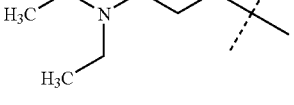 | —Br | —Cl | —$CF_3$ |
| 4.64 | 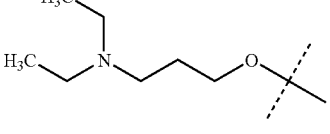 | —$CH_3$ | —Cl | —$CF_3$ |
| 4.65 | 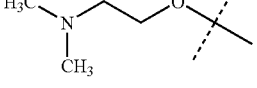 | —$CH_3$ | —Cl | —$CF_3$ |
| 4.66 | 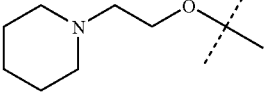 | —$CH_3$ | —Cl | —$CF_3$ |

-continued
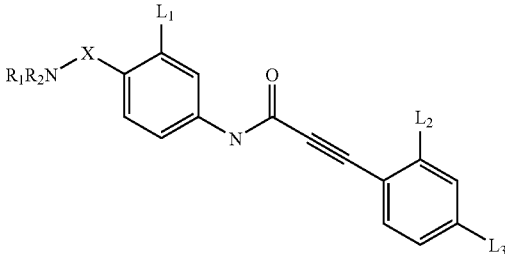
| | R₁R₂N-X | L₁ | L₂ | L₃ |
|---|---|---|---|---|
| 4.67 | 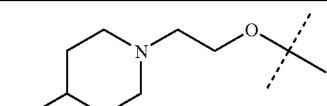 | —CH₃ | —Cl | —CF₃ |
| 4.68 | 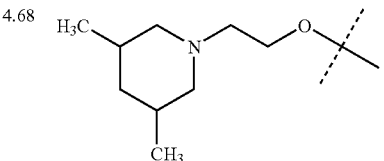 | —CH₃ | —Cl | —CF₃ |
| 4.69 | 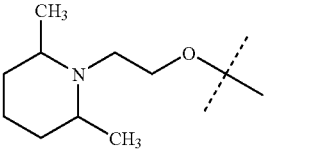 | —CH₃ | —Cl | —CF₃ |
| 4.70 | 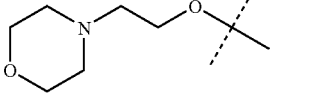 | —CH₃ | —Cl | —CF₃ |
| 4.71 | 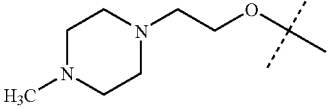 | —CH₃ | —Cl | —CF₃ |
| 4.72 | 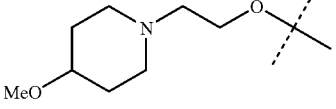 | —CH₃ | —Cl | —CF₃ |
| 4.73 | 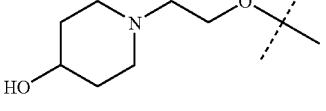 | —CH₃ | —Cl | —CF₃ |
| 4.74 | 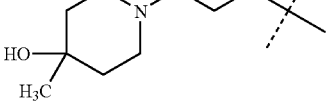 | —CH₃ | —Cl | —CF₃ |
| 4.75 | 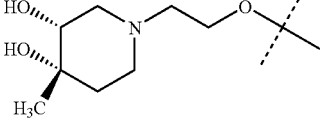 | —CH₃ | —Cl | —CF₃ |

-continued
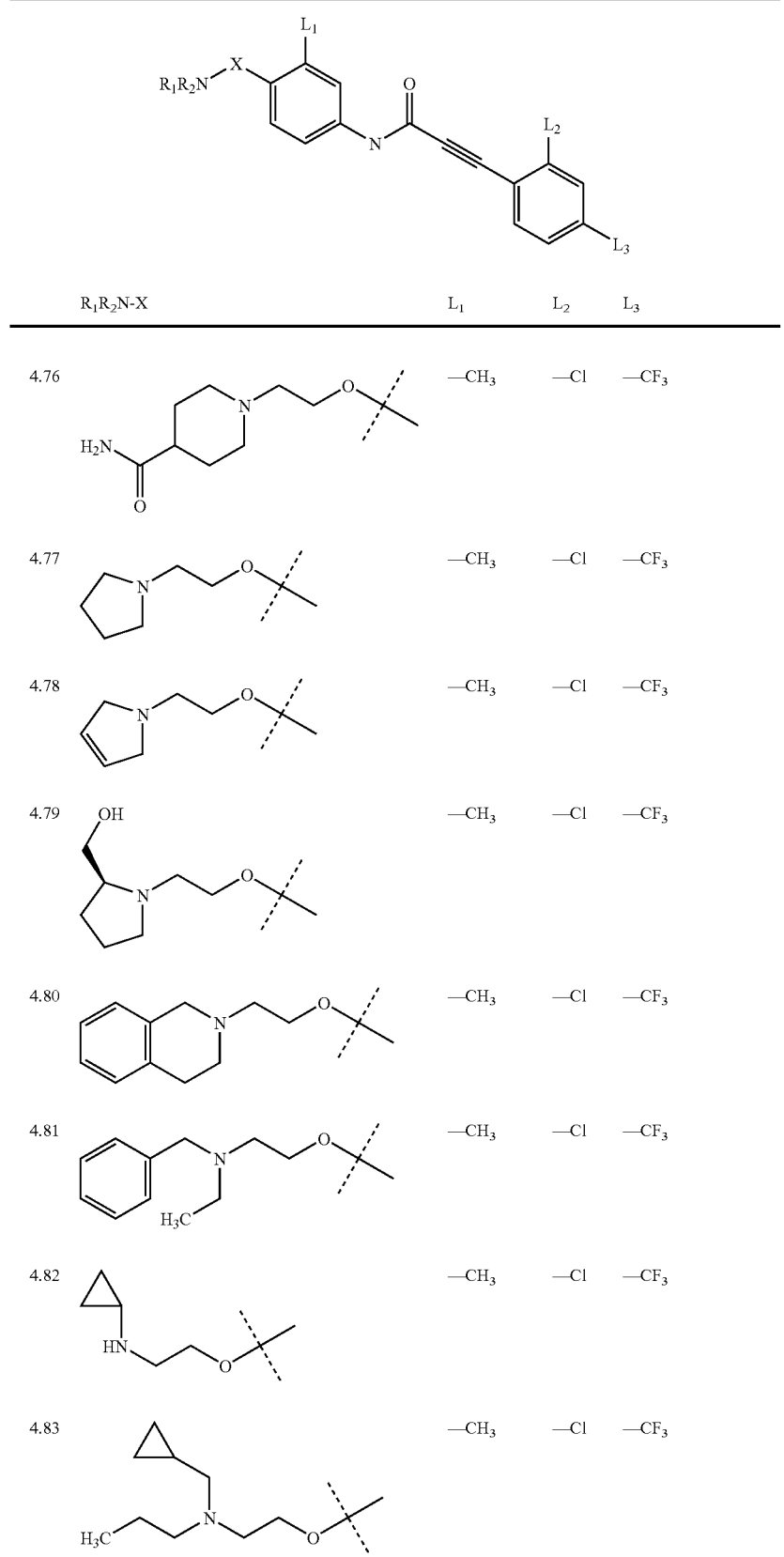
| | $R_1R_2N-X$ | $L_1$ | $L_2$ | $L_3$ |
|---|---|---|---|---|
| 4.76 | | —CH₃ | —Cl | —CF₃ |
| 4.77 | | —CH₃ | —Cl | —CF₃ |
| 4.78 | | —CH₃ | —Cl | —CF₃ |
| 4.79 | | —CH₃ | —Cl | —CF₃ |
| 4.80 | | —CH₃ | —Cl | —CF₃ |
| 4.81 | | —CH₃ | —Cl | —CF₃ |
| 4.82 | | —CH₃ | —Cl | —CF₃ |
| 4.83 | | —CH₃ | —Cl | —CF₃ |

-continued
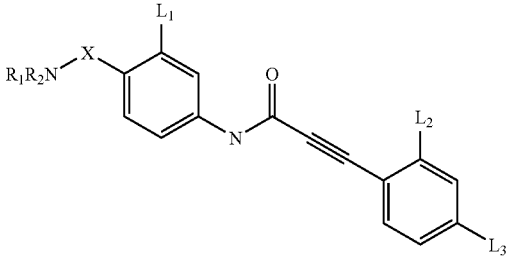
| | $R_1R_2N-X$ | $L_1$ | $L_2$ | $L_3$ |
|---|---|---|---|---|
| 4.84 | 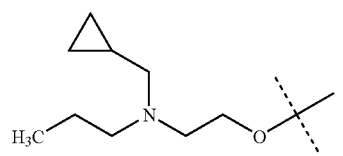 | —CH₃ | —Cl | —CF₃ |
| 4.85 | 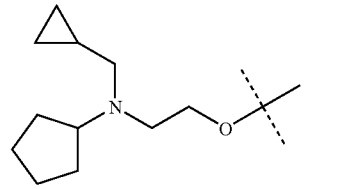 | —CH₃ | —Cl | —CF₃ |
| 4.86 | 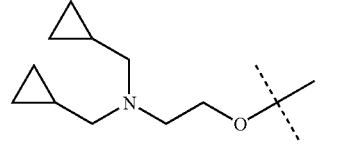 | —CH₃ | —Cl | —CF₃ |
| 4.87 | 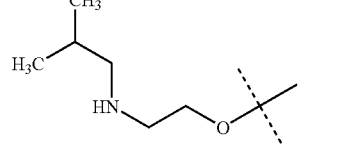 | —CH₃ | —Cl | —CF₃ |
| 4.88 | 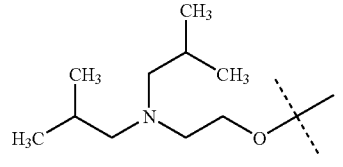 | —CH₃ | —Cl | —CF₃ |
| 4.89 | 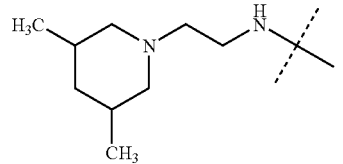 | —CH₃ | —Cl | —CF₃ |
| 4.90 | 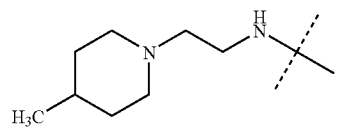 | —CH₃ | —Cl | —CF₃ |

-continued
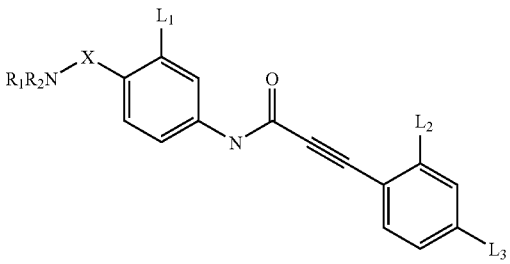
| | R₁R₂N-X | L₁ | L₂ | L₃ |
|---|---|---|---|---|
| 4.91 | 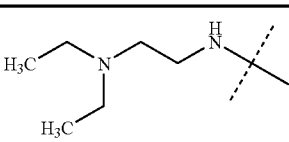 | —CH₃ | —Cl | —CF₃ |
| 4.92 | 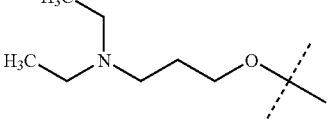 | —H | —Cl | —CF₃ |
| 4.93 | 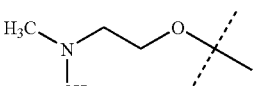 | —H | —Cl | —CF₃ |
| 4.94 | 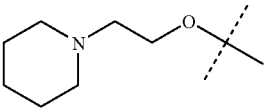 | —H | —Cl | —CF₃ |
| 4.96 | 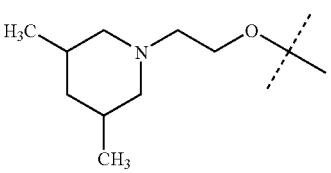 | —H | —Cl | —CF₃ |
| 4.97 | 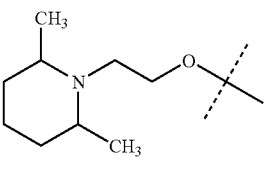 | —H | —Cl | —CF₃ |
| 4.98 | 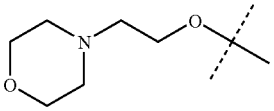 | —H | —Cl | —CF₃ |
| 4.99 | 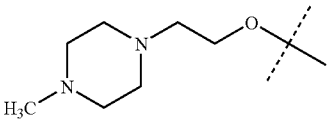 | —H | —Cl | —CF₃ |
| 4.100 | 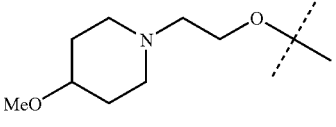 | —H | —Cl | —CF₃ |

-continued

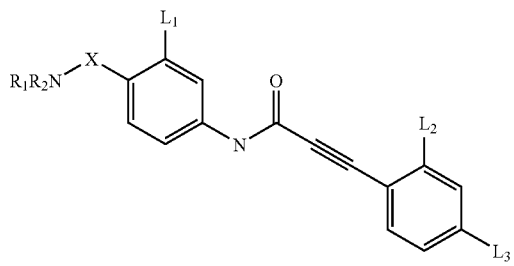

| | R₁R₂N-X | L₁ | L₂ | L₃ |
|---|---|---|---|---|
| 4.101 | (4-hydroxypiperidin-1-yl)ethoxy- | —H | —Cl | —CF₃ |
| 4.102 | (4-hydroxy-4-methylpiperidin-1-yl)ethoxy- | —H | —Cl | —CF₃ |
| 4.103 | (3,4-dihydroxy-4-methylpiperidin-1-yl)ethoxy- | —H | —Cl | —CF₃ |
| 4.104 | (4-carbamoylpiperidin-1-yl)ethoxy- | —H | —Cl | —CF₃ |
| 4.105 | (pyrrolidin-1-yl)ethoxy- | —H | —Cl | —CF₃ |
| 4.106 | (2,5-dihydropyrrol-1-yl)ethoxy- | —H | —Cl | —CF₃ |
| 4.107 | (2-(hydroxymethyl)pyrrolidin-1-yl)ethoxy- | —H | —Cl | —CF₃ |
| 4.108 | (1,2,3,4-tetrahydroisoquinolin-2-yl)ethoxy- | —H | —Cl | —CF₃ |
| 4.109 | (N-benzyl-N-ethylamino)ethoxy- | —H | —Cl | —CF₃ |

-continued
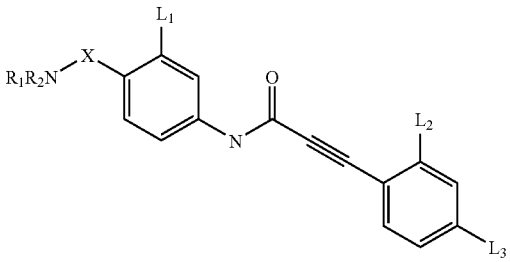
| | $R_1R_2N$-X | $L_1$ | $L_2$ | $L_3$ |
|---|---|---|---|---|
| 4.110 | 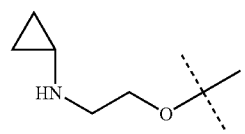 | —H | —Cl | —CF$_3$ |
| 4.111 | 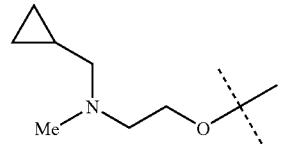 | —H | —Cl | —CF$_3$ |
| 4.112 | 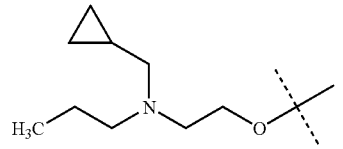 | —H | —Cl | —CF$_3$ |
| 4.113 | 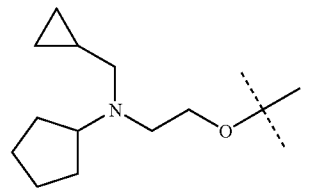 | —H | —Cl | —CF$_3$ |
| 4.114 | 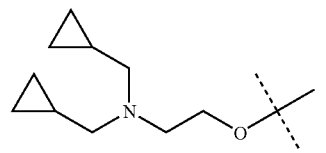 | —H | —Cl | —CF$_3$ |
| 4.115 | 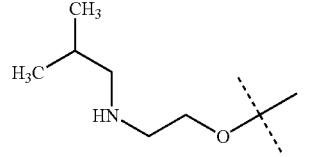 | —H | —Cl | —CF$_3$ |
| 4.116 | 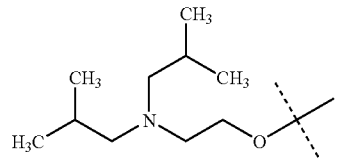 | —H | —Cl | —CF$_3$ |

-continued
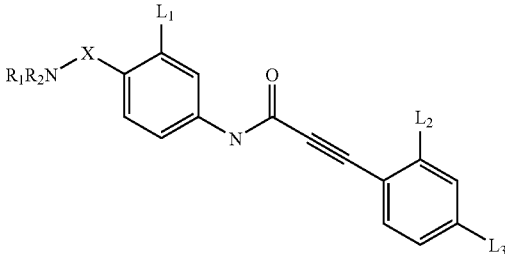
| | R₁R₂N-X | L₁ | L₂ | L₃ |
|---|---|---|---|---|
| 4.117 | 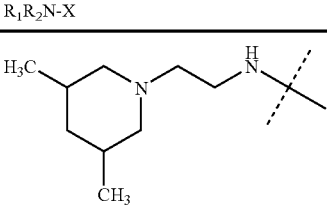 | —H | —Cl | —CF₃ |
| 4.118 | 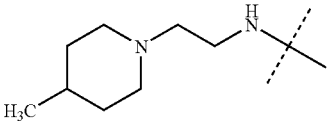 | —H | —Cl | —CF₃ |
| 4.119 | 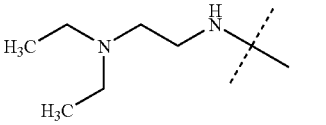 | —H | —Cl | —CF₃ |
| 4.120 | 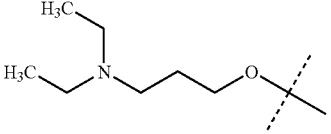 | —OCH₃ | —Cl | —CF₃ |
| 4.121 | 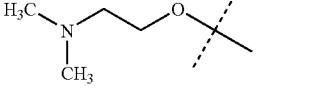 | —OCH₃ | —Cl | —CF₃ |
| 4.122 | 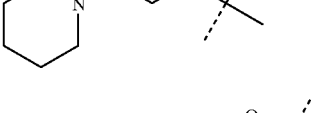 | —OCH₃ | —Cl | —CF₃ |
| 4.123 | 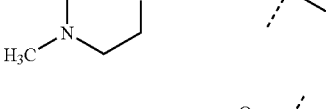 | —OCH₃ | —Cl | —CF₃ |
| 4.124 | 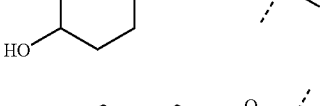 | —OCH₃ | —Cl | —CF₃ |
| 4.125 | 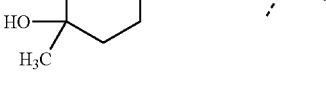 | —OCH₃ | —Cl | —CF₃ |

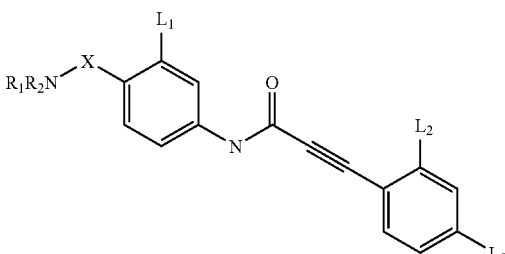

-continued
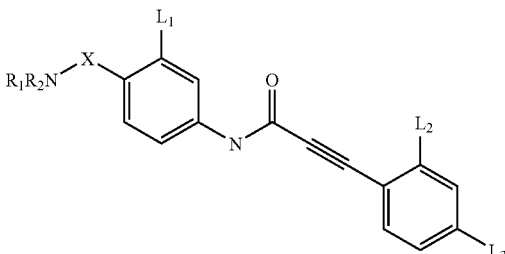
| | $R_1R_2N-X$ | $L_1$ | $L_2$ | $L_3$ |
|---|---|---|---|---|
| 4.134 | 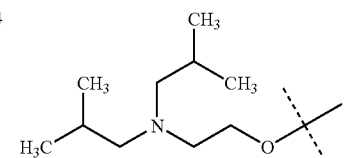 | —OCH₃ | —Cl | —CF₃ |
| 4.135 | 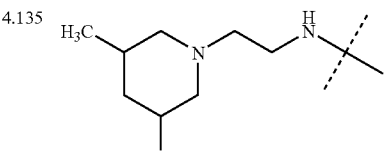 | —OCH₃ | —Cl | —CF₃ |
| 4.136 | 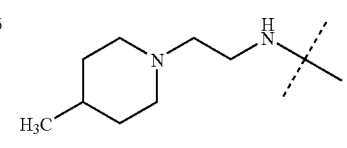 | —OCH₃ | —Cl | —CF₃ |
| 4.137 | 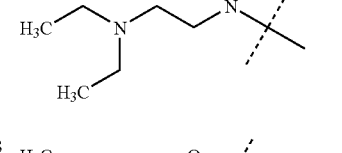 | —OCH₃ | —Cl | —CF₃ |
| 4.138 | 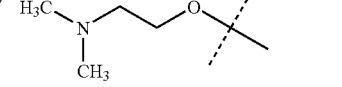 | —Cl | —Cl | —CF₃ |
| 4.139 | 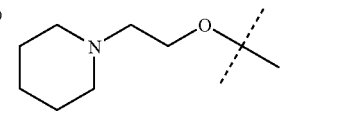 | —Cl | —Cl | —CF₃ |
| 4.140 | 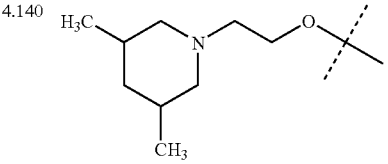 | —Cl | —Cl | —CF₃ |
| 4.141 | 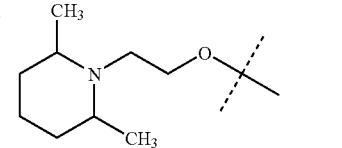 | —Cl | —Cl | —CF₃ |

-continued
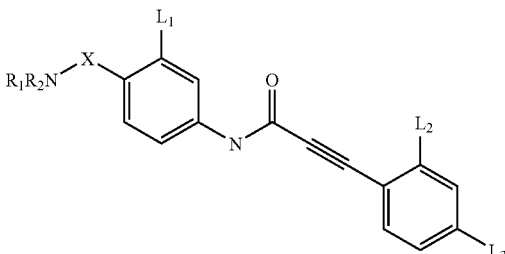
| | R₁R₂N-X | L₁ | L₂ | L₃ |
|---|---|---|---|---|
| 4.142 | 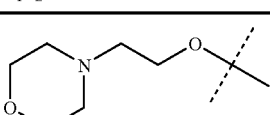 | —Cl | —Cl | —CF₃ |
| 4.143 | 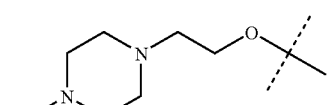 | —Cl | —Cl | —CF₃ |
| 4.144 | 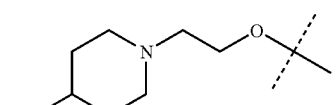 | —Cl | —Cl | —CF₃ |
| 4.145 | 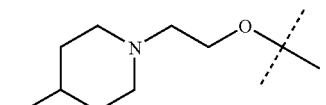 | —Cl | —Cl | —CF₃ |
| 4.146 | 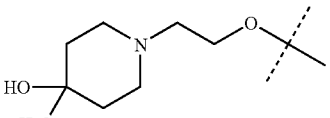 | —Cl | —Cl | —CF₃ |
| 4.147 | 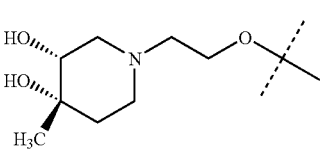 | —Cl | —Cl | —CF₃ |
| 4.148 | 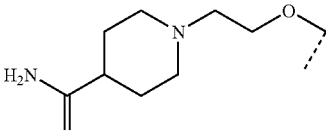 | —Cl | —Cl | —CF₃ |
| 4.149 | 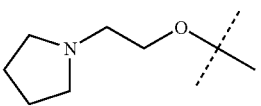 | —Cl | —Cl | —CF₃ |
| 4.150 | 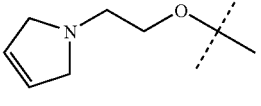 | —Cl | —Cl | —CF₃ |

-continued

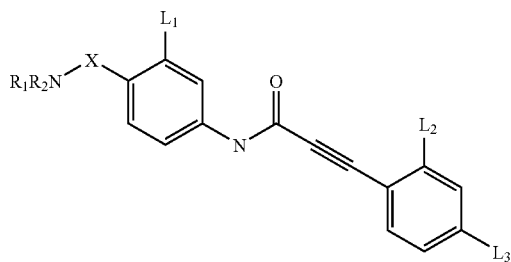

| | R₁R₂N-X | L₁ | L₂ | L₃ |
|---|---|---|---|---|
| 4.151 | (S)-2-(hydroxymethyl)pyrrolidin-1-yl-CH₂CH₂-O- | —Cl | —Cl | —CF₃ |
| 4.152 | 1,2,3,4-tetrahydroisoquinolin-2-yl-CH₂CH₂-O- | —Cl | —Cl | —CF₃ |
| 4.153 | N-benzyl-N-ethylamino-CH₂CH₂-O- | —Cl | —Cl | —CF₃ |
| 4.154 | cyclopropylmethylamino-CH₂CH₂-O- | —Cl | —Cl | —CF₃ |
| 4.155 | N-(cyclopropylmethyl)-N-methylamino-CH₂CH₂-O- | —Cl | —Cl | —CF₃ |
| 4.156 | N-(cyclopropylmethyl)-N-propylamino-CH₂CH₂-O- | —Cl | —Cl | —CF₃ |
| 4.157 | N-(cyclopropylmethyl)-N-cyclopentylamino-CH₂CH₂-O- | —Cl | —Cl | —CF₃ |
| 4.158 | N,N-bis(cyclopropylmethyl)amino-CH₂CH₂-O- | —Cl | —Cl | —CF₃ |

-continued
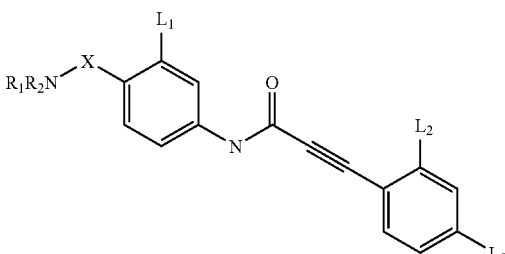
| R₁R₂N-X | L₁ | L₂ | L₃ |
|---|---|---|---|
| 4.159 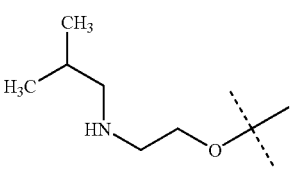 | —Cl | —Cl | —CF₃ |
| 4.160 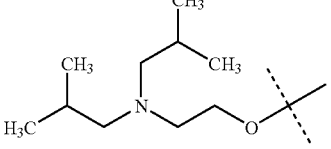 | —Cl | —Cl | —CF₃ |
| 4.161 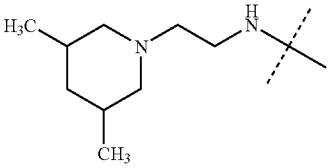 | —Cl | —Cl | —CF₃ |
| 4.162 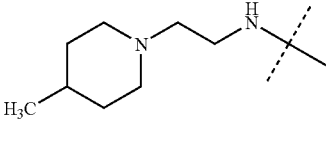 | —Cl | —Cl | —CF₃ |
| 4.163 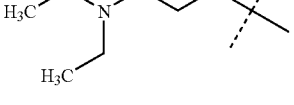 | —Cl | —Cl | —CF₃ |
| 4.164 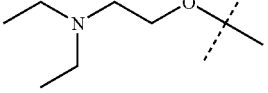 | —Cl | —Cl | —NH₂ |
| 4.165 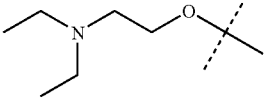 | —Cl | —Cl | 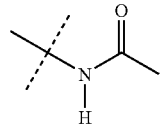 |
| 4.166 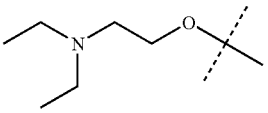 | —Cl | —Cl | 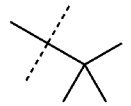 |

-continued
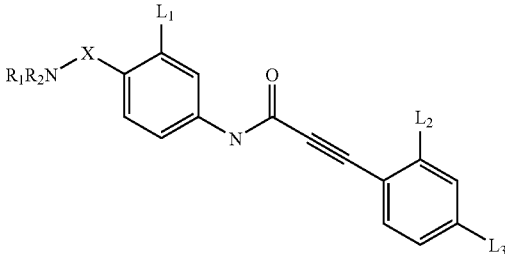
| | R₁R₂N-X | L₁ | L₂ | L₃ |
|---|---|---|---|---|
| 4.167 | 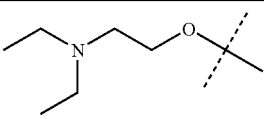 | —Cl | —Cl | —OMe |
| 4.168 | 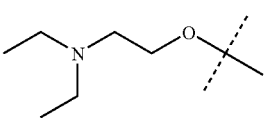 | —Cl | —Cl | -Me |
| 4.169 | 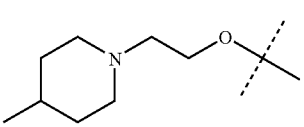 | —Cl | —Cl | —Br |
| 4.170 | 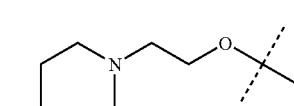 | —Cl | —Cl | —NO₂ |
| 4.171 | 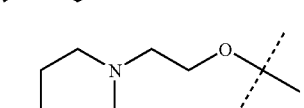 | —Cl | —Cl | —NH₂ |
| 4.172 | 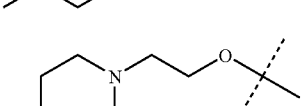 | —Cl | —Cl | 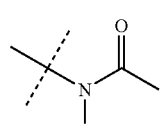 |
| 4.173 | 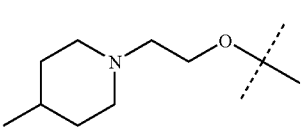 | —Cl | —Cl |  |
| 4.174 | 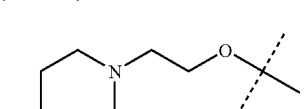 | —Cl | —Cl | —OMe |
| 4.175 | 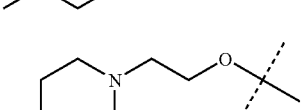 | —Cl | —Cl | -Me |
| 4.176 |  | —Cl | —Cl | —CF₃ |

-continued

| R₁R₂N-X | L₁ | L₂ | L₃ |
|---|---|---|---|
| 4.177 | —Cl | —Cl | —CF₃ |
| 4.178 | —Cl | —Cl | —CF₃ |
| 4.179 | —Cl | —Cl | —CF₃ |
| 4.180 | —Cl | —Cl | —CF₃ |
| 4.181 | —Cl | —Cl | —CF₃ |
| 4.182 | —Cl | —Cl | —CF₃ |
| 4.183 | —Cl | —Cl | —CF₃ |

-continued
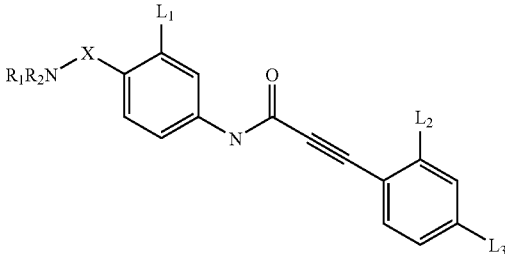
| | R₁R₂N-X | L₁ | L₂ | L₃ |
|---|---|---|---|---|
| 4.184 | 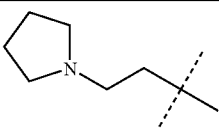 | —Cl | —Cl | —CF₃ |
| 4.185 | 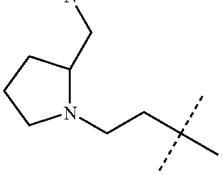 | —Cl | —Cl | —CF₃ |
| 4.186 | 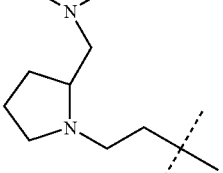 | —Cl | —Cl | —CF₃ |
| 4.187 | 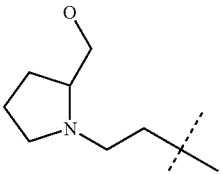 | —Cl | —Cl | —CF₃ |
| 4.188 | 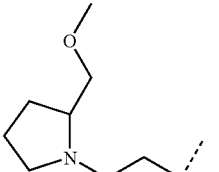 | —Cl | —Cl | —CF₃ |
| 4.189 | 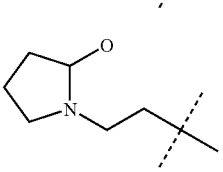 | —Cl | —Cl | —CF₃ |
| 4.190 | 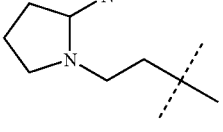 | —Cl | —Cl | —CF₃ |

-continued
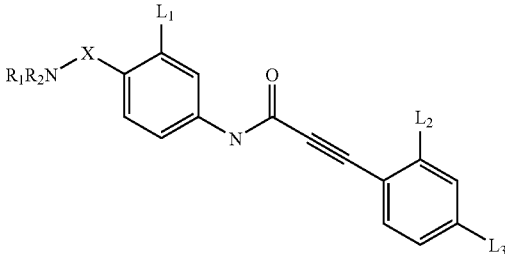
| R₁R₂N-X | L₁ | L₂ | L₃ |
|---|---|---|---|
| 4.191 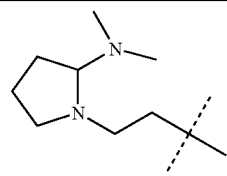 | —Cl | —Cl | —CF₃ |
| 4.192 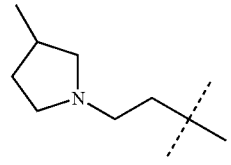 | —Cl | —Cl | —CF₃ |
| 4.193 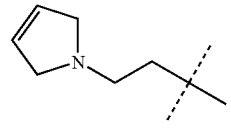 | —Cl | —Cl | —CF₃ |
| 4.194 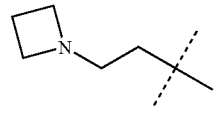 | —Cl | —Cl | —CF₃ |
| 4.195 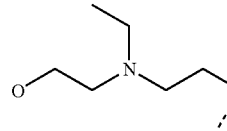 | —Cl | —Cl | —CF₃ |
| 4.196 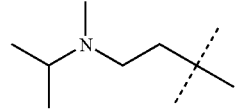 | —Cl | —Cl | —CF₃ |
| 4.197 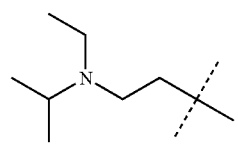 | —Cl | —Cl | —CF₃ |
| 4.198 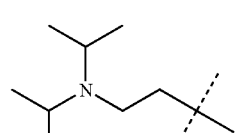 | —Cl | —Cl | —CF₃ |
| 4.199 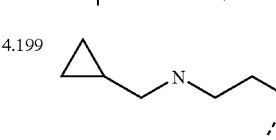 | —Cl | —Cl | —CF₃ |

-continued
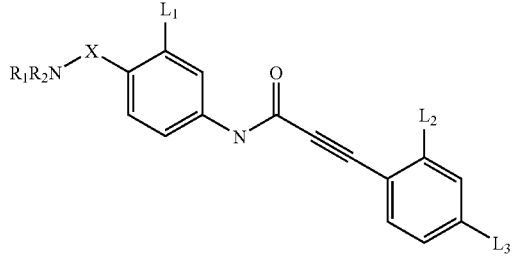
| | R₁R₂N-X | L₁ | L₂ | L₃ |
|---|---|---|---|---|
| 4.200 | 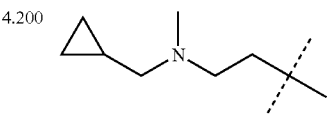 | —Cl | —Cl | —CF₃ |
| 4.201 | 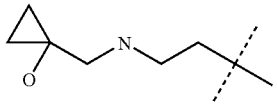 | —Cl | —Cl | —CF₃ |
| 4.202 | 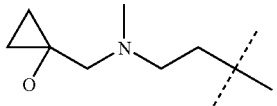 | —Cl | —Cl | —CF₃ |
| 4.203 | 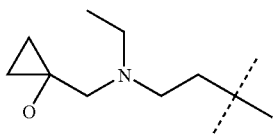 | —Cl | —Cl | —CF₃ |
| 4.204 | 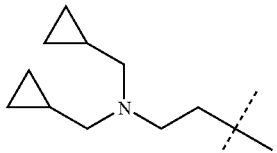 | —Cl | —Cl | —CF₃ |
| 4.205 | 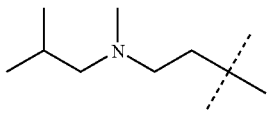 | —Cl | —Cl | —CF₃ |
| 4.206 | 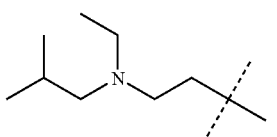 | —Cl | —Cl | —CF₃ |
| 4.207 | 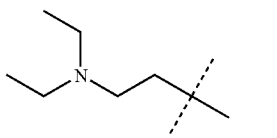 | -Me | —Cl | —CF₃ |
| 4.208 | 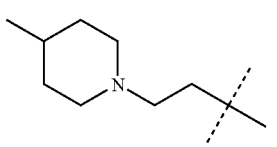 | -Me | —Cl | —CF₃ |

-continued

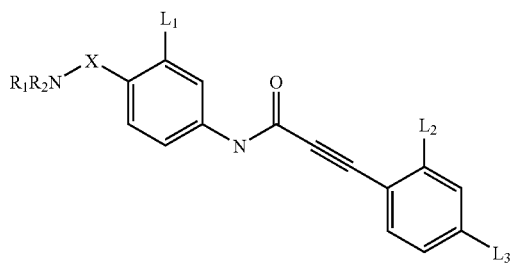

| | R₁R₂N-X | L₁ | L₂ | L₃ |
|---|---|---|---|---|
| 4.209 | pyrrolidine-CH₂CH₂C(CH₃)₂- | -Me | —Cl | —CF₃ |
| 4.210 | azetidine-CH₂CH₂C(CH₃)₂- | -Me | —Cl | —CF₃ |
| 4.211 | (cyclopropylmethyl)(methyl)N-CH₂CH₂C(CH₃)₂- | -Me | —Cl | —CF₃ |
| 4.212 | (cyclopropylmethyl)(ethyl)N-CH₂CH₂C(CH₃)₂- | -Me | —Cl | —CF₃ |
| 4.213 | bis(cyclopropylmethyl)N-CH₂CH₂C(CH₃)₂- | -Me | —Cl | —CF₃ |
| 4.214 | (isopropyl)(methyl)N-CH₂CH₂C(CH₃)₂- | -Me | —Cl | —CF₃ |
| 4.215 | (isopropyl)(ethyl)N-CH₂CH₂C(CH₃)₂- | -Me | —Cl | —CF₃ |
| 4.216 | (isobutyl)(methyl)N-CH₂CH₂C(CH₃)₂- | -Me | —Cl | —CF₃ |
| 4.217 | (isobutyl)(ethyl)N-CH₂CH₂C(CH₃)₂- | -Me | —Cl | —CF₃ |

-continued
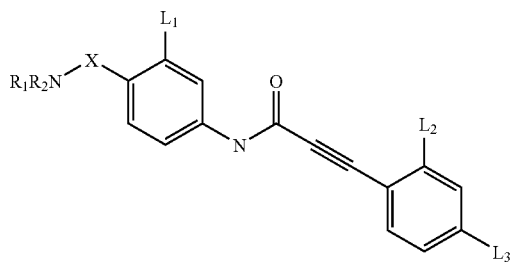
| | R₁R₂N-X | L₁ | L₂ | L₃ |
|---|---|---|---|---|
| 4.218 | | —Br | —Cl | —CF₃ |
| 4.219 | | —Br | —Cl | —CF₃ |
| 4.220 | | —Br | —Cl | —CF₃ |
| 4.221 | | —Br | —Cl | —CF₃ |
| 4.222 | | —Br | —Cl | —CF₃ |
| 4.223 | | —Br | —Cl | —CF₃ |
| 4.224 | | —Br | —Cl | —CF₃ |
| 4.225 | | —Br | —Cl | —CF₃ |
| 4.226 | | —Br | —Cl | —CF₃ |

-continued
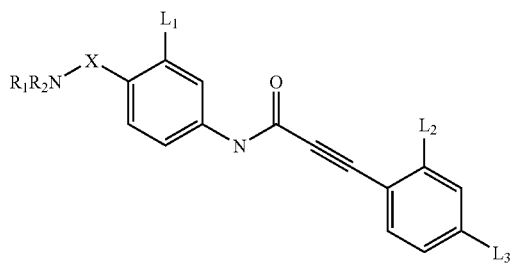
| | $R_1R_2N-X$ | $L_1$ | $L_2$ | $L_3$ |
|---|---|---|---|---|
| 4.227 | | —Br | —Cl | —CF$_3$ |
| 4.228 | | —Br | —Cl | —CF$_3$ |
| 4.229 | | —Br | —Cl | —CF$_3$ |
| 4.230 | | —Br | —Cl | —CF$_3$ |
| 4.231 | | —OMe | —Cl | —CF$_3$ |
| 4.232 | | —OMe | —Cl | —CF$_3$ |
| 4.233 | | —OMe | —Cl | —CF$_3$ |
| 4.234 | | —OMe | —Cl | —CF$_3$ |
| 4.235 | | —OMe | —Cl | —CF$_3$ |

-continued
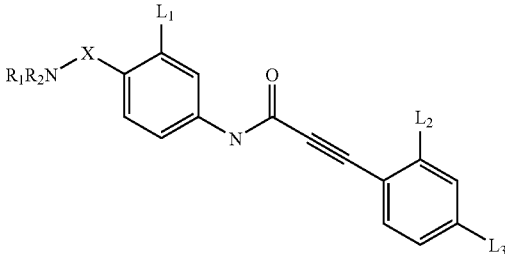
| | R₁R₂N-X | L₁ | L₂ | L₃ |
|---|---|---|---|---|
| 4.236 | 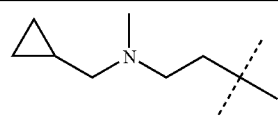 | —OMe | —Cl | —CF₃ |
| 4.237 | 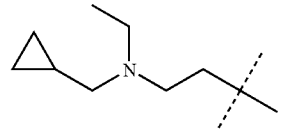 | —OMe | —Cl | —CF₃ |
| 4.238 | 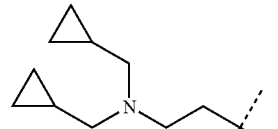 | —OMe | —Cl | —CF₃ |
| 4.239 | 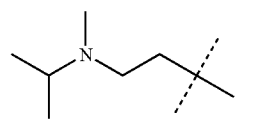 | —OMe | —Cl | —CF₃ |
| 4.240 | 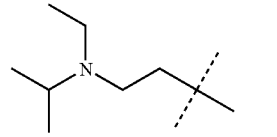 | —OMe | —Cl | —CF₃ |
| 4.241 | 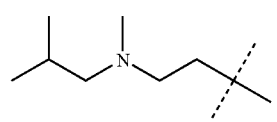 | —OMe | —Cl | —CF₃ |
| 4.242 | 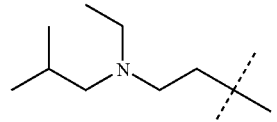 | —OMe | —Cl | —CF₃ |
| 4.243 | 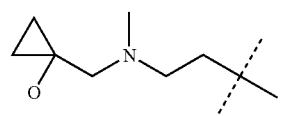 | —OMe | —Cl | —CF₃ |
| 4.244 | 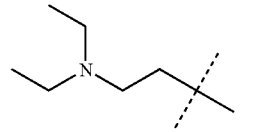 | —Cl | —Cl | —Cl |

-continued
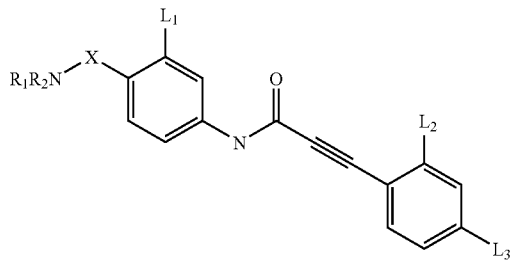
| | $R_1R_2N-X$ | $L_1$ | $L_2$ | $L_3$ |
|---|---|---|---|---|
| 4.245 | 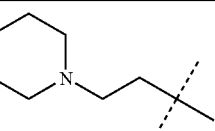 | —Cl | —Cl | —Cl |
| 4.246 | 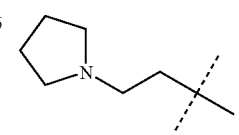 | —Cl | —Cl | —Cl |
| 4.247 | 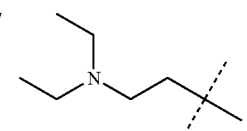 | —Cl | —Cl | -Me |
| 4.248 | 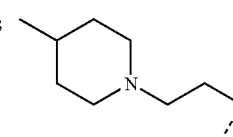 | —Cl | —Cl | -Me |
| 4.249 | 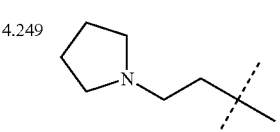 | —Cl | —Cl | -Me |
| 4.250 | 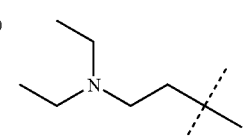 | —Cl | —Cl | —OMe |
| 4.251 | 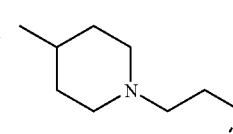 | —Cl | —Cl | —OMe |
| 4.252 | 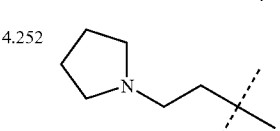 | —Cl | —Cl | —OMe |
| 4.253 | 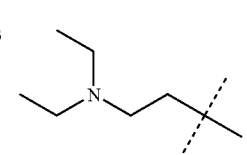 | —Cl | —Cl | 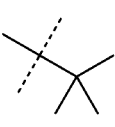 |

-continued
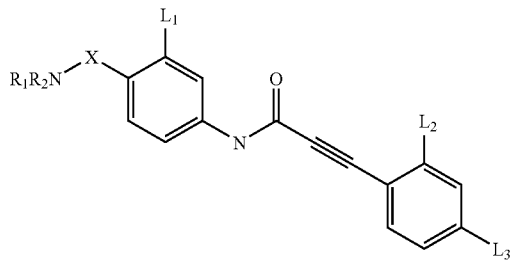
| | R₁R₂N-X | L₁ | L₂ | L₃ |
|---|---|---|---|---|
| 4.254 | 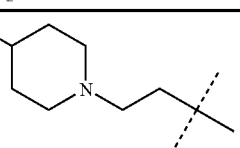 | —Cl | —Cl | 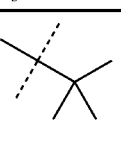 |
| 4.255 | 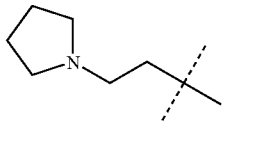 | —Cl | —Cl | 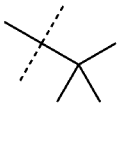 |
| 4.256 | 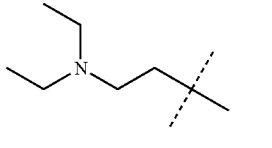 | —Cl | —Br | —CF₃ |
| 4.257 | 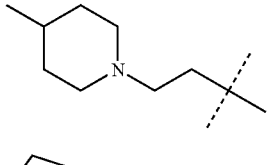 | —Cl | —Br | —CF₃ |
| 4.258 | 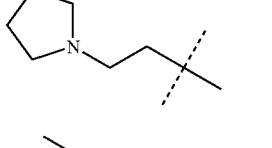 | —Cl | —Br | —CF₃ |
| 4.259 | 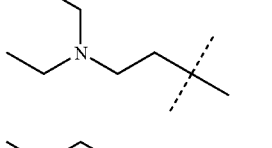 | —Cl | -Me | —CF₃ |
| 4.260 | 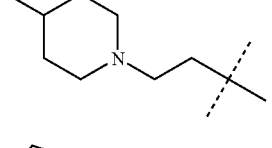 | —Cl | -Me | —CF₃ |
| 4.261 | 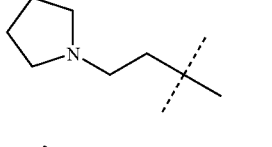 | —Cl | -Me | —CF₃ |
| 4.262 | 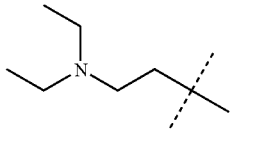 | —Cl | —OMe | —CF₃ |

-continued
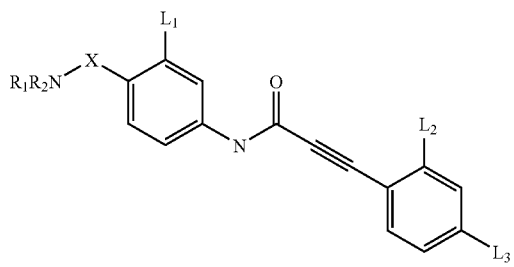
| | $R_1R_2N-X$ | $L_1$ | $L_2$ | $L_3$ |
|---|---|---|---|---|
| 4.263 |  | —Cl | —OMe | —CF₃ |
| 4.264 | 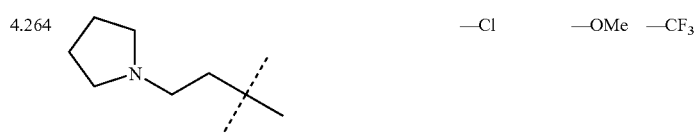 | —Cl | —OMe | —CF₃ |
| 4.265 |  | —Cl | —F | —CF₃ |
| 4.266 | 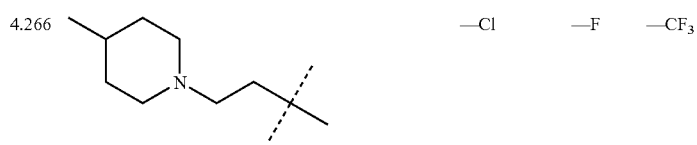 | —Cl | —F | —CF₃ |
| 4.267 |  | —Cl | —F | —CF₃ |
| 4.268 | 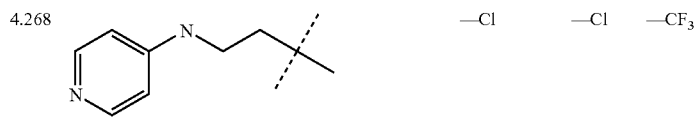 | —Cl | —Cl | —CF₃ |
| 4.269 |  | —Cl | —Cl | —CF₃ |

EXAMPLE 4.270

3-(2-chloro-4-trifluoromethylphenyl)propynoic acid-{3-methoxy-4-[2-(4-methylpiperidin-1-yl)ethoxy]phenyl}amide

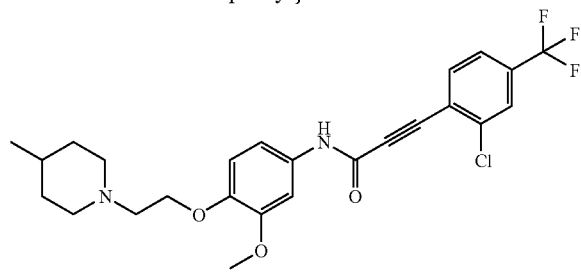

4.270.a. 1-[2-(2-methoxy-4-nitrophenoxy)ethyl]-4-methylpiperidine

Prepared analogously to Example 1.1 C. from 1-(2-bromoethoxy)-2-methoxy-4-nitrobenzene and 4-methylpiperidine. Yield: 0.7 g (88.2% of theory); $C_{15}H_{22}N_2O_4$ (M=294.35); calc.: molecular ion peak (M+H)$^+$: 295; found: molecular ion peak (M+H)$^+$: 295; $R_f$ value: 0.5 (silica gel, dichloromethane/methanol (9:1)).

4.270.b. 3-methoxy-4-[2-(4-methylpiperidin-1-yl)ethoxy]phenylamine

Prepared analogously to Example 3.1.b. from 1-[2-(2-methoxy-4-nitrophenoxy)ethyl]-4-methylpiperidine. Yield: 0.51 g (81.1% of theory); $C_{15}H_{24}N_2O_2$ (M=264.37); calc.: molecular ion peak (M+H)$^+$: 265; found: molecular ion peak (M+H)$^+$: 265; $R_f$ value: 0.3 (silica gel, dichloromethane/methanol (9:1)).

4.270.c. 3-(2-chloro-4-trifluoromethylphenyl)propynoic acid-{3-methoxy-4-[2-(4-methylpiperidin-1-yl)ethoxy]phenyl}amide Prepared analogously to Example 2.3.f. from (2-chloro-4-trifluoromethylphenyl)propynoic acid and 3-methoxy-4-[2-(4-methylpiperidin-1-yl)ethoxy]phenylamine. Yield: 70 mg (23.5% of theory); melting point: 207° C.-209° C.; $C_{25}H_{26}ClF_3N_2O_3$ (M=494.94); calc.: molecular ion peak (M+H)$^+$: 495/497; found: molecular ion peak (M+H)$^+$: 495/497; $R_f$ value: 0.45 (silica gel, dichloromethane/methanol (9:1)).

EXAMPLE 4.271

3-(2-chloro-4-trifluoromethylphenyl)propynoic acid-{4-[2-(3,5-dimethylpiperidin-1-yl)ethoxy]-3-methoxyphenyl}amide

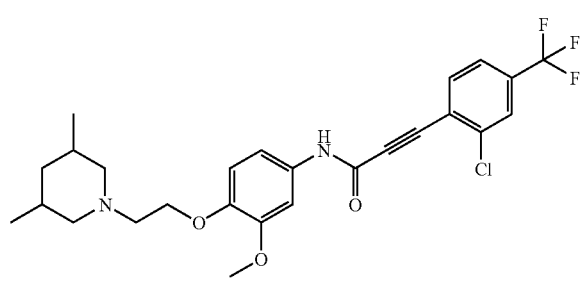

4.271.a. 1-[2-(2-methoxy-4-nitrophenoxy)ethyl]-3,5-dimethylpiperidine

Prepared analogously to Example 1.1.c. from 1-(2-bromoethoxy)-2-methoxy-4-nitrobenzene and 3,5-dimethylpiperidine. Yield: 0.4 g (48.1% of theory); $C_{16}H_{24}N_2O_4$ (M=308.38); calc.: molecular ion peak (M+H)$^+$: 309; found: molecular ion peak (M+H)$^+$: 309; $R_f$ value: 0.5 (silica gel, dichloromethane/methanol (9:1)).

4.271.b. 4-[2-(3,5-dimethylpiperidin-1-yl)ethoxy]-3-methoxyphenylamine

Prepared analogously to Example 3.1.b. from 1-[2-(2-methoxy-4-nitrophenoxy)ethyl]-3,5-dimethylpiperidine. Yield: 0.35 g (96.9% of theory); $C_{15}H_{24}N_2O_2$ (M=264.37); calc.: molecular ion peak (M+H)$^+$: 279; found: molecular ion peak (M+H)$^+$: 279; $R_f$ value: 0.3 (silica gel, dichloromethane/methanol (9:1)).

4.271.c. 3-(2-chloro-4-trifluoromethylphenyl)propynoic acid-{4-[2-(3,5-methylpiperidin-1-yl)ethoxy]-3-methoxyphenyl}amide Prepared analogously to Example 2.3.f. from (2-chloro-4-trifluoromethylphenyl)propynoic acid and 4-[2-(3,5-dimethylpiperidin-1-yl)ethoxy]-3-methoxyphenylamine. Yield: 160 mg (52.1% of theory); melting point: 196° C.-201° C.; $C_{26}H_{28}ClF_3N_2O_3$ (M=508.97); calc.: molecular ion peak (M+H)$^+$: 509/511; found: molecular ion peak (M+H)$^+$: 509/511; $R_f$ value: 0.5 (silica gel, dichloromethane/methanol (9:1)).

EXAMPLE 4.272

3-(2-chloro-4-trifluoromethylphenyl)propynoic acid-{4-[2-((S)-2-hydroxymethylpyrrolidin-1-yl)ethoxy]-3-methoxyphenyl}amide

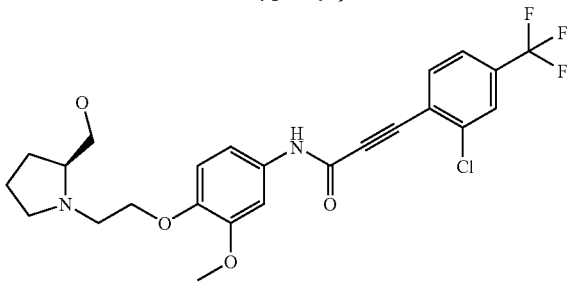

4.272.a. {(S)-1-[2-(2-methoxy-4-nitrophenoxy)ethyl]pyrrolidin-2-yl}methanol

Prepared analogously to Example 1.1.c. from 1-(2-bromoethoxy)-2-methoxy-4-nitrobenzene and (S)-1-pyrrolidin-2-ylmethanol. Yield: 0.2 g (25% of theory); $C_{14}H_{20}N_2O_5$ (M=296.32); calc.: molecular ion peak (M+H)$^+$: 297; found: molecular ion peak (M+H)$^+$: 297; $R_f$ value: 0.55 (silica gel, dichloromethane/methanol (9:1)).

4.272.b. {(S)-1-[2-(4-amino-2-methoxyphenoxy)ethyl]pyrrolidin-2-yl}methanol

Prepared analogously to Example 3.1.b. from {(S)-1-[2-(2-methoxy-4-nitrophenoxy)ethyl]pyrrolidin-2-yl}methanol. Yield: 0.15 g (83.4% of theory); $C_{14}H_{22}N_2O_3$ (M=266.34); calc.: molecular ion peak (M+H)$^+$: 267; found: molecular ion peak (M+H)$^+$: 267; $R_f$ value: 0.15 (silica gel, dichloromethane/methanol 9:1)).

4.272.c. 3-(2-chloro-4-trifluoromethylphenyl)propynoic acid-{4-[2-((S)-2-hydroxymethylpyrrolidin-1-yl)ethoxy]-3-methoxyphenyl}amide Prepared analogously to Example 2.3.f. from (2-chloro-4-trifluoromethylphenyl)propynoic acid and {(S)-1-[2-(4-amino-2-methoxyphenoxy)ethyl]pyrrolidin-2-yl}methanol. Yield: 140 mg (58.9% of theory); melting point: decomposition at 300° C.; $C_{24}H_{24}ClF_3N_2O_4$ (M=496.91); calc.: molecular ion peak (M+H)$^+$: 497/499; found: molecular ion peak (M+H)$^+$: 497/499; $R_f$ value: 0.2 (silica gel, dichloromethane/methanol (9:1).

EXAMPLE 4.273

3-(2-chloro-4-trifluoromethylphenyl)propynoic acid-[3-methoxy-4-(2-morpholin-4-ylethoxy)phenyl]amide

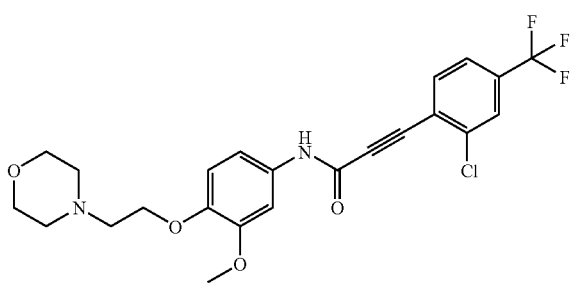

4.273.a. 4-[2-(2-methoxy-4-nitrophenoxy)ethyl]morpholine

Prepared analogously to Example 1.1.c. from 1-(2-bromoethoxy)-2-methoxy-4-nitrobenzene and morpholine. Yield: 0.3 g (39.4% of theory); $C_{13}H_{18}N_2O_5$ (M=282.29); calc.: molecular ion peak (M+H)$^+$: 283; found: molecular ion peak (M+H)$^+$: 283; $R_f$ value: 0.6 (silica gel, dichloromethane/methanol (9:1)).

4.273.b. 3-methoxy-4-(2-morpholin-4-ylethoxy)phenylamine

Prepared analogously to Example 3.1.b. from 4-[2-(2-methoxy-4-nitrophenoxy)ethyl]morpholine. Yield: 0.23 g (85.8% of theory); $C_{13}H_{20}N_2O_3$ (M=252.31); calc.: molecular ion peak (M+H)$^+$: 253; found: molecular ion peak (M+H)$^+$: 253; $R_f$ value: 0.5 (silica gel, dichloromethane/methanol (9:1)).

4.273.c. 3-(2-chloro-4-trifluoromethylphenyl)propynoic acid-[3-methoxy-4-(2-morpholin-4-ylethoxy)phenyl]amide Prepared analogously to Example 2.3.f. from (2-chloro-4-trifluoromethylphenyl)propynoic acid and 3-methoxy-4-(2-morpholin-4-ylethoxy)phenylamine. Yield: 20 mg (6.9% of theory); melting point: 209° C.-211° C.; $C_{23}H_{22}ClF_3N_2O_4$ (M=482.89); calc.: molecular ion peak (M+H)$^+$: 483/485; found: molecular ion peak (M+H)$^+$: 483/485; $R_f$ value: 0.5 (silica gel, dichloromethane/methanol (9:1)).

EXAMPLE 4.274

3-(2-chloro-4-trifluoromethylphenyl)propynoic acid-{3-methoxy-4-[2-(4-methoxypiperidin-1-yl)ethoxy]phenyl}amide

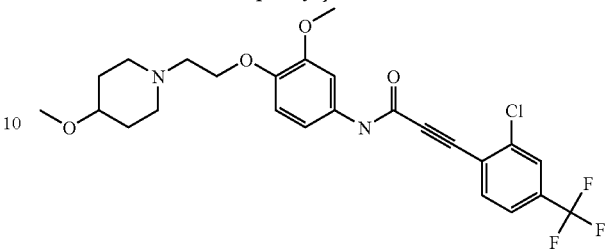

4.274.a. 4-methoxy-1-[2-(2-methoxy-4-nitrophenoxy)ethyl]piperidine

Prepared analogously to Example 1.1.c. from 1 g (3.62 mmol) of 1-(2-bromoethoxy)-2-methoxy-4-nitrobenzene and 1.25 g (10.87 mmol) of 4-methoxypiperidine. Yield: 1 g (89% of theory); $C_{15}H_{22}N_2O_5$ (M=310.35); calc.: molecular ion peak (M+H)$^+$: 311; found: molecular ion peak (M+H)$^+$: 311; $R_f$ value: 0.5 (silica gel, dichloromethane/methanol (9:1)).

4.274.b. 3-methoxy-4-[2-(4-methoxypiperidin-1-yl)ethoxy]phenylamine

Prepared analogously to Example 3.1.b. from 1 g (3.22 mmol) of 4-methoxy-1-[2-(2-methoxy-4-nitrophenoxy)ethyl]piperidine. Yield: 0.85 g (94% of theory); $C_{15}H_{24}N_2O_3$ (M=280.36); calc.: molecular ion peak (M+H)$^+$: 281; found: molecular ion peak (M+H)$^+$: 281; $R_f$ value: 0.6 (silica gel, dichloromethane/methanol (9:1)).

4.274.c. 3-(2-chloro-4-trifluoromethylphenyl)propynoic acid-{3-methoxy-4-[2-(4-methoxypiperidin-1-yl)ethoxy]phenyl}amide Prepared analogously to Example 2.3.f. from 150 mg (0.6 mmol) of (2-chloro-4-trifluoromethylphenyl)propynoic acid and 186 mg (0.66 mmol) of 3-methoxy-4-[2-(4-methoxypiperidin-1-yl)ethoxy]phenylamine. Yield: 20 mg (7% of theory); melting point: 195° C.-197° C.; $C_{25}H_{26}ClF_3N_2O_4$ (M=510.93); calc.: molecular ion peak (M+H)$^+$: 511/513 (Cl); found: molecular ion peak (M+H)$^+$: (M+H)$^+$: 511/513 (Cl); $R_f$ value: 0.3 (silica gel, dichloromethane/methanol (9:1)).

EXAMPLE 4.275

3-(2-chloro-4-trifluoromethylphenyl)propynoic acid-{4-[2-(3,4-dihydro-1H-isoquinolin-2-yl)ethoxy]-3-methoxyphenyl}amide formate

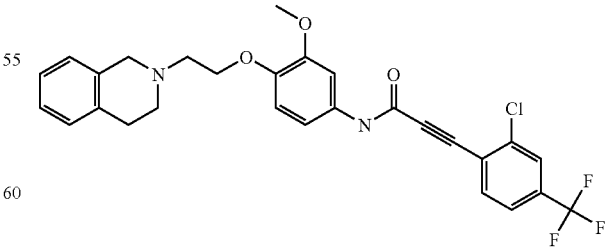

4.275.a. 2-[2-(2-methoxy-4-nitrophenoxy)ethyl]-1,2,3,4-tetrahydroisoquinoline Prepared analogously to Example 1.1.c. from 1 g (3.622 mmol) of 1-(2-bromoethoxy)-2-methoxy-4-nitrobenzene and 1.36 mL (10.87 mmol) of 1,2,3,4-tetrahydroisoquinoline. Yield: 1.4 g (77% of theory); $C_{18}H_{20}N_2O_4$ (M=328.36); calc.: molecular ion peak (M+H)$^+$: 329; found: molecular ion peak (M+H)$^+$: 329; $R_f$ value: 0.7 (silica gel, dichloromethane/methanol (9:1)).

4.275.b. 4-[2-(3,4-dihydro-1H-isoquinolin-2-yl)ethoxy]-3-methoxyphenylamine

Prepared analogously to Example 3.1.b. from 1.4 g (2.77 mmol) of 2-[2-(2-methoxy-4-nitrophenoxy)ethyl]-1,2,3,4-tetrahydroisoquinoline (65%). Yield: 1.2 g (94% of theory); $C_{18}H_{22}N_2O_2$ (M=298.38); calc.: molecular ion peak (M+H)$^+$: 299; found: molecular ion peak (M+H)$^+$: 299; $R_f$ value: 0.5 (silica gel, dichloromethane/methanol (9:1)).

4.275.c. 3-(2-chloro-4-trifluoromethylphenyl)propynoic acid-{4-[2-(3,4-dihydro-1H-isoquinolin-2-yl)ethoxy]-3-methoxyphenyl}amide formate Prepared analogously to Example 2.3.f. from 150 mg (0.6 mmol) of (2-chloro-4-trifluoromethylphenyl)propynoic acid and 304 mg (0.66 mmol) of 4-[2-(3,4-dihydro-1H-isoquinolin-2-yl)ethoxy]-3-methoxyphenylamine (65%). Yield: 17 mg (5% of theory); melting point: 92° C.-95° C.; $C_{28}H_{24}ClF_3N_2O_3$ (M=528.96)*$CH_2O_2$; calc.: molecular ion peak (M+H)$^+$: 529/531 (Cl); found: molecular ion peak (M+H)$^+$: 529/531 (Cl); $R_f$ value: 0.55 (silica gel, dichloromethane/methanol (9:1)).

EXAMPLE 4.276

1-(2-{4-[3-(2-chloro-4-trifluoromethylphenyl)propynoylamino]-2-methoxyphenoxy}ethyl)piperidine-4-carboxylic acid amide

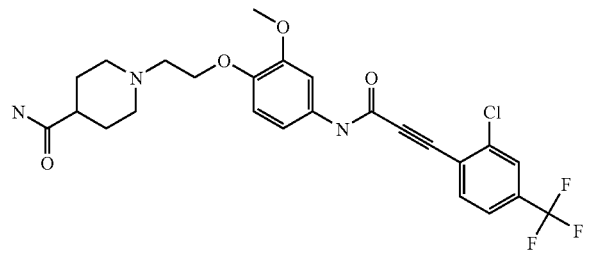

4.276.a. 1-[2-(2-methoxy-4-nitrophenoxy)ethyl]piperidine-4-carboxylic acid amide Prepared analogously to Example 1.1.c. from 1 g (3.622 mmol) of 1-(2-bromoethoxy)-2-methoxy-4-nitrobenzene and 1.4 g (10.87 mmol) of piperidine-4-carboxylic acid amide. Yield: 1.05 g (90% of theory); $C_{15}H_{21}N_3O_5$ (M=323.34); calc.: molecular ion peak (M+H)$^+$: 324; found: molecular ion peak (M+H)$^+$: 324; $R_f$ value: 0.4 (silica gel, dichloromethane/methanol/ammonia (9:1:0.1)).

4.276.b. 1-[2-(4-amino-2-methoxyphenoxy)ethyl]piperidine-4-carboxylic acid amide Prepared analogously to Example 3.1.b. from 1 g (3.1 mmol) of 1-[2-(2-methoxy-4-nitrophenoxy)ethyl]piperidine-4-carboxylic acid amide. Yield: 0.8 g (88% of theory); $C_{15}H_{23}N_3O_3$ (M=298.38); calc.: molecular ion peak (M+H)$^+$: 294; found: molecular ion peak (M+H)$^+$: 294; $R_f$ value: 0.3 (silica gel, dichloromethane/methanol/ammonia (9:1:0.1)).

4.276.c. 3-(1-(2-{4-[3-(2-chloro-4-trifluoromethylphenyl)propinoylamino]-2-methoxyphenoxy}ethyl)piperidine-4-carboxylic acid amide Prepared analogously to Example 2.3.f. from 150 mg (0.6 mmol) of (2-chloro-4-trifluoromethylphenyl)propynoic acid and 194 mg (0.66 mmol) of 1-[2-(4-amino-2-methoxyphenoxy)ethyl]piperidine-4-carboxylic acid amide. Yield: 310 mg (98% of theory); melting point: 150° C.; $C_{25}H_{25}ClF_3N_3O_4$ (M=523.93); calc.: molecular ion peak (M+H)$^+$: 524/526 (Cl); found: molecular ion peak (M+H)$^+$: 524/526 (Cl); $R_f$ value: 0.4 (silica gel, dichloromethane/methanol/ammonia (9:1:0.1)).

EXAMPLE 4.277

3-(2-chloro-4-trifluoromethylphenyl)propynoic acid-{4-[2-(2,6-dimethylpiperidin-1-yl)ethoxy]-3-methoxyphenyl}amide

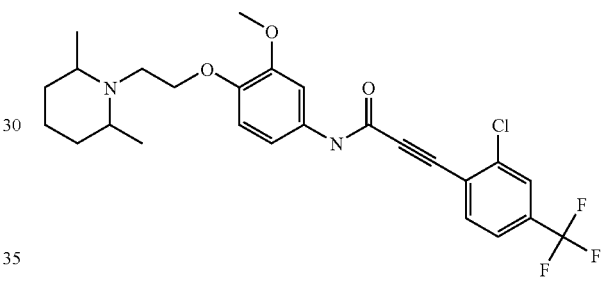

4.277.a. 1-[2-(2-methoxy-4-nitrophenoxy)ethyl]-2,6-dimethylpiperidine

Prepared analogously to Example 1.1.c. from 1 g (3.622 mmol) of 1-(2-bromoethoxy)-2-methoxy-4-nitrobenzene and 1.5 mL (10.87 mmol) of 2,6-dimethylpiperidine. Yield: 0.85 g (76% of theory); $C_{16}H_{24}N_2O_4$ (M=308.37); calc.: molecular ion peak (M+H)$^+$: 309; found: molecular ion peak (M+H)$^+$: 309; $R_f$ value: 0.55 (silica gel, dichloromethane/methanol (9:1)).

4.277.b. 4-[2-(2,6-dimethylpiperidin-1-yl)ethoxy]-3-methoxyphenylamine

Prepared analogously to Example 3.1.b. from 0.84 g (2.72 mmol) of 1-[2-(2-methoxy-4-nitrophenoxy)ethyl]-2,6-dimethylpiperidine. Yield: 0.65 g (86% of theory); $C_{16}H_{26}N_2O_2$ (M=278.39); calc.: molecular ion peak (M+H)$^+$: 279; found: molecular ion peak (M+H)$^+$: 279; $R_f$ value: 0.1 (silica gel, dichloromethane/methanol (9:1)).

4.277.c. 3-(2-chloro-4-trifluoromethylphenyl)propynoic acid-{4-[2-(2,6-dimethylpiperidin-1-yl)ethoxy]-3-methoxyphenyl}amide Prepared analogously to Example 2.3.f. from 150 mg (0.6 mmol) of (2-chloro-4-trifluoromethylphenyl)propynoic acid and 185 mg (0.663 mmol) of 4-[2-(2,6-dimethylpiperidin-1-yl)ethoxy]-3-methoxyphenylamine. Yield: 150 mg (49% of theory); melting point: 225° C.-227° C.; $C_{26}H_{28}ClF_3N_2O_3$ (M=508.96); calc.: molecular ion peak $(M+H)^+$: 509/511 (Cl); found: molecular ion peak $(M+H)^+$: 509/511 (Cl); $R_f$ value: 0.2 (silica gel, dichloromethane/methanol (9:1)).

EXAMPLE 4.278

3-(2-chloro-4-trifluoromethylphenyl)propynoic acid-{4-[2-(cyclopropylmethylmethylamino)ethoxy]-3-methoxyphenyl}amide hydrochloride

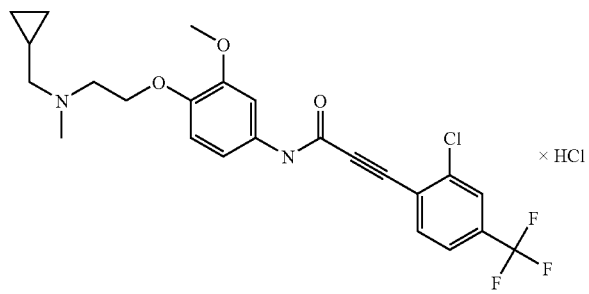

4.278.a. cyclopropylmethyl-[2-(2-methoxy-4-nitro-phenoxy)ethyl]methylamine

Prepared analogously to Example 1.1.c. from 1 g (3.62 mmol) of 1-(2-bromoethoxy)-2-methoxy-4-nitrobenzene and 900 mg (10.57 mmol) of cyclopropylmethylamine. Yield: 0.95 g (94% of theory); $C_{14}H_{20}N_2O_4$ (M=280.32); calc.: molecular ion peak $(M+H)^+$: 281; found: molecular ion peak $(M+H)^+$: 281; $R_f$ value: 0.4 (silica gel, dichloromethane/methanol (9:1)).

4.278.b. 4-[2-(cyclopropylmethylmethylamine)ethoxy]-3-methoxyphenylamine

Prepared analogously to Example 3.1.b. from 950 mg (3.4 mmol) of cyclopropylmethyl-[2-(2-methoxy-4-nitrophenoxy)ethyl]methylamine. Yield: 0.68 g (80% of theory); $C_{14}H_{22}N_2O_2$ (M=250.34); calc.: molecular ion peak $(M+H)^+$: 251; found: molecular ion peak $(M+H)^+$: 251; $R_f$ value: 0.35 (silica gel, dichloromethane/methanol/ammonia (9:1:0.1)).

4.278.c. 3-(2-chloro-4-trifluoromethylphenyl)propynoic acid-{4-[2-(cyclopropylmethylmethylamino)ethoxy]-3-methoxyphenyl}amide hydrochloride Prepared analogously to Example 2.3.f. from 150 mg (0.6 mmol) of (2-chloro-4-trifluoromethylphenyl)propynoic acid and 166 mg (0.66 mmol) of 4-[2-(cyclopropylmethylmethylamine)ethoxy]-3-methoxyphenylamine. Yield: 130 mg (45% of theory); melting point: 173° C.-176° C.; $C_{24}H_{24}ClF_3N_2O_3$ (M=480.91)*HCl; calc.: molecular ion peak $(M+H)^+$: 481/483 (Cl); found: molecular ion peak $(M+H)^+$: 481/483 (Cl); $R_f$ value: 0.2 (silica gel, dichloromethane/methanol (9:1)).

EXAMPLE 4.279

3-(2-chloro-4-trifluoromethylphenyl)propynoic acid-{4-[2-(cyclopropylmethylpropylamino)ethoxy]-3-methoxyphenyl}amide hydrochloride

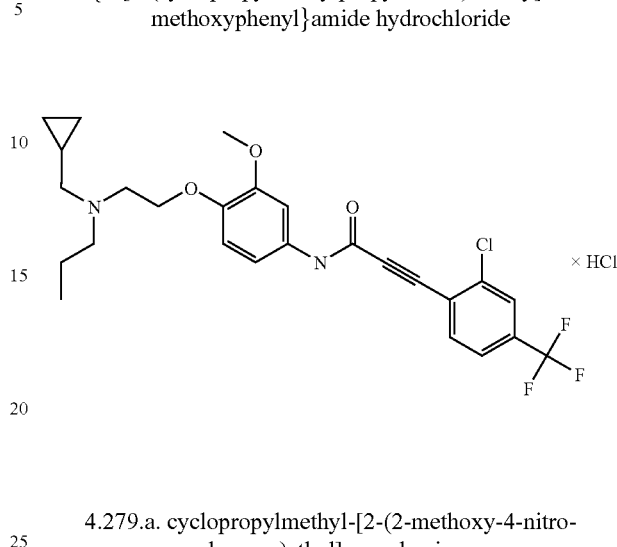

4.279.a. cyclopropylmethyl-[2-(2-methoxy-4-nitro-phenoxy)ethyl]propylamine

Prepared analogously to Example 1.1.c. from 1 g (3.62 mmol) of 1-(2-bromoethoxy)-2-methoxy-4-nitrobenzene and 1.51 mL (10.57 mmol) of cyclopropylmethylpropylamine. Yield: 0.95 g (85% of theory); $C_{16}H_{24}N_2O_4$ (M=308.37); calc.: molecular ion peak $(M+H)^+$: 309; found: molecular ion peak $(M+H)^+$: 309; $R_f$ value: 0.4 (silica gel, dichloromethane/methanol (9:1)).

4.279.b. 4-[2-(cyclopropylmethylpropylamino)ethoxy]-3-methoxyphenylamine

Prepared analogously to Example 3.1.b. from 950 mg (3.1 mmol) of cyclopropylmethyl-[2-(2-methoxy-4-nitrophenoxy)ethyl]propylamine. Yield: 0.74 g (86% of theory); $C_{16}H_{26}N_2O_2$ (M=278.39); calc.: molecular ion peak $(M+H)^+$: 279; found: molecular ion peak $(M+H)^+$: 279; $R_f$ value: 0.4 (silica gel, dichloromethane/methanol/ammonia (9:1:0.1)).

4.279.c. 3-(2-chloro-4-trifluoromethylphenyl)propynoic acid-{4-[2-(cyclopropylmethylpropylamino)ethoxy]-3-methoxyphenyl}amide hydrochloride Prepared analogously to Example 2.3.f. from 150 mg (0.6 mmol) of (2-chloro-4-trifluoromethylphenyl)propynoic acid and 185 mg (0.66 mmol) of 4-[2-(cyclopropylmethylpropylamino)ethoxy]-3-methoxyphenylamine. Yield: 180 mg (59% of theory); melting point: 185° C.-188° C.; $C_{26}H_{28}ClF_3N_2O_3$ (M=508.96)*HCl; calc.: molecular ion peak $(M+H)^+$: 509/511 (Cl); found: molecular ion peak $(M+H)^+$: 509/511 (Cl); $R_f$ value: 0.35 (silica gel, dichloromethane/methanol (9:1)).

EXAMPLE 4.281

3-(3-bromobiphenyl-4-yl)propynoic acid-{3-chloro-4-[2-(4-methylpiperidin-1-yl)ethyl]phenyl}amide

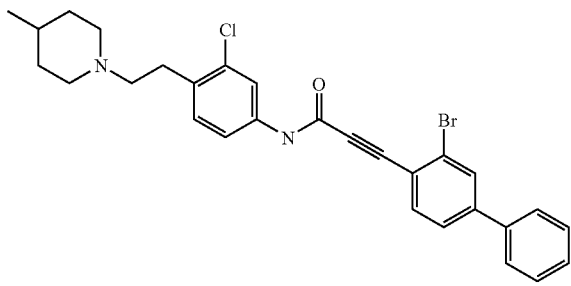

4.281.a. 3-bromobiphenyl-4-ylamine 8.7 mL (76.8 mmol) of a 48% hydrogen bromide solution is added dropwise to a solution of 13.008 g (76.8 mmol) of biphenyl-4-ylamine in 60 mL of DMSO at ambient temperature and the mixture is stirred for 14 hours. Then it is heated to 100° C. for 1 hour, the mixture is then cooled and poured onto water. By the addition of ammonia solution, the reaction mixture is made alkaline and the precipitate formed is filtered off and washed with water. The purification is carried out by column chromatography on silica gel (eluant: dichloromethane). Yield: 11.3 g (60% of theory); $C_{12}H_{10}BrNO$ (M=248.19); calc.: molecular ion peak $(M+H)^+$: 248/250 (Cl); found: molecular ion peak $(M+H)^+$: 248/250 (Cl).

4.281.b. 3-iodobiphenyl-4-ylamine

A solution of 7.3 g (29.4 mmol) of 3-bromobiphenyl-4-ylamine in 120 mL of acetic acid is mixed with 6 mL of concentrated hydrochloric acid at ambient temperature, cooled to 15° C., and stirred for 30 minutes. A solution of 2 g (28.9 mmol) of sodium nitrite in 7 mL of water is slowly added dropwise to this reaction mixture at 15° C. and stirred for 30 minutes. Then at 5° C., a solution of 5.4 g (32.5 mmol) of potassium iodide in 28 mL of water is slowly added dropwise and the mixture is stirred. After 30 minutes, 2.95 g of sodium thiosulfate is added and the mixture is stirred for a further 30 minutes. Then the reaction mixture is evaporated down and combined with water/ethyl acetate. The aqueous phase is again extracted with ethyl acetate, the combined aqueous phases are extracted once with water and dried over sodium sulfate. The purification is carried out by column chromatography on silica gel (eluant: petroleum ether). Yield: 6.6 g (85% of theory); $C_{12}H_8BrI$ (M=359.00); calc.: molecular ion peak $(M)^+$: 358/360 (Br); found: molecular ion peak $(M)^+$: 358/360 (Br).

4.281.c. (3-bromobiphenyl-4-ylethynyl)-tert-butyldimethylsilane

Prepared analogously to Example 1.1.d. from 3-iodobiphenyl-4-ylamine and tert-butylethynyldimethylsilane. Yield: 0.52 g (72% of theory); $C_{20}H_{23}BrSi$ (M=371.38); calc.: molecular ion peak $(M+H)^+$: 371/373 (Br); found: molecular ion peak $(M+H)^+$: 371/373 (Br).

4.281.d. 3-bromo-4-ethynylbiphenyl 1.99 mL (1.99 mmol) of a 1M tetrabutylammonium fluoride solution in THF is added batchwise at 5° C. to a solution of 495 mg (1.33 mmol) of (3-bromobiphenyl-4-ylethynyl)-tert-butyldimethylsilane in 8 mL of anhydrous THF. The reaction mixture is stirred for another 30 minutes at ambient temperature and evaporated down. The residue is combined with diethyl ether and water and the organic phase is dried over sodium sulfate. Yield: 0.34 g (99% of theory); $C_{14}H_9Br$ (M=257.12); calc.: molecular ion peak $(M-H)^-$: 255/257 (Br); found: molecular ion peak $(M-H)^-$: 255/257 (Br).

4.281.e. (3-bromobiphenyl-4-yl)propynoic acid

Prepared analogously to Example 4.3.a. from 3-bromo-4-ethynylbiphenyl and carbon dioxide. Yield: 2.5 g (89% of theory); $C_{15}H_9BrO_2$ (M=301.13); calc.: molecular ion peak $(M+H)^+$: 301/303 (Br); found: molecular ion peak $(M+H)^+$: 301/303 (Br); $R_f$ value: 0.3 (silica gel, dichloromethane/methanol (90:10)).

4.281.f. 3-(3-bromobiphenyl-4-yl)propynoic acid-{3-chloro-4-[2-(4-methylpiperidin-1-yl)ethyl]phenyl}amide Prepared analogously to Example 2.3.f. from (3-bromobiphenyl-4-yl)propynoic acid and 3-chloro-4-[2-(4-methylpiperidin-1-yl)ethyl]phenylamine. Yield: 0.24 g (50% of theory); $C_{29}H_{28}BrClN_2O$ (M=535.90); calc.: molecular ion peak $(M+H)^+$: 535/37/39; found: molecular ion peak $(M+H)^+$: 535/37/39; $R_f$ value: 0.48 (silica gel, dichloromethane/methanol (90:10)).

EXAMPLE 4.282

3-(3-bromobiphenyl-4-yl)propynoic acid-[3-chloro-4-(2-diethylaminoethyl)phenyl]amide hydrochloride

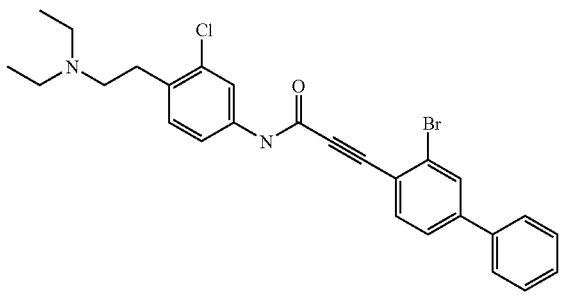

Prepared analogously to Example 2.3.f. from (3-bromobiphenyl-4-yl)propynoic acid and 3-chloro-4-(2-diethylaminoethyl)phenylamine. Yield: 95 mg (23.8% of theory); $C_{27}H_{26}BrClN_2O*HCl$ (M=546.32); calc.: molecular ion peak $(M+H)^+$: 509/11/13; found: molecular ion peak $(M+H)^+$: 509/11/13; $R_f$ value: 0.3 (silica gel, dichloromethane/methanol (90:10)).

EXAMPLE 4.283

3-(3-bromobiphenyl-4-yl)propynoic acid-[3-chloro-4-(2-pyrrolidin-1-ylethyl)phenyl]amide

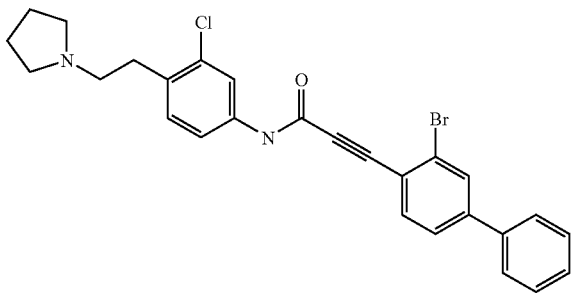

Prepared analogously to Example 2.3.f. from (3-bromobiphenyl-4-yl)propynoic acid and 3-chloro-4-(2-pyrrolidin-1-ylethyl)phenylamine. Yield: 140 mg (27.2% of theory); $C_{27}H_{24}BrClN_2O_1$ (M=507.84); calc.: molecular ion peak $(M+H)^+$: 507/09/11; found: molecular ion peak $(M+H)^+$: 507/09/11.

EXAMPLE 4.284

3-(3-bromobiphenyl-4-yl)propynoic acid-{3-chloro-4-[2-(4-hydroxy-4-trifluoromethylpiperidin-1-yl)ethyl]phenyl}amide

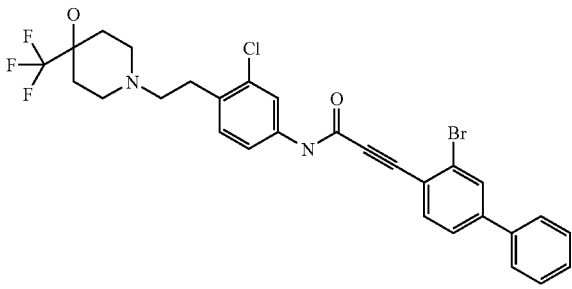

Prepared analogously to Example 2.3.f. from (3-bromobiphenyl-4-yl)propynoic acid and 1-[2-(4-amino-2-chlorophenyl)ethyl]4-trifluoromethylpiperidin-4-ol. Yield: 36 mg (10.5% of theory); $C_{29}H_{25}BrClF_3N_2O_2$ (M=605.87); calc.: molecular ion peak $(M+H)^+$: 605/07/09; found: molecular ion peak $(M+H)^+$: 605/07/09.

EXAMPLE 4.285

3-pyridin-3-ylpropynoic acid-[3-chloro-4-(2-diethylaminoethoxy)phenyl]amide

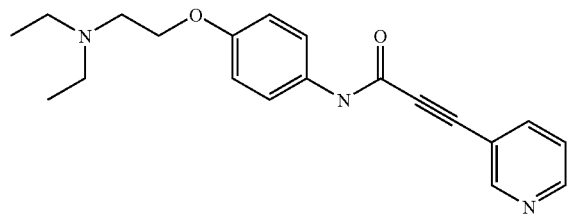

Prepared analogously to Example 2.3.f. from pyridin-3-ylpropynoic acid and [2-(2-chloro-4-aminophenoxy)ethyl] diethylamine. Yield: 0.42 g (66.4% of theory); melting point: 118° C.-120° C.; $C_{20}H_{22}ClN_3O_2$ (M=371.86); calc.: molecular ion peak $(M+H)^+$: 372/374; found: molecular ion peak $(M+H)^+$: 372/374; $R_f$ value: 0.4 (silica gel, dichloromethane/methanol/ammonia (9:1:0.1)).

EXAMPLE 5.1

(E)-N-(4'-methoxybiphenyl-4-yl)-3-(4-pyrrolidin-1-ylmethylphenyl)acrylamide

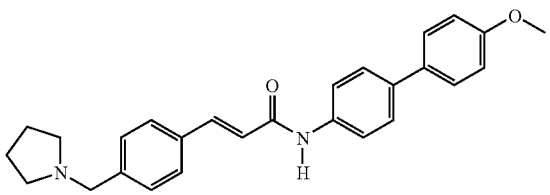

5.1.a.
ethyl(E)-3-(4-pyrrolidin-1-ylmethylphenyl)acrylate 2 g (7.43 mmol) of ethyl (E)-3-(4-bromomethylphenyl)acrylate is added to a suspension of 0.69 mL (8.2 mmol) of pyrrolidine and 2.05 g (14.86 mmol) of potassium carbonate in 40 mL of DMF and stirred for 18 hours at ambient temperature. The reaction mixture is evaporated down and the residue is extracted with water and ethyl acetate. The organic phase is dried over sodium sulfate, evaporated down, and the residue is purified by column chromatography on silica gel (eluant: dichloromethane/methanol/ammonia (90:10:1)). Yield: 0.3 g (15.6% of theory); $C_{16}H_{21}NO_2$ (M=259.35); calc.: molecular ion peak $(M+H)^+$: 260; found: molecular ion peak $(M+H)^+$: 260; $R_f$ value: 0.5 (silica gel, dichloromethane/methanol/ammonia (90:10:1)).

5.1.b. (E)-3-(4-pyrrolidin-1-ylmethylphenyl)acrylic acid

A reaction mixture of 0.3 g (1.15 mmol) of ethyl (E)-3-(4-pyrrolidin-1-ylmethylphenyl)acrylate and 0.4 g (9.53 mmol) of lithium hydroxide monohydrate in 20 mL of a 1:1 mixture of methanol, THF, and water is stirred for 48 hours at ambient temperature. Then the reaction mixture is evaporated down, the residue is diluted with water and acidified with hydrochloric acid. The mixture is evaporated down, combined with methanol and dichloromethane, filtered, and the filtrate is evaporated to dryness. Yield: 0.27 g, $C_{14}H_{17}NO_2$ (M=231.29); calc.: molecular ion peak $(M+H)^+$: 232; found: molecular ion peak $(M+H)^+$: 232; $R_f$ value: starting spot (silica gel, dichloromethane/methanol/ammonia (90:10:1)).

5.1.c. (E)-N-(4'-methoxybiphenyl-4-yl)-3-(4-pyrrolidin-1-ylmethylphenyl)acrylamide Prepared analogously to Example 3.1.e. from (E)-3-(4-pyrrolidin-1-ylmethylphenyl)acrylic acid and 4'-methoxybiphenyl-4-ylamine. Yield: 74 mg (15.4% of theory); melting point: 199° C.-200° C.; $C_{27}H_{28}N_2O_2$ (M=412.53); calc.: molecular ion peak $(M+H)^+$: 413; found: molecular ion peak (M+H)$^+$: 413; $R_f$ value: 0.77 (silica gel, dichloromethane/methanol/ammonia (80:20:1)).

EXAMPLE 5.2

(E)-N-(4'-chlorobiphenyl-4-yl)-3-[4-(4-methylpiperidin-1-ylmethyl)phenyl]acrylamide

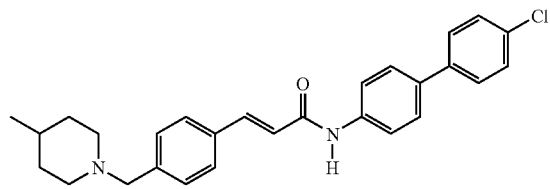

5.2.a. (E)-3-(4-dimethoxymethylphenyl)acrylic acid 38.81 mL (0.354 mmol) of trimethylorthoformate is added to a suspension of 25 g (0.141 mol) of (E)-3-(4-formylphenyl)acrylic acid in 350 mL of methanol and the mixture is refluxed for 48 hours. After cooling, the reaction mixture is filtered and the filtrate is evaporated down. The residue is taken up in 500 mL of dichloromethane and filtered through CELITE® filter aid. The filtrate is evaporated down to 150 mL and cooled to 0° C. The precipitate formed is filtered off, washed with dichloromethane/petroleum ether (1:1), and dried at 60° C. in the circulating air dryer. Yield: 12.05 g (31.5% of theory); $C_{12}H_{14}O_4$ (M=222.24); calc.: molecular ion peak (M+H)$^+$: 245; found: molecular ion peak (M+H)$^+$: 245; $R_f$ value: 0.6 (silica gel, petroleum ether/ethyl acetate (1:1)).

5.2.b. (E)-N-(4'-chlorobiphenyl-4-yl)-3-(4-dimethoxymethylphenyl)acrylamide

Prepared analogously to Example 3.1.e. from (E)-3-(4-dimethoxymethylphenyl)acrylic acid and 4'-chlorobiphenyl-4-ylamine. Yield: 9.8 g, $C_{24}H_{22}ClNO_3$ (M=407.90); calc.: molecular ion peak (M+H)$^+$: 408/410; found: molecular ion peak (M+H)$^+$: 408/410; $R_f$ value: 0.3 (silica gel, dichloromethane/ethanol (20:1)).

5.2.c. (E)-N-(4'-chlorobiphenyl-4-yl)-3-(4-formylphenyl)acrylamide 70 mL of water and 21 mL of trifluoroacetic acid are added to a suspension of 9.8 g (24.02 mmol) of (E)-N-(4'-chlorobiphenyl-4-yl)-3-(4-dimethoxymethylphenyl)acrylamide in 280 mL of chloroform and the reaction mixture is stirred for 8 hours at ambient temperature. It is diluted with chloroform and water, the organic phase is separated off and extracted with water. The organic phase is dried, filtered through silica gel, and the solvent is distilled off. Yield: 5.5 g; $C_{22}H_{16}ClNO_2$ (M=361.83); calc.: molecular ion peak (M+H)$^+$: 362/364; found: molecular ion peak (M+H)$^+$: 362/364; $R_f$ value: 0.6 (silica gel, cyclohexane/ethyl acetate (1:1)).

5.2.d. (E)-N-(4'-chlorobiphenyl-4-yl)-3-[4-(4-methylpiperidin-1-ylmethyl)phenyl]acrylamide Prepared analogously to Example 4.30.c. from (E)-N-(4'-chlorobiphenyl-4-yl)-3-(4-formylphenyl)acrylamide and 4-methylpiperidine. Yield: 80 mg (21.7% of theory); melting point: 207° C.-208° C.; $C_{28}H_{29}ClN_2O$ (M=445.00); calc.: molecular ion peak (M+H)$^+$: 445/447; found: molecular ion peak (M+H)$^+$: 445/447; $R_f$ value: 0.76 (silica gel, dichloromethane/methanol (10:1)).

EXAMPLE 5.3

(E)-N-(4'-chlorobiphenyl-4-yl)-3-[4-(cis-3,5-dimethylpiperidin-1-ylmethyl)phenyl]acrylamide

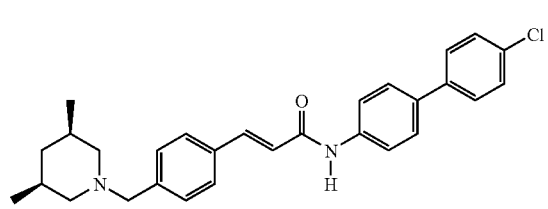

5.3.a. (E)-N-(4'-chlorobiphenyl-4-yl)-3-(4-hydroxymethylphenyl)acrylamide

A solution of 4.4 g (12.16 mmol) of (E)-N-(4'-chlorobiphenyl-4-yl)-3-(4-formylphenyl)acrylamide in 200 mL of THF is adjusted with glacial acetic acid to a pH of three, combined with 8.14 g (36.48 mmol) of sodium triacetoxyborohydride, and stirred for 18 hours at ambient temperature. Then the reaction mixture is poured into water and the precipitate is filtered off. The filtrate is extracted with ethyl acetate, washed with water, and dried over sodium sulfate. The solvent is removed and the residue is combined with the solid which has been filtered off. The purification is carried out by column chromatography on silica gel (eluant: dichloromethane/ethanol/ammonia (30:1:0.1)). Yield: 3.2 g (72.4% of theory); $C_{22}H_{18}ClNO_2$ (M=363.84); calc.: molecular ion peak (M+H)$^+$: 364/366; found: molecular ion peak (M+H)$^+$: 364/366; $R_f$ value: 0.2 (silica gel, dichloromethane/ethanol (20:1)).

5.3.b. (E)-N-(4'-chlorobiphenyl-4-yl)-3-(4-chloromethylphenyl)acrylamide

A suspension of 2.1 g (5.77 mmol) of (E)-N-(4'-chlorobiphenyl-4-yl)-3-(4-hydroxymethylphenyl)acrylamide in 100 mL of dichloromethane is combined with 1.7 mL (12.19 mmol) of triethylamine and then combined with 0.46 mL (5.88 mmol) of methanesulfonic acid chloride. The reaction mixture is stirred for 3 hours at ambient temperature, diluted with water, and extracted several times with dichloromethane. The combined organic phases are dried over sodium sulfate, filtered through silica gel, and the filtrate is evaporated down. Yield: 0.4 g (18.1% of theory); $C_{22}H_{17}Cl_2NO$ (M=382.29); calc.: molecular ion peak (M+H)$^+$: 381/383/385; found: molecular ion peak (M+H)$^+$: 381/383/385.

5.3.c. (E)-N-(4'-chlorobiphenyl-4-yl)-3-[4-(cis-3,5-dimethylpiperidin-1-ylmethyl)phenyl]acrylamide Prepared analogously to Example 1.2.c. from (E)-N-(4'-chlorobiphenyl-4-yl)-3-(4-chloromethylphenyl)acrylamide and cis-3,5-dimethylpiperidine. Yield: 30 mg (30% of theory); melting point: 217° C.-218° C.; $C_{29}H_{31}ClN_2O$ (M=459.03); calc.: molecular ion peak (M+H)$^+$: 459/461; found: molecular ion peak (M+H)$^+$: 459/461.

The following compounds are prepared analogously to Example 5.3.c.:

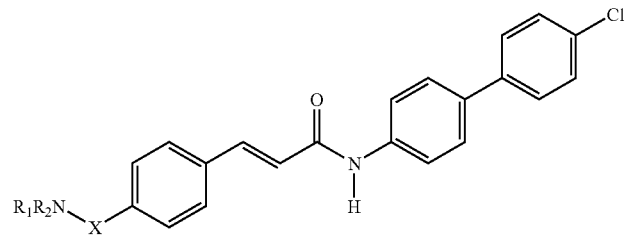
| Example | R₁R₂N—X | educt | empirical formula | mass spectrum | mp [° C.] | $R_f$ value |
|---|---|---|---|---|---|---|
| 5.4 | | 5.3.b | $C_{28}H_{29}ClN_2O_2$ | 461/463 $[M + H]^+$ | 205-206 | 0.4 (A) |
| 5.5 | | 5.3.b | $C_{26}H_{25}ClN_2O_2$ | 432/435 $[M + H]^+$ | 184-185 | 0.6 (A) |
| 5.6 | | 5.3.b | $C_{28}H_{28}ClN_3O_2$ | 474/476 $[M + H]^+$ | 254-255 | 0.05 (A) |
| 5.7 | | 5.3.b | $C_{28}H_{29}ClN_2O_2$ | 461/463 $[M + H]^+$ | 196-197 | 0.2 (A) |
| 5.8 | | 5.3.b | $C_{28}H_{29}ClN_2O_2$ | 461/463 $[M + H]^+$ | 190-191 | 0.1 (A) |
| 5.9 | | 5.3.b | $C_{26}H_{25}ClN_2O_2$ | 433/435 $[M + H]^+$ | 178-179 | 0.14 (A) |
| 5.10 | | 5.3.b | $C_{27}H_{27}ClN_2O_2$ | 447/449 $[M + H]^+$ | 192-193 | 0.2 (A) |
| 5.11 | | 5.3.b | $C_{28}H_{29}ClN_2O_2$ | 461/463 $[M + H]^+$ | 212 | 0.25 (B) |

-continued

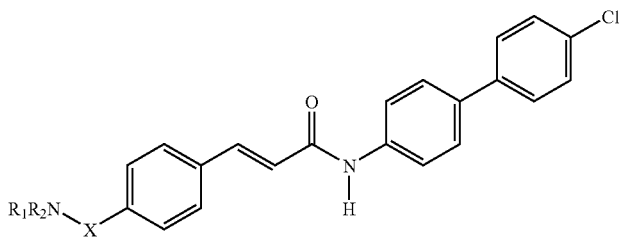

| Example | R₁R₂N—X | educt | empirical formula | mass spectrum | mp [° C.] | $R_f$ value |
|---|---|---|---|---|---|---|
| 5.12 | (4-methylpiperazinyl-methyl) | 5.3.b | $C_{27}H_{28}ClN_3O$ | 446/448 [M + H]⁺ | 216 | 0.2 (B) |
| 5.13 | (pyrrolidinyl-methyl) | 5.3.b | $C_{26}H_{25}ClN_2O$ | 417/419 [M + H]⁺ | 219 | 0.25 (B) |

$R_f$ value:
A = (silica gel, dichloromethane/methanol (10:1))
B = (silica gel, dichloromethane/methanol/ammonia (10:1:0.1))

EXAMPLE 5.14

(E)-N-(4'-chlorobiphenyl-4-yl)-3-(4-cyclopropylaminomethylphenyl)acrylamide

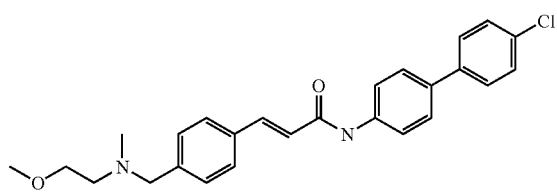

A reaction mixture of 100 mg (0.26 mmol) of (E)-N-(4'-chlorobiphenyl-4-yl)-3-(4-chloromethylphenyl)acrylamide, 70 mg (0.77 mmol) of 2-methoxyethylmethylamine, and 140 mg (1 mmol) of potassium carbonate in 10 mL of acetone is agitated for 24 hours at reflux temperature. The reaction mixture is evaporated down. The residue is purified by column chromatography on silica gel (eluant: dichloromethane/ethanol/ammonia (20/1/0.1)). Yield: 92 mg (81% of theory); melting point: 222° C.-223° C.; $C_{26}H_{27}ClN_2O_2$ (M=434.96); calc.: molecular ion peak (M+H)⁺: 435/37(Cl); found: molecular ion peak (M+H)⁺: 435/37(Cl); $R_f$ value: 0.4 (silica gel, dichloromethane/methanol/ammonia (20:1:0.1)).

The following compounds are prepared analogously to Example 5.14:

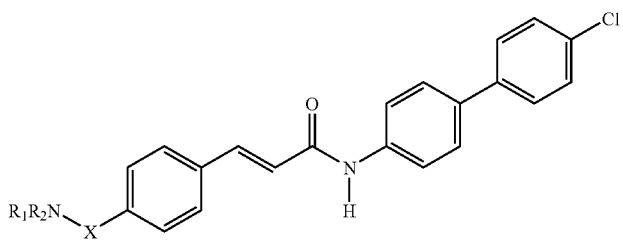

| Example | R₁R₂N—X | educt | empirical formula | mass spectrum | mp [° C.] | $R_f$ value |
|---|---|---|---|---|---|---|
| 5.15 | (diazabicyclic-methyl) | 5.3.b | $C_{28}H_{28}ClN_3O$ | 458/460 [M + H]⁺ | 206-207 | 0.1 (B) |

-continued

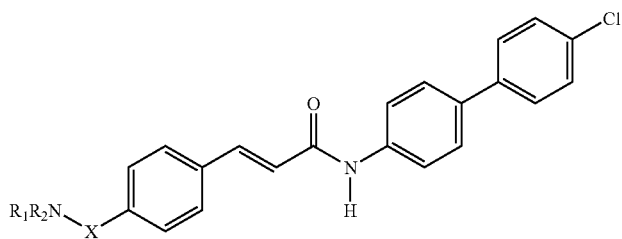

| Example | R₁R₂N—X | educt | empirical formula | mass spectrum | mp [° C.] | $R_f$-value |
|---|---|---|---|---|---|---|
| 5.16 | pyrrolo-piperazinyl-CH₂- | 5.3.b | $C_{29}H_{30}ClN_3O$ | 472/474 [M + H]⁺ | 223-224 | 0.2 (A) |
| 5.17 | cyclopropylmethyl(methyl)N-CH₂- | 5.3.b | $C_{27}H_{27}ClN_2O$ | 431/433 [M + H]⁺ | 246-247 | 0.4 (B) |
| 5.18 | benzyl(methyl)N-CH₂- | 5.3.b | $C_{30}H_{27}ClN_2O$ | 467/469 [M + H]⁺ | 210-212 | 0.6 (A) |
| 5.19 | (tetrahydropyran-4-yl)methyl(methyl)N-CH₂- | 5.3.b | $C_{29}H_{31}ClN_2O_2$ | 475/477 [M + H]⁺ | 181 | 0.35 (A) |
| 5.20 | 2-phenoxyethyl(methyl)N-CH₂- | 5.3.b | $C_{31}H_{29}ClN_2O_2$ | 497 [M + H]⁺ | 188-189 | 0.35 (A) |
| 5.21 | cyclohexyl(methyl)N-CH₂- | 5.3.b | $C_{29}H_{31}ClN_2O$ | 459/461 [M + H]⁺ | 262-263 | 0.4 (A) |
| 5.22 | cyclopropyl(methyl)N-CH₂- | 5.3.b | $C_{26}H_{25}ClN_2O$ | 417/419 [M + H]⁺ | 238-239 | 0.5 (B) |
| 5.23 | 2,6-dimethylmorpholinyl-CH₂- | 5.3.b | $C_{28}H_{29}ClN_2O_2$ | 461/463 [M + H]⁺ | 212-213 | 0.45 (A) |
| 5.24 | thiomorpholine-1,1-dioxide-N-CH₂- | 5.3.b | $C_{26}H_{25}ClN_2O_3S$ | 481/83 [M + H]⁺ | 264-266 | 0.45 (B) |

-continued

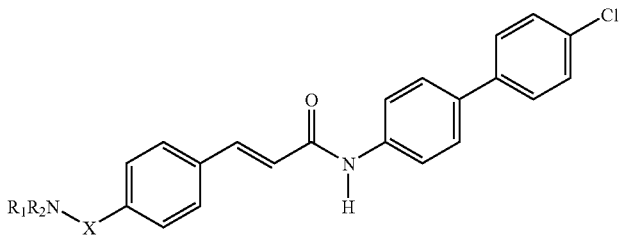

| Example | R₁R₂N—X | educt | empirical formula | mass spectrum | mp [° C.] | $R_f$-value |
|---|---|---|---|---|---|---|
| 5.25 | (spiro cyclopentane-piperidine-CH₂-) | 5.3.b | $C_{31}H_{33}ClN_2O$ | 485/87 [M + H]⁺ | 250 | 0.35 (B) |
| 5.26 | (N≡C-CH₂CH₂-N(CH₃)-CH₂-) | 5.3.b | $C_{26}H_{24}ClN_3O$ | 430/32 [M + H]⁺ | 160-161 | 0.45 (B) |
| 5.27 | (MeO-CH₂CH₂-N(CH₂C(CH₃)₂OMe)-CH₂-) | 5.3.b | $C_{29}H_{33}ClN_2O_3$ | 493/95 [M + H]⁺ | 125-126 | 0.4 (A) |
| 5.28 | (1-piperidinyl-pyrrolidinyl-CH₂-) | 5.3.b | $C_{31}H_{34}ClN_3O$ | 500/02 [M + H]⁺ | 209-210 | 0.15 (A) |

$R_f$-value:
A = (silica gel, dichloromethane/ethanol/ammonia (20:1:0.1))
B = (silica gel, dichloromethane/methanol/ammonia (10:1:0.1))

EXAMPLE 5.29

(E)-N-(4'-chlorobiphenyl-4-yl)-3-(4-{[methyl-(4-methylcyclohexyl)amino]methyl}phenyl)acrylamide

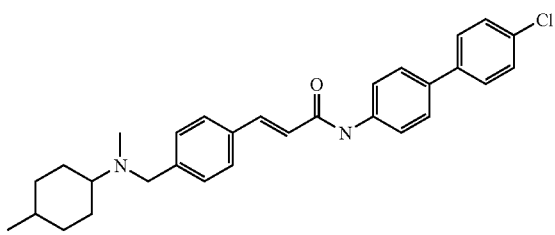

5.29.a. 4-[(E)-2-(4'-chlorobiphenyl-4-ylcarbamoyl) vinyl]benzyl methanesulfonate A suspension of 2.3 g (6.3 mmol) of (E)-N-(4'-chlorobiphenyl-4-yl)-3-(4-hydroxymethylphenyl)acrylamide in 200 mL of dichloromethane is combined with 1.94 mL (13.9 mmol) of triethylamine and then with 0.54 mL (6.92 mmol) of methanesulfonic acid chloride. The reaction mixture is stirred for 18 hours at ambient temperature, diluted with water, and extracted several times with dichloromethane. The combined organic phases are dried over sodium sulfate, filtered through silica gel and the filtrate is evaporated down. Yield: 1.85 g (67% of theory); $C_{23}H_{20}ClNO_4S$ (M=441.93); calc.: molecular ion peak (M+H)⁺: 442/444 (Cl); found: molecular ion peak (M+H)⁺: 442/444 (Cl); $R_f$-value: 0.73 (silica gel, dichloromethane/methanol/ammonia (90:10:1)).

5.29.b. (E)-N-(4'-chlorobiphenyl-4-yl)-3-(4-{[methyl-(4-methylcyclohexyl)amino]methyl}phenyl) acrylamide A reaction mixture of 100 mg (0.226 mmol) of 4-[(E)-2-(4'-chlorobiphenyl-4-ylcarbamoyl)vinyl]benzyl methanesulfonate, 37.34 mg (0.29 mmol) of methyl-(4-methylcyclohexyl)amine, and 0.1 mL of triethylamine in 10 mL of dichloromethane is stirred for 18 hours at ambient temperature. Then the reaction mixture is extracted between water and dichloromethane, the organic phase is separated off, dried, and evaporated down. The residue is purified by column chromatography on silica gel (eluant: dichloromethane/methanol/ammonia (90:10:1)). Yield: 52 mg (49% of theory); $C_{30}H_{33}ClN_2O$ (M=473.05); melting point: 227° C.-258° C.; calc.: molecular ion peak $(M+H)^+$: 473/475 (Cl); found: molecular ion peak $(M+H)^+$: 473/475 (Cl); $R_f$ value: 0.48 (silica gel, dichloromethane/methanol/ammonia (90:10:1)).

The following compounds are prepared analogously to Example 5.29.b.:

nyl-4-yl)-3-(4-chloromethylphenyl)acrylamide in 5 mL of THF and the mixture is refluxed for 18 hours. Then the reaction mixture is poured onto water and the precipitate formed is suction filtered. Further purification is carried out by column chromatography on silica gel (eluant: dichloromethane/methanol (95:5 to 50:50)). Yield: 70 mg (40% of theory); $C_{28}H_{29}ClN_2O$ (M=444.99); melting point: 247° C.-248° C.; Calc.: molecular ion peak $(M+H)^+$: 445/447 (Cl); found: molecular ion peak $(M+H)^+$: 445/447 (Cl).

| Example | $R_1R_2N$—X | educt | empirical formula | mass spectrum | mp [° C.] | $R_f$ value |
|---|---|---|---|---|---|---|
| 5.30 | | 5.29.a | $C_{29}H_{31}ClN_2O_2$ | 475/477 (Cl) $[M + H]^+$ | 225-265 | 0.37 (A) |
| 5.31 | | 5.29.a | $C_{29}H_{32}ClN_3O$ | 474/476 (Cl) $[M + H]^+$ | 226-254 | 0.6 (A) |
| 5.32 | | 5.29.a | $C_{30}H_{33}ClN_2O$ | 473/475 (Cl) $[M + H]^+$ | 205-210 | 0.42 (A) |

$R_f$ value: A = (silica gel, dichloromethane/methanol/ammonia (90:10:1))

EXAMPLE 5.33

(E)-N-(4'-chlorobiphenyl-4-yl)-3-(4-cyclohexylaminomethylphenyl)acrylamide 0.082 mL (0.72 mmol) of cyclohexylamine is added to a suspension of 150 mg (0.39 mmol) of (E)-N-(4'-chlorobiphe-

EXAMPLE 5.34

(E)-N-(4'-chlorobiphenyl-4-yl)-3-(4-{[(2-hydroxycyclohexyl)methylamino]methyl}phenyl)acrylamide

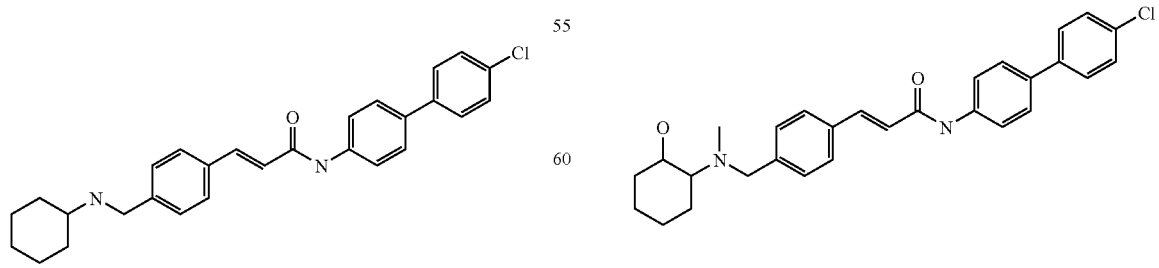

Prepared analogously to Example 5.33 from (E)-N-(4'-chlorobiphenyl-4-yl)-3-(4-chloromethylphenyl)acrylamide and 2-methylaminocyclohexanol. Yield: 90 mg (48% of theory); $C_{29}H_{31}ClN_2O_2$ (M=475.02); melting point: 210° C.-211° C.; calc.: molecular ion peak $(M+H)^+$: 475/477 (Cl); found: molecular ion peak $(M+H)^+$: 475/477 (Cl).

EXAMPLE 5.35 tert-butyl 4-({-[(E)-2-(4'-chlorobiphenyl-4-ylcarbamoyl)vinyl]benzyl}methylamino)piperidine-1-carboxylate

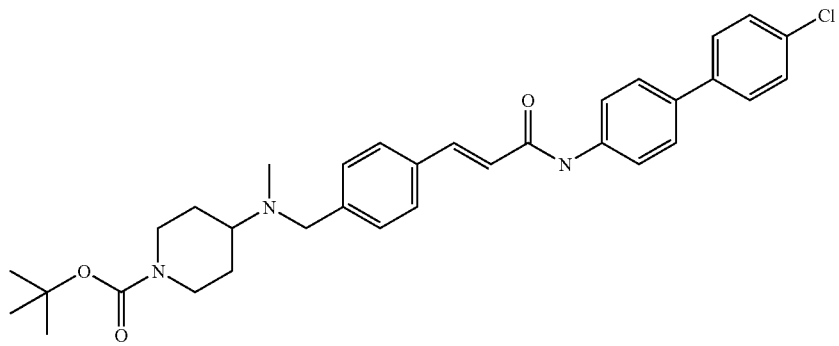

0.5 g (2.34 mmol) of tert-butyl 4-methylaminopiperidine-1-carboxylate is added to a suspension of 300 mg (0.79 mmol) of (E)-N-(4'-chlorobiphenyl-4-yl)-3-(4-chloromethylphenyl)acrylamide in 5 mL of DMF and the mixture is stirred for 18 hours at 80° C. Then the reaction mixture is poured onto water and the precipitate formed is suction filtered. Further purification is carried out by stirring out from a little methanol. Yield: 200 mg (45% of theory); $C_{33}H_{38}ClN_3O_3$ (M=560.13); melting point: 168° C.-169° C.; calc.: molecular ion peak $(M+H)^+$: 560/562 (Cl); found: molecular ion peak $(M+H)^+$: 560/562 (Cl).

1 mL of trifluoroacetic acid is added to a suspension of 170 mg (0.3 mmol) of tert-butyl 4-({-[(E)-2-(4'-chlorobiphenyl-4-ylcarbamoyl)vinyl]benzyl}methylamino)piperidine-1-carboxylate (Example 5.35) in 25 mL of dichloromethane and the mixture is stirred for 18 hours at ambient temperature. Then the solvent is evaporated down and the residue is crystallized from ethyl acetate/diisopropylether (1:1). The precipitated solid is suction filtered and dried at 60° C. in the circulating air dryer. Yield: 70 mg (40% of theory); $C_{28}H_{30}ClN_3O$ (M=460.02) *trifluoroacetic acid acetate; melting point: 207° C.-208° C.; calc.: molecular ion peak $(M+H)^+$: 460/462 (Cl); found: molecular ion peak $(M+H)^+$: 460/462 (Cl).

EXAMPLE 5.37

(E)-3-(4-{[(1-acetylpiperidin-4-yl)methylamino]methyl}phenyl)-N-(4'-chlorobiphenyl-4-yl)acrylamide

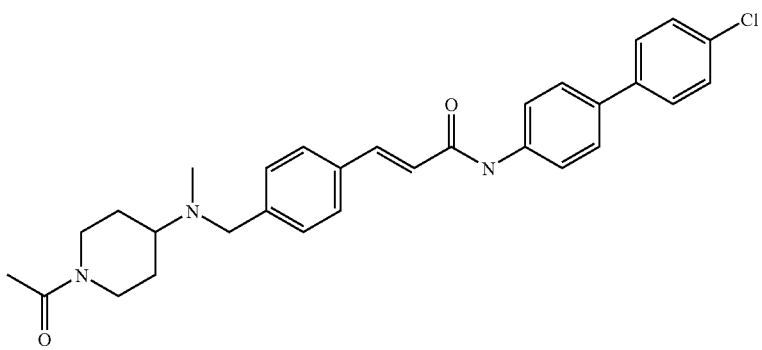

EXAMPLE 5.36

(E)-N-(4'-chlorobiphenyl-4-yl)-3-{4[(methylpiperidin-4-ylamino)methyl]phenyl}acrylamidextrifluoroacetic acid acetate

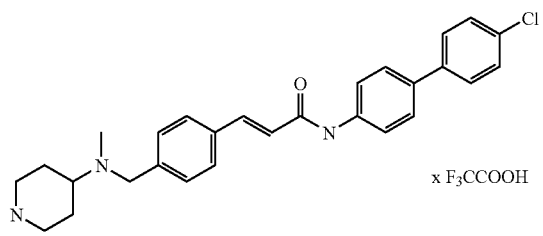

0.017 mL (0.18 mmol) of acetic anhydride is added to a solution of 50 mg (0.087 mmol) of (E)—N-(4'-chlorobiphenyl-4-yl)-3-{4[(methylpiperidin-4-ylamino)methyl]phenyl}acrylamidextrifluoroacetic acid acetate in 4 mL of acetic acid and the mixture is stirred for 18 hours at ambient temperature. Then the reaction mixture is poured onto water and made basic with ammonia. The precipitate formed is suction filtered and washed with water. The product is dried at 60° C. in the circulating air dryer. Yield: 20 mg (46% of theory); $C_{30}H_{32}ClN_3O_2$ (M=502.05); melting point: 225° C.-226° C.; calc.: molecular ion peak $(M+H)^+$: 502/504 (Cl); found: molecular ion peak $(M+H)^+$: 502/504 (Cl).

EXAMPLE 5.38

(E)-N-(4'-chlorobiphenyl-4-yl)-3-(4-{[cyclohexyl-(2-hydroxyethyl)amino]methyl}phenyl)acrylamide

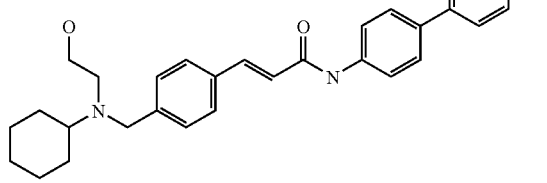

0.24 g (1.7 mmol) of 2-cyclohexylaminoethanol are added to a suspension of 130 mg (0.34 mmol) of (E)-N-(4'-chlorobiphenyl-4-yl)-3-(4-chloromethylphenyl)acrylamide in 10 mL of DMF and the mixture is stirred for 48 hours at 80° C. Then the reaction mixture is poured onto water and the precipitate formed is suction filtered and washed with water. The solid is dried in the circulating air dryer at 50° C. Yield: 20 mg (10% of theory); $C_{30}H_{33}ClN_2O_2$ (M=489.05); melting point: 178° C.-179° C.; calc.: molecular ion peak (M+H)$^+$: 489/491 (Cl); found: molecular ion peak (M+H)$^+$: 489/491 (Cl).

EXAMPLE 5.39

(E)-N-(4'-chlorobiphenyl-4-yl)-3-{4-[(cyclopentylmethylamino)methyl]phenyl}acrylamide

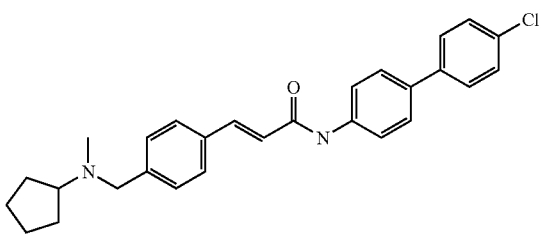

A reaction mixture of 200 mg (0.523 mmol) of (E)-N-(4'-chlorobiphenyl-4-yl)-3-(4-chloromethylphenyl)acrylamide, 295 mg (1.56 mmol) of cyclopentylmethylamine oxalic acid acetate and 0.44 mL (3.12 mmol) of triethylamine in 5 mL of THF is refluxed for 18 hours. Then the reaction mixture is poured onto water and the precipitate formed is suction filtered. Further purification is carried out by column chromatography on silica gel (eluant: dichloromethane/methanol (10:1)). Yield: 10 mg (4% of theory); $C_{28}H_{29}ClN_2O$ (M=445.0); melting point: 209° C.-210° C.; calc.: molecular ion peak (M+H)$^+$: 445/447 (Cl); found: molecular ion peak (M+H)$^+$: 445/447 (Cl).

The following compounds are prepared analogously to Example 5.3.c.:

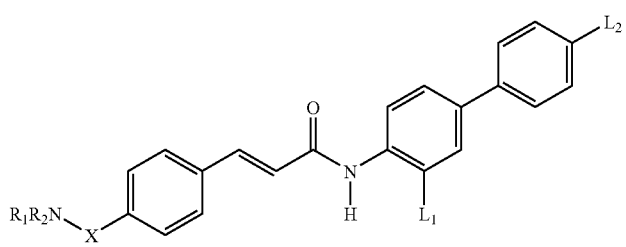

| Example | R$_1$R$_2$N—X | L$_1$ | L$_2$ |
|---|---|---|---|
| 5.40 | | H | Cl |
| 5.41 | | H | Cl |
| 5.42 | | H | Cl |

-continued

| Example | R₁R₂N—X | L₁ | L₂ |
|---|---|---|---|
| 5.43 | 4-methoxypiperidin-1-yl-neopentyl | F | Cl |
| 5.44 | N-(cyclopropylmethyl)-N-methyl-neopentyl | F | Cl |
| 5.45 | N-methyl-N-(tetrahydropyran-4-yl)-neopentyl | F | Cl |
| 5.46 | N-(2-methoxyethyl)-N-(2,2-dimethyl-3-oxopropyl)-neopentyl | F | Cl |
| 5.47 | 2-azaspiro[4.5]decan-2-yl-neopentyl (spiro N) | F | Cl |
| 5.48 | piperidin-1-yl-neopentyl | F | Cl |
| 5.49 | N-cyclopropyl-N-methyl-neopentyl | F | Cl |
| 5.50 | 4-methylpiperidin-1-yl-neopentyl | F | Cl |
| 5.51 | 4-ethylpiperidin-1-yl-neopentyl | F | Cl |

-continued
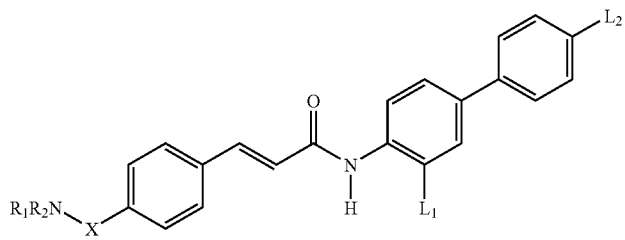
| Example | R₁R₂N—X | L₁ | L₂ |
|---|---|---|---|
| 5.52 | | F | Cl |
| 5.53 | | F | Cl |
| 5.54 | | F | Cl |
| 5.55 | | F | Cl |
| 5.56 | | F | Cl |
| 5.57 | | F | Cl |
| 5.58 | | F | Cl |
| 5.59 | | F | Cl |
| 5.60 | | F | Cl |

-continued
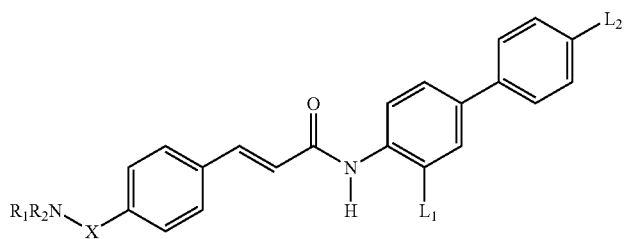
| Example | R₁R₂N—X | L₁ | L₂ |
|---|---|---|---|
| 5.61 | (N-methyl-N-benzyl) | F | Cl |
| 5.62 | (N-methyl-N-(2-cyanoethyl)) | F | Cl |
| 5.63 | (N-methyl-N-((tetrahydropyran-4-yl)methyl)) | F | Cl |
| 5.64 | (N-methyl-N-(2-phenoxyethyl)) | F | Cl |
| 5.65 | (N-methyl-N-cyclohexyl) | F | Cl |
| 5.66 | (2,6-dimethylmorpholino) | F | Cl |
| 5.67 | (4-methoxypiperidino) | H | CF₃ |
| 5.68 | (N-methyl-N-(cyclopropylmethyl)) | H | CF₃ |
| 5.69 | (N-methyl-N-(tetrahydropyran-4-yl)) | H | CF₃ |

-continued

| Example | R₁R₂N—X | L₁ | L₂ |
|---|---|---|---|
| 5.70 | (2,2-dimethyl-2-oxo with methoxyethyl N-) | H | CF₃ |
| 5.71 | (2-azaspiro[4.5] piperidine group) | H | CF₃ |
| 5.72 | (piperidin-1-yl-methyl) | H | CF₃ |
| 5.73 | (N-cyclopropyl-N-methylamino-methyl) | H | CF₃ |
| 5.74 | (4-methylpiperidin-1-yl-methyl) | H | CF₃ |
| 5.75 | (4-ethylpiperidin-1-yl-methyl) | H | CF₃ |
| 5.76 | (3,5-dimethylpiperidin-1-yl-methyl) | H | CF₃ |
| 5.77 | (octahydropyrrolo[1,2-a]pyrazin-2-yl-methyl) | H | CF₃ |
| 5.78 | (3-hydroxypyrrolidin-1-yl-methyl) | H | CF₃ |

-continued

| Example | R₁R₂N—X | L₁ | L₂ |
|---|---|---|---|
| 5.79 | (2-hydroxymethyl-pyrrolidin-1-yl)methyl | H | CF₃ |
| 5.80 | 4-carbamoyl-piperidin-1-yl-methyl | H | CF₃ |
| 5.81 | morpholin-4-yl-methyl | H | CF₃ |
| 5.82 | diethylamino-methyl | H | CF₃ |
| 5.83 | pyrrolidin-1-yl-methyl | H | CF₃ |
| 5.84 | [(2-methoxyethyl)(methyl)amino]methyl | H | CF₃ |
| 5.85 | [benzyl(methyl)amino]methyl | H | CF₃ |
| 5.86 | [(2-cyanoethyl)(methyl)amino]methyl | H | CF₃ |
| 5.87 | [((tetrahydropyran-3-yl)methyl)(methyl)amino]methyl | H | CF₃ |
| 5.88 | [(2-phenoxyethyl)(methyl)amino]methyl | H | CF₃ |

-continued

| Example | R₁R₂N—X | L₁ | L₂ |
|---|---|---|---|
| 5.89 | cyclohexyl(methyl)amino-neopentyl | H | CF₃ |
| 5.90 | 2,6-dimethylmorpholino-neopentyl | H | CF₃ |
| 5.91 | 4-methoxypiperidino-neopentyl | H | Me |
| 5.92 | (cyclopropylmethyl)(methyl)amino-neopentyl | H | Me |
| 5.93 | (tetrahydro-2H-pyran-4-yl)(methyl)amino-neopentyl | H | Me |
| 5.94 | (2-methoxyethyl)amino-2,2-dimethyl-3-oxo derivative | H | Me |
| 5.95 | 2-azaspiro[4.5]decane-neopentyl | H | Me |
| 5.96 | piperidino-neopentyl | H | Me |
| 5.97 | cyclopropyl(methyl)amino-neopentyl | H | Me |

-continued

| Example | R₁R₂N—X | L₁ | L₂ |
|---|---|---|---|
| 5.98 | 4-methylpiperidin-1-ylmethyl | H | Me |
| 5.99 | 4-ethylpiperidin-1-ylmethyl | H | Me |
| 5.100 | 3,5-dimethylpiperidin-1-ylmethyl | H | Me |
| 5.101 | hexahydropyrrolo[1,2-a]pyrazin-2-ylmethyl | H | Me |
| 5.102 | 3-hydroxypyrrolidin-1-ylmethyl | H | Me |
| 5.103 | 2-(hydroxymethyl)pyrrolidin-1-ylmethyl | H | Me |
| 5.104 | 4-carbamoylpiperidin-1-ylmethyl | H | Me |
| 5.105 | morpholin-4-ylmethyl | H | Me |
| 5.106 | diethylaminomethyl | H | Me |

-continued

| Example | R₁R₂N—X | L₁ | L₂ |
|---|---|---|---|
| 5.107 | pyrrolidin-1-ylmethyl | H | Me |
| 5.108 | (2-methoxyethyl)(methyl)aminomethyl | H | Me |
| 5.109 | benzyl(methyl)aminomethyl | H | Me |
| 5.110 | (2-cyanoethyl)(methyl)aminomethyl | H | Me |
| 5.111 | methyl((tetrahydro-2H-pyran-4-yl)methyl)aminomethyl | H | Me |
| 5.112 | methyl(2-phenoxyethyl)aminomethyl | H | Me |
| 5.113 | cyclohexyl(methyl)aminomethyl | H | Me |
| 5.114 | (2,6-dimethylmorpholin-4-yl)methyl | H | Me |
| 5.115 | (4-methoxypiperidin-1-yl)methyl | H | F |
| 5.116 | (cyclopropylmethyl)(methyl)aminomethyl | H | F |

-continued

| Example | R₁R₂N—X | L₁ | L₂ |
|---|---|---|---|
| 5.117 | 4-(N-methyl)-tetrahydropyran-4-yl-amino-neopentyl | H | F |
| 5.118 | N-(2-methoxyethyl)-N-(2-hydroxy-2-methylpropyl)amino-neopentyl | H | F |
| 5.119 | 2,8-diazaspiro[4.5]decan-8-yl-neopentyl | H | F |
| 5.120 | piperidin-1-yl-neopentyl | H | F |
| 5.121 | N-methyl-N-cyclopropylamino-neopentyl | H | F |
| 5.122 | 4-methylpiperidin-1-yl-neopentyl | H | F |
| 5.123 | 4-ethylpiperidin-1-yl-neopentyl | H | F |
| 5.124 | 3,5-dimethylpiperidin-1-yl-neopentyl | H | F |
| 5.125 | octahydropyrrolo[1,2-a]pyrazin-2-yl-neopentyl | H | F |

-continued

| Example | R₁R₂N—X | L₁ | L₂ |
|---|---|---|---|
| 5.126 | (3-hydroxypyrrolidin-1-yl)methyl | H | F |
| 5.127 | (2-(hydroxymethyl)pyrrolidin-1-yl)methyl | H | F |
| 5.128 | (4-carbamoylpiperidin-1-yl)methyl | H | F |
| 5.129 | morpholinomethyl | H | F |
| 5.130 | (diethylamino)methyl | H | F |
| 5.131 | pyrrolidin-1-ylmethyl | H | F |
| 5.132 | ((2-methoxyethyl)(methyl)amino)methyl | H | F |
| 5.133 | (benzyl(methyl)amino)methyl | H | F |
| 5.134 | ((2-cyanoethyl)(methyl)amino)methyl | H | F |
| 5.135 | (methyl((tetrahydro-2H-pyran-4-yl)methyl)amino)methyl | H | F |

-continued

| Example | R₁R₂N—X | L₁ | L₂ |
|---|---|---|---|
| 5.136 | phenoxyethyl-N(methyl)- | H | F |
| 5.137 | cyclohexyl-N(methyl)- | H | F |
| 5.138 | 2,6-dimethylmorpholin-4-yl- | H | F |
| 5.139 | 4-methoxypiperidin-1-yl- | F | $CF_3$ |
| 5.140 | cyclopropylmethyl-N(methyl)- | F | $CF_3$ |
| 5.141 | tetrahydropyran-4-yl-N(methyl)- | F | $CF_3$ |
| 5.142 | (2-methoxyethyl)-N-(2,2-dimethyl-3-oxopropyl)- | F | $CF_3$ |
| 5.143 | 2-azaspiro[4.5]decan-... (spiro piperidine) | F | $CF_3$ |
| 5.144 | piperidin-1-yl- | F | $CF_3$ |

-continued

| Example | R₁R₂N—X | L₁ | L₂ |
|---|---|---|---|
| 5.145 | N-methyl-N-cyclopropylaminomethyl | F | CF₃ |
| 5.146 | 4-methylpiperidin-1-ylmethyl | F | CF₃ |
| 5.147 | 4-ethylpiperidin-1-ylmethyl | F | CF₃ |
| 5.148 | 3,5-dimethylpiperidin-1-ylmethyl | F | CF₃ |
| 5.149 | hexahydropyrrolo[1,2-a]pyrazin-2-ylmethyl | F | CF₃ |
| 5.150 | 3-hydroxypyrrolidin-1-ylmethyl | F | CF₃ |
| 5.151 | 2-(hydroxymethyl)pyrrolidin-1-ylmethyl | F | CF₃ |
| 5.152 | 4-carbamoylpiperidin-1-ylmethyl | F | CF₃ |
| 5.153 | morpholin-4-ylmethyl | F | CF₃ |

-continued

| Example | R₁R₂N—X | L₁ | L₂ |
|---|---|---|---|
| 5.154 | diethylamino-neopentyl | F | CF₃ |
| 5.155 | pyrrolidinyl-neopentyl | F | CF₃ |
| 5.156 | (2-methoxyethyl)(methyl)amino-neopentyl | F | CF₃ |
| 5.157 | benzyl(methyl)amino-neopentyl | F | CF₃ |
| 5.158 | (2-cyanoethyl)(methyl)amino-neopentyl | F | CF₃ |
| 5.159 | ((tetrahydro-2H-pyran-4-yl)methyl)(methyl)amino-neopentyl | F | CF₃ |
| 5.160 | (2-phenoxyethyl)(methyl)amino-neopentyl | F | CF₃ |
| 5.161 | cyclohexyl(methyl)amino-neopentyl | F | CF₃ |
| 5.162 | 2,6-dimethylmorpholinyl-neopentyl | F | CF₃ |
| 5.163 | 4-methoxypiperidinyl-neopentyl | F | Me |

-continued

| Example | R₁R₂N—X | L₁ | L₂ |
|---|---|---|---|
| 5.164 | cyclopropylmethyl(methyl)amino | F | Me |
| 5.165 | methyl(tetrahydropyran-4-yl)amino | F | Me |
| 5.166 | (2-methoxyethyl)(2-methyl-2-oxopropyl... ) amino | F | Me |
| 5.167 | 2-azaspiro[4.5]... (spiro piperidine) | F | Me |
| 5.168 | piperidin-1-yl | F | Me |
| 5.169 | cyclopropyl(methyl)amino | F | Me |
| 5.170 | 4-methylpiperidin-1-yl | F | Me |
| 5.171 | 4-ethylpiperidin-1-yl | F | Me |
| 5.172 | 3,5-dimethylpiperidin-1-yl | F | Me |

-continued

| Example | R₁R₂N—X | L₁ | L₂ |
|---|---|---|---|
| 5.173 | (octahydropyrrolo[1,2-a]pyrazin-2-yl)methyl | F | Me |
| 5.174 | (3-hydroxypyrrolidin-1-yl)methyl | F | Me |
| 5.175 | (2-(hydroxymethyl)pyrrolidin-1-yl)methyl | F | Me |
| 5.176 | (4-carbamoylpiperidin-1-yl)methyl | F | Me |
| 5.177 | morpholinomethyl | F | Me |
| 5.178 | (diethylamino)methyl | F | Me |
| 5.179 | pyrrolidin-1-ylmethyl | F | Me |
| 5.180 | ((2-methoxyethyl)(methyl)amino)methyl | F | Me |
| 5.181 | (benzyl(methyl)amino)methyl | F | Me |
| 5.182 | ((2-cyanoethyl)(methyl)amino)methyl | F | Me |

-continued

| Example | R₁R₂N—X | L₁ | L₂ |
|---------|---------|-----|-----|
| 5.183 | (tetrahydropyran-4-ylmethyl)(methyl)amino- | F | Me |
| 5.184 | (2-phenoxyethyl)(methyl)amino- | F | Me |
| 5.185 | cyclohexyl(methyl)amino- | F | Me |
| 5.186 | (2,6-dimethylmorpholin-4-yl)- | F | Me |
| 5.187 | (4-methoxypiperidin-1-yl)- | F | F |
| 5.188 | (cyclopropylmethyl)(methyl)amino- | F | F |
| 5.189 | (tetrahydropyran-4-yl)(methyl)amino- | F | F |
| 5.190 | (2-methoxyethyl)(2-hydroxy-2-methylpropyl)amino- | F | F |
| 5.191 | 2,8-diazaspiro[4.5]decan-8-yl- | F | F |

-continued

| Example | R₁R₂N—X | L₁ | L₂ |
|---|---|---|---|
| 5.192 | piperidin-1-ylmethyl | F | F |
| 5.193 | (cyclopropyl)(methyl)aminomethyl | F | F |
| 5.194 | (4-methylpiperidin-1-yl)methyl | F | F |
| 5.195 | (4-ethylpiperidin-1-yl)methyl | F | F |
| 5.196 | (3,5-dimethylpiperidin-1-yl)methyl | F | F |
| 5.197 | (hexahydropyrrolo[1,2-a]pyrazin-2-yl)methyl | F | F |
| 5.198 | (3-hydroxypyrrolidin-1-yl)methyl | F | F |
| 5.199 | (2-(hydroxymethyl)pyrrolidin-1-yl)methyl | F | F |
| 5.200 | (4-carbamoylpiperidin-1-yl)methyl | F | F |

-continued

| Example | R₁R₂N—X | L₁ | L₂ |
|---|---|---|---|
| 5.201 | morpholin-4-ylmethyl | F | F |
| 5.202 | (diethylamino)methyl | F | F |
| 5.203 | pyrrolidin-1-ylmethyl | F | F |
| 5.204 | (2-methoxyethyl)(methyl)aminomethyl | F | F |
| 5.205 | benzyl(methyl)aminomethyl | F | F |
| 5.206 | (2-cyanoethyl)(methyl)aminomethyl | F | F |
| 5.207 | methyl((tetrahydro-2H-pyran-4-yl)methyl)aminomethyl | F | F |
| 5.208 | methyl(2-phenoxyethyl)aminomethyl | F | F |
| 5.209 | cyclohexyl(methyl)aminomethyl | F | F |
| 5.210 | (2,6-dimethylmorpholin-4-yl)methyl | F | F |

EXAMPLE 6.1

N-(4'-methoxybiphenyl-4-yl)-3-(4-pyrrolidin-1-ylm-ethylphenyl)propionamide

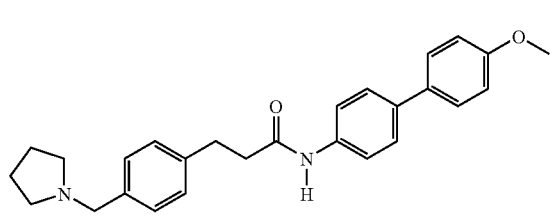

A reaction mixture of 60 mg (0.14 mmol) of (E)-N-(4'-methoxybiphenyl-4-yl)-3-(4-pyrrolidin-1-ylmethylphenyl)acrylamide and 10 mg of Raney nickel in 30 mL of methanol is hydrogenated for 4 hours. The catalyst is filtered off and the filtrate is evaporated to dryness. Yield: 56 mg (93.2% of theory); melting point: 185° C.-188° C.; $C_{27}H_{30}N_2O_2$ (M=414.55); calc.: molecular ion peak (M+H)$^+$: 415; found: molecular ion peak (M+H)$^+$: 415; $R_f$ value: 0.29 (silica gel, dichloromethane/methanol/ammonia (90:10:1)).

EXAMPLE 6.2

N-(4'-chlorobiphenyl-4-yl)-3-[4-(4-methylpiperidin-1-ylmethyl)phenyl]propionamide

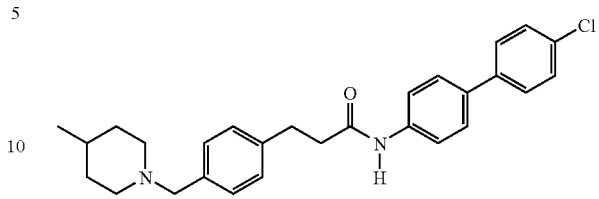

A reaction mixture of 80 mg (0.18 mmol) of (E)-N-(4'-chlorobiphenyl-4-yl)-3-[4-(4-methylpiperidin-1-ylmethyl)phenyl]acrylamide and 20 mg of Raney nickel in 15 mL of ethyl acetate and 15 mL of methanol is hydrogenated for 1 hour at 50 psi and ambient temperature. The catalyst is filtered off, the filtrate is evaporated to dryness and stirred with diisopropylether. Yield: 40 mg (49.7% of theory); melting point: 150° C.-151° C.; $C_{28}H_{31}ClN_2O$ (M=447.02); calc.: molecular ion peak (M+H)$^+$: 447/449; found: molecular ion peak (M+H)$^+$: 447/449; $R_f$ value: 0.5 (silica gel, dichloromethane/methanol (10:1)).

The following compounds are prepared analogously to Example 6.2:

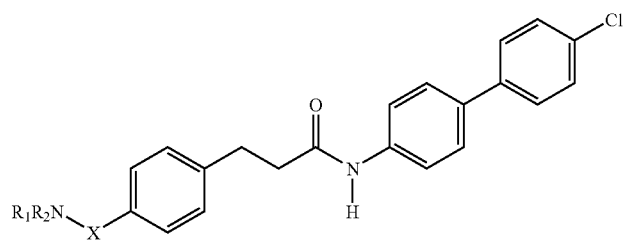

| Example | $R_1R_2N$—X | educt | empirical formula | mass spectrum | mp [° C.] | $R_f$ value |
|---|---|---|---|---|---|---|
| 6.3 | | 5.4 | $C_{28}H_{31}ClN_2O_2$ | 463/465 [M + H]$^+$ | 143-144 | 0.4 (A) |
| 6.4 | | 5.5 | $C_{26}H_{27}ClN_2O_2$ | 435/437 [M + H]$^+$ | 193-194 | |
| 6.5 | ![](piperidinyl carboxamide) | 5.6 | $C_{28}H_{30}ClN_3O_2$ | 476/478 [M + H]$^+$ | 240-241 | |
| 6.6 | | 5.8 | $C_{28}H_{31}ClN_2O_2$ | 463/465 [M + H]$^+$ | 185-186 | 0.1 (A) |

-continued

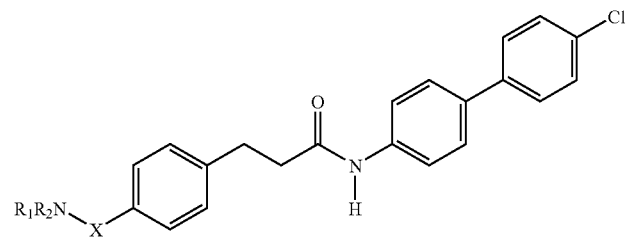

| Example | R₁R₂N—X | educt | empirical formula | mass spectrum | mp [° C.] | $R_f$ value |
|---|---|---|---|---|---|---|
| 6.7 | (3-hydroxypyrrolidinyl) | 5.9 | $C_{26}H_{27}ClN_2O_2$ | 435/437 $[M + H]^+$ | 171-172 | 0.14 (A) |
| 6.8 | (2-hydroxymethylpyrrolidinyl) | 5.10 | $C_{27}H_{29}ClN_2O_2$ | 449/451 $[M + H]^+$ | 156-157 | 0.2 (A) |
| 6.9 | (4-hydroxy-4-methylpiperidinyl) | 5.11 | $C_{28}H_{31}ClN_2O_2$ | 463/465 $[M + H]^+$ | 192 | 0.25 (B) |
| 6.10 | (4-methylpiperazinyl) | 5.12 | $C_{27}H_{30}ClN_3O$ | 448/450 $[M + H]^+$ | 172 | 0.2 (B) |
| 6.11 | (pyrrolidinyl) | 5.13 | $C_{26}H_{27}ClN_2O$ | 419 $[M + H]^+$ | 183-184 | 0.25 (B) |

$R_f$ value:
A, B as specified hereinbefore;
C = (silica gel, dichloromethane/ethanol/ammonia 20/1/0.1)).

EXAMPLE 6.12

N-(4'-chlorobiphenyl-4-yl)-3-(4-{[methyl(tetrahydropyran-4-yl)amino]methyl}phenyl)propionamide

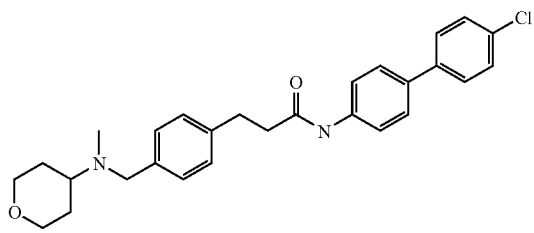

A reaction mixture of 60 mg (0.13 mmol) of (E)-N-(4'-chlorobiphenyl-4-yl)-3-(4-{[methyl-(tetrahydropyran-4-yl)amino]methyl}phenyl)acrylamide and 20 mg of Raney nickel in 10 mL of DMF is hydrogenated for 3 hours at 50 psi and ambient temperature. The catalyst is filtered off and the filtrate is evaporated to dryness. The purification is carried out by column chromatography on silica gel (eluant: dichloromethane/methanol/ammonia (20:1:0.1)). Yield: 22 mg (29% of theory); melting point: 167° C.-173° C.; $C_{28}H_{31}ClN_2O_2$ (M=463.01); calc.: molecular ion peak $(M+H)^+$: 463/65 (Cl); found: molecular ion peak $(M+H)^+$: 463/65 (Cl).

The following compounds are prepared analogously to Example 6.12:

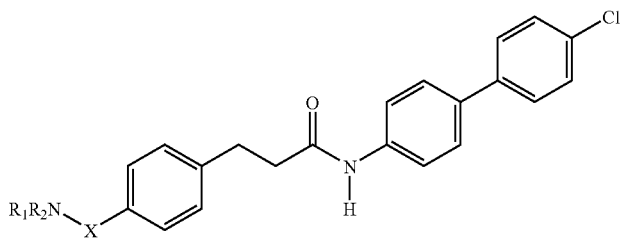
| Example | R₁R₂N—X | educt | empirical formula | mass spectrum | mp [° C.] |
|---|---|---|---|---|---|
| 6.13 | (cyclopropylmethyl)(methyl)N— | 5.17 | $C_{27}H_{29}ClN_2O$ | 433/35 (Cl) $[M + H]^+$ | 156 |
| 6.14 | | 5.27 | $C_{29}H_{35}ClN_2O_3$ | 495/97 (Cl) $[M + H]^+$ | 108-109 |
| 6.15 | | 5.22 | $C_{26}H_{27}ClN_2O$ | 418/20 (Cl) $[M + H]^+$ | 191-192 |
| 6.16 | | 5.16 | $C_{29}H_{32}ClN_3O$ | 474/76 (Cl) $[M + H]^+$ | 177 |
| 6.17 | | 5.14 | $C_{26}H_{29}ClN_2O_2$ | 437/39 (Cl) $[M + H]^+$ | 138 |
| 6.18 | | 5.18 | $C_{30}H_{29}ClN_2O$ | 469/71 (Cl) $[M + H]^+$ | 174-175 |
| 6.19 | | 5.19 | $C_{29}H_{33}ClN_2O_2$ | 477/79 (Cl) $[M + H]^+$ | 162-163 |
| 6.20 | | 5.20 | $C_{31}H_{31}ClN_2O_2$ | 499/501 (Cl) $[M + H]^+$ | 122-124 |
| 6.21 | | 5.23 | $C_{28}H_{31}ClN_2O_2$ | 463/65 (Cl) $[M + H]^+$ | 158.5-160.5 |

-continued
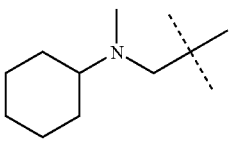
| Example | R₁R₂N—X | educt | empirical formula | mass spectrum | mp [° C.] |
|---|---|---|---|---|---|
| 6.22 | 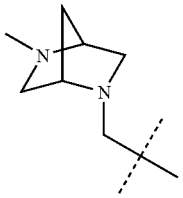 | 5.21 | $C_{29}H_{33}ClN_2O$ | 461/63 (Cl) [M + H]⁺ | 201-204 |
| 6.23 | 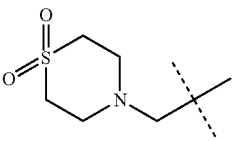 | 5.15 | $C_{28}H_{30}ClN_3O$ | 460/62 (Cl) [M + H]⁺ | 143-144 |
| 6.24 | 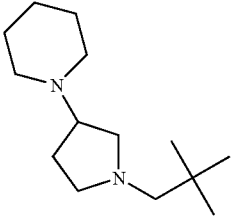 | 5.24 | $C_{26}H_{27}ClN_2O_3S$ | 483/85 (Cl) [M + H]⁺ | 198-201 |
| 6.25 | 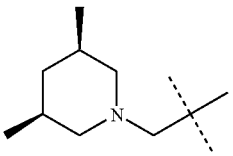 | 5.28 | $C_{31}H_{36}ClN_3O$ | 502/04 (Cl) [M + H]⁺ | 168.8 |
| 6.26 | 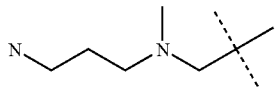 | 5.3.c | $C_{29}H_{33}ClN_2O$ | 461/63 (Cl) [M + H]⁺ | 164-169 |
| 6.27 | 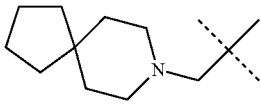 | 5.26 | $C_{26}H_{30}ClN_3O$ | 436/38 (Cl) [M + H]⁺ | 165 |
| 6.28 |  | 5.25 | $C_{31}H_{35}ClN_2O$ | 487/89 (Cl) [M + H]⁺ | 201.5 |

EXAMPLE 6.29

N-(4'-chlorobiphenyl-4-yl)-3-[4-(R)-3-hydroxypyr-rolidin-1-ylmethyl)phenyl]propionamide

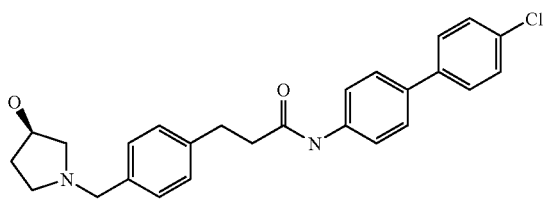

A reaction mixture of 40 mg (0.09 mmol) of 3-[4-((R)-3-hydroxypyrrolidin-1-ylmethyl)phenyl]propynoic acid-(4'-chlorobiphenyl-4-yl)amide and 10 mg of Raney nickel in 10 mL of DMF is hydrogenated for 3 hours at 50 psi and ambient temperature. The catalyst is filtered off and the filtrate is evaporated to dryness. The purification is carried out by column chromatography on silica gel (eluant: dichloromethane/methanol/ammonia (15:1:0.1)). Yield: 20 mg (50% of theory); melting point: 169° C.-170° C.; $C_{26}H_{27}ClN_2O_2$ (M=434.96); calc.: molecular ion peak $(M+H)^+$: 435/37 (Cl); found: molecular ion peak $(M+H)^+$: 435/37 (Cl).

The following compounds are prepared analogously to Example 6.29:

EXAMPLE 6.32

N-(4'-chlorobiphenyl-4-yl)-3-{4-[(methylpyridin-4-ylmethylamino)methyl]phenyl}propionamide

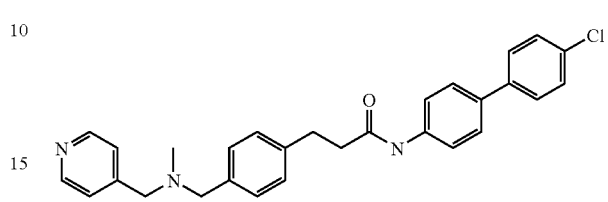

6.32.a. N-(4'-chlorobiphenyl-4-yl)-3-(4-cyanophenyl)propionamide 6 mL (43.04 mmol) of triethylamine and 13.73 g (42.75 mmol) of TBTU are added to a reaction mixture of 7.5 g (42.81 mmol) of 4-cyanophenylpropionic acid in 150 mL of DMF and the mixture is stirred for 30 minutes at RT. Then a further 6 mL (43.04 mmol) of triethylamine and 8.72 g (42.83 mmol) of 4'-chlorobiphenyl-4-ylamine are added and the mixture is stirred for 24 hours at RT. The solution is mixed with plenty of water and the precipitated N-(4'-chlorobiphenyl-4-yl)-3-(4-cyanophenyl)propionamide is suction filtered, washed with water, and finally with diisopropyl ether. The

| Example | $R_1R_2N$—X | educt | empirical formula | mass spectrum | mp [° C.] |
|---|---|---|---|---|---|
| 6.30 | | 1.47 | $C_{31}H_{31}ClN_2O$ | 483/85 (Cl) $[M + H]^+$ | 137-138 |
| 6.31 | | 1.48 | $C_{31}H_{31}ClN_2O$ | 483/85 (Cl) $[M + H]^+$ | 133-136 | yellow solid is dried for 6 hours at 50° C. and 20 mbar in the vacuum drying chamber. Yield: 14.22 g (92% of theory); $C_{22}H_{17}ClN_2O$ (M=360.84); calc.: molecular ion peak $(M+H)^+$: 361/63 (Cl); found: molecular ion peak $(M+H)^+$: 361/63 (Cl); $R_f$ value: 0.5 (silica gel, dichloromethane/ethanol (20:1)).

6.32.b. N-(4'-chlorobiphenyl-4-yl)-3-(4-formylphenyl)propionamide 100 mL of formic acid is added to a reaction mixture of 3 g of Raney nickel moistened with water and 14.22 g (39.41 mmol) of N-(4'-chlorobiphenyl-4-yl)-3-(4-cyanophenyl)propionamide and refluxed for 20 hours. Then the catalyst is suction filtered and the filtrate is diluted with plenty of water. The precipitated N-(4'-chlorobiphenyl-4-yl)-3-(4-formylphenyl)propionamide is suction filtered and dissolved in ethyl acetate. The organic phase is washed first of all with 2 molar sodium hydroxide solution, then with water and finally with saturated sodium chloride solution, dried over sodium sulfate and activated charcoal, and freed from solvent by rotary evaporation. Yield: 11.7 g (57% of theory); $C_{22}H_{18}ClNO_2$ (M=363.84); calc.: molecular ion peak $(M+H)^+$: 364/66 (Cl); found: molecular ion peak $(M+H)^+$: 364/66 (Cl); $R_f$ value: 0.5 (silica gel, cyclohexane/ethyl acetate (1:1)).

6.32.c. N-(4'-chlorobiphenyl-4-yl)-3-(4-hydroxymethylphenyl)propionamide

First 8 mL of glacial acetic acid is added to a reaction solution of 11.7 g (22.51 mmol) of N-(4'-chlorobiphenyl-4-yl)-3-(4-formylphenyl)propionamide in 200 mL of THF and then 15.1 g (67.53 mmol) of sodium triacetoxyborohydride is added and the mixture is stirred for 20 hours at RT. The reaction mixture is poured onto plenty of water and the precipitate formed is suction filtered. This is purified by column chromatography on silica gel (eluant: dichloromethane/acetone (15:1 to 10:1)). Yield: 5.46 g (66% of theory); $C_{22}H_{20}ClNO_2$ (M=365.85); calc.: molecular ion peak $(M+H)^+$: 366/68 (Cl); found: molecular ion peak $(M+H)^+$: 366/68 (Cl); $R_f$ value: 0.35 (silica gel, dichloromethane/acetone (10:1)).

6.32.d. N-(4'-chlorobiphenyl-4-yl)-3-(4-chloromethylphenyl)propionamide 0.43 mL (5.6 mmol) of methanesulfonic acid chloride is slowly added dropwise at ambient temperature to a solution of 2 g (5.47 mmol) of N-(4'-chlorobiphenyl-4-yl)-3-(4-hydroxymethylphenyl)propionamide and 1.56 mL (11.2 mmol) of triethylamine in 50 mL of dichloromethane and the reaction mixture is stirred for 24 hours at ambient temperature. It is extracted with water and the organic phase is dried over sodium sulfate. The solvent is distilled off and the residue is stirred with diisopropyl ether and suction filtered. Yield: 1.45 g (69% of theory); $C_{22}H_{19}Cl_2NO$ (M=384.3); calc.: molecular ion peak $(M+H)^+$: 384/86/88 (Cl2) Found: molecular ion peak $(M+H)^+$: 384/86/88 ($Cl_2$); $R_f$ value: 0.45 (silica gel, dichloromethane/ethanol (50:1)).

6.32.e. N-(4'-chlorobiphenyl-4-yl)-3-{4-[(methylpyridin-4-ylmethylamino)methyl]phenyl}propionamide A reaction mixture of 70 mg (0.18 mmol) of N-(4'-chlorobiphenyl-4-yl)-3-(4-chloromethylphenyl)propionamide, 18 mg (0.15 mmol) of methylpyridin-4-ylmethylamine, and 41 mg (0.3 mmol) of potassium carbonate in 5 mL of acetone is agitated for 24 hours at reflux temperature. The reaction mixture is evaporated down. The residue is triturated with water and diisopropyl ether, suction filtered and dried in the air. Yield: 52 mg (87% of theory); melting point: 102° C.; $C_{29}H_{28}ClN_3O$ (M=470.01); calc.: molecular ion peak $(M+H)^+$: 470/72 (Cl); found: molecular ion peak $(M+H)^+$: 470/72 (Cl).

The following compounds are prepared analogously to Example 6.32.e.:

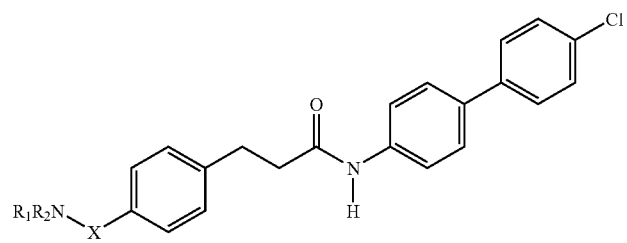

| Example | $R_1R_2N$—X | educt | empirical formula | mass spectrum | mp [° C.] |
|---|---|---|---|---|---|
| 6.33 | (pyridin-3-ylmethyl)(methyl)amino- | 6.32.d | $C_{29}H_{28}ClN_3O$ | 470/72 (Cl) $[M+H]^+$ | 168-169 |
| 6.34 | (pyridin-2-ylmethyl)(methyl)amino- | 6.32.d | $C_{29}H_{28}ClN_3O$ | 470/72 (Cl) $[M+H]^+$ | 144-145 |

-continued

| Example | $R_1R_2N-X$ | educt | empirical formula | mass spectrum | mp [° C.] |
|---|---|---|---|---|---|
| 6.35 | cyclohexyl-N-ethyl-neopentyl | 6.32.d | $C_{30}H_{35}ClN_2O$ | 475/77 (Cl) [M + H]$^+$ | 149-150.5 |
| 6.36 | 4-trifluoromethyl-4-hydroxypiperidinyl-neopentyl | 6.32.d | $C_{28}H_{28}ClF_3N_2O_2$ | 517/19 (Cl) [M + H]$^+$ | 193 |
| 6.37 | cyclopentyl-N-methyl-neopentyl | 6.32.d | $C_{28}H_{31}ClN_2O$ | 447/49 (Cl) [M + H]$^+$ | 182.5-184 |

EXAMPLE 6.38

3-[4-(benzylaminomethyl)phenyl]-N-(4'-chlorobiphenyl-4-yl)propionamide

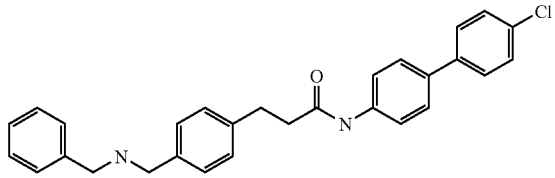

A reaction mixture of 70 mg (0.18 mmol) of N-(4'-chlorobiphenyl-4-yl)-3-(4-chloromethylphenyl)propionamide, 16 mg (0.15 mmol) of benzylamine, and 41 mg (0.3 mmol) of potassium carbonate in 5 mL of acetone is agitated for 24 hours at reflux temperature. The reaction mixture is evaporated down. The residue is triturated with water and diisopropyl ether, suction filtered, and dried in the air. The residue is purified by column chromatography on silica gel (eluant: dichloromethane/ethanol/ammonia (30:1:0.1)). Yield: 23 mg (40% of theory); melting point: 176° C.; $C_{29}H_{27}ClN_2O$ (M=454.99); calc.: molecular ion peak (M+H)$^+$: 455/57 (Cl); found: molecular ion peak (M+H)$^+$: 455/57 (Cl).

The following compounds are prepared analogously to Example 6.38:

| Example | $R_1R_2N-X$ | educt | empirical formula | mass spectrum | mp [° C.] | $R_f$ value |
|---|---|---|---|---|---|---|
| 6.39 | cyclohexyl-N-methyl | 6.32.d | $C_{28}H_{31}ClN_2O$ | 447/49 (Cl) [M + H]$^+$ | 208 | |
| 6.40 | cyclohexyl-N-isopropyl | 6.32.d | $C_{31}H_{37}ClN_2O$ | 489/91 (Cl) [M + H]$^+$ | 165 | |

-continued

| Example | R₁R₂N—X | educt | empirical formula | mass spectrum | mp [° C.] | R_f value |
|---|---|---|---|---|---|---|
| 6.41 | | 6.32.d | $C_{27}H_{29}ClN_2O$ | 432/34 (Cl) [M + H]⁺ | 196-197 | |
| 6.42 | | 6.32.d | $C_{28}H_{33}ClN_2O_2$ | 465/67 (Cl) [M + H]⁺ | 135 | 0.3 (A) |

R_f value: A = (silica gel, dichloromethane/ethanol/ammonia (20:1:0.1))

EXAMPLE 6.43

N-(4'-chlorobiphenyl-4-yl)-3-(4-cyclopropylaminomethylphenyl)propionamide trifluoroacetate

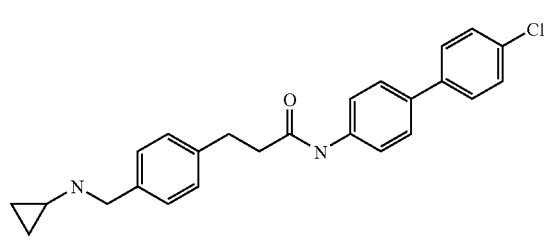

A reaction mixture of 70 mg (0.18 mmol) of N-(4'-chlorobiphenyl-4-yl)-3-(4-chloromethylphenyl)propionamide, 16 mg (0.15 mmol) of cyclopropylamine, and 41 mg (0.3 mmol) of potassium carbonate in 5 mL of acetone is shaken for 24 hours at reflux temperature. The reaction mixture is evaporated down. The residue is triturated with water and diisopropylether, suction filtered, and dried in the air. The residue is purified by column chromatography on silica gel (eluant: dichloromethane/ethanol/ammonia (30:1:0.1) and then by column chromatography on RP-18 (eluant: water+0.1% trifluoroacetic acid/acetonitrile+0.1% trifluoroacetic acid (100:0 to 50:50)). Yield: 24 mg (36% of theory); melting point: 208° C.; $C_{25}H_{25}ClN_2O*C_2HF_3O_2$ (M=518.96); calc.: molecular ion peak (M+H)⁺: 405/07 (Cl); found: molecular ion peak (M+H)⁺: 405/07 (Cl).

The following compound is prepared analogously to Example 6.43:

EXAMPLE 6.45

3-[4-(8-azaspiro[4.5]dec-8-ylmethyl)phenyl]-N-(4'-chlorobiphenyl-4-yl)-N-methylpropionamide

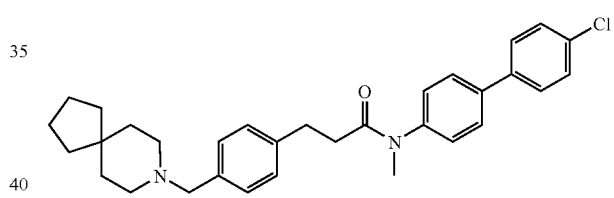

Prepared analogously to Example 6.29 from 3-[4-(8-azaspiro[4.5]dec-8-ylmethyl)phenyl]propynoic acid (4'-chlorobiphenyl-4-yl)methylamide. Yield: 43 mg (86% of theory); melting point: 119° C.; $C_{32}H_{37}ClN_2O$ (M=501.10); calc.: molecular ion peak (M+H)⁺: 501/07(Cl); found: molecular ion peak (M+H)⁺: 501/03 (Cl).

The following compounds are prepared analogously to Example 6.2:

| Example | R₁R₂N—X | educt | empirical formula | mass spectrum | mp [° C.] |
|---|---|---|---|---|---|
| 6.44 | | 6.32.d | $C_{26}H_{26}ClN_3O$ | 432/34 (Cl) [M + H]⁺ | 148-149 |

| Example | R₁R₂N—X | L₁ | L₂ |
|---|---|---|---|
| 6.46 | 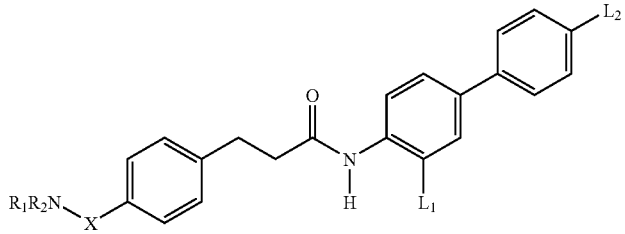 | H | Cl |
| 6.47 | 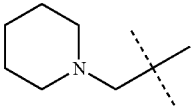 | H | Cl |
| 6.48 | 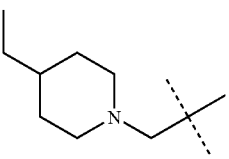 | H | Cl |
| 6.49 | 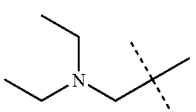 | F | Cl |
| 6.50 | 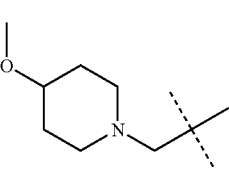 | F | Cl |
| 6.51 | 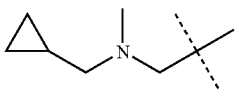 | F | Cl |
| 6.52 | 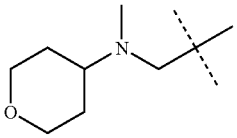 | F | Cl |
| 6.53 | 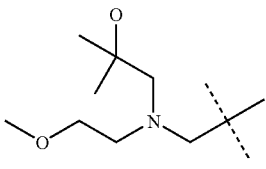 | F | Cl |
| 6.54 | 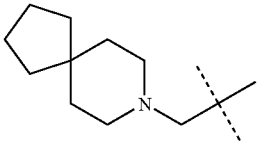 | F | Cl |

-continued

| Example | R₁R₂N—X | L₁ | L₂ |
|---------|---------|----|----|
| 6.55 | N-methyl-N-cyclopropylaminomethyl | F | Cl |
| 6.56 | 4-methylpiperidin-1-ylmethyl | F | Cl |
| 6.57 | 4-ethylpiperidin-1-ylmethyl | F | Cl |
| 6.58 | 3,5-dimethylpiperidin-1-ylmethyl | F | Cl |
| 6.59 | hexahydropyrrolo[1,2-a]pyrazin-2-ylmethyl | F | Cl |
| 6.60 | 3-hydroxypyrrolidin-1-ylmethyl | F | Cl |
| 6.61 | 2-(hydroxymethyl)pyrrolidin-1-ylmethyl | F | Cl |
| 6.62 | 4-carbamoylpiperidin-1-ylmethyl | F | Cl |
| 6.63 | morpholin-4-ylmethyl | F | Cl |

-continued

| Example | R₁R₂N—X | L₁ | L₂ |
|---------|---------|----|----|
| 6.64 | diethylaminomethyl (neopentyl) | F | Cl |
| 6.65 | pyrrolidin-1-ylmethyl (neopentyl) | F | Cl |
| 6.66 | (2-methoxyethyl)(methyl)aminomethyl | F | Cl |
| 6.67 | benzyl(methyl)aminomethyl | F | Cl |
| 6.68 | (2-cyanoethyl)(methyl)aminomethyl | F | Cl |
| 6.69 | ((tetrahydro-2H-pyran-4-yl)methyl)(methyl)aminomethyl | F | Cl |
| 6.70 | (2-phenoxyethyl)(methyl)aminomethyl | F | Cl |
| 6.71 | cyclohexyl(methyl)aminomethyl | F | Cl |
| 6.72 | (2,6-dimethylmorpholin-4-yl)methyl | F | Cl |
| 6.73 | (4-methoxypiperidin-1-yl)methyl | H | CF₃ |

-continued

| Example | R₁R₂N—X | L₁ | L₂ |
|---|---|---|---|
| 6.74 | cyclopropylmethyl(methyl)amino-neopentyl | H | $CF_3$ |
| 6.75 | (tetrahydro-2H-pyran-4-yl)(methyl)amino-neopentyl | H | $CF_3$ |
| 6.76 | (2-methoxyethyl)(2-methoxy-2-methylpropyl)amino-neopentyl | H | $CF_3$ |
| 6.77 | 2-azaspiro[4.5]... (2-azaspiro[4.5]decan-2-yl)neopentyl | H | $CF_3$ |
| 6.78 | piperidin-1-yl-neopentyl | H | $CF_3$ |
| 6.79 | cyclopropyl(methyl)amino-neopentyl | H | $CF_3$ |
| 6.80 | 4-methylpiperidin-1-yl-neopentyl | H | $CF_3$ |
| 6.81 | 4-ethylpiperidin-1-yl-neopentyl | H | $CF_3$ |
| 6.82 | 3,5-dimethylpiperidin-1-yl-neopentyl | H | $CF_3$ |

-continued

| Example | R₁R₂N—X | L₁ | L₂ |
|---|---|---|---|
| 6.83 | (octahydropyrrolo[1,2-a]pyrazin-2-yl)methyl | H | CF₃ |
| 6.84 | (3-hydroxypyrrolidin-1-yl)methyl | H | CF₃ |
| 6.85 | (2-(hydroxymethyl)pyrrolidin-1-yl)methyl | H | CF₃ |
| 6.86 | (4-carbamoylpiperidin-1-yl)methyl | H | CF₃ |
| 6.87 | (morpholin-4-yl)methyl | H | CF₃ |
| 6.88 | (diethylamino)methyl | H | CF₃ |
| 6.89 | (pyrrolidin-1-yl)methyl | H | CF₃ |
| 6.90 | ((2-methoxyethyl)(methyl)amino)methyl | H | CF₃ |
| 6.91 | (benzyl(methyl)amino)methyl | H | CF₃ |
| 6.92 | ((2-cyanoethyl)(methyl)amino)methyl | H | CF₃ |

-continued

| Example | R₁R₂N—X | L₁ | L₂ |
|---|---|---|---|
| 6.93 | (tetrahydropyran-4-ylmethyl)(methyl)N– | H | CF₃ |
| 6.94 | (2-phenoxyethyl)(methyl)N– | H | CF₃ |
| 6.95 | cyclohexyl(methyl)N– | H | CF₃ |
| 6.96 | (2,6-dimethylmorpholin-4-yl)– | H | CF₃ |
| 6.97 | (4-methoxypiperidin-1-yl)– | H | Me |
| 6.98 | (cyclopropylmethyl)(methyl)N– | H | Me |
| 6.99 | (tetrahydropyran-4-yl)(methyl)N– | H | Me |
| 6.100 | (2-methoxyethyl)(2-hydroxy-2-methylpropyl)N– | H | Me |
| 6.101 | 2,8-diazaspiro[4.5]decan-8-yl– | H | Me |

-continued

| Example | R₁R₂N—X | L₁ | L₂ |
|---|---|---|---|
| 6.102 | piperidinyl-CH₂C(CH₃)₂- | H | Me |
| 6.103 | N-methyl-N-cyclopropyl-aminomethyl-C(CH₃)₂- | H | Me |
| 6.104 | 4-methylpiperidinyl-CH₂C(CH₃)₂- | H | Me |
| 6.105 | 4-ethylpiperidinyl-CH₂C(CH₃)₂- | H | Me |
| 6.106 | 3,5-dimethylpiperidinyl-CH₂C(CH₃)₂- | H | Me |
| 6.107 | octahydropyrrolo[1,2-a]pyrazin-2-yl-CH₂C(CH₃)₂- | H | Me |
| 6.108 | 3-hydroxypyrrolidin-1-yl-CH₂C(CH₃)₂- | H | Me |
| 6.109 | 2-(hydroxymethyl)pyrrolidin-1-yl-CH₂C(CH₃)₂- | H | Me |
| 6.110 | 4-carbamoylpiperidin-1-yl-CH₂C(CH₃)₂- | H | Me |

-continued
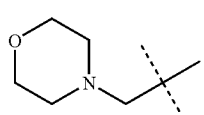
| Example | R₁R₂N—X | L₁ | L₂ |
| --- | --- | --- | --- |
| 6.111 | 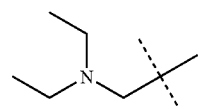 | H | Me |
| 6.112 | 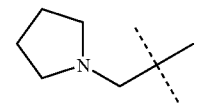 | H | Me |
| 6.113 | 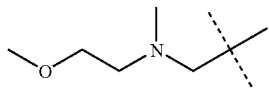 | H | Me |
| 6.114 | 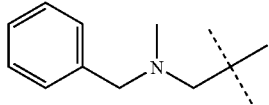 | H | Me |
| 6.115 | 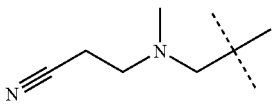 | H | Me |
| 6.116 | 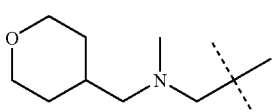 | H | Me |
| 6.117 | 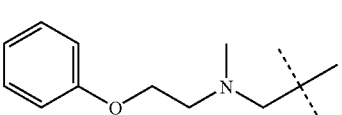 | H | Me |
| 6.118 | 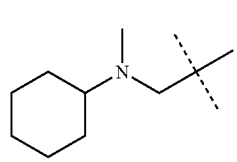 | H | Me |
| 6.119 | 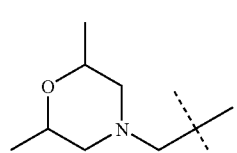 | H | Me |
| 6.120 | | H | Me |

-continued

| Example | R₁R₂N—X | L₁ | L₂ |
|---|---|---|---|
| 6.121 | 4-methoxypiperidin-1-yl-CH₂-C(CH₃)₂- | H | F |
| 6.122 | (cyclopropylmethyl)(methyl)N-CH₂-C(CH₃)₂- | H | F |
| 6.123 | (tetrahydro-2H-pyran-4-yl)(methyl)N-CH₂-C(CH₃)₂- | H | F |
| 6.124 | (2,2-dimethyl-3-methoxypropyl)(2-methoxyethyl)N-CH₂-C(CH₃)₂- | H | F |
| 6.125 | 2-azaspiro[4.5]dec... (spiro piperidine)-N-CH₂-C(CH₃)₂- | H | F |
| 6.126 | piperidin-1-yl-CH₂-C(CH₃)₂- | H | F |
| 6.127 | cyclopropyl(methyl)N-CH₂-C(CH₃)₂- | H | F |
| 6.128 | 4-methylpiperidin-1-yl-CH₂-C(CH₃)₂- | H | F |
| 6.129 | 4-ethylpiperidin-1-yl-CH₂-C(CH₃)₂- | H | F |

-continued
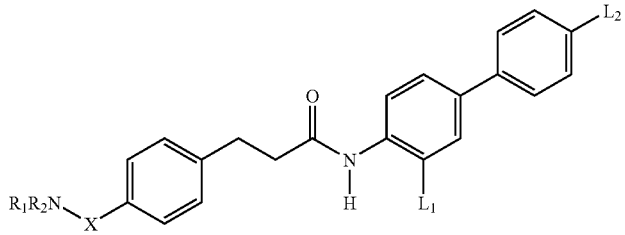
| Example | R₁R₂N—X | L₁ | L₂ |
|---|---|---|---|
| 6.130 | 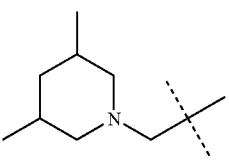 | H | F |
| 6.131 | 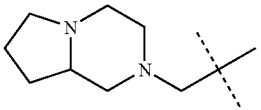 | H | F |
| 6.132 | 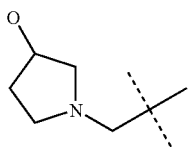 | H | F |
| 6.133 | 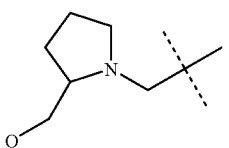 | H | F |
| 6.134 | 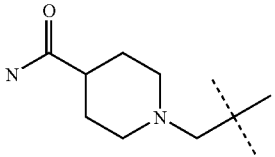 | H | F |
| 6.135 | 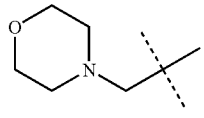 | H | F |
| 6.136 | 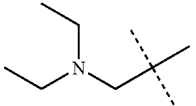 | H | F |
| 6.137 | 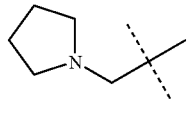 | H | F |
| 6.138 | 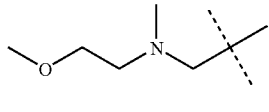 | H | F |

-continued
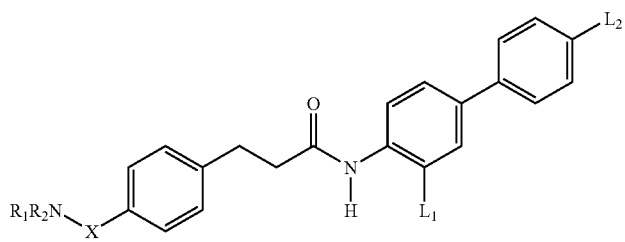
| Example | R₁R₂N—X | L₁ | L₂ |
|---|---|---|---|
| 6.139 | N-benzyl-N-methyl | H | F |
| 6.140 | N-(2-cyanoethyl)-N-methyl | H | F |
| 6.141 | N-methyl-N-((tetrahydropyran-4-yl)methyl) | H | F |
| 6.142 | N-methyl-N-(2-phenoxyethyl) | H | F |
| 6.143 | N-cyclohexyl-N-methyl | H | F |
| 6.144 | 2,6-dimethylmorpholin-4-yl | H | F |
| 6.145 | 4-methoxypiperidin-1-yl | F | CF₃ |
| 6.146 | N-(cyclopropylmethyl)-N-methyl | F | CF₃ |
| 6.147 | N-methyl-N-(tetrahydropyran-4-yl) | F | CF₃ |

-continued

| Example | R₁R₂N—X | L₁ | L₂ |
|---|---|---|---|
| 6.148 | (2-methoxyethyl)(2-methoxy-2-methylpropyl)amino-CH₂C(CH₃)₂- | F | CF₃ |
| 6.149 | 2,8-diazaspiro[4.5]decan-8-yl-CH₂C(CH₃)₂- (8-azaspiro[4.5]) | F | CF₃ |
| 6.150 | piperidin-1-yl-CH₂C(CH₃)₂- | F | CF₃ |
| 6.151 | N-cyclopropyl-N-methylamino-CH₂C(CH₃)₂- | F | CF₃ |
| 6.152 | 4-methylpiperidin-1-yl-CH₂C(CH₃)₂- | F | CF₃ |
| 6.153 | 4-ethylpiperidin-1-yl-CH₂C(CH₃)₂- | F | CF₃ |
| 6.154 | 3,5-dimethylpiperidin-1-yl-CH₂C(CH₃)₂- | F | CF₃ |
| 6.155 | octahydropyrrolo[1,2-a]pyrazin-2-yl-CH₂C(CH₃)₂- | F | CF₃ |
| 6.156 | 3-hydroxypyrrolidin-1-yl-CH₂C(CH₃)₂- | F | CF₃ |

-continued

| Example | R₁R₂N—X | L₁ | L₂ |
|---|---|---|---|
| 6.157 | (2-(hydroxymethyl)pyrrolidin-1-yl)methyl | F | CF₃ |
| 6.158 | 1-methylpiperidine-4-carboxamide | F | CF₃ |
| 6.159 | morpholinomethyl | F | CF₃ |
| 6.160 | N,N-diethylaminomethyl | F | CF₃ |
| 6.161 | pyrrolidin-1-ylmethyl | F | CF₃ |
| 6.162 | N-(2-methoxyethyl)-N-methylaminomethyl | F | CF₃ |
| 6.163 | N-benzyl-N-methylaminomethyl | F | CF₃ |
| 6.164 | N-(2-cyanoethyl)-N-methylaminomethyl | F | CF₃ |
| 6.165 | N-methyl-N-((tetrahydro-2H-pyran-3-yl)methyl)aminomethyl | F | CF₃ |
| 6.166 | N-methyl-N-(2-phenoxyethyl)aminomethyl | F | CF₃ |

-continued

| Example | R₁R₂N—X | L₁ | L₂ |
|---|---|---|---|
| 6.167 | cyclohexyl(methyl)amino-neopentyl | F | CF₃ |
| 6.168 | 2,6-dimethylmorpholino-neopentyl | F | CF₃ |
| 6.169 | 4-methoxypiperidin-1-yl-neopentyl | F | Me |
| 6.170 | (cyclopropylmethyl)(methyl)amino-neopentyl | F | Me |
| 6.171 | methyl(tetrahydro-2H-pyran-4-yl)amino-neopentyl | F | Me |
| 6.172 | (2-methoxyethyl)(2-methoxy-2-methylpropyl)amino-neopentyl | F | Me |
| 6.173 | 2-azaspiro[4.5]decan-2-yl-neopentyl | F | Me |
| 6.174 | piperidin-1-yl-neopentyl | F | Me |
| 6.175 | cyclopropyl(methyl)amino-neopentyl | F | Me |

-continued
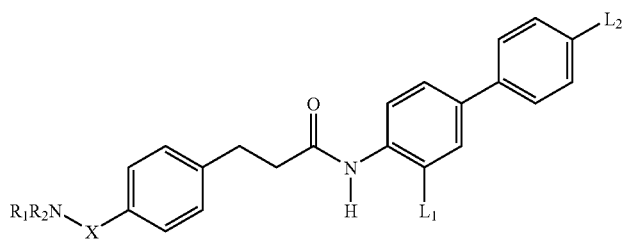
| Example | R₁R₂N—X | L₁ | L₂ |
|---|---|---|---|
| 6.176 | 4-methylpiperidinyl-CH₂- | F | Me |
| 6.177 | 4-ethylpiperidinyl-CH₂- | F | Me |
| 6.178 | 3,5-dimethylpiperidinyl-CH₂- | F | Me |
| 6.179 | octahydropyrrolo[1,2-a]pyrazinyl-CH₂- | F | Me |
| 6.180 | 3-hydroxypyrrolidinyl-CH₂- | F | Me |
| 6.181 | 2-(hydroxymethyl)pyrrolidinyl-CH₂- | F | Me |
| 6.182 | 4-carbamoylpiperidinyl-CH₂- | F | Me |
| 6.183 | morpholinyl-CH₂- | F | Me |
| 6.184 | Et₂N-CH₂- | F | Me |

-continued

| Example | R₁R₂N—X | L₁ | L₂ |
|---|---|---|---|
| 6.185 | pyrrolidin-1-ylmethyl | F | Me |
| 6.186 | N-(2-methoxyethyl)-N-methylaminomethyl | F | Me |
| 6.187 | N-benzyl-N-methylaminomethyl | F | Me |
| 6.188 | N-(2-cyanoethyl)-N-methylaminomethyl | F | Me |
| 6.189 | N-methyl-N-((tetrahydro-2H-pyran-4-yl)methyl)aminomethyl | F | Me |
| 6.190 | N-methyl-N-(2-phenoxyethyl)aminomethyl | F | Me |
| 6.191 | N-cyclohexyl-N-methylaminomethyl | F | Me |
| 6.192 | (2,6-dimethylmorpholin-4-yl)methyl | F | Me |
| 6.193 | (4-methoxypiperidin-1-yl)methyl | F | F |
| 6.194 | N-(cyclopropylmethyl)-N-methylaminomethyl | F | F |

-continued

| Example | R₁R₂N—X | L₁ | L₂ |
|---|---|---|---|
| 6.195 | (N-methyl-N-(tetrahydropyran-4-yl)amino)methyl | F | F |
| 6.196 | (N-(2-methoxyethyl)-N-(2-hydroxy-2-methylpropyl)amino)methyl | F | F |
| 6.197 | 2,8-diazaspiro[4.5]decan-8-ylmethyl | F | F |
| 6.198 | piperidin-1-ylmethyl | F | F |
| 6.199 | (N-cyclopropyl-N-methylamino)methyl | F | F |
| 6.200 | 4-methylpiperidin-1-ylmethyl | F | F |
| 6.201 | 4-ethylpiperidin-1-ylmethyl | F | F |
| 6.202 | 3,5-dimethylpiperidin-1-ylmethyl | F | F |
| 6.203 | octahydropyrrolo[1,2-a]pyrazin-2-ylmethyl | F | F |

-continued
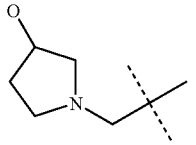
| Example | R₁R₂N—X | L₁ | L₂ |
| --- | --- | --- | --- |
| 6.204 | 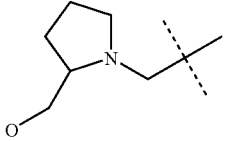 | F | F |
| 6.205 | 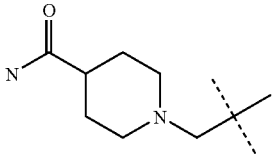 | F | F |
| 6.206 | 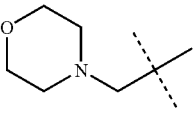 | F | F |
| 6.207 | 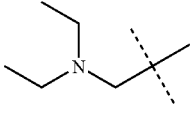 | F | F |
| 6.208 | 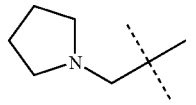 | F | F |
| 6.209 | 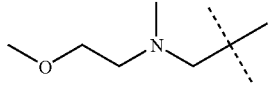 | F | F |
| 6.210 | 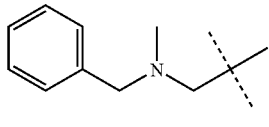 | F | F |
| 6.211 | 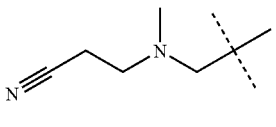 | F | F |
| 6.212 | 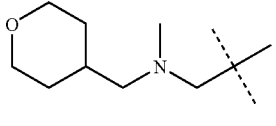 | F | F |
| 6.213 | | F | F |

-continued

| Example | R₁R₂N—X | L₁ | L₂ |
|---|---|---|---|
| 6.214 | (phenoxyethyl)(methyl)amino-CH₂- | F | F |
| 6.215 | (cyclohexyl)(methyl)amino-CH₂- | F | F |
| 6.216 | (2,6-dimethylmorpholin-4-yl)-CH₂- | F | F |

EXAMPLE 6.217

2-(4-morpholin-4-ylmethylphenyl)cyclopropanecarboxylic acid (4'-chlorobiphenyl-4-yl)amide

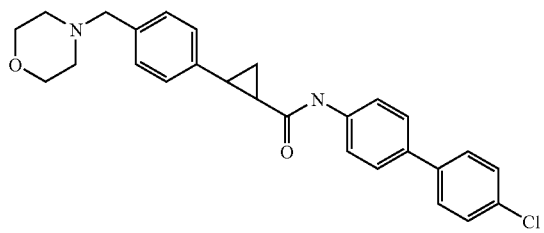

Preparation of diazomethane: 0.15 g (1.48 mmol) of N-nitroso-N-methylurea is added with manual shaking to 10 mL of diethyl ether, over a lower layer of 3 mL of 40% potassium hydroxide solution, at 5° C. to 0° C. The reaction mixture is left to stand for 10 minutes and then the yellow ether solution is decanted off and dried over potassium hydroxide.

The yellow diazomethane solution prepared is slowly added dropwise at 0° C. to a suspension of 80 mg (0.19 mmol) of (E)-N-(4'-chlorobiphenyl-4-yl)-3-(4-morpholin-4-ylmethylphenyl)-acrylamide (for preparation see 6.4) and 202 mg (0.001 mmol) of palladium (II) acetate in 20 mL of diethyl ether. The dark reaction mixture is stirred for 30 minutes. Then the reaction mixture is mixed twice with double the amount of a diazomethane solution. After the reaction has ended, 10 mL of glacial acetic acid is added dropwise to the suspension and extracted several times with a sodium hydrogen carbonate solution. The organic phase is dried over sodium sulfate, the desiccant is filtered off, and the filtrate is evaporated down. Further purification is carried out by column chromatography on silica gel (eluant: dichloromethane/ethanol/ammonia (30:1:0.1)). Yield: 32 mg (82.6% of theory); $C_{27}H_{27}ClN_2O_2$ (M=446.97); melting point: 187° C.-188° C.; calc.: molecular ion peak (M+H)⁺: 447/449 (Cl); found: molecular ion peak (M+H)⁺: 447/449 (Cl); $R_f$ value: 0.3 (silica gel, dichloromethane/ethanol/ammonia (20:1:0.1)).

EXAMPLE 7.1

3-(2-chloro-4-trifluoromethylphenyl)propynoic acid-(2-piperidin-1-ylquinolin-6-yl)amide

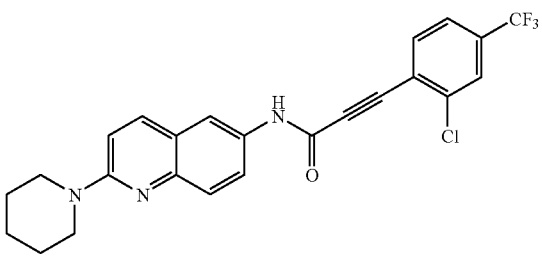

7.1.a. 6-amino-2-piperidin-2-yl-quinoline

Prepared analogously to Example 3.1.b. from 6-nitro-2-piperidin-2-yl-quinoline. Yield: 0.79 g (59.6% of theory); $C_{14}H_{17}N_3$ (M=227.31); calc.: molecular ion peak (M+H)⁺: 228; found: molecular ion peak (M+H)⁺: 228; $R_f$ value: 0.37 (silica gel, dichloromethane/methanol (19:1)).

7.1.b. 3-(2-chloro-4-trifluoromethylphenyl)propynoic acid-(2-piperidin-1-yl-quinolin-6-yl)amide Prepared analogously to Example 2.3.f. from (2-chloro-4-trifluoromethylphenyl)propynoic acid and 6-amino-2-piperidin-2-ylquinoline. Yield: 170 mg (37.1% of theory); melting point: 176° C.-179° C.; $C_{24}H_{19}ClF_3N_3O$ (M=457.88); calc.: molecular ion peak (M+H)$^+$: 456/458; found: molecular ion peak (M+H)$^+$: 456/458; $R_f$ value: 0.62 (silica gel, dichloromethane/methanol (19:1)).

EXAMPLE 7.2

3-(2-chloro-4-trifluoromethylphenyl)propynoic acid-(2-isopropylaminoquinolin-6-yl)amide

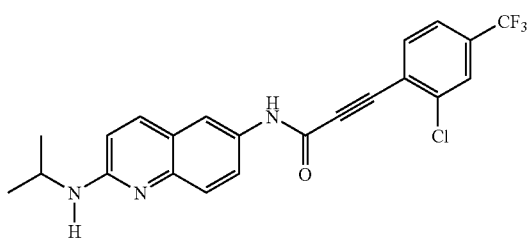

7.2.a. isopropyl(6-nitroquinolin-2-yl)amine 2.55 mL (29.96 mmol) of isopropylamine is added to a solution of 1.25 g (5.99 mmol) of 2-chloro-6-nitroquinoline in 50 mL of ethanol and the mixture is stirred for 18 hours at ambient temperature. Then the reaction mixture is heated to 65° C. in the microwave for 2 hours. The reaction mixture is then evaporated down, the residue is taken up in 20 mL of DMF, combined with 2.55 mL (29.96 mmol) of isopropylamine, and stirred for 18 hours at ambient temperature. The reaction mixture is evaporated down and the residue is combined with ethyl acetate and water. The organic phase is extracted twice with water. The aqueous phases are extracted twice with ethyl acetate. The combined organic phases are dried over sodium sulfate and the solvent is then removed. Yield: 0.75 g (54.1% of theory); $C_{12}H_{13}N_3O_2$ (M=221.25); calc.: molecular ion peak (M+H)$^+$: 232; found: molecular ion peak (M+H)$^+$: 232; $R_f$ value: 0.48 (silica gel, petroleum ether/ethyl acetate (2:1)).

7.2.b. $N^2$-isopropyl-quinoline-2,6-diamine

Prepared analogously to Example 3.1.b. from isopropyl-(6-nitroquinolin-2-yl)amine. Yield: 0.51 g (78.1% of theory); $C_{12}H_{15}N_3$ (M=201.27); calc.: molecular ion peak (M+H)$^+$: 202; found: molecular ion peak (M+H)$^+$: 202; $R_f$ value: 0.25 (silica gel, dichloromethane/methanol (19:1)).

7.2.c. 3-(2-chloro-4-trifluoromethylphenyl)propynoic acid-(2-isopropylaminoquinolin-6-yl)amide Prepared analogously to Example 2.3.f. from (2-chloro-4-trifluoromethylphenyl)propynoic acid and $N^2$-isopropyl-quinoline-2,6-diamine. Yield: 140 mg (46.3% of theory); melting point: 57° C.-60° C.; $C_{22}H_{17}ClF_3N_3O$ (M=431.84); calc.: molecular ion peak (M+H)$^+$: 432/434; found: molecular ion peak (M+H)$^+$: 432/434; $R_f$ value: 0.49 (silica gel, petroleum ether/ethyl acetate (2:1)).

The following compounds are prepared analogously to Example 7.1:

| Example | R₁R₂N—X— | L₁ | L₂ | L₃ |
|---|---|---|---|---|
| 7.3 | (dimethylamino) | —Cl | —CF₃ | —H |
| 7.4 | (4-methylpiperidin-1-yl) | —Cl | —CF₃ | —H |
| 7.5 | (diethylamino) | —Cl | —CF₃ | —H |

-continued
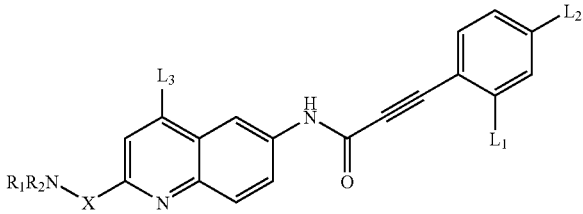
| Example | R₁R₂N—X— | L₁ | L₂ | L₃ |
|---|---|---|---|---|
| 7.6 | 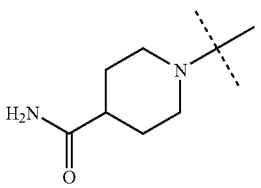 | —Cl | —CF₃ | —H |
| 7.7 | 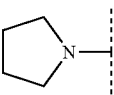 | —Cl | —CF₃ | —H |
| 7.8 | 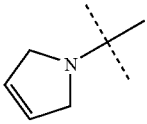 | —Cl | —CF₃ | —H |
| 7.9 | 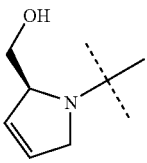 | —Cl | —CF₃ | —H |
| 7.10 | 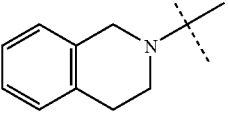 | —Cl | —CF₃ | —H |
| 7.11 | 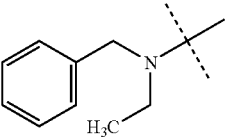 | —Cl | —CF₃ | —H |
| 7.12 | 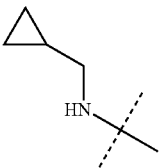 | —Cl | —CF₃ | —H |
| 7.13 | 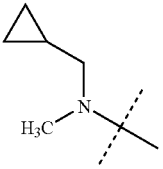 | —Cl | —CF₃ | —H |

-continued

[Structure: quinoline core with R₁R₂N-X- at position 2, L₃ at position 4, and at position 6 an NH-C(O)-C≡C-phenyl group where the phenyl bears L₂ (para) and L₁ (ortho)]

| Example | R₁R₂N—X— | L₁ | L₂ | L₃ |
| --- | --- | --- | --- | --- |
| 7.14 | N-(cyclopropylmethyl)(n-propyl)amino, attached via C(CH₃)₂ | —Cl | —CF₃ | —H |
| 7.15 | N-(cyclopropylmethyl)(cyclopentyl)amino, attached via C(CH₃)₂ | —Cl | —CF₃ | —H |
| 7.16 | N,N-bis(cyclopropylmethyl)amino, attached via C(CH₃)₂ | —Cl | —CF₃ | —H |
| 7.17 | isobutylamino (HN-CH₂-CH(CH₃)₂), attached via C(CH₃)₂ | —Cl | —CF₃ | —H |
| 7.18 | 4-carbamoylpiperidin-1-yl, attached via C(CH₃)₂ | —Cl | —CF₃ | —H |
| 7.19 | ethylamino (Me-CH₂-NH-), attached via C(CH₃)₂ | —Cl | —CF₃ | —H |
| 7.20 | methylamino (Me-NH-), attached via C(CH₃)₂ | —Cl | —CF₃ | —H |

-continued
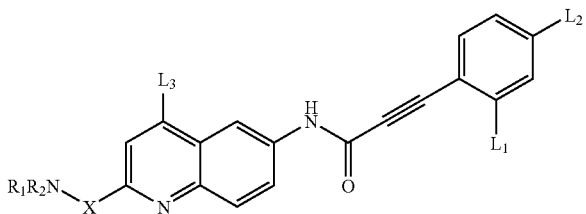
| Example | R₁R₂N—X— | L₁ | L₂ | L₃ |
|---|---|---|---|---|
| 7.21 | cyclopentyl-NH- | —Cl | —CF₃ | —H |
| 7.22 | cyclopentyl-N(Me)- | —Cl | —CF₃ | —H |
| 7.23 | 4-methylpiperidin-1-yl | —Cl | —CF₃ | —H |
| 7.24 | Me₂N- | —Cl | —CF₃ | -Me |
| 7.25 | 4-methylpiperidin-1-yl | —Cl | —CF₃ | -Me |
| 7.26 | Et₂N- | —Cl | —CF₃ | -Me |
| 7.27 | 4-carbamoylpiperidin-1-yl | —Cl | —CF₃ | -Me |
| 7.28 | pyrrolidin-1-yl | —Cl | —CF₃ | -Me |

-continued

| Example | R₁R₂N—X— | L₁ | L₂ | L₃ |
|---|---|---|---|---|
| 7.29 | 2,5-dihydropyrrol-1-yl | —Cl | —CF₃ | -Me |
| 7.30 | (2-hydroxymethyl-2,5-dihydropyrrol-1-yl) | —Cl | —CF₃ | -Me |
| 7.31 | 1,2,3,4-tetrahydroisoquinolin-2-yl | —Cl | —CF₃ | -Me |
| 7.32 | N-benzyl-N-ethylamino | —Cl | —CF₃ | -Me |
| 7.33 | (cyclopropylmethyl)amino | —Cl | —CF₃ | -Me |
| 7.34 | N-(cyclopropylmethyl)-N-methylamino | —Cl | —CF₃ | -Me |
| 7.35 | N-(cyclopropylmethyl)-N-propylamino | —Cl | —CF₃ | -Me |
| 7.36 | N-(cyclopropylmethyl)-N-cyclopentylamino | —Cl | —CF₃ | -Me |

-continued

| Example | R₁R₂N—X— | L₁ | L₂ | L₃ |
| --- | --- | --- | --- | --- |
| 7.37 | bis(cyclopropylmethyl)amino group | —Cl | —CF₃ | -Me |
| 7.38 | isobutylamino group | —Cl | —CF₃ | -Me |
| 7.39 | 4-carbamoylpiperidin-1-yl group | —Cl | —CF₃ | -Me |
| 7.19 | ethylamino group | —Cl | —CF₃ | -Me |
| 7.20 | methylamino group | —Cl | —CF₃ | -Me |
| 7.21 | cyclopentylamino group | —Cl | —CF₃ | -Me |
| 7.21 | N-methyl-N-cyclopentylamino group | —Cl | —CF₃ | -Me |

-continued

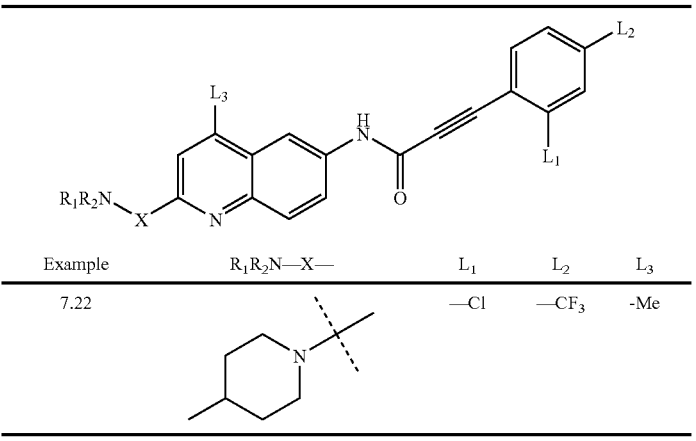

| Example | $R_1R_2N$—X— | $L_1$ | $L_2$ | $L_3$ |
|---|---|---|---|---|
| 7.22 | (4-methylpiperidin-1-yl) | —Cl | —$CF_3$ | -Me |

Some test methods for determining an MCH-receptor antagonistic activity will now be described. In addition, other test methods known to the skilled man may be used, e.g., by inhibiting the MCH-receptor-mediated inhibition of cAMP production, as described in M. Hoogduijn, et al., *Melanin-concentrating hormone and its receptor are expressed and functional in human skin*, Biochem. Biophys. Res Commun. 296 (2002) 698-701 and by biosensory measurement of the binding of MCH to the MCH receptor in the presence of antagonistic substances by plasmon resonance, as described in O. P. Karlsson and S. Lofas, *Flow-Mediated On-Surface Reconstitution of G-Protein Coupled Receptors for Applications in Surface Plasmon Resonance Biosensors*, Anal. Biochem. 300 (2002), 132-138. Other methods of testing antagonistic activity to MCH receptors are contained in the references and patent documents mentioned hereinbefore, and the description of the test methods used is hereby incorporated in this application.

MCH-1 Receptor Binding Test
  Method: MCH binding to hMCH-1R transfected cells
  Species: Human
  Test cell: hMCH-1R stably transfected into CHO/Galpha16 cells
    Results: $IC_{50}$ values Membranes from CHO/Galpha16 cells stably transfected with human hMCH-1R are resuspended using a syringe (needle 0.6×25 mm) and diluted in test buffer (50 mM HEPES, 10 mM $MgCl_2$, 2 mM EGTA, pH 7.00; 0.1% bovine serum albumin (protease-free), 0.021% bacitracin, 1 μg/mL aprotinin, 1 μg/mL leupeptin and 1 μM phosphoramidone) to a concentration of 5 to 15 μg/mL. 200 L of this membrane fraction (contains 1 to 3/g of protein) are incubated for 60 minutes at ambient temperature with 100 pM of $^{125}I$-tyrosyl melanin concentrating hormone ($^{125}I$-MCH commercially obtainable from NEN) and increasing concentrations of the test compound in a final volume of 250 μL. After the incubation the reaction is filtered using a cell harvester through 0.5% PEI treated fiberglass filters (GF/B, Unifilter Packard). The membrane-bound radioactivity retained on the filter is then determined after the addition of scintillator substance (Packard Microscint 20) in a measuring device (TopCount of Packard). The non-specific binding is defined as bound radioactivity in the presence of 1 micromolar MCH during the incubation period. The analysis of the concentration binding curve is carried out on the assumption of one receptor binding site. Standard: Non-labeled MCH competes with labeled $^{125}I$-MCH for the receptor binding with an IC50 value of between 0.06 and 0.15 nM. The KD value of the radioligand is 0.156 nM.

MCH-1 Receptor-Coupled $Ca^{2+}$ Mobilization Test
  Method: Calcium mobilization test with human MCH (FLIPR$^{384}$)
  Species: Human
  Test cells: CHO/Galpha 16 cells stably transfected with hMCH-$R^1$
  Results: 1st measurement: % stimulation of the reference (MCH $10^{-6}M$); 2nd measurement: pKB value

| Reagents: | HBSS (10x) | (GIBCO) |
|---|---|---|
| | HEPES buffer (1 M) | (GIBCO) |
| | Pluronic F-127 | (Molecular Probes) |
| | Fluo-4 | (Molecular Probes) |
| | Probenecid | (Sigma) |
| | MCH | (Bachem) |
| | bovine serum albumin (protease-free) | (Serva) |
| | DMSO | (Serva) |
| | Ham's F12 | (BioWhittaker) |
| | FCS | (BioWhittaker) |
| | L-Glutamine | (GIBCO) |
| | Hygromycin B | (GIBCO) |
| | PENStrep | (BioWhittaker) |
| | Zeocin | (Invitrogen) |

Clonal CHO/Galpha16 hMCH-$R^1$ cells are cultivated in Ham's F12 cell culture medium (with L-glutamine; BioWhittaker; Cat. No.: BE12-615F). This contains per 500 mL: 10% FCS, 1% PENStrep, 5 mL of L-glutamine (200 mM stock solution), 3 mL of hygromycin B (50 mg/mL in PBS), and 1.25 mL of zeocin (100 μg/mL stock solution). One day before the experiment the cells are plated on a 384-well microtiter plate (black-walled with a transparent base, made by Costar) in a density of 2500 cells per cavity and cultivated in the above medium overnight at 37° C., 5% $CO_2$, and 95% relative humidity. On the day of the experiment, the cells are incubated with cell culture medium to which 2 mM Fluo-4 and 4.6 mM Probenicid have been added, at 37° C. for 45 minutes. After charging with fluorescent dye, the cells are washed four times with Hanks buffer solution (1×HBSS, 20 mM HEPES), which has been combined with 0.07% Probenicid. The test substances are diluted in Hanks buffer solution, combined with 2.5% DMSO. The background fluorescence of non-stimulated cells is measured in the presence of substance in the 384-well microtiter plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular $Ca^{2+}$ mobilization is measured as the peak of the relative fluorescence minus the background and is expressed as the percentage of the maximum signal of the reference (MCH $10^{-6}$M). This measurement serves to identify any possible agonistic effect of a test substance.

2nd measurement: The cellular $Ca^{2+}$ mobilization is measured as the peak of the relative fluorescence minus the background and is expressed as the percentage of the maximum signal of the reference (MCH $10^{-6}$M, signal is standardized to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)} - 1) - \log C_{(testsubstance)}$$

The compounds according to the invention, including their salts, exhibit an MCH-receptor antagonistic activity in the tests mentioned above. Using the MCH-1 receptor binding test described above an antagonistic activity is obtained in a dosage range from about $10^{-10}$ to $10^{-5}$ M, particularly from $10^{-9}$ to $10^{-6}$ M.

The following $IC_{50}$ values were determined using the MCH-1 receptor binding test described above:

| Compound according to Example No. | Structure | $IC_{50}$ value |
|---|---|---|
| 1.23 | 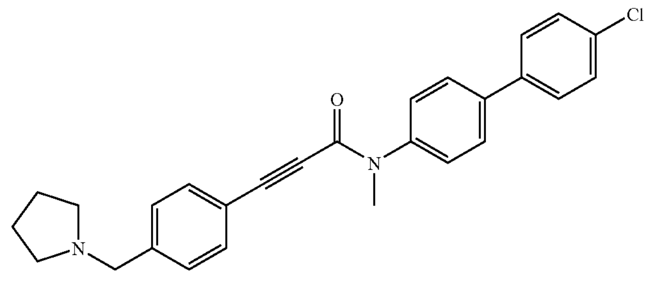 | 7.5 nM |
| 5.1 | 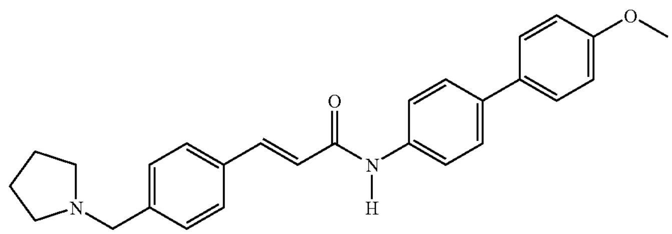 | 20 nM |
| 4.8 | 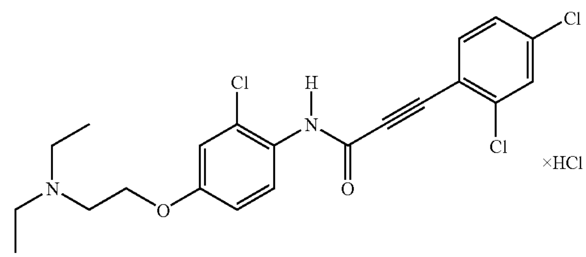 | 50 nM |

Some examples of formulations will be described hereinafter, wherein the term "active substance" denotes one or more compounds according to the invention, including their salts. In the case of one of the combinations with one or more active substances described, the term "active substance" also includes the additional active substances.

EXAMPLE A

Capsules for Powder Inhalation Containing 1 mg Active Substance

Composition:

| Composition: 1 capsule for powder inhalation contains: | |
|---|---|
| active substance | 1.0 mg |
| lactose | 20.0 mg |
| hard gelatine capsules | 50.0 mg |
| | 71.0 mg |

Preparation: The active substance is ground to the particle size required for inhalation. The ground active substance is homogeneously mixed with the lactose. The mixture is packed into hard gelatine capsules.

EXAMPLE B

Inhalable Solution for Respimat® Containing 1 mg Active Substance

| Composition: 1 spray contains: | |
| --- | --- |
| active substance | 1.0 mg |
| benzalkonium chloride | 0.002 mg |
| disodium edetate | 0.0075 mg |
| purified water | to 15.0 μL |

Preparation: The active substance and benzalkonium chloride are dissolved in water and packed into Respimat® cartridges.

EXAMPLE C

Inhalable Solution for Nebulizer Containing 1 mg Active Substance

| Composition: 1 vial contains: | |
| --- | --- |
| active substance | 0.1 g |
| sodium chloride | 0.18 g |
| benzalkonium chloride | 0.002 g |
| purified water | to 20.0 mL |

Preparation: The active substance, sodium chloride, and benzalkonium chloride are dissolved in water.

EXAMPLE D

Propellant Type Metered Dose Aerosol Containing 1 mg Active Substance

| Composition: 1 spray contains: | |
| --- | --- |
| active substance | 1.0 mg |
| lecithin | 0.1% |
| propellant gas | to 50.0 μL |

Preparation: The micronized active substance is homogeneously suspended in the mixture of lecithin and propellant gas. The suspension is transferred into a pressurised container with a metering valve.

EXAMPLE E

Nasal Spray Containing 1 mg Active Substance

| Composition: | |
| --- | --- |
| active substance | 1.0 mg |
| sodium chloride | 0.9 mg |
| benzalkonium chloride | 0.025 mg |
| disodium edetate | 0.05 mg |
| purified water | to 0.1 mL |

Preparation: The active substance and the excipients are dissolved in water and transferred into a corresponding container.

EXAMPLE F

Injectable Solution Containing 5 Mg of Active Substance Per 5 mL

| Composition: | |
| --- | --- |
| active substance | 5 mg |
| glucose | 250 mg |
| human serum albumin | 10 mg |
| glycofurol | 250 mg |
| water for injections | to 5 mL |

Preparation: Glycofurol and glucose are dissolved in water for injections (WfI); human serum albumin is added; active ingredient is dissolved with heating; made up to specified volume with WfI; transferred into ampoules under nitrogen gas.

EXAMPLE G

Injectable Solution Containing 100 Mg of Active Substance Per 20 mL

| Composition: | |
| --- | --- |
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections | to 20 mL |

Preparation: Polysorbate 80, sodium chloride, monopotassium dihydrogen phosphate, and disodium hydrogen phosphate are dissolved in water for injections (WfI); human serum albumin is added; active ingredient is dissolved with heating; made up to specified volume with WfI; transferred into ampoules.

EXAMPLE H

Lyophilisate Containing 10 mg of Active Substance

| Composition: | |
| --- | --- |
| Active substance | 10 mg |
| Mannitol | 300 mg |
| human serum albumin | 20 mg |

Preparation: Mannitol is dissolved in water for injections (WfI); human serum albumin is added; active ingredient is dissolved with heating; made up to specified volume with WfI; transferred into vials; freeze-dried.

| Solvent for lyophilisate: | |
|---|---|
| Polysorbate 80 = Tween 80 | 20 mg |
| mannitol | 200 mg |
| water for injections | to 10 mL |

Preparation: Polysorbate 80 and mannitol are dissolved in water for injections (WfI); transferred into ampoules.

EXAMPLE I

Tablets Containing 20 mg of Active Substance

| Composition: | |
|---|---|
| active substance | 20 mg |
| lactose | 120 mg |
| maize starch | 40 mg |
| magnesium stearate | 2 mg |
| Povidone K 25 | 18 mg |

Preparation: Active substance, lactose, and maize starch are homogeneously mixed; granulated with an aqueous solution of povidone; mixed with magnesium stearate; compressed in a tablet press; weight of tablet: 200 mg.

EXAMPLE J

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation: Active substance, maize starch, and silica are homogeneously mixed; mixed with magnesium stearate; the mixture is packed into size 3 hard gelatine capsules in a capsule filling machine.

EXAMPLE K

Suppositories Containing 50 mg of Active Substance

| Composition: | |
|---|---|
| active substance | 50 mg |
| hard fat (Adeps solidus) | q.s. ad 1700 mg |

Preparation: Hard fat is melted at about 38° C.; ground active substance is homogeneously dispersed in the molten hard fat; after cooling to about 35° C. it is poured into chilled moulds.

EXAMPLE L

Injectable Solution Containing 10 mg of Active Substance Per 1 mL

| Composition: | |
|---|---|
| active substance | 10 mg |
| mannitol | 50 mg |
| human serum albumin | 10 mg |
| water for injections | to 1 mL |

Preparation: Mannitol is dissolved in water for injections (WfI); human serum albumin is added; active ingredient is dissolved with heating; made up to specified volume with WfI; transferred into ampoules under nitrogen gas.

We claim:

1. A compound of formula I

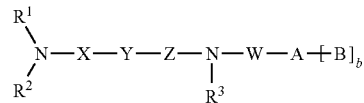

wherein:
- $R^1$ and $R^2$ are each independently H, a $C_{1-8}$-alkyl, or $C_{3-7}$-cycloalkyl group optionally mono- or polysubstituted by the group $R^{11}$, wherein a —$CH_2$— group in position 3 or 4 of a 5-, 6-, or 7-membered cycloalkyl group is optionally replaced by —O—, —S—, or —$NR^{13}$—, or a phenyl or pyridinyl group optionally mono- or polysubstituted by the group $R^{12}$ and/or monosubstituted by nitro, or
- $R^1$ and $R^2$ form a $C_{2-8}$-alkylene bridge, wherein: one or two —$CH_2$— groups are optionally independently replaced by —CH=N— or —CH=CH— and/or one or two —$CH_2$— groups are optionally independently replaced by —O—, —S—, —SO—, —($SO_2$)—, —C=N—O—$R^{18}$—, —CO—, —C(=$CH_2$)—, or —$NR^{13}$— such that heteroatoms are not directly joined together and that a group —C=N—O—$R^{18}$ or —CO— is not directly linked to the group $R^1R^2N$—,
  wherein in the alkylene bridge one or more H atoms are optionally replaced by $R^{14}$, and the alkylene bridge is optionally independently substituted by one or two Cy group such that the bond between the alkylene bridge and the Cy group is made via (a) a single or double bond, (b) a common C atom forming a spirocyclic ring system, (c) two common adjacent C and/or N atoms forming a fused bicyclic ring system, or (d) three or more C and/or N atoms forming a bridged ring system;
- $R^3$ is H, $C_{1-6}$-alkyl, $C_{3-7}$-cycloalkyl, $C_{3-7}$-cycloalkyl-$C_{1-4}$-alkyl, or phenyl-$C_{1-3}$-alkyl;
- X is a $C_{1-8}$-alkylene bridge, wherein:
  - (a) a —$CH_2$— group not directly linked to the group $R^1R^2N$— is optionally replaced by —CH=CH— or —C≡C—, and/or
  - (b) one or two non-adjacent —$CH_2$— groups not directly linked to the group $R^1R^2N$— are each optionally independently replaced by —O—, —S—, —(SO)—, —(SO$_2$), —CO—, or —NR$^4$— such that in each case two O, S, or N atoms or an O and an S atom are not directly joined together, and wherein (i) the bridge X is optionally connected to R$^1$ including the N atom linked to R$^1$ and X forming a heterocyclic group, (ii) the bridge X is optionally additionally connected to R$^2$ including the N atom connected to R$^2$ and X, forming a heterocyclic group, (iii) two C atoms of the alkylene bridge are optionally joined together by an additional C$_{1-4}$-alkylene bridge, and (iv) a C atom is optionally substituted with R$^{10}$ and/or one or two C atoms are optionally independently substituted by one or two substituents selected from C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, C$_{4-7}$-cycloalkenyl, and C$_{4-7}$-cycloalkenyl-C$_{1-3}$-alkyl, while two alkyl and/or alkenyl substituents are optionally joined together, forming a carbocyclic ring system;

W is a single bond and Z is —C≡C—C(=O)—, —CR$^{7a}$=CR$^{7c}$—C(=O)—, or —CR$^{7a}$R$^{7b}$—CR$^{7c}$R$^{7d}$—C(=O)—, or W is —C(=O)—C≡C— and Z is a single bond;

Y has one of the meanings given for Cy, wherein X is optionally connected to Y, forming a carbo- or heterocyclic group fused to Y, and/or R$^1$ is optionally connected to Y, including the group X and the N atom connected to R$^1$ and X, forming a heterocyclic group fused to Y;

A is independently Cy, wherein if b has the value 0, the group Cy does not have an amino group as substituent in the ortho position to W;

B is independently Cy;

b is 0 or 1;

Cy is a carbo- or heterocyclic group selected from (a) a saturated 3- to 7-membered carbocyclic group, (b) a unsaturated 4- to 7-membered carbocyclic group, (c) a phenyl group, (d) a saturated 4- to 7-membered or unsaturated 5- to 7-membered heterocyclic group with an N, O, or S atom as heteroatom, (e) a saturated or unsaturated 5- to 7-membered heterocyclic group with two or more N atoms or with one or two N atoms and one O or S atom as heteroatoms, (f) an aromatic heterocyclic 5- or 6-membered group with one or more identical or different heteroatoms selected from N, O and/or S, wherein the 4-, 5-, 6-, or 7-membered groups are optionally fused to a phenyl or pyridine ring via two common adjacent C atoms, in the 5-, 6-, or 7-membered groups one or two nonadjacent —CH$_2$— groups are optionally independently replaced by a —CO—, —C(=CH$_2$)—, —(SO)—, or —(SO$_2$)— group, the saturated 6- or 7-membered groups optionally occur as bridged ring systems with an imino, N—(C$_{1-4}$-alkyl)-imino, methylene, C$_{1-4}$-alkylmethylene, or di-(C$_{1-4}$-alkyl)methylene bridge, and the cyclic groups are optionally mono- or polysubstituted by R$^{20}$ at one or more C atoms, and in the case of a phenyl group are optionally also additionally be monosubstituted by nitro, and/or one or more NH groups are optionally substituted by R$^{21}$;

R$^4$ is independently R$^{17}$ or C$_{2-6}$-alkenyl or C$_{3-6}$-alkynyl;

R$^{7a}$ and R$^{7c}$ are each independently H, F, Cl, C$_{1-4}$-alkyl, or CF$_3$, R$^{7b}$ and R$^{7d}$ are each independently H, F, or C$_{1-4}$-alkyl, wherein, if R$^{7b}$ and R$^{7d}$ are alkyl, they are optionally joined together to form a cyclopropyl group;

R$^{10}$ is hydroxy, hydroxy-C$_{1-3}$-alkyl, C$_{1-4}$-alkoxy, C$_{1-4}$-alkoxy-C$_{1-3}$-alkyl, carboxy, C$_{1-4}$-alkoxycarbonyl, amino, C$_{1-4}$-alkylamino, di-(C$_{1-4}$-alkyl)amino, cyclo-C$_{3-6}$-alkyleneimino, amino-C$_{1-3}$-alkyl, C$_{1-4}$-alkylamino-C$_{1-3}$-alkyl, di-(C$_{1-4}$-alkyl)amino-C$_{1-3}$-alkyl, cyclo-C$_{3-6}$-alkyleneimino-C$_{1-3}$-alkyl, amino-C$_{1-3}$-alkoxy, C$_{1-4}$-alkylamino-C$_{1-3}$-alkoxy, di-(C$_{1-4}$-alkyl)amino-C$_{1-3}$-alkoxy, cyclo-C$_{3-6}$-alkyleneimino-C$_{1-3}$-alkoxy, aminocarbonyl, C$_{1-4}$-alkylaminocarbonyl, di-(C$_{1-4}$-alkyl)aminocarbonyl, or cyclo-C$_{3-6}$-alkyleneiminocarbonyl;

R$^{11}$ is C$_{2-6}$-alkenyl, C$_{2-6}$-alkynyl, R$^{15}$—O—, R$^{15}$—O—C$_{1-3}$-alkyl, R$^{15}$—O—CO—, R$^{15}$—CO—O—, R$^{16}$R$^{17}$N, cyano, R$^{18}$R$^{19}$N—CO—, or Cy;

R$^{12}$ is independently R$^{20}$;

R$^{13}$ is independently R$^{17}$ excluding carboxy;

R$^{14}$ is halogen, C$_{1-6}$-alkyl, C$_{2-6}$-alkenyl, C$_{2-6}$-alkynyl, R$^{15}$—O, R$^{15}$—O—CO, R$^{15}$—CO, R$^{15}$—CO—O, R$^{16}$R$^{17}$N, R$^{18}$R$^{19}$N—CO—, R$^{15}$—O—C$_{1-3}$-alkyl, R$^{15}$—O—CO—C$_{1-3}$-alkyl, R$^{15}$—O—CO—NH, R$^{15}$—SO$_2$—NH, R$^{15}$—O—CO—NH—C$_{1-3}$-alkyl, R$^{15}$—SO$_2$—NH—C$_{1-3}$-alkyl, R$^{15}$—CO—C$_{1-3}$-alkyl, R$^{15}$—CO—O—C$_{1-3}$-alkyl, R$^{16}$R$^{17}$N—C$_{1-3}$-alkyl, R$^{18}$R$^{19}$N—CO—C$_{1-3}$-alkyl, or Cy-C$_{1-3}$-alkyl;

R$^{15}$ is H, C$_{1-4}$-alkyl, C$_{3-7}$-cycloalkyl, C$_{3-7}$-cycloalkyl-C$_{1-3}$-alkyl, phenyl, phenyl-C$_{1-3}$-alkyl, pyridinyl, or pyridinyl-C$_{1-3}$-alkyl;

R$^{16}$ is H, C$_{1-6}$-alkyl, C$_{3-7}$-cycloalkyl, C$_{3-7}$-cycloalkyl-C$_{1-3}$-alkyl, C$_{4-7}$-cycloalkenyl, C$_{4-7}$-cycloalkenyl-C$_{1-3}$-alkyl, hydroxy-C$_{2-3}$-alkyl, C$_{1-4}$-alkoxy-C$_{2-3}$-alkyl, amino-C$_{2-6}$-alkyl, C$_{1-4}$-alkylamino-C$_{2-6}$-alkyl, di-(C$_{1-4}$-alkyl)amino-C$_{2-6}$-alkyl, or cyclo-C$_{3-6}$-alkyleneimino-C$_{2-6}$-alkyl;

R$^{17}$ is independently R$^{16}$, phenyl, phenyl-C$_{1-3}$-alkyl, pyridinyl, dioxolan-2-yl, —CHO, C$_{1-4}$-alkylcarbonyl, carboxy, hydroxycarbonyl-C$_{1-3}$-alkyl, C$_{1-4}$-alkoxycarbonyl, C$_{1-4}$-alkoxycarbonyl-C$_{1-3}$-alkyl, C$_{1-4}$-alkylcarbonylamino-C$_{2-3}$-alkyl, N-(C$_{1-4}$-alkylcarbonyl)-N-(C$_{1-4}$-alkyl)amino-C$_{2-3}$-alkyl, C$_{1-4}$-alkylsulfonyl, C$_{1-4}$-alkylsulfonylamino-C$_{2-3}$-alkyl, or N-(C$_{1-4}$-alkylsulfonyl)-N(C$_{1-4}$-alkyl)amino-C$_{2-3}$-alkyl;

R$^{18}$ and R$^{19}$ are each independently H or C$_{1-6}$-alkyl;

R$^{20}$ is independently R$^{22}$, halogen, hydroxy, cyano, C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, hydroxy-C$_{1-4}$-alkyl, or R$^{22}$—C$_{1-3}$-alkyl;

R$^{21}$ is C$_{1-4}$-alkyl, hydroxy-C$_{2-3}$-alkyl, C$_{1-4}$-alkoxy-C$_{2-6}$-alkyl, C$_{1-4}$-alkylamino-C$_{2-6}$-alkyl, di-(C$_{1-4}$-alkyl)amino-C$_{2-6}$-alkyl, cyclo-C$_{3-6}$-alkyleneimino-C$_{2-6}$-alkyl, phenyl-C$_{1-3}$-alkyl, C$_{1-4}$-alkyl-carbonyl, C$_{1-4}$-alkoxy-carbonyl, or C$_{1-4}$-alkylsulfonyl; and R$^{22}$ is phenyl-C$_{1-3}$-alkoxy, cyclo-C$_{3-6}$-alkyleneimino-C$_{2-4}$-alkoxy, OHC—, HO—N=HC—, C$_{1-4}$-alkoxy-N=HC—, C$_{1-4}$-alkoxy, C$_{1-4}$-alkylthio, carboxy, C$_{1-4}$-alkylcarbonyl, C$_{1-4}$-alkoxycarbonyl, aminocarbonyl, C$_{1-4}$-alkylaminocarbonyl, di-(C$_{1-4}$-alkyl)aminocarbonyl, cyclo-C$_{3-6}$-alkylaminocarbonyl, cyclo-C$_{3-6}$-alkyleneiminocarbonyl, cyclo-C$_{3-6}$-alkyleneimino-C$_{2-4}$-alkylaminocarbonyl, phenylaminocarbonyl, C$_{1-4}$-alkylsulfonyl, C$_{1-4}$-alkyl-sulfinyl, C$_{1-4}$-alkyl-sulfonylamino, amino, C$_{1-4}$-alkylamino, di-(C$_{1-4}$-alkyl)amino, C$_{1-4}$-alkyl-carbonylamino, cyclo-C$_{3-6}$-alkyleneimino, phenyl-C$_{1-3}$-alkylamino, N-(C$_{1-4}$-alkyl)phenyl-C$_{1-3}$-alkylamino, acetylamino, propionylamino, phenylcarbonylamino, phenylcarbonylmethylamino, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, or alkylaminocarbonylamino-, wherein in each of the above groups and radicals, one or more C atoms are optionally additionally mono- or polysubstituted by F and/or one or two C atoms independently of one another are optionally additionally monosubstituted by Cl or Br and/or one or more phenyl rings optionally independently additionally comprise one, two, or three substituents selected from the group F, Cl, Br, I, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)amino, acetylamino, aminocarbonyl, cyano, difluoromethoxy, trifluoromethoxy, amino-$C_{1-3}$-alkyl, $C_{1-3}$-alkylamino-$C_{1-3}$-alkyl and di-($C_{1-3}$-alkyl)amino-$C_{1-3}$-alkyl and/or are optionally monosubstituted by nitro, and the H atom of a carboxy group present or an H atom bound to an N atom are optionally replaced by a group which can be cleaved in vivo, or a tautomer, enantiomer, salt, or mixture thereof, excluding the following compounds (M1) to (M14):

(M1) N-[4-[[(methylamino)sulfonyl]methyl]phenyl]-3-[2-(dimethylamino)ethyl]-1H-indole-5-propanamide oxalate, (M2) 3-[2-[3-[3,6-dihydro-4-(2-naphthyl)-1(2H)pyridinyl]-2-hydroxypropoxy]phenyl]-N-methyl-N-phenyl-2-propenamide, (M3) 3-[2-[2-hydroxy-3-[4-(1-naphthyl)-1-piperidinyl]propoxy]phenyl]-N-methyl-N-phenyl-2-propenamide, (M4) 3-[2-[2-hydroxy-3-[4-(2-naphthyl)-1-piperidinyl]propoxy]phenyl]-N-methyl-N-phenyl-2-propenamide, (M5) 3-[2-[2-hydroxy-3-[4-(2-naphthalyl)-1-piperidinyl]propoxy]phenyl]-N-phenyl-2-propenamide, (M6) N-[4-[1-(1H-imidazol-1-yl)-2-methylpropyl]phenyl]-3-phenyl-2-propinamide, (M7) 2'-[[3-(dimethylamino)propyl]thio]-3-phenylpropiolanilide, (M8) 2-(methylthio)-5-[[3-[4-(octadecylamino)phenyl]-1-oxopropyl]amino]benzoic acid, including the trifluoroacetate salt, (M9) 4-amino-N-(4-hydroxy-3,5-dimethylphenyl)benzenepropanamide, (M10) 4-(dimethylamino)-N-(4-hydroxy-3,5-dimethylphenyl)benzenepropanamide, (M11) β-methyl-4-[[3-[2-[(2-methylphenyl)amino]-6-benzoxazolyl]-1-oxopropylamino]benzenepropanoic acid, (M12) 4-[3-[[1-oxo-3-[2-(phenylamino)-6-benzoxazolyl]propyl]amino]phenoxy]butanoic acid, (M13) 2-chloro-5-[[1-oxo-3-[4-[(5-phenylpentyl)amino]phenyl]propyl]amino]benzoic acid, and (M14) methyl 2-chloro-5-[[1-oxo-3-[4-[(5-phenylpentyl)amino]phenyl]propyl]amino]-benzoate.

2. The compound of formula (I) according to claim 1, wherein the compound of formula (I) has the following formula Ia or Ib:

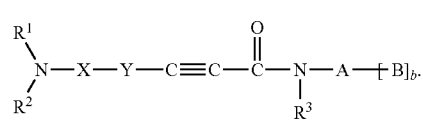

Ia

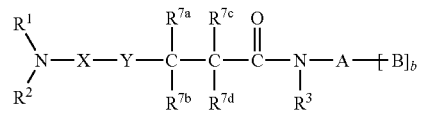

Ib

3. The compound of formula (I) according to claim 1, wherein the compound of formula (I) has the following formula Ic or Id:

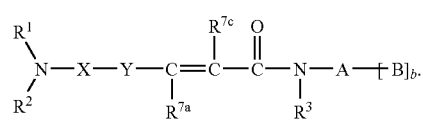

Ic

Id

4. The compound of formula (I) according to one of claims 1, 2, or 3, wherein:

$R^1$ and $R^2$ are each independently $C_{1-6}$-alkyl, $C_{3-7}$-cycloalkyl, $C_{3-7}$-cycloalkyl-$C_{1-3}$-alkyl, hydroxy-$C_{2-4}$-alkyl, NC—$C_{2-4}$-alkyl, $C_{1-4}$-alkoxy-$C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkylamino-$C_{2-4}$-alkyl, di-($C_{1-4}$-alkyl)amino-$C_{2-4}$-alkyl, cyclo-$C_{3-6}$-alkyleneimino-$C_{2-4}$-alkyl, pyrrolidin-3-yl wherein the NH group is optionally independently substituted by $R^{13}$, pyrrolidinyl-$C_{1-3}$-alkyl wherein the NH group is optionally independently substituted by $R^{13}$, piperidin-3-yl or 4-yl wherein the NH group is optionally independently substituted by $R^{13}$, piperidinyl-$C_{1-3}$-alkyl wherein the NH group is optionally independently substituted by $R^{13}$, tetrahydropyran-3-yl or -4-yl, tetrahydropyranyl-$C_{1-3}$-alkyl, tetrahydrofuran-3-yl, tetrahydrofuranyl-$C_{1-3}$-alkyl, phenyl, phenyl-$C_{1-3}$-alkyl, pyridyl, or pyridyl-$C_{1-3}$-alkyl, wherein one of $R^1$ or $R^2$ is optionally H, and wherein in each of the above groups and radicals, one or more C atoms are optionally independently mono- or polysubstituted by F and/or one or two C atoms; the phenyl or pyridyl groups are optionally independently mono- or polysubstituted by $R^{12}$ and/or monosubstituted by nitro; cycloalkyl rings are optionally mono- or polysubstituted by substituents selected from hydroxy, hydroxy-$C_{1-3}$-alkyl, $C_{1-3}$-alkyl, or $C_{1-3}$-alkyloxy; $C_{2-4}$-alkyl bridges contained in hydroxy-$C_{2-4}$-alkyl- and $C_{1-4}$-alkoxy-$C_{2-4}$-alkyl- are optionally independently additionally monosubstituted by hydroxy, hydroxy-$C_{1-3}$-alkyl, $C_{1-3}$-alkyl, or $C_{1-3}$-alkyloxy.

5. The compound of formula (I) according to one of claims 1, 2, or 3, wherein:

$R^1$ and $R^2$ form an alkylene bridge such that $R^1R^2N$— is azetidine, pyrrolidine, piperidine, azepan, 2,5-dihydro-1H-pyrrole, 1,2,3,6-tetrahydropyridine, 2,3,4,7-tetrahydro-1H-azepine, 2,3,6,7-tetrahydro-1H-azepine, piperazine wherein the free imine function is substituted by $R^{13}$, piperidin-4-one-oxime, piperidin-4-one-O—$C_{1-4}$-alkyl-oxime, morpholine, and thiomorpholine, wherein in the alkylene bridge one or more H atoms are optionally replaced by $R^{14}$, and the alkylene bridge is optionally independently substituted by one or two Cy group such that the bond between the alkylene bridge and the Cy group is made via (a) a single or double bond, (b) a common C atom forming a spirocyclic ring system, (c) two common adjacent C and/or N atoms forming a fused bicyclic ring system, or (d) three or more C and/or N atoms forming a bridged ring system.

6. The compound of formula (I) according to one of claims 1, 2, or 3, wherein the group

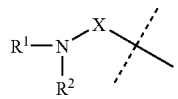

thereof is defined according to one of the following partial formulae

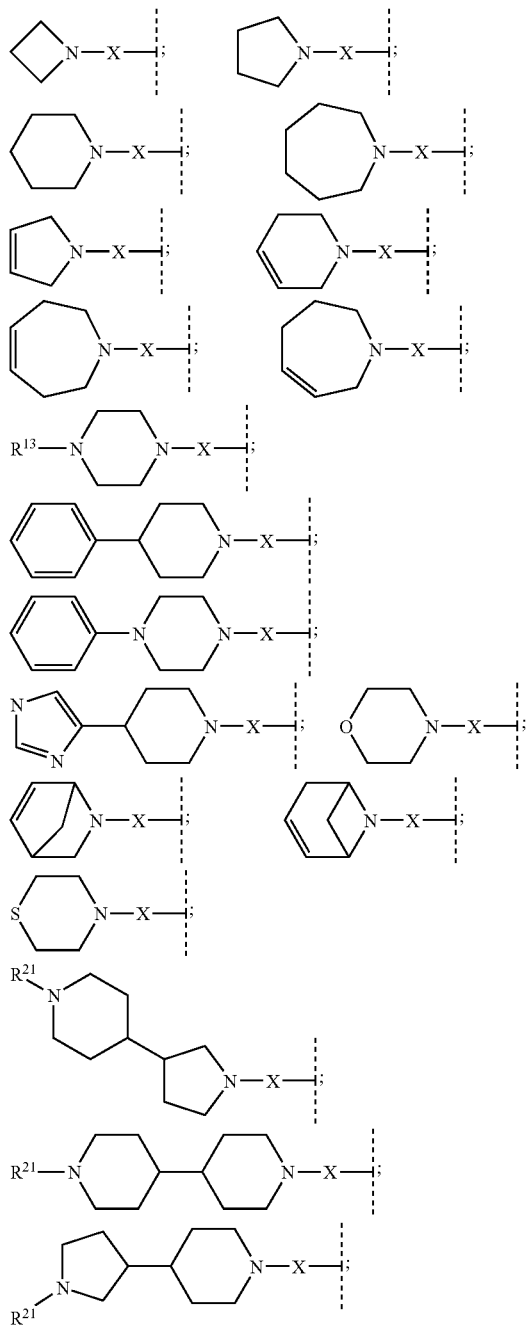

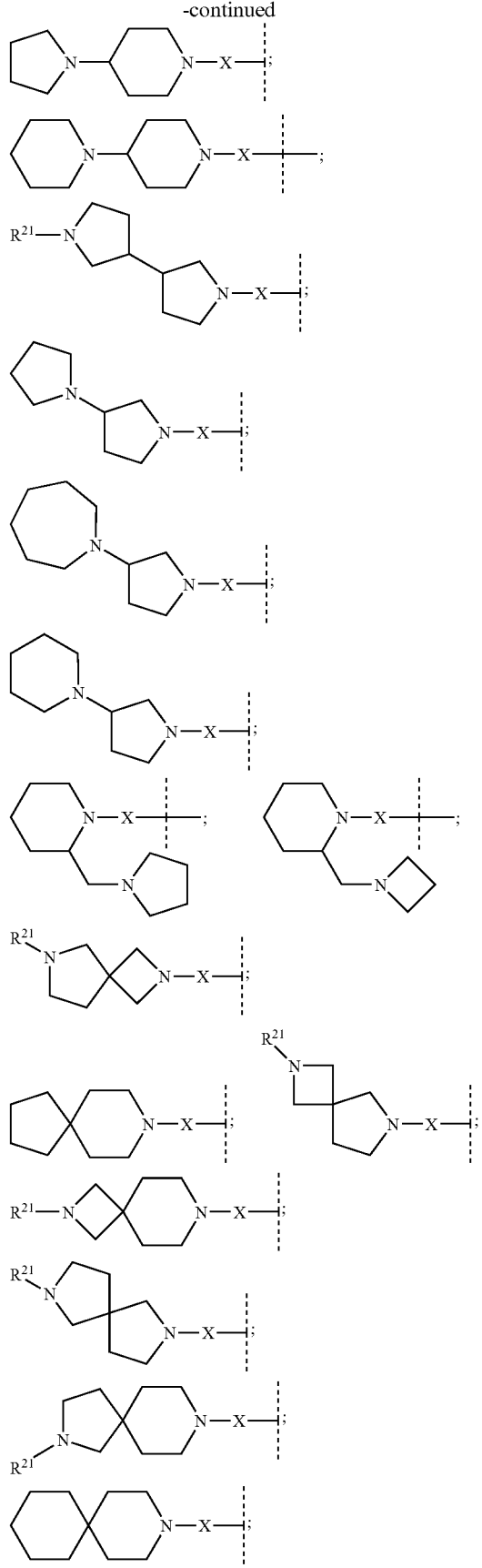

-continued

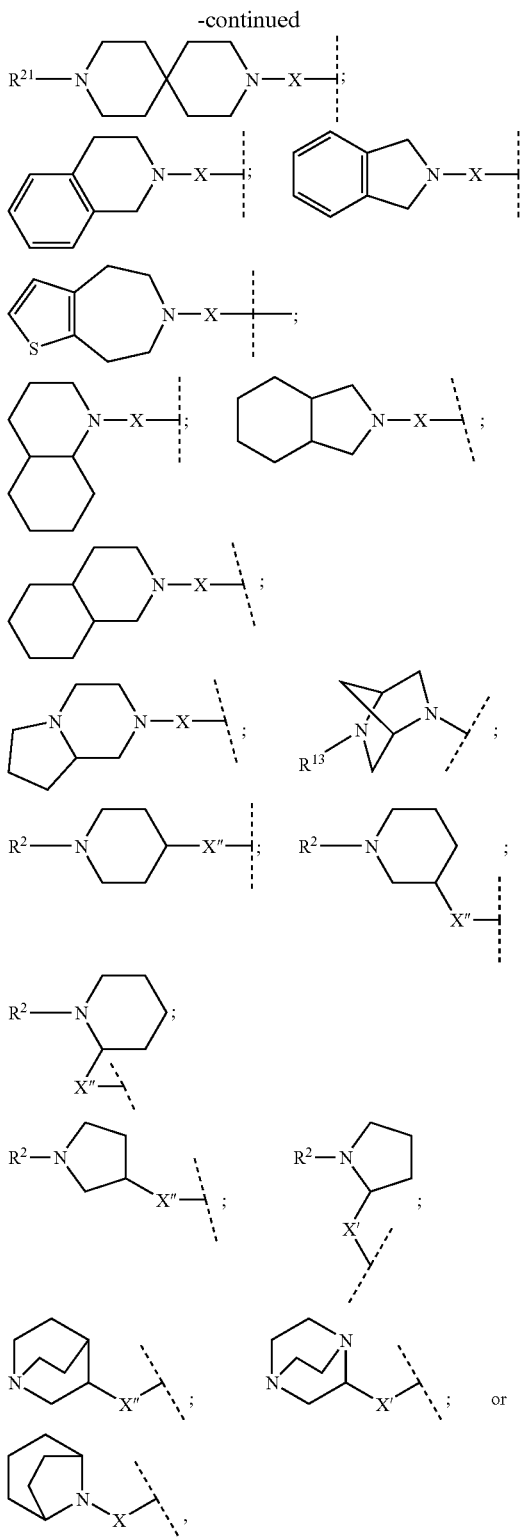

wherein in the heterocycle formed by the group $R^1R^2N—$ one or more H atoms are optionally replaced by $R^{14}$ and/or a H atom is optionally substituted by $C_{3-7}$-cycloalkyl optionally mono- or polysubstituted by $R^{20}$, and the ring connected to the heterocycle formed by the group $R^1R^2N—$ is optionally mono- or polysubstituted at one or more C atoms by $R^{20}$, and, in the case of a phenyl ring, is additionally optionally monosubstituted by nitro;

X' or X" are each independently a single bond or $C_{1-3}$-alkylene, and in the event that the group Y is linked to X' or X" via a C atom, X' or X" are each additionally —$C_{1-3}$-alkylene-O—, —$C_{1-3}$-alkylene-NH— or —$C_{1-3}$-alkylene-N($C_{1-3}$-alkyl)-, and X" is additionally —O—$C_{1-3}$-alkylene-, —NH—$C_{1-3}$-alkylene-, or —N($C_{1-3}$-alkyl)-$C_{1-3}$-alkylene- and, in the event that the group Y is linked to X" via a C atom, X" is additionally —NH—, —N($C_{1-3}$-alkyl)-, or —O—, wherein in X' or X" a C atom is optionally substituted by $R^{10}$ and/or one or two C atoms are optionally independently substituted by substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, wherein two alkyl and/or alkenyl substituents are optionally joined together forming a carbocyclic ring system, and in X' or X" one or more C atoms are each optionally independently mono- or polysubstituted by F and/or one or two C atoms are each optionally independently monosubstituted by Cl or Br.

7. The compound of formula (I) according to one of claims 1, 2, or 3, wherein:

X is an unbranched $C_{1-4}$-alkylene bridge and, if Y is linked to X via a C atom, X is also a single bond, —$CH_2$—CH=CH—, —$CH_2$—C≡C—, $C_{2-4}$-alkylenoxy, or $C_{2-4}$-alkylene-$NR^4$, wherein X is optionally connected to $R^1$, including the N atom connected to $R^1$ and X, forming a heterocyclic group, and in X a C atom is optionally substituted by $R^{10}$ and/or one or two C atoms are optionally independently substituted by one or two substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, wherein two alkyl and/or alkenyl substituents are optionally joined together forming a carbocyclic ring system, and wherein in each of the above groups and radicals, one or more C atoms are optionally mono- or polysubstituted by F and/or one or two C atoms are optionally independently monosubstituted by Cl or Br.

8. The compound of formula (I) according to claim 7, wherein:

X is —$CH_2$—, —$CH_2$—$CH_2$—, or —$CH_2$—$CH_2$—$CH_2$—, and if Y is linked to X via a C atom, X is also a single bond, —$CH_2$—CH=CH—, —$CH_2$—C≡C—, —$CH_2$—$CH_2$—O—, —$CH_2$—$CH_2$—$CH_2$—O—, —$CH_2$—$CH_2$-$NR^4$—, or —$CH_2$—$CH_2$—$CH_2$—$NR^4$—, wherein X is optionally connected to $R^1$, including the N atom linked to $R^1$ and X, forming a heterocyclic group, and in X a C atom is optionally substituted by $R^{10}$, and/or one or two C atoms are optionally independently substituted by one or two substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, wherein two alkyl and/or alkenyl substituents are optionally joined together forming a carbocyclic ring system.

9. The compound of formula (I) according to one of claims 1, 2, or 3, wherein:

Y is phenyl, pyridinyl, naphthyl, tetrahydronaphthyl, indolyl, dihydroindolyl, quinolinyl, dihydroquinolinyl, tetrahydroquinolinyl, isoquinolinyl, dihydroisoquinolinyl, tetrahydroisoquinolinyl, or benzoxazolinyl, each optionally independently mono- or polysubstituted by $R^{20}$ at one or more C atoms and, in the case of a phenyl group, additionally optionally monosubstituted by nitro, and/or optionally independently substituted by $R^{21}$ at one or more N atoms.

10. The compound of formula (I) according to one of claims 1, 2, or 3, wherein:

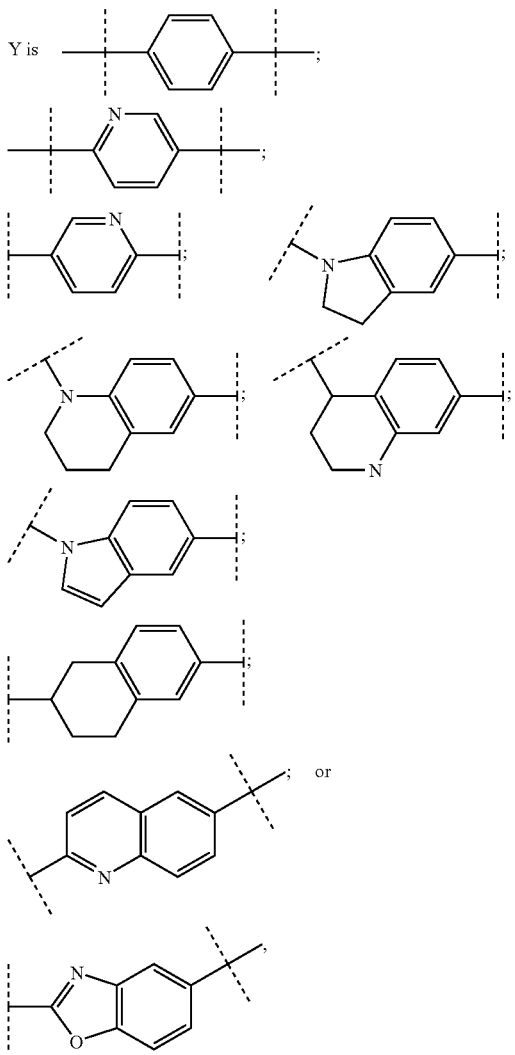

each optionally independently mono- or polysubstituted by $R^{20}$ at one or more C atoms and, in the case of a phenyl group, optionally additionally monosubstituted by nitro, and/or one or more NH groups are optionally independently substituted by $R^{21}$.

11. The compound of formula (I) according to one of claims 1, 2, or 3, wherein:

Y is linked to X, forming a carbocyclic group fused to Y, wherein the carbocyclic group —X—Y— formed is selected from the carbocyclic group —X—Y—, the phenyl ring is optionally mono- or polysubstituted by $R^{20}$ or is optionally additionally monosubstituted by nitro, and the saturated carbocyclic ring is optionally mono- or disubstituted by $C_{1-3}$-alkyl.

12. The compound of formula (I) according to one of claims 1, 2, or 3, wherein:

A is phenyl, pyridyl, or naphthyl, each optionally independently mono- or polysubstituted by $R^{20}$ at one or more C atoms, and in the case of a phenyl ring, optionally additionally monosubstituted by nitro, and/or one or more NH groups are optionally independently substituted by $R^{21}$, wherein if b is 0, A cannot have an amino group as substituent in the ortho position to W.

13. The compound of formula (I) according to claim 1, wherein b is 0.

14. The compound of formula (I) according to claim 1, wherein:

b is 1; and

B is phenyl, furanyl, thienyl, or pyridyl, each optionally independently mono- or polysubstituted by $R^{20}$ at one or more C atoms and, in the case of a phenyl ring, optionally additionally monosubstituted by nitro.

15. The compound of formula (I) according to one of claims 1, 2, or 3, wherein the compound is a physiologically acceptable salt.

16. A pharmaceutical composition comprising the compound of formula (I) according to one of claims 1, 2, or 3, and one or more physiologically acceptable excipients, inert carriers, or diluents.

17. The compound of formula (I) according to one of claims 1, 2, or 3, wherein the group

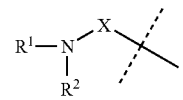

thereof is defined according to one of the following partial formulae

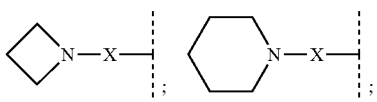

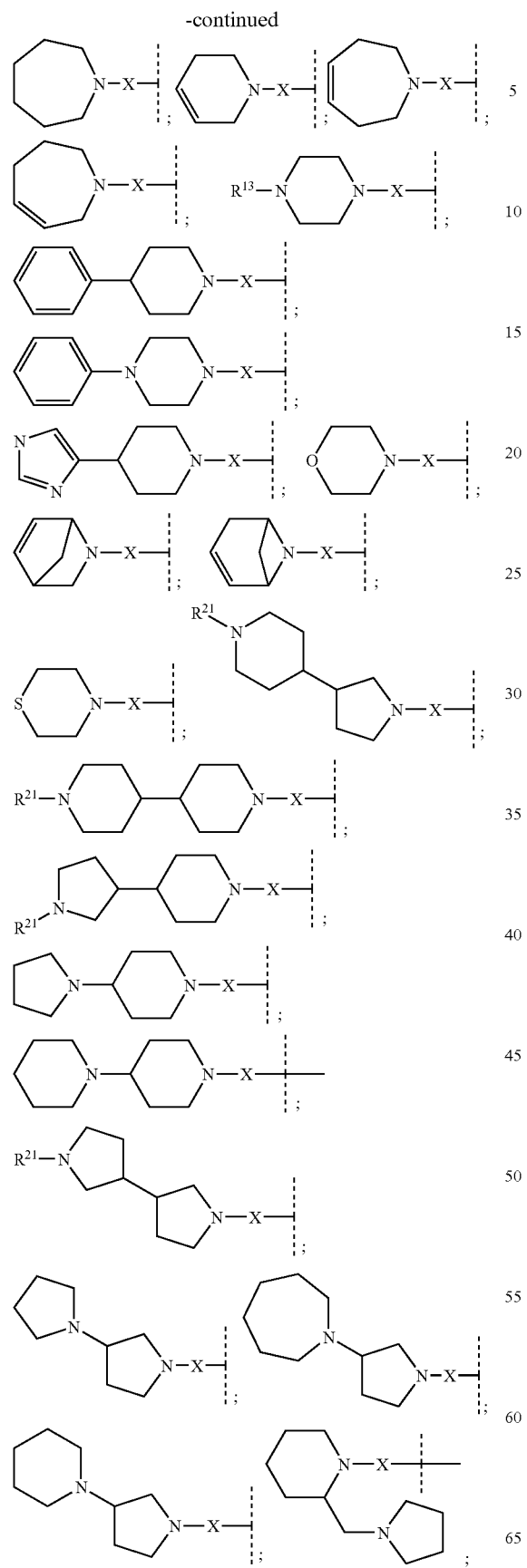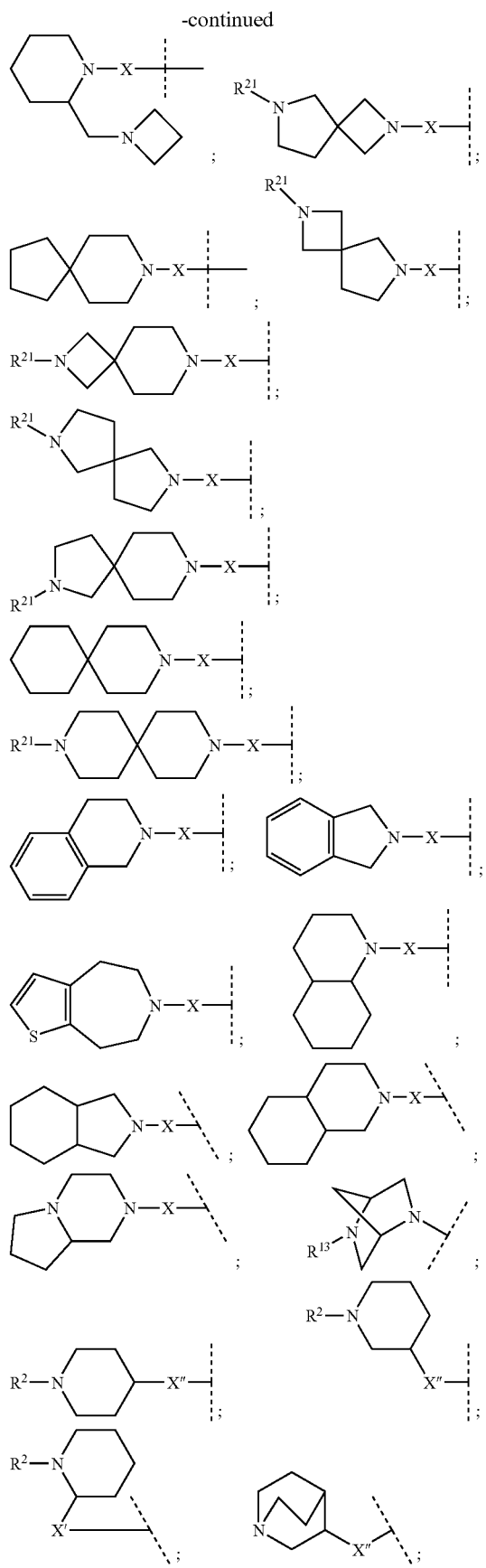

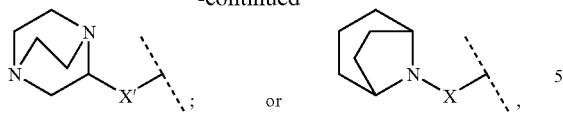

wherein in the heterocycle formed by the group R¹R²N— one or more H atoms are optionally replaced by $R^{14}$ and/or a H atom is optionally substituted by $C_{3-7}$cycloalkyl optionally mono- or polysubstituted by $R^{20}$, and the ring connected to the heterocycle formed by the group R¹R²N— is optionally mono- or polysubstituted at one or more C atoms by $R^{20}$, and, in the case of a phenyl ring, is additionally optionally monosubstituted by nitro;

X' and X" are each independently a single bond or $C_{1-3}$-alkylene, and in the event that the group Y is linked to X' or X" via a C atom, X' and X" are each additionally —$C_{1-3}$-alkylene-O—, -$C_{1-3}$-alkylene-NH— or —$C_{1-3}$-alkylene-N($C_{1-3}$alkyl)-, and X" is additionally —O—$C_{1-3}$-alkylene-, —NH—$C_{1-3}$-alkylene-, or —N($C_{1-3}$-alkyl)-$C_{1-3}$-alkylene- and, in the event that the group Y is linked to X" via a C atom, X" is additionally —NH—, —N($C_{1-3}$-alkyl)-, or —O—, wherein in X' and X" a C atom is optionally substituted by $R^{10}$ and/or one or two C atoms are optionally independently substituted by substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, wherein two alkyl and/or alkenyl substituents are optionally joined together forming a carbocyclic ring system, and in X' and X" one or more C atoms are each optionally independently mono- or polysubstituted by F and/or one or two C atoms are each optionally independently monosubstituted by Cl or Br.

18. The compound of formula (I) according to one of claims 1, 2, or 3, wherein R¹ and R² are each independently H, a $C_{1-8}$-alkyl, or $C_{3-7}$-cycloalkyl group optionally mono- or polysubstituted by the group $R^{11}$, wherein a —$CH_2$— group in position 3 or 4 of a 5-, 6-, or 7-membered cycloalkyl group is optionally replaced by —O—, —S—, or —$NR^{13}$—, or a phenyl or pyridinyl group optionally mono- or polysubstituted by the group $R^{12}$ and/or monosubstituted by nitro.

* * * * *